US010738113B2

(12) United States Patent
Rondon et al.

(10) Patent No.: US 10,738,113 B2
(45) Date of Patent: Aug. 11, 2020

(54) ANTI-IL-2 ANTIBODIES AND COMPOSITIONS AND USES THEREOF

(71) Applicants: Pfizer Inc., New York, NY (US); The Regents of the University of California, Oakland, CA (US); The Board of Trustees of the Leland Stanford Junior University, Stanford, CA (US)

(72) Inventors: Isaac J. Rondon, San Francisco, CA (US); Natasha Crellin, San Carlos, CA (US); Paul Bessette, San Francisco, CA (US); Eleonora Trotta, San Francisco, CA (US); Jeffrey A. Bluestone, San Francisco, CA (US); Lauren K. Ely, Palo Alto, CA (US); Kenan C. Garcia, Menlo Park, CA (US)

(73) Assignees: THE REGENTS OF THE UNIVERSITY OF CALIFORNIA, Oakland, CA (US); PFIZER INC., New York, NY (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 64 days.

(21) Appl. No.: 16/133,939

(22) Filed: Sep. 18, 2018

(65) Prior Publication Data
US 2019/0106488 A1 Apr. 11, 2019

Related U.S. Application Data

(62) Division of application No. 15/331,038, filed on Oct. 21, 2016, now Pat. No. 10,138,298.

(60) Provisional application No. 62/408,360, filed on Oct. 14, 2016, provisional application No. 62/245,600, filed on Oct. 23, 2015.

(51) Int. Cl.
| C12N 5/00 | (2006.01) |
| C12N 15/00 | (2006.01) |
| C07H 21/04 | (2006.01) |
| C07K 16/24 | (2006.01) |
| A61K 39/00 | (2006.01) |

(52) U.S. Cl.
CPC ...... *C07K 16/246* (2013.01); *A61K 2039/505* (2013.01); *C07K 2317/21* (2013.01); *C07K 2317/33* (2013.01); *C07K 2317/51* (2013.01); *C07K 2317/565* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

WO 2014028748 A1 2/2014
WO 2015109212 A1 7/2015

OTHER PUBLICATIONS

Boyman et al., "Potential use of IL-2/anti-IL-2 antibody immune complexes for the treatment of cancer and autoimmune disease", Expert Opinion on Biological Therapy, Informa Healthcare. Ashley, vol. 6. No. 12, Dec. 2006, pp. 1323-1331.
Krieg et al., "Improved IL-2 immunotherapy by selective stimulation of IL-2 receptors on lymphocytes and endothelial cells", Proceedings of the National Academy of Sciences. National Academy of Sciences, vol. 107. No. 26, Jun. 29, 2010, pp. 11906-11911.
León et al., "Mathematical Models of the Impact of IL2 Modulation Therapies on T Cell Dynamics", Frontiers in Immunology, vol. 4, Jan. 2013.
Littwitz-Salomon et al., "Activated regulatory T cells suppress effector NK cell responses by an IL-2-mediated mechanism during an acute retroviral infection", Retrovirology. Biomed Central Ltd., vol. 12, Jul. 30, 2015, 13 pages.
PCT/US2016/058249 , "International Preliminary Report on Patentability", dated May 3, 2018, 14 pages.
PCT/US2016/058249 , "International Search Report and Written Opinion", dated Mar. 31, 2017, 20 pages.
Rojas et al., "Deciphering the molecular bases of the biological effects of antibodies against Interleukin-2: a versatile platform for fine epitope mapping", Immunobiology, vol. 218, No. 1, Jan. 2013, pp. 105-113.
Rojas et al., "Fine epitope specificity of antibodies against interleukin-2 explains their paradoxical immunomodulatory effects", MAbs, vol. 6, No. 1, Nov. 2013, pp. 273-285.
Spangler et al., "Antibodies to Interleukin-2 elicit selective T cell subset potentiation through distinct conformational mechanisms", Immunity, vol. 42. No. 5, May 2015, pp. 815-825.

*Primary Examiner* — Shulamith H Shafer
(74) *Attorney, Agent, or Firm* — Kilpatrick Townsend & Stockton LLP

(57) ABSTRACT

The present invention provides antibodies, or antigen-binding portions thereof, which specifically bind to IL-2 and reduce the affinity of IL-2 binding to IL-2Rα and IL-2Rβ. The invention further provides a method of obtaining such antibodies and nucleic acids encoding the same. The invention further relates to compositions and therapeutic methods for use of these antibodies for the treatment and/or prevention of autoimmune diseases, disorders or conditions and for immunosuppression, including, but not limited to, administering a complex comprising the antibody and IL-2.

6 Claims, 52 Drawing Sheets
Specification includes a Sequence Listing.

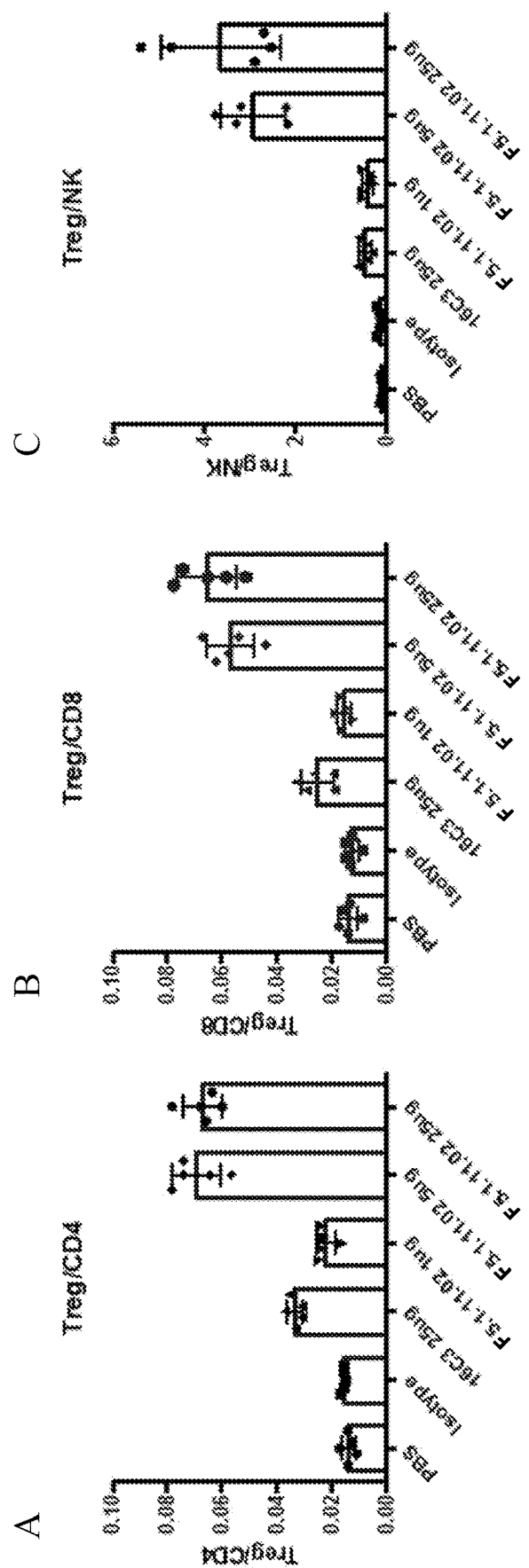
Fig. 4A-C

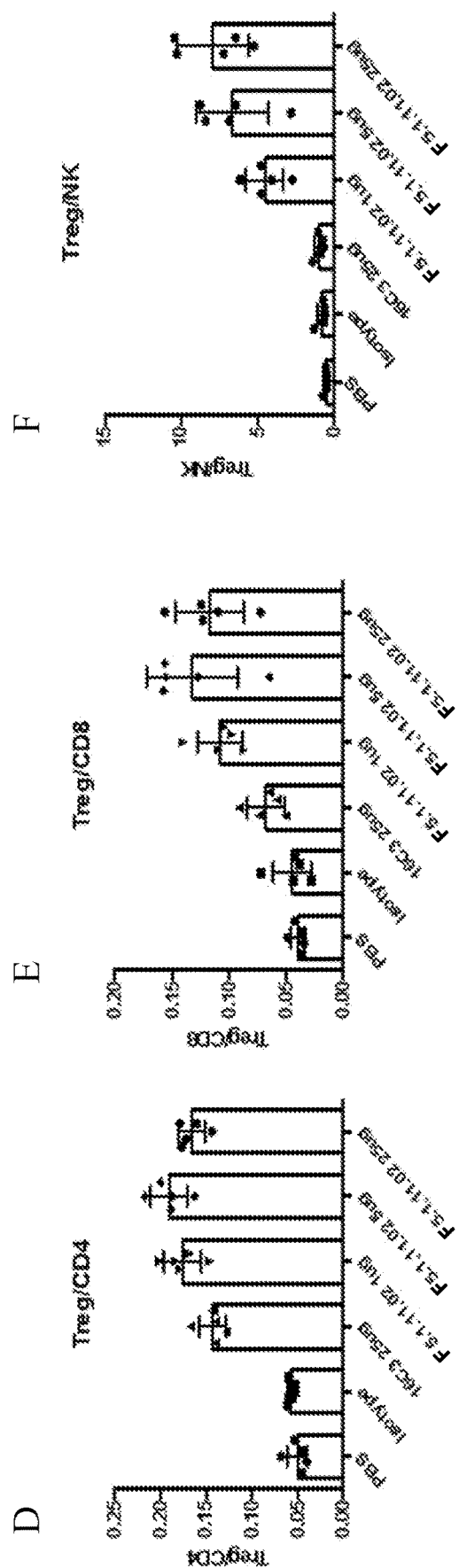
Fig. 4D-F

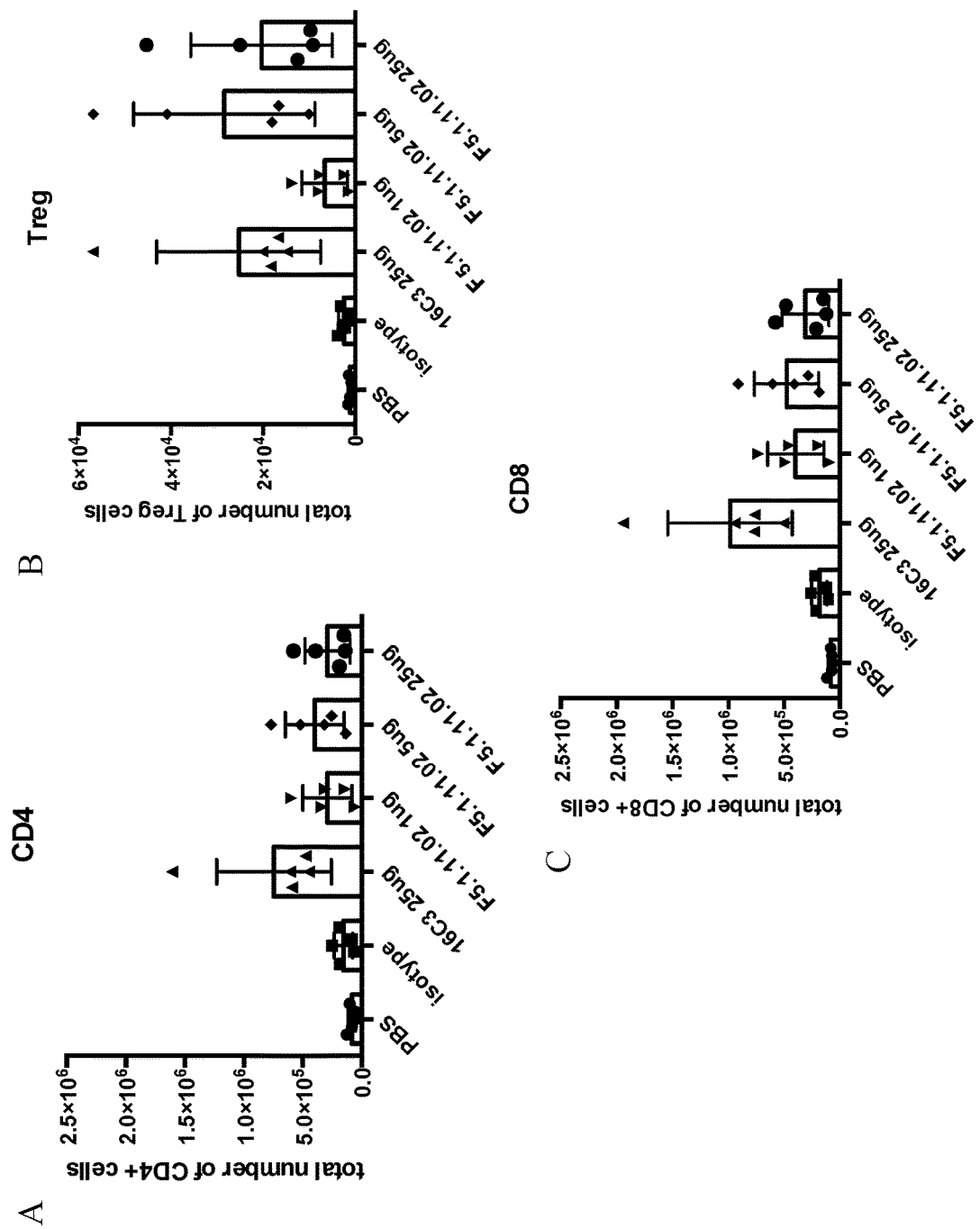
Fig. 5A-C

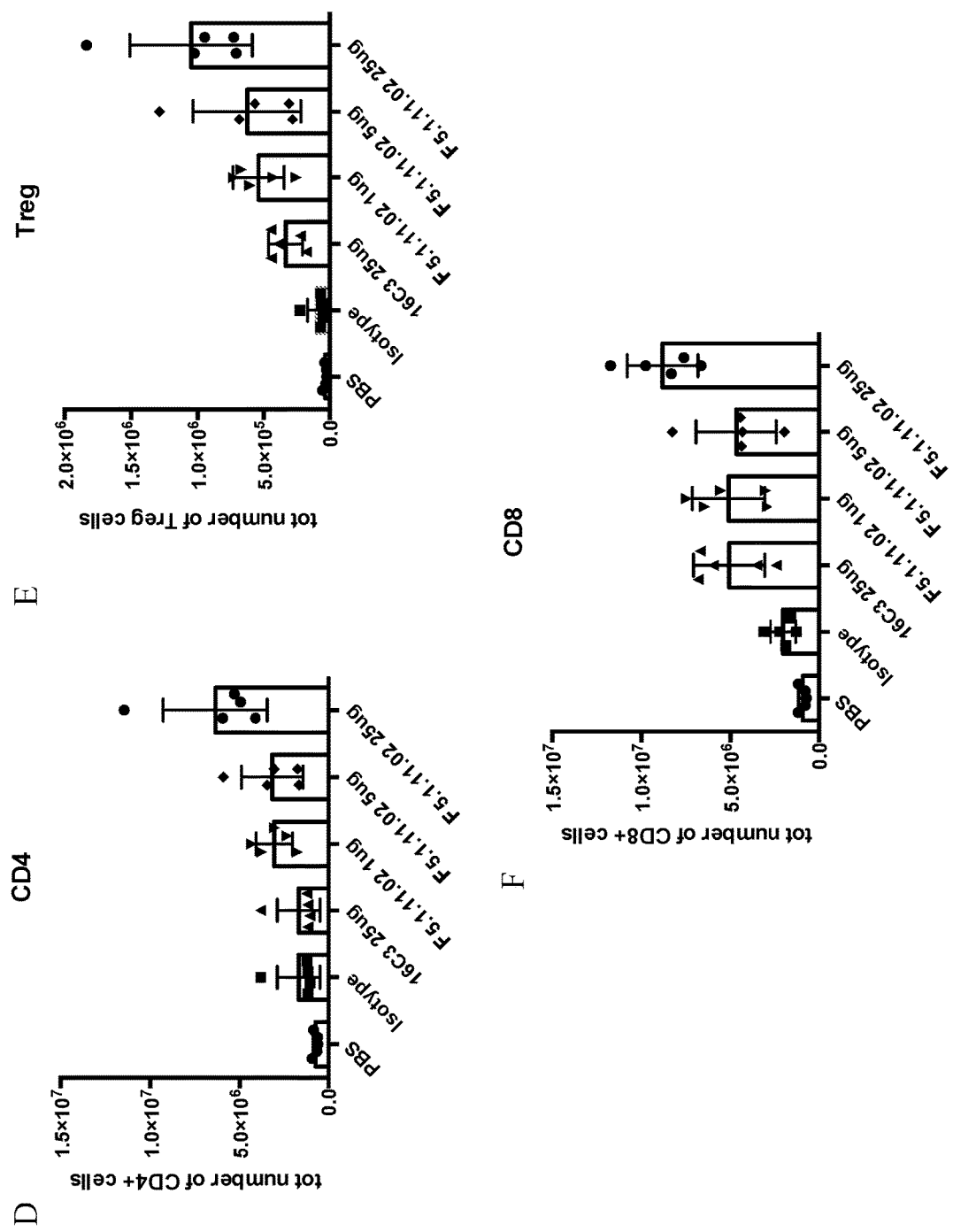
Fig. 5D-F

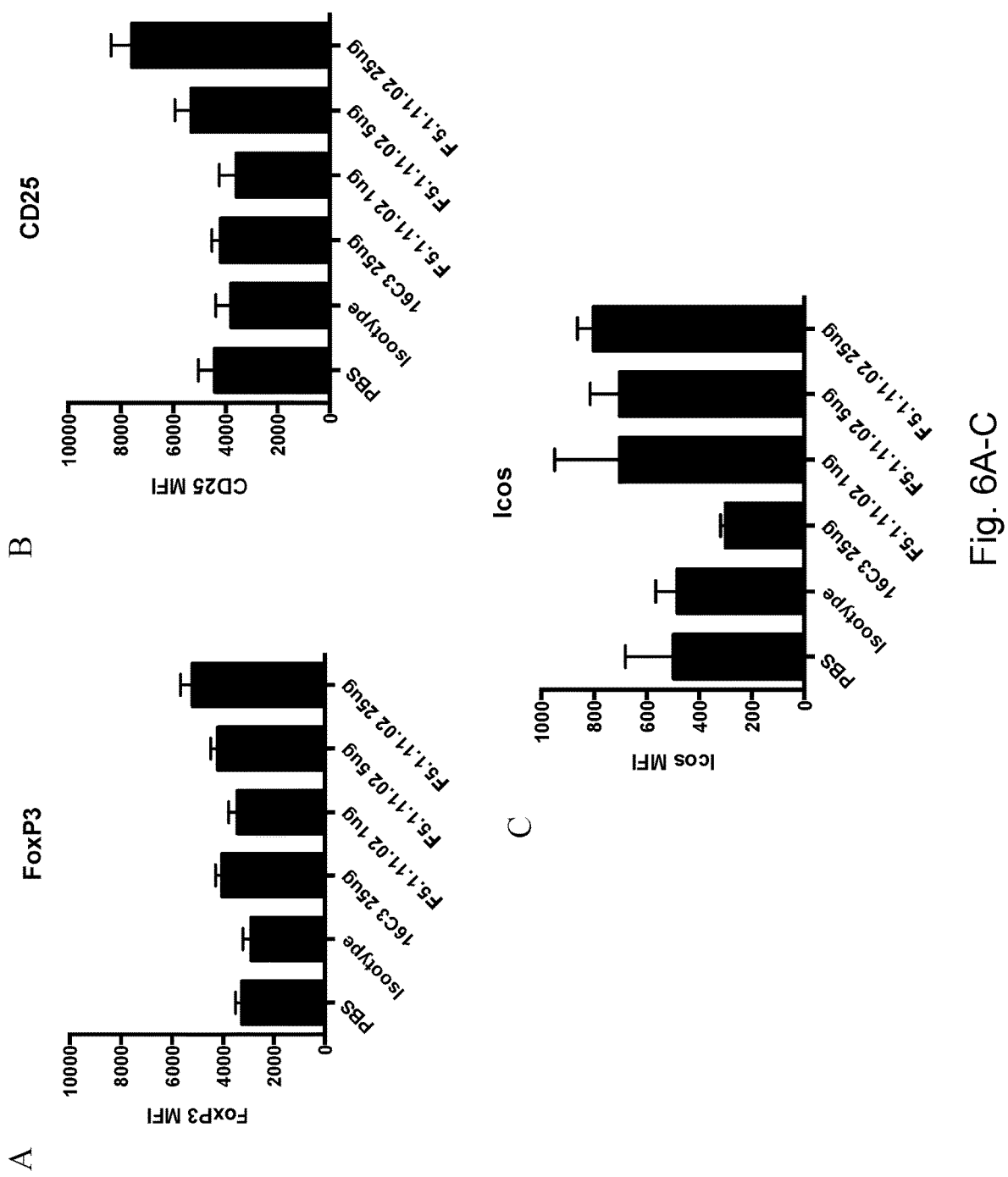
Fig. 6A-C

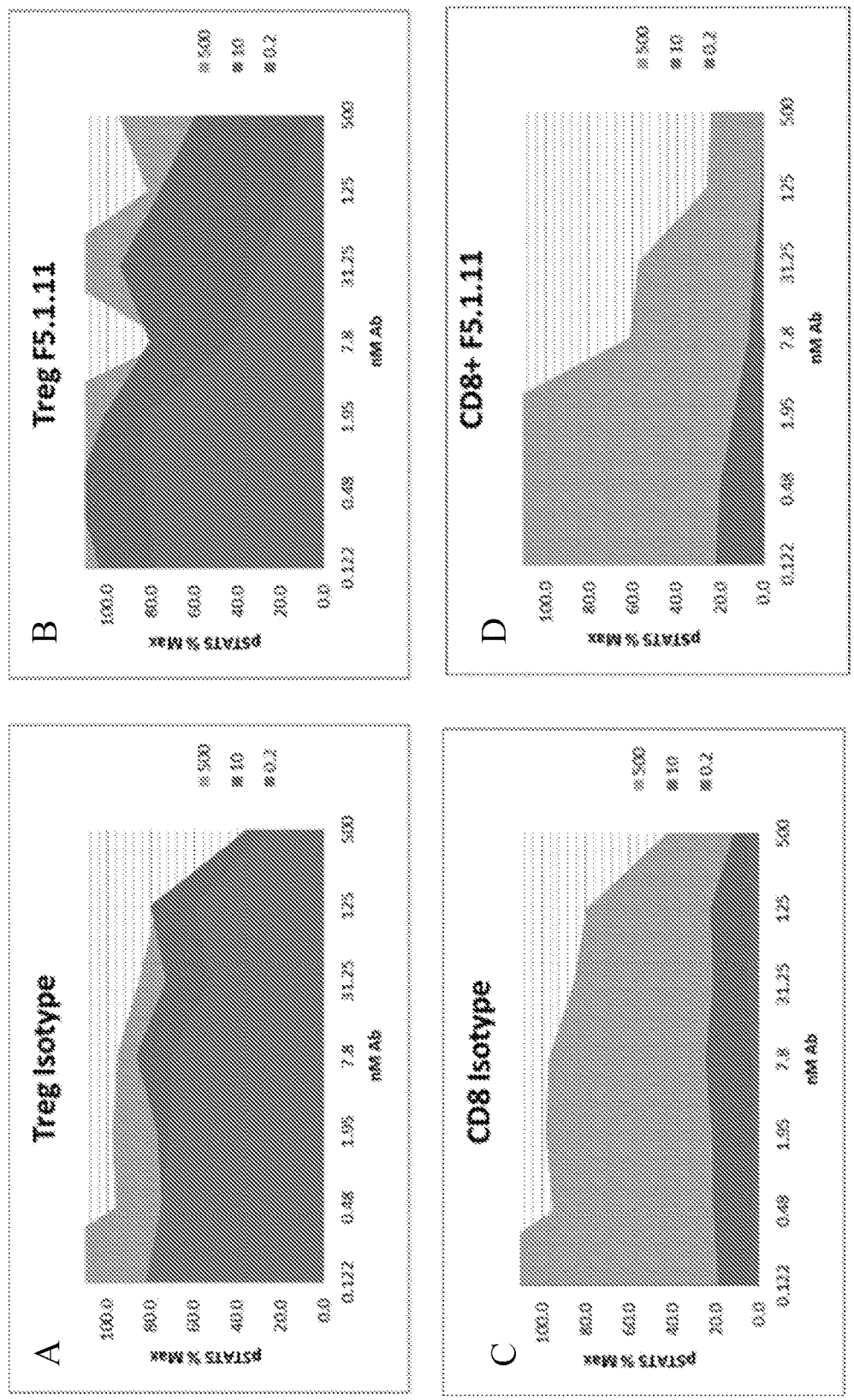
Fig. 7A-D

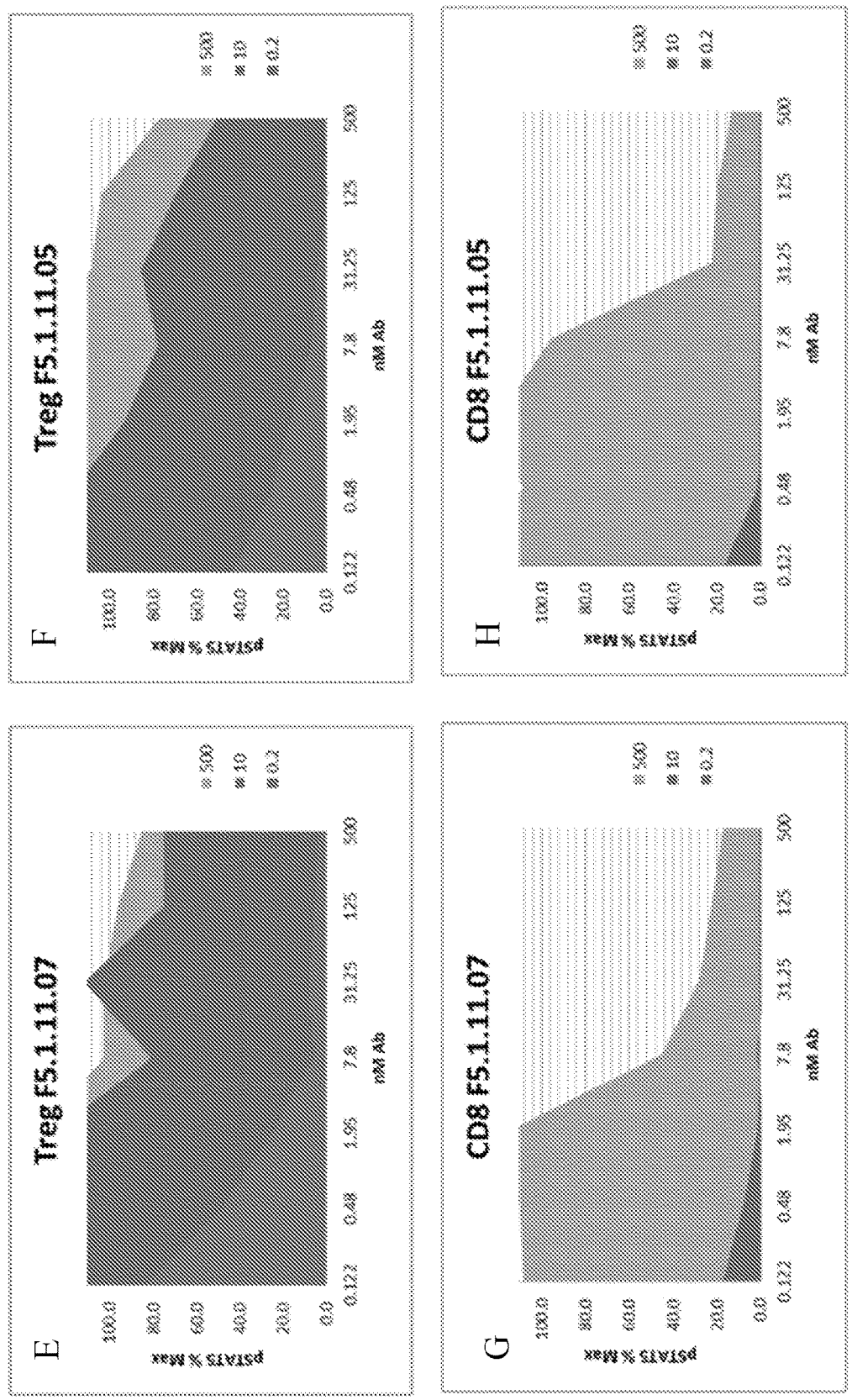
Fig. 7E-H

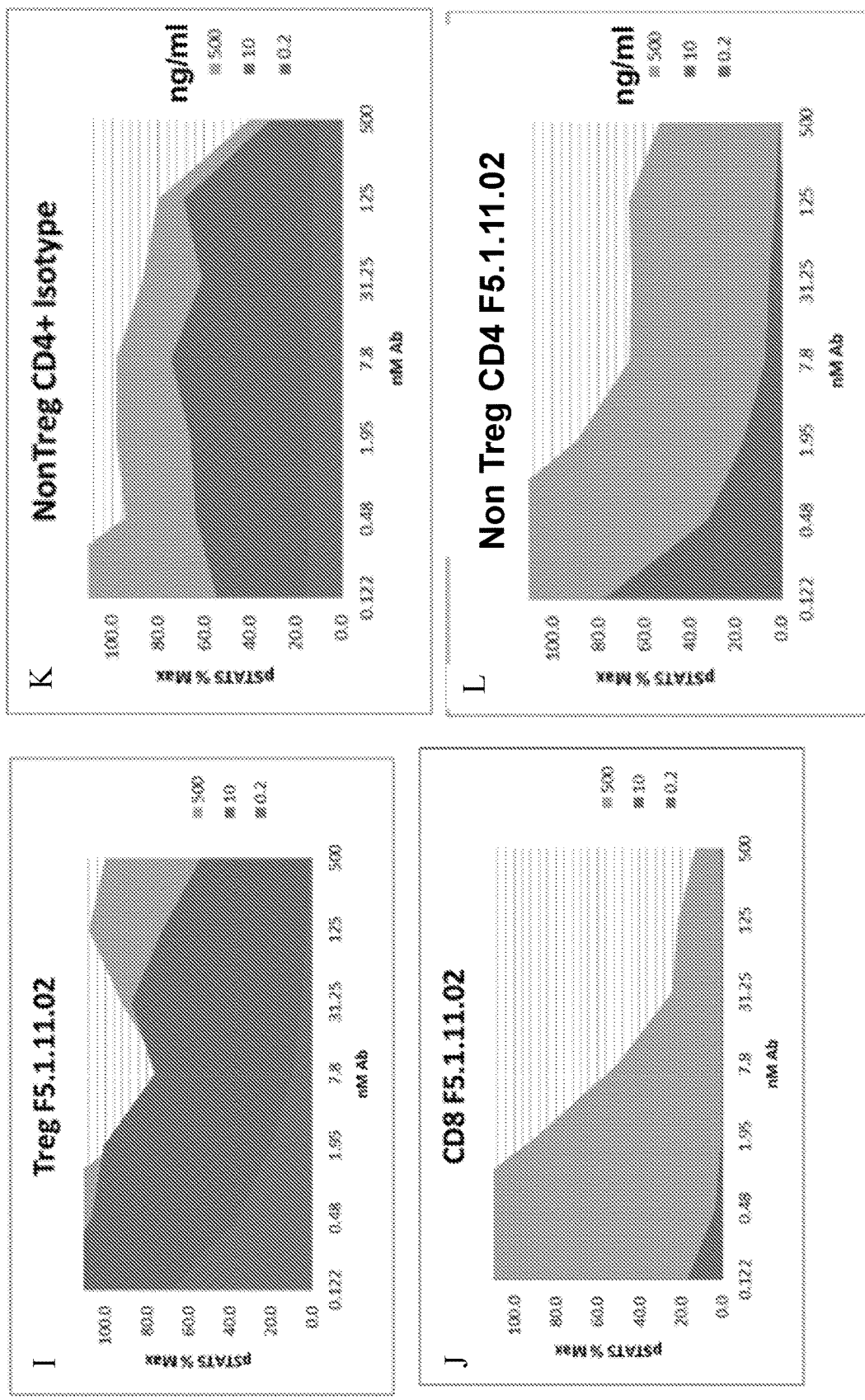
Fig. 7I-L

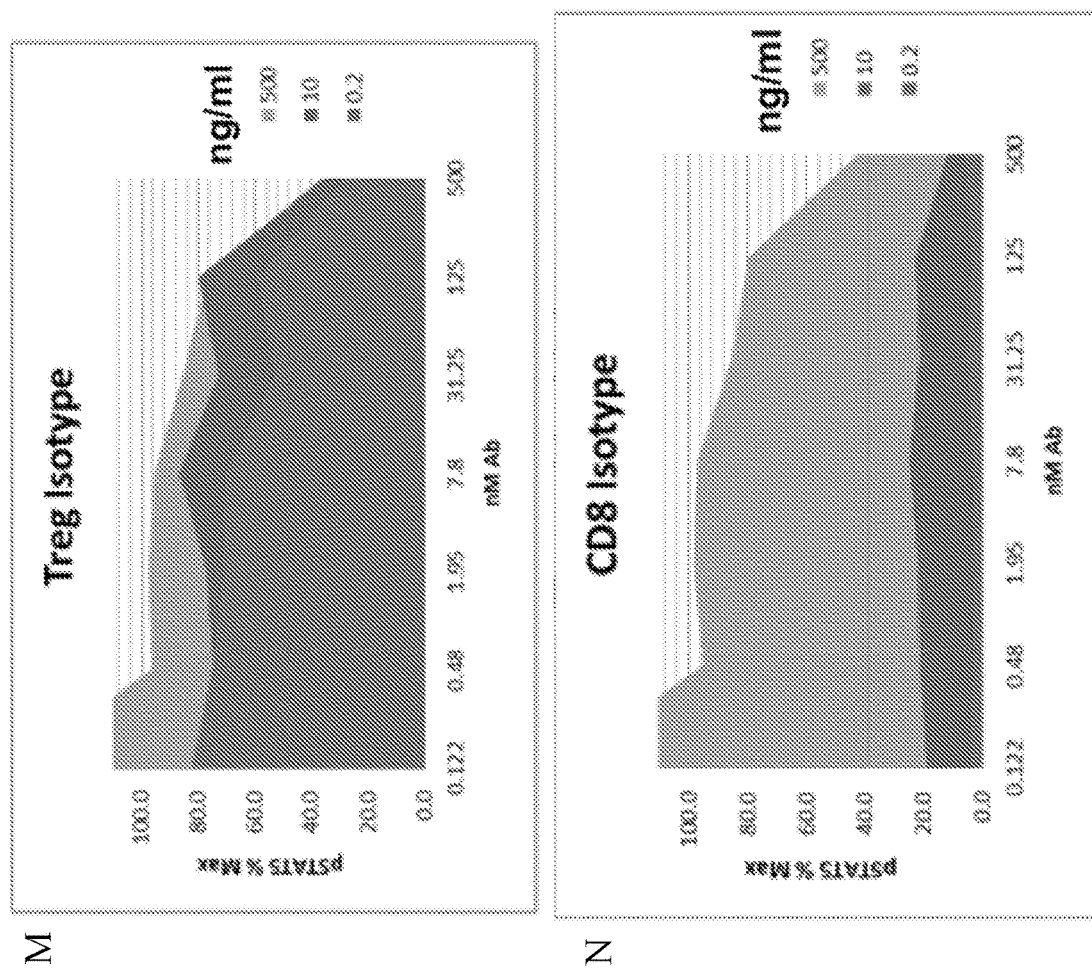
Fig. 7M-N

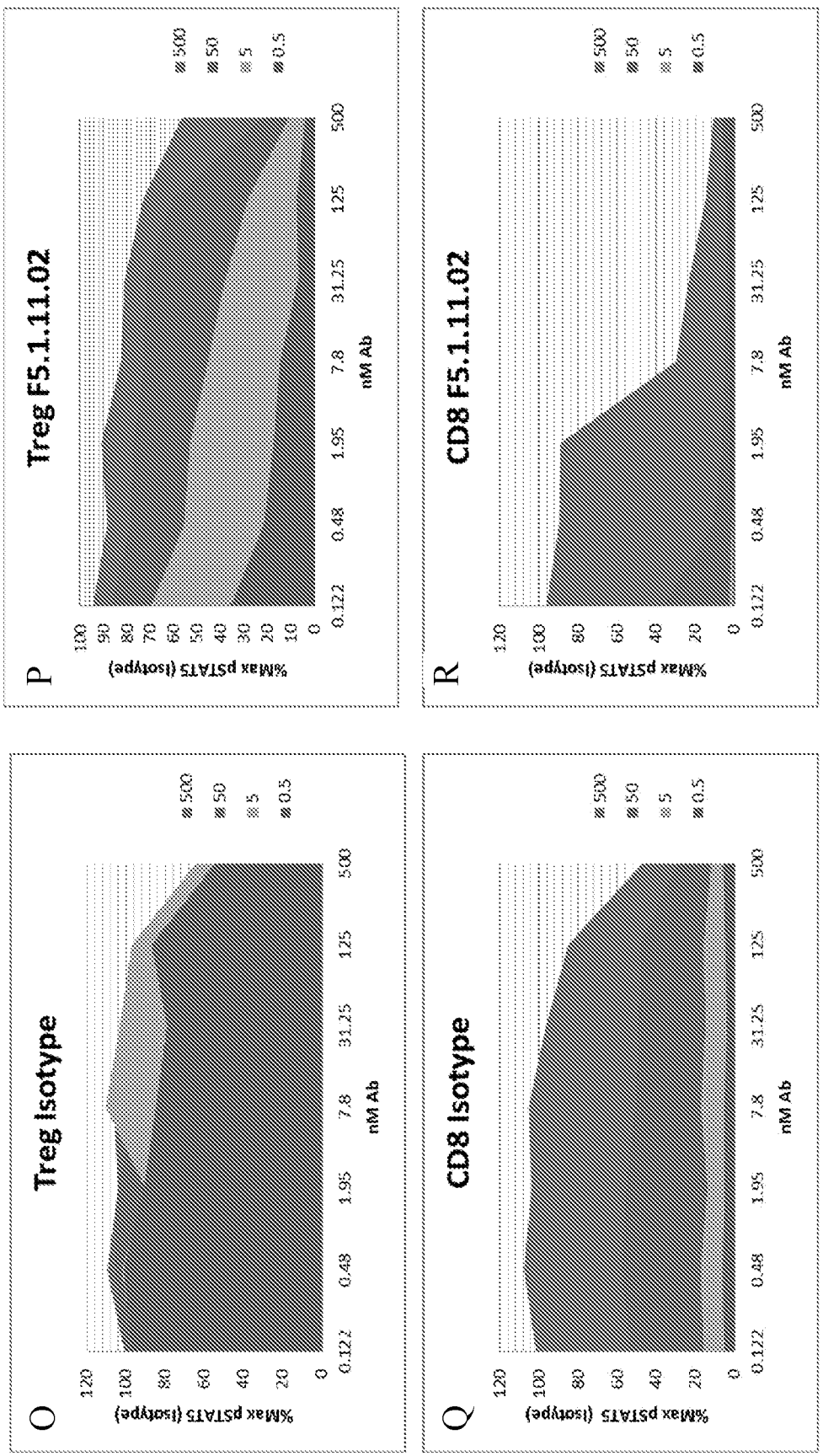
Fig. 7O-R

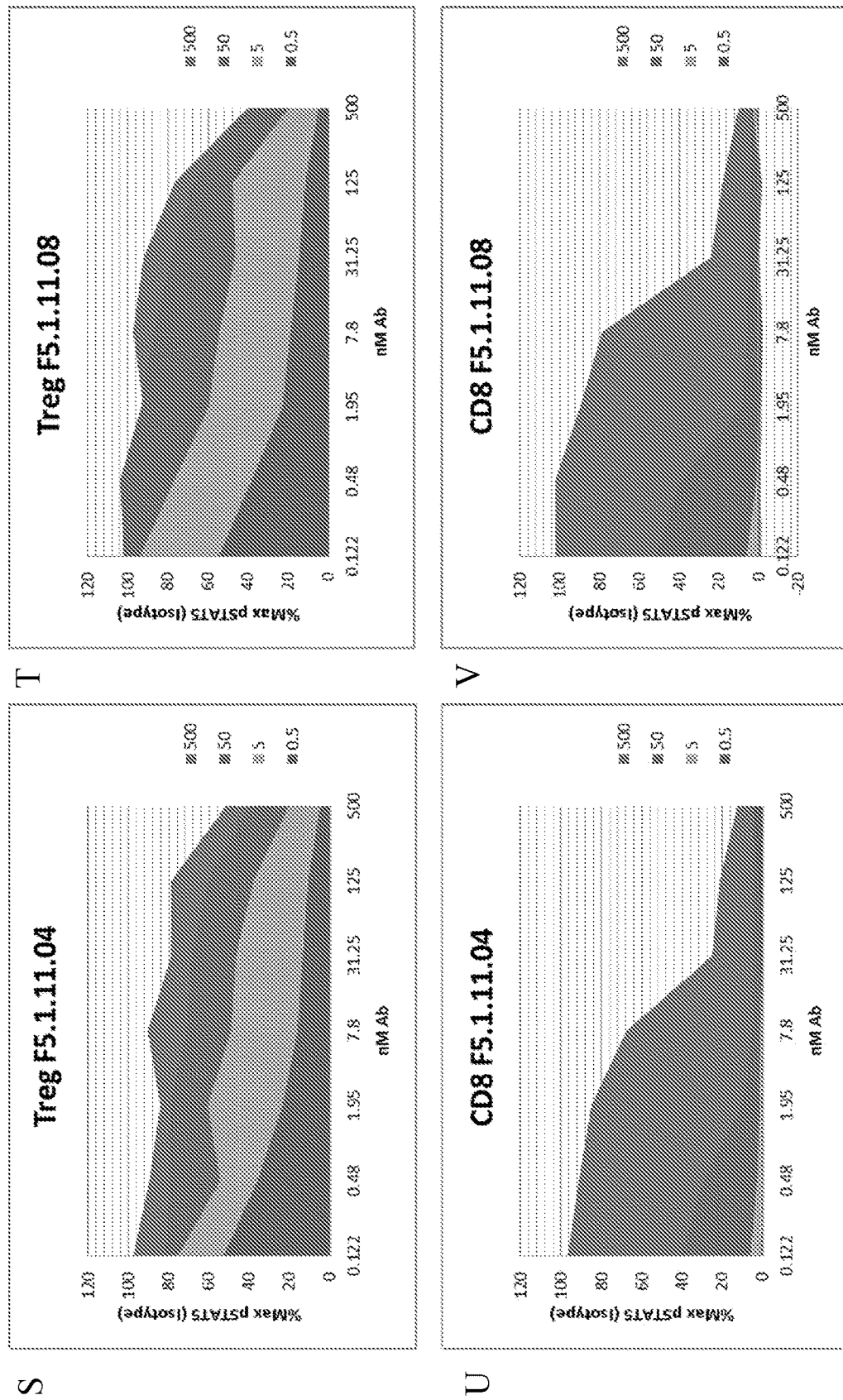
Fig. 7S-V

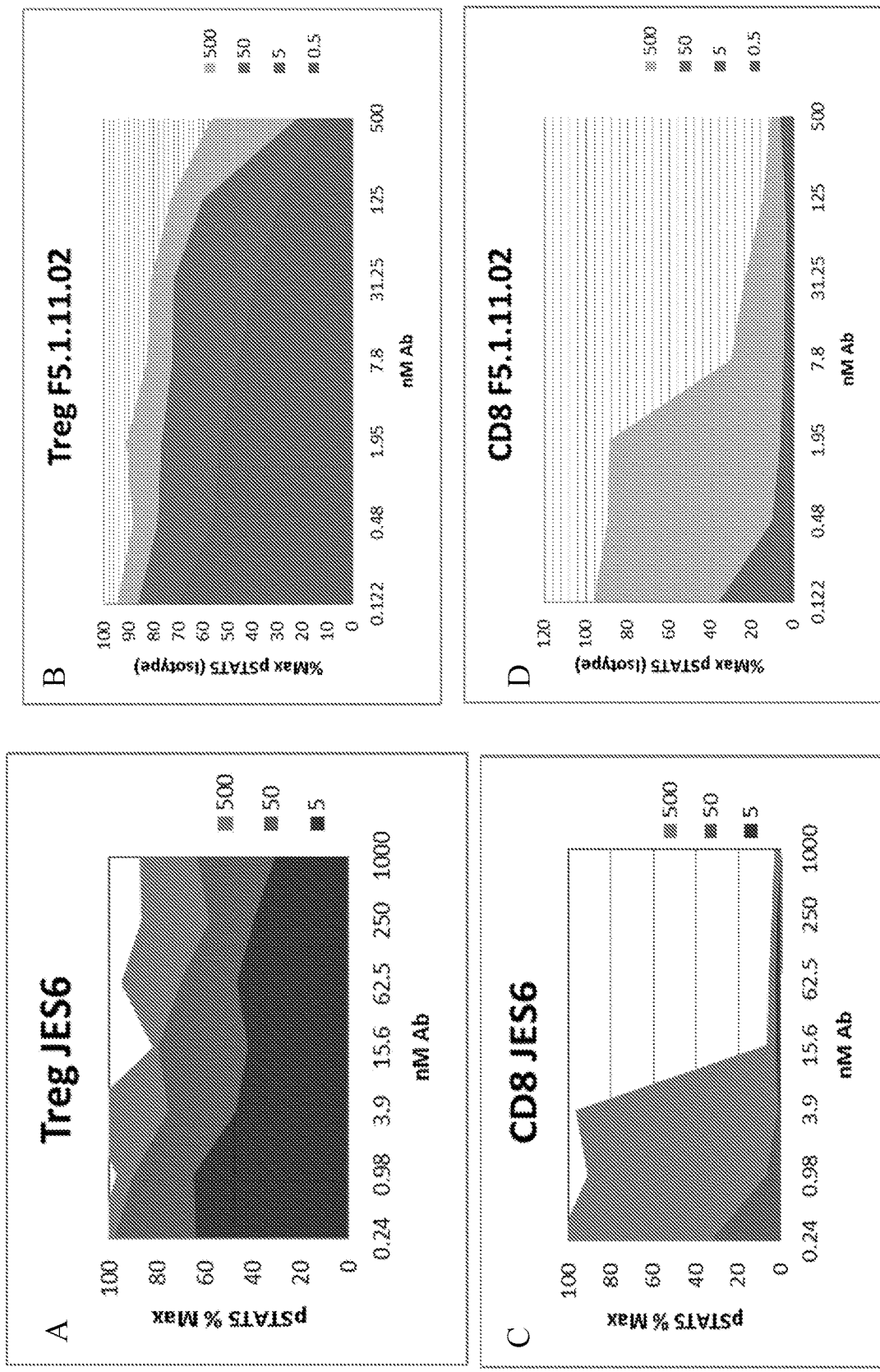
Fig. 8A-D

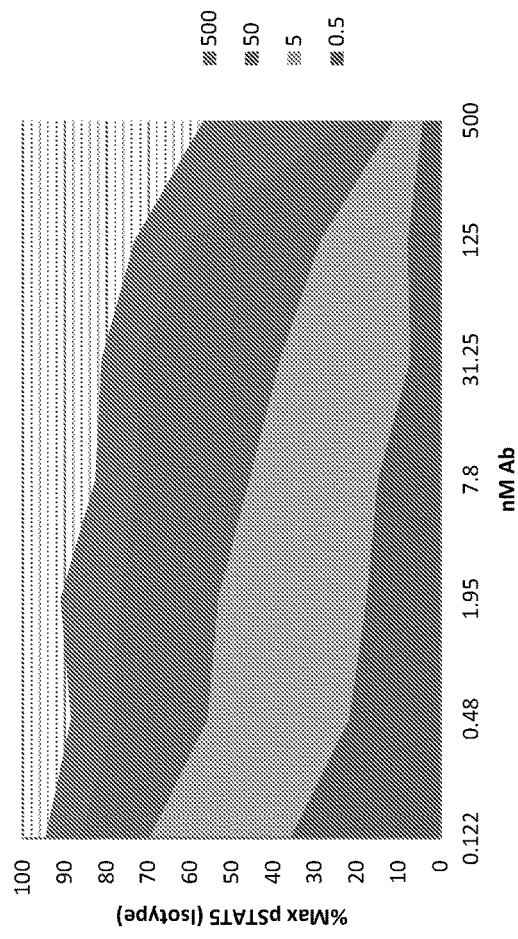
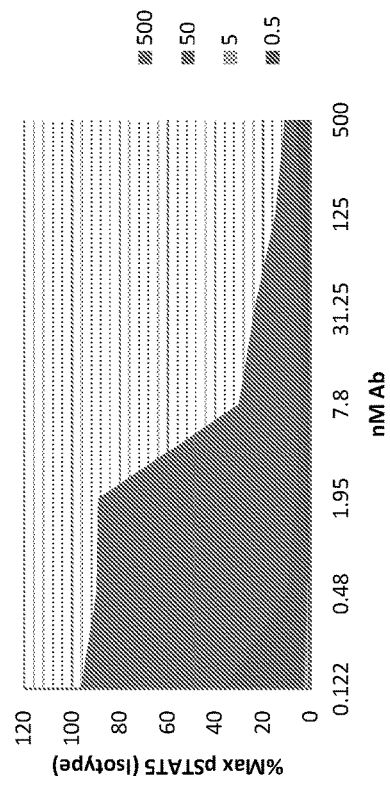
Fig. 8E-F

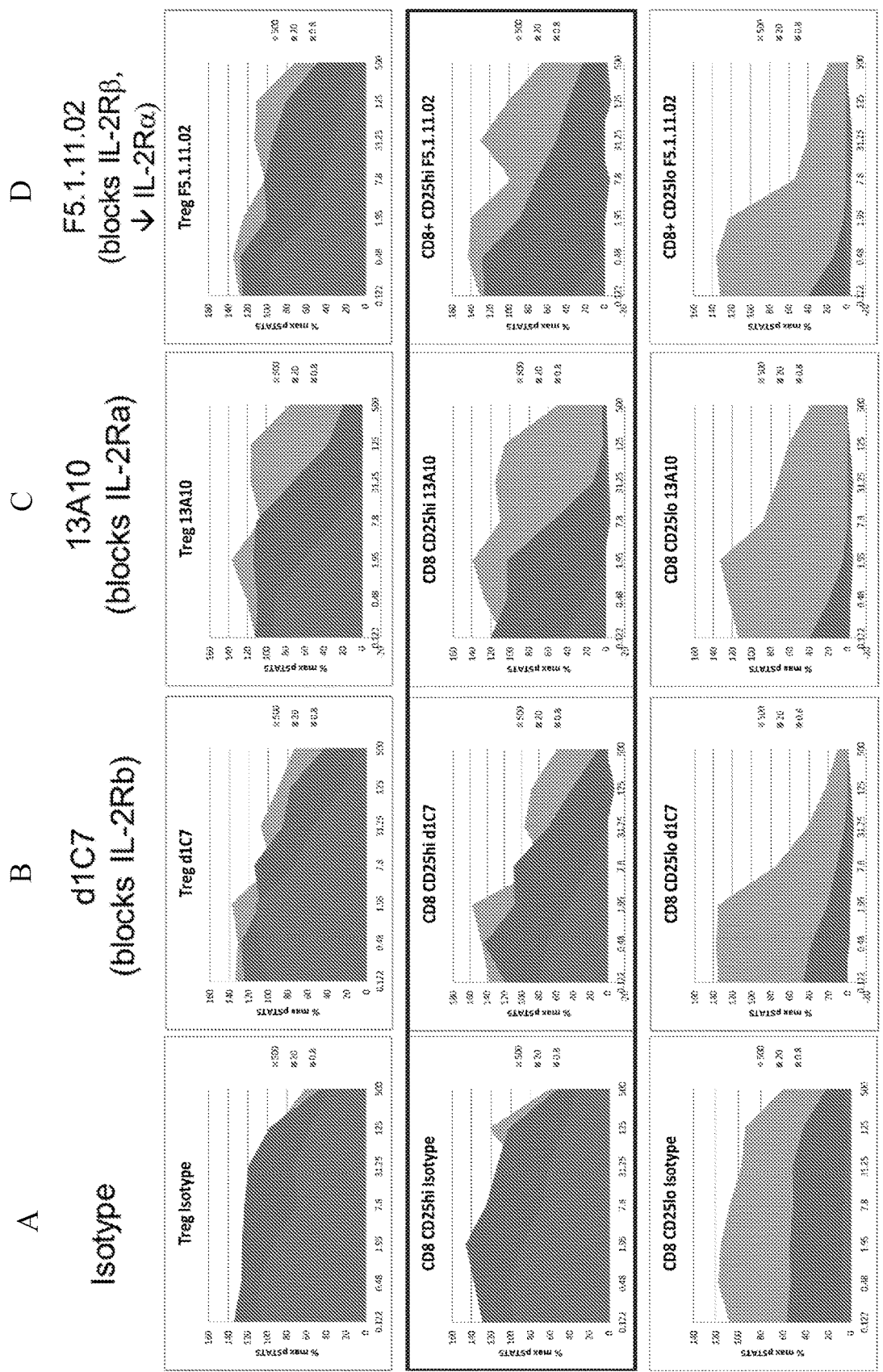
Fig. 9A-D

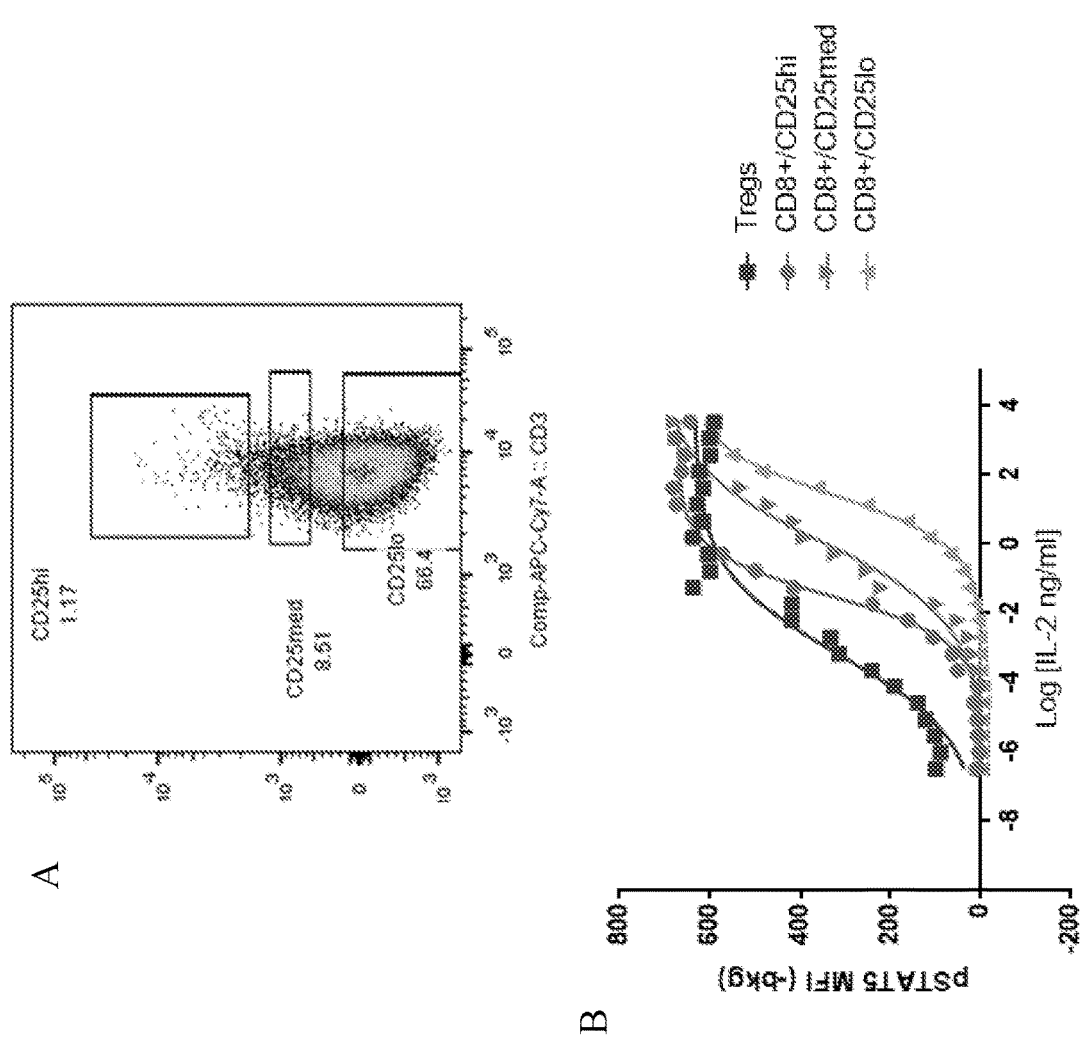
Fig. 10A-B

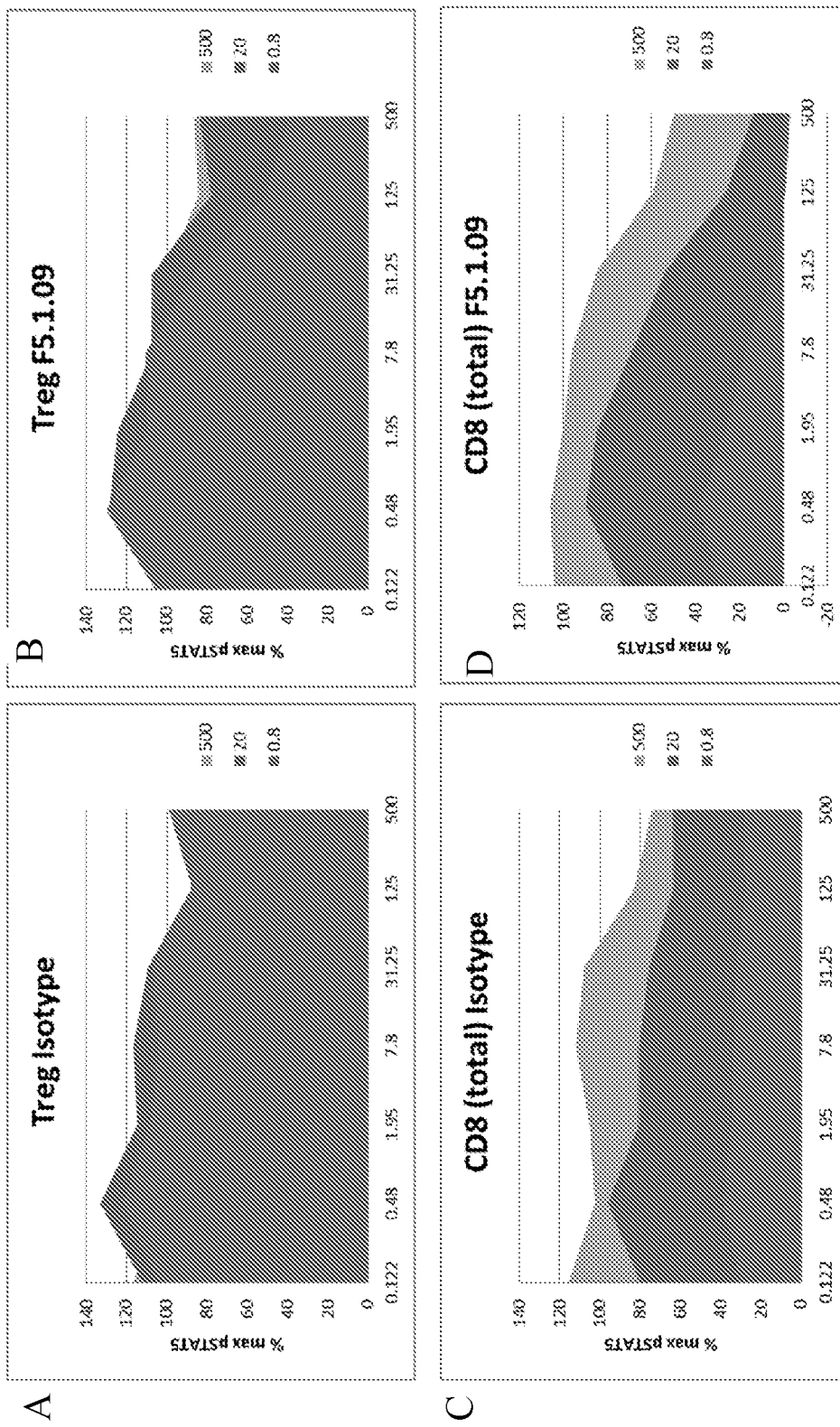
Fig. 11A-D

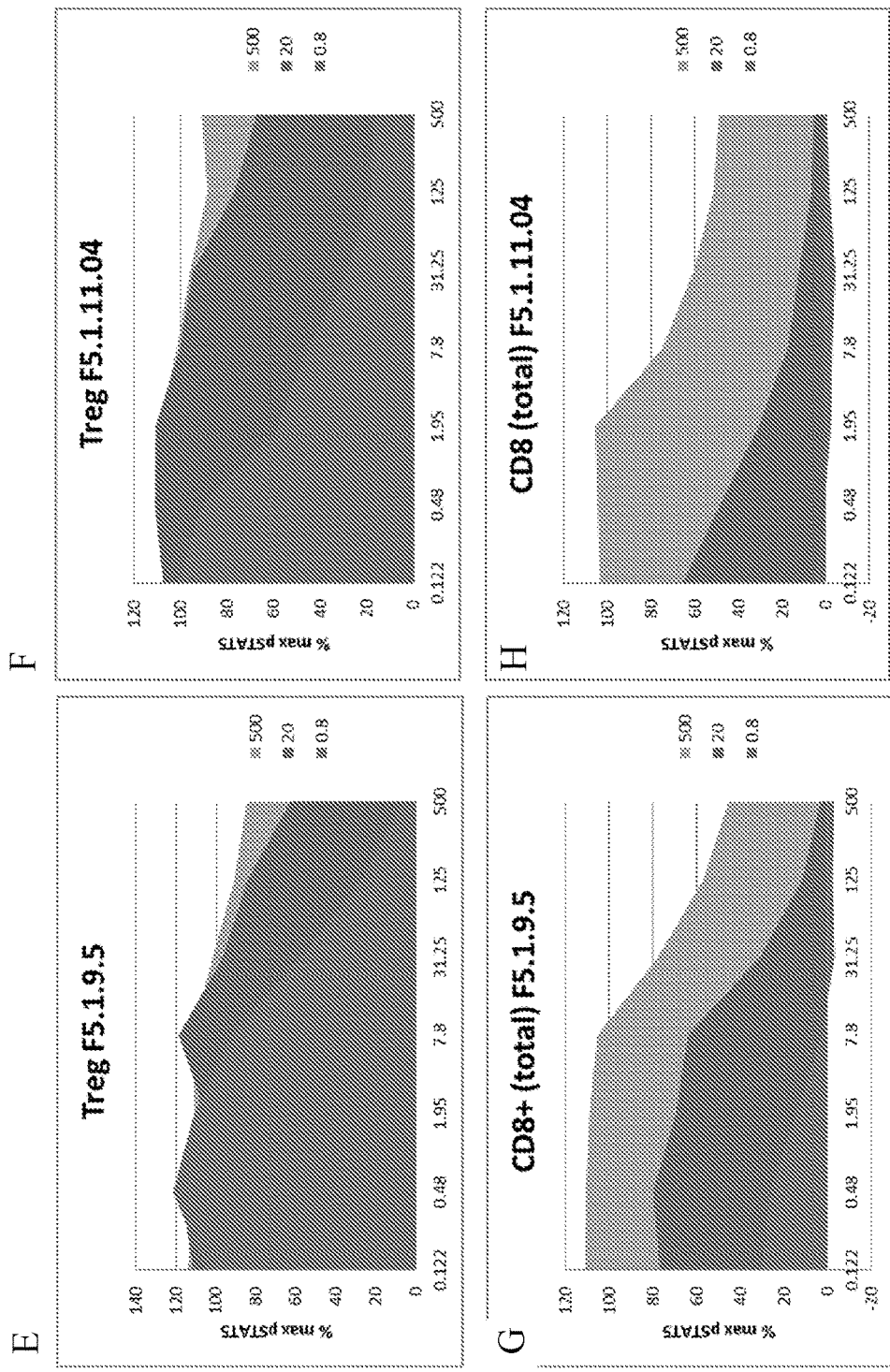
Fig. 11E-H

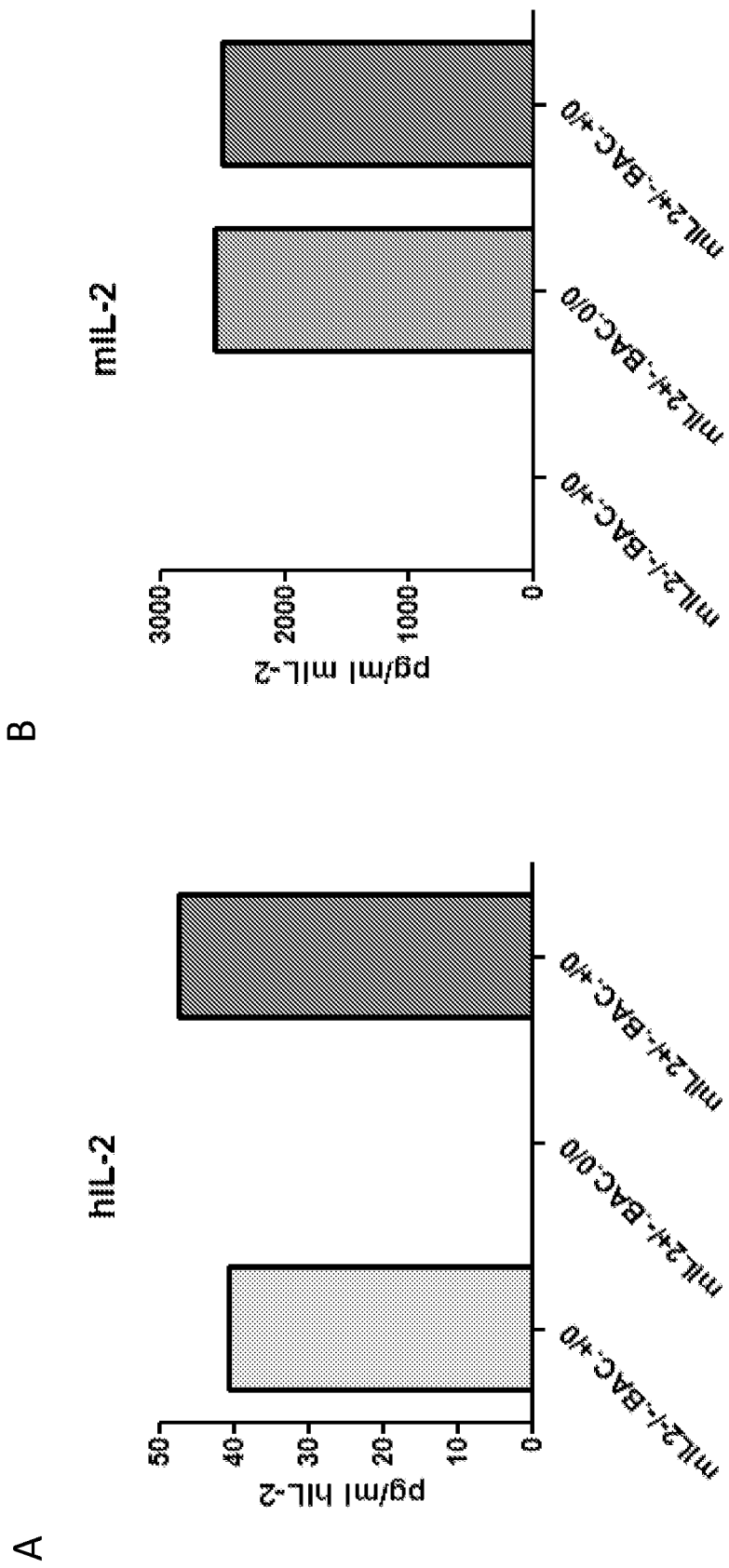
Fig. 12A-B

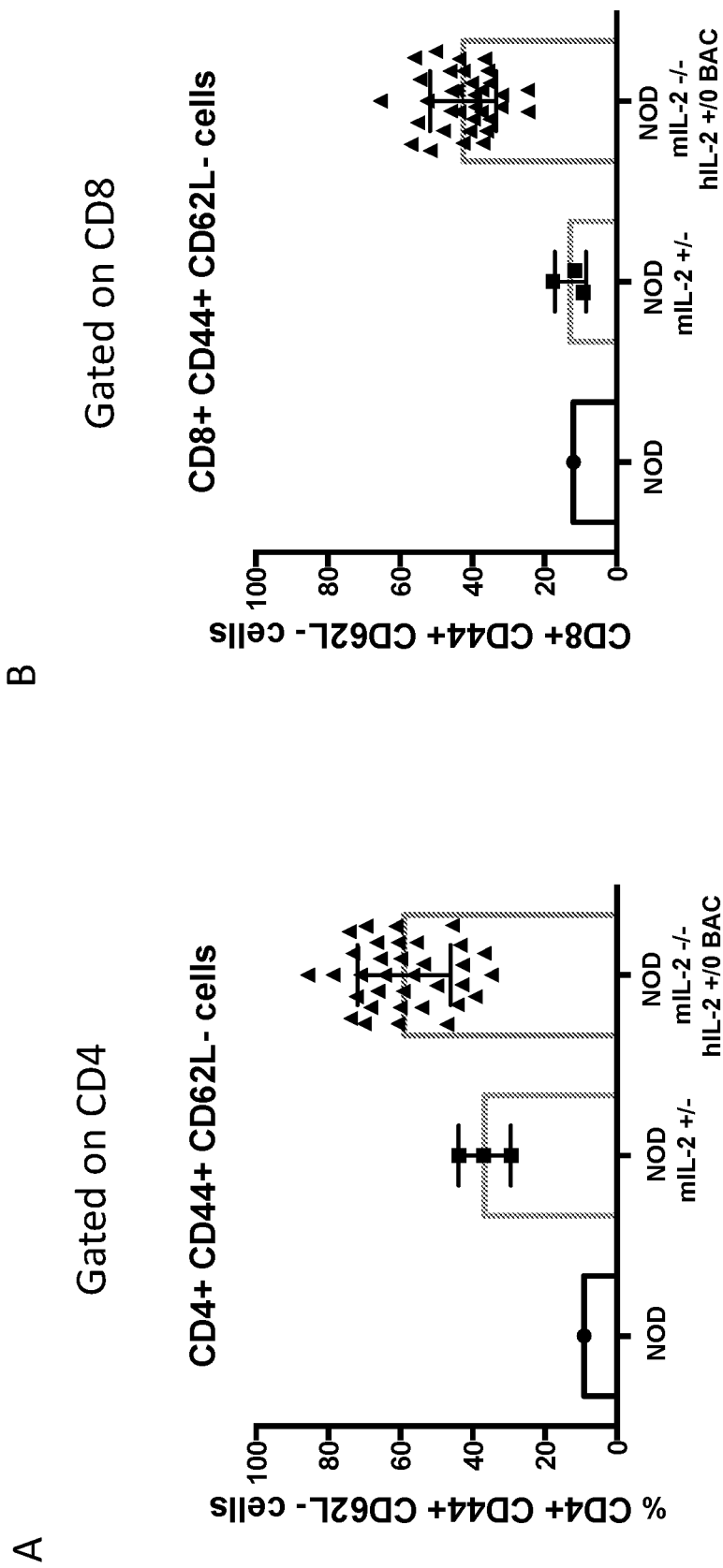
Fig. 13A-B

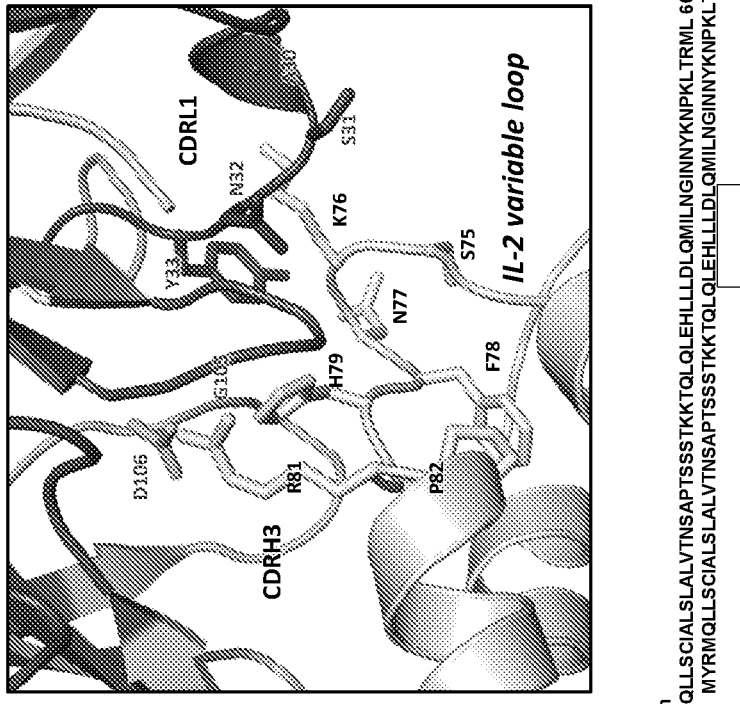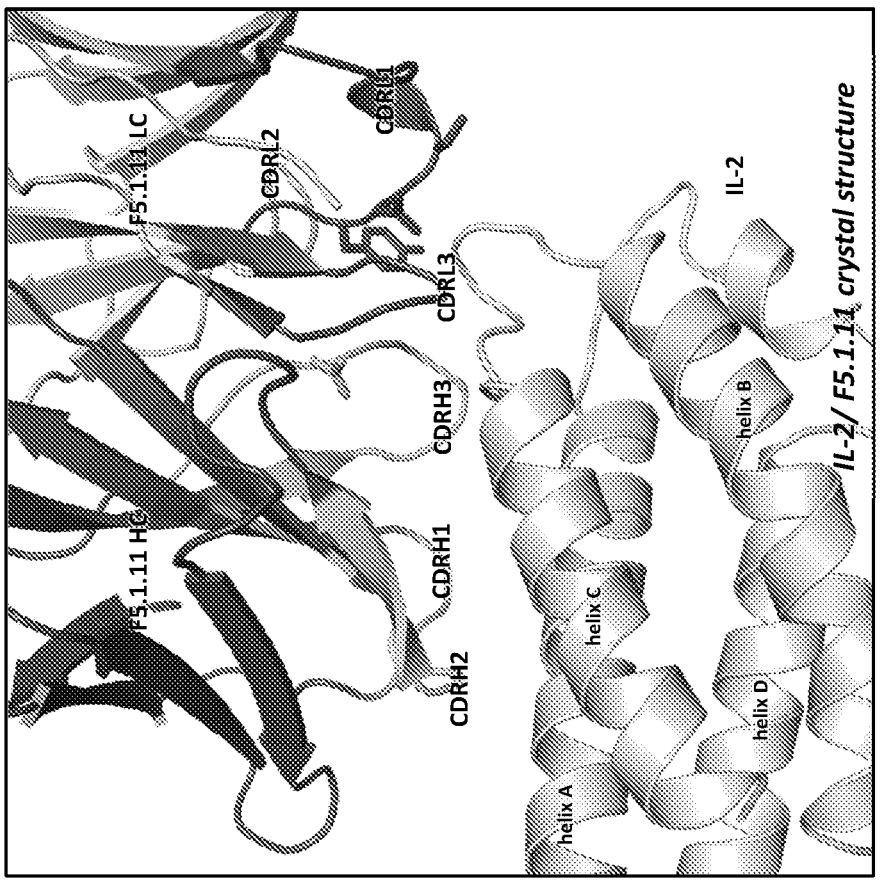
Fig. 32

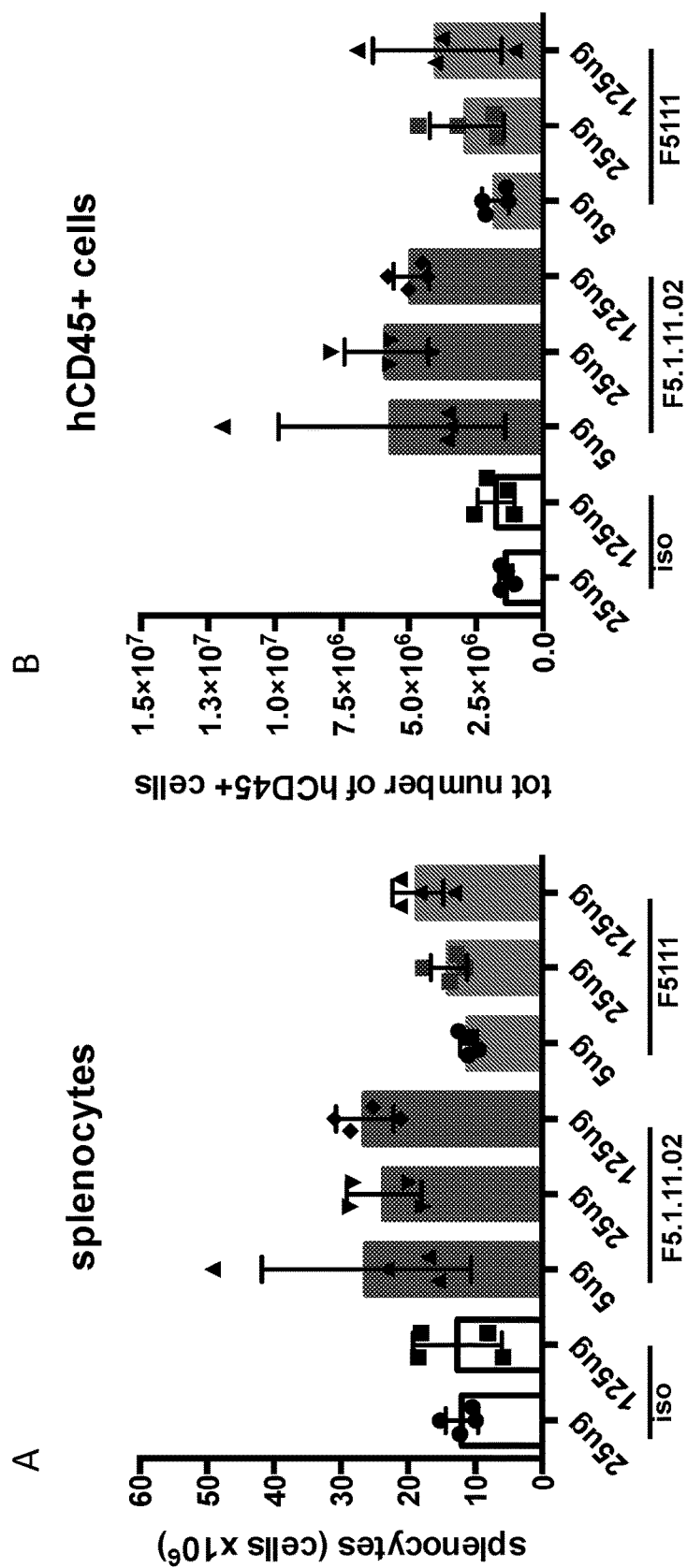
Fig. 33A-B

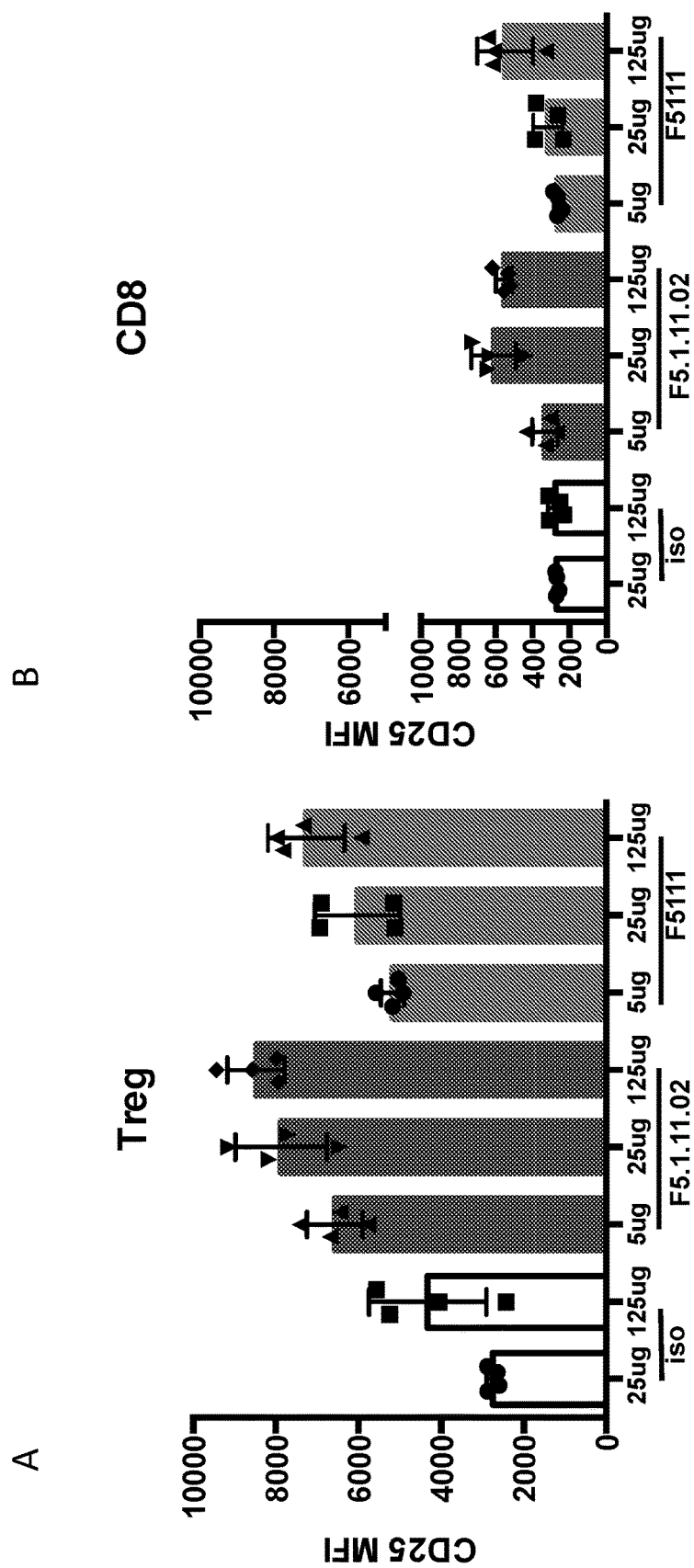
Fig. 34A-B

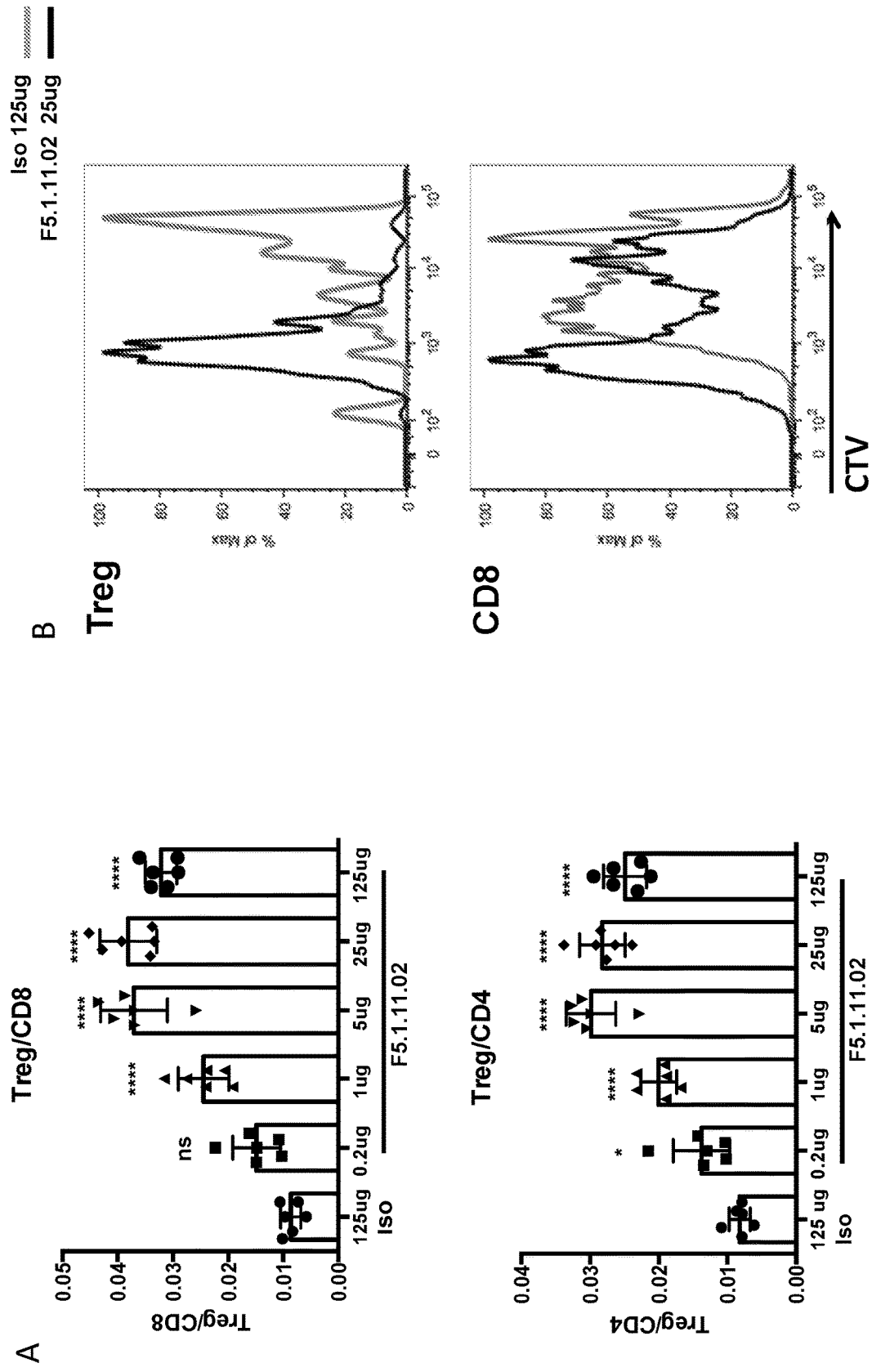
Figs. 36A-B

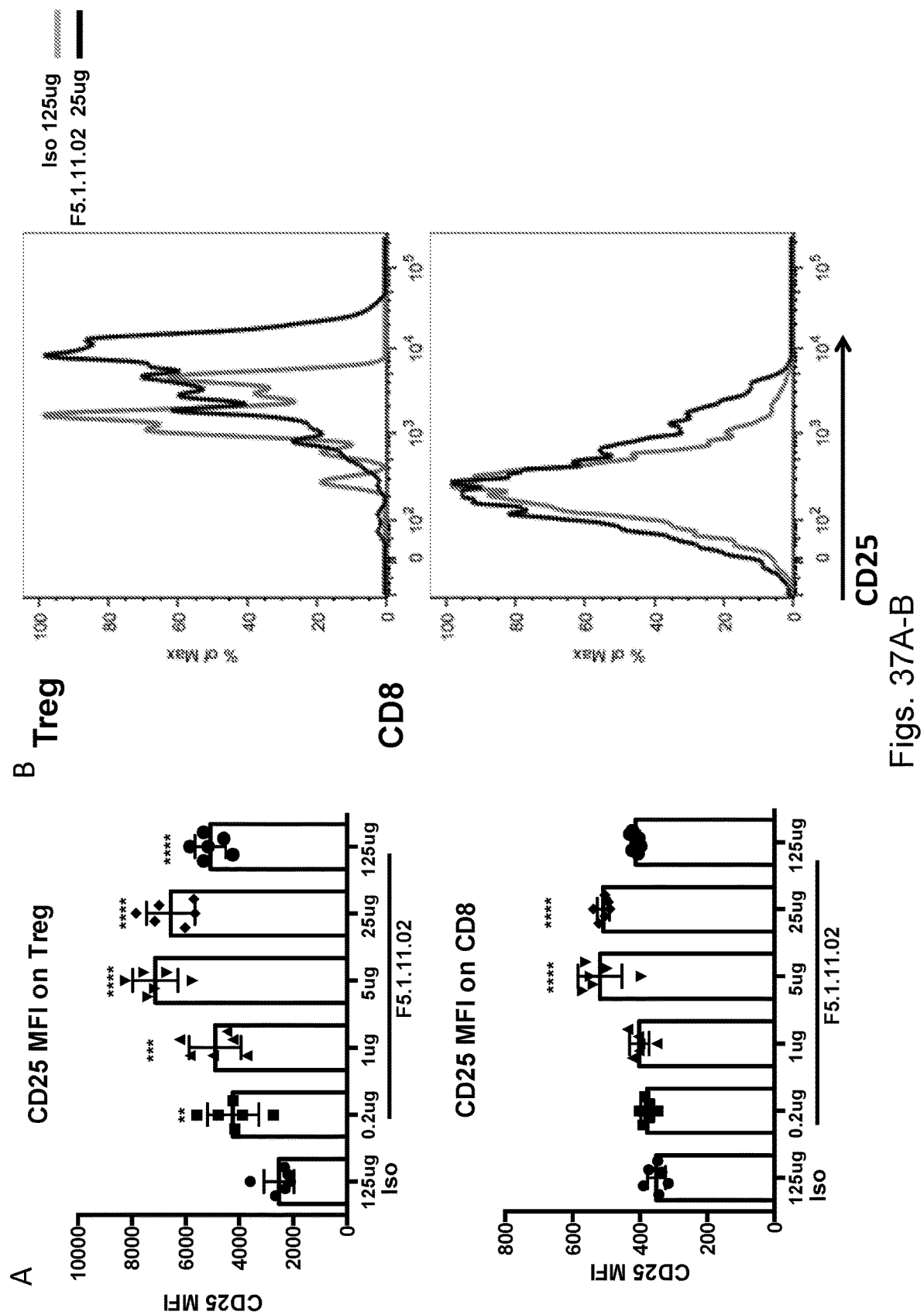
Figs. 37A-B

Figs. 39A-B

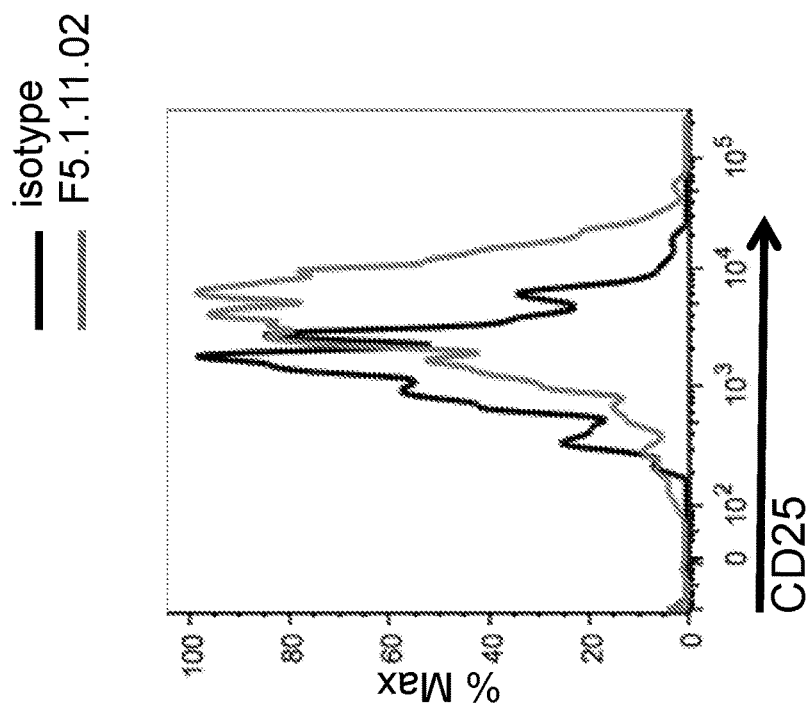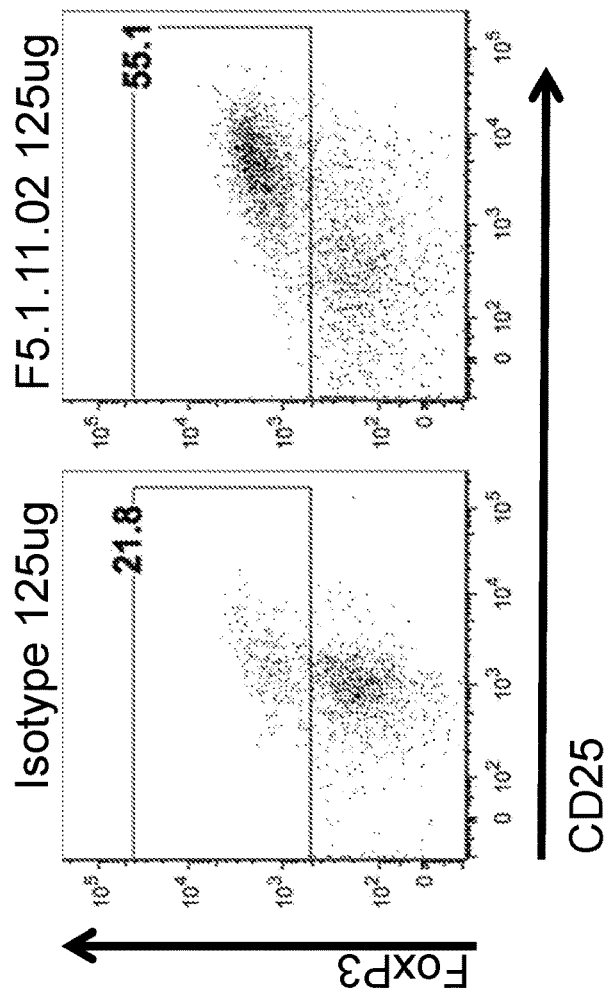
Fig. 42

ANTI-IL-2 ANTIBODIES AND COMPOSITIONS AND USES THEREOF

RELATED APPLICATIONS

This application is a Divisional of U.S. application Ser. No. 15/331,038, filed Oct. 21, 2016, which claims the benefit of U.S. Provisional Application No. 62/408,360, filed Oct. 14, 2016, and of U.S. Provisional Application No. 62/245,600, filed Oct. 23, 2015, the contents of each of which applications are hereby incorporated by reference in their entireties.

PARTIES TO A JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are PFIZER INC. and THE REGENTS OF THE UNIVERSITY OF CALIFORNIA.

SEQUENCE LISTING

The instant application contains a Sequence Listing which has been submitted electronically as a text file in ASCII format and is hereby incorporated by reference in its entirety. Said text file, created on Aug. 7, 2018, is named 081906-1097999-226020US_Seq_Listing.TXT and is 106,611 bytes in size.

FIELD OF THE DISCLOSURE

The present disclosure relates to antibodies, e.g., full length antibodies and antigen-binding portions thereof that specifically bind interleukin-2 (IL-2). The disclosure further relates to compositions comprising antibodies to IL-2, and methods of using the antibodies as a medicament. The anti-IL-2 antibodies are useful for treating and preventing autoimmune diseases, disorders and conditions and for immunosuppression.

BACKGROUND OF THE DISCLOSURE

Interleukin-2 (IL-2) plays an important role in the immune response and is a potential target for treating diseases associated with the immune response, such as autoimmune diseases, disorders and conditions and for immunosuppression. There is a long-felt unmet need for novel therapeutics to treat IL-2 mediated diseases, disorders, and conditions. The present disclosure meets these needs.

SUMMARY OF THE DISCLOSURE

The present inventors have generated new and advantageous anti-IL-2 antibodies. In certain aspects, the disclosure relates to an isolated antibody or an antigen-binding portion thereof that specifically binds human IL-2 (hIL-2), wherein the antibody reduces hIL-2 binding to IL-2 receptor chains IL-2Rα and IL-2Rβ, and inhibits an activity in CD8$^+$ T cells to a higher degree than in regulatory T (Treg) cells.

In certain aspects, the disclosure relates to an isolated antibody or an antigen-binding portion thereof that specifically binds human IL-2 (hIL-2), wherein the antibody binds helices A and C and the B-C loop of hIL-2.

In certain aspects, the disclosure relates to an isolated antibody or an antigen-binding portion thereof that competes for binding to human IL-2 (hIL-2) with, or binds the same epitope of hIL-2 as, an antibody comprising the amino acid sequences of SEQ ID NOs: 13 and 14.

In certain aspects, the disclosure relates to an isolated antibody or an antigen-binding portion thereof that specifically binds human IL-2 (hIL-2), wherein the antibody reduces the binding affinity of hIL-2 to IL-2Rα by 1 to 199 fold. In certain embodiments, the antibody reduces the binding affinity of hIL-2 to IL-2Rα by 10 fold.

In certain aspects, the disclosure relates to an isolated antibody or an antigen-binding portion thereof that specifically binds hIL-2, wherein the antibody or portion reduces hIL-2 binding to IL-2Rα and IL-2Rβ, and inhibits STAT5 phosphorylation in CD8$^+$ T cells to a higher degree than in Treg cells.

In certain aspects, the disclosure relates to an isolated antibody or an antigen-binding portion thereof that specifically binds hIL-2, wherein the antibody or portion reduces hIL-2 binding to IL-2Rα and IL-2Rβ, and increases the ratio of Treg cells to CD8$^+$ or CD4$^+$ T cells or to NK cells in the body, as measured in a peripheral blood mononuclear cell (PBMC) culture or reconstitution assay.

In certain aspects, the disclosure relates to an isolated antibody or an antigen-binding portion thereof that specifically binds hIL-2, wherein the antibody or portion reduces hIL-2 binding to IL-2Rα and IL-2Rβ, and increases expression of one or more of FOXP3, CD25, and Icos in Treg cells.

In certain aspects, the disclosure relates to an isolated antibody or antigen-binding portion, wherein the antibody or portion has a) an hIL-2 binding off-rate of equal or greater than about $4.53 \times 10^{-4}$ s$^{-1}$; and/or b) a binding affinity to hIL-2 of equal or greater than about $1.14 \times 10^{-10}$ M.

In certain aspects, the disclosure relates to an isolated antibody or antigen-binding portion, wherein the antibody or portion comprises:

(a) a HCDR1 comprising SEQ ID NO: 73 (Kabat), 74 (Chothia), or 75 (extended); a HCDR2 comprising SEQ ID NO: 76 (Kabat), or 77 (Chothia); a HCDR3 comprising SEQ ID NO: 78; a LCDR1 comprising SEQ ID NO: 79; a LCDR2 comprising SEQ ID NO: 80; and a LCDR3 comprising SEQ ID NO: 81;

(b) a HCDR1 comprising SEQ ID NO: 82 (Kabat), 83 (Chothia), or 84 (extended); a HCDR2 comprising SEQ ID NO: 85 (Kabat), or 86 (Chothia); a HCDR3 comprising SEQ ID NO: 87; a LCDR1 comprising SEQ ID NO: 88; a LCDR2 comprising SEQ ID NO: 89; and a LCDR3 comprising SEQ ID NO: 90;

(c) a HCDR1 comprising SEQ ID NO: 91 (Kabat), 92 (Chothia), or 93 (extended); a HCDR2 comprising SEQ ID NO: 94 (Kabat), or 95 (Chothia); a HCDR3 comprising SEQ ID NO: 96; a LCDR1 comprising SEQ ID NO: 97; a LCDR2 comprising SEQ ID NO: 98; and a LCDR3 comprising SEQ ID NO: 99;

(d) a HCDR1 comprising SEQ ID NO: 100 (Kabat), 101 (Chothia), or 102 (extended); a HCDR2 comprising SEQ ID NO: 103 (Kabat), or 104 (Chothia); a HCDR3 comprising SEQ ID NO: 105; a LCDR1 comprising SEQ ID NO: 106; a LCDR2 comprising SEQ ID NO: 107; and a LCDR3 comprising SEQ ID NO: 108;

(e) a HCDR1 comprising SEQ ID NO: 109 (Kabat), 110 (Chothia), or 111 (extended); a HCDR2 comprising SEQ ID NO: 112 (Kabat), or 113 (Chothia); a HCDR3 comprising SEQ ID NO: 114; a LCDR1 comprising SEQ ID NO: 115;

a LCDR2 comprising SEQ ID NO: 116; and a LCDR3 comprising SEQ ID NO: 117;

(f) a HCDR1 comprising SEQ ID NO: 118 (Kabat), 119 (Chothia), or 120 (extended); a HCDR2 comprising SEQ ID NO: 121 (Kabat), or 122 (Chothia); a HCDR3 comprising SEQ ID NO: 123; a LCDR1 comprising SEQ ID NO: 124; a LCDR2 comprising SEQ ID NO: 125; and a LCDR3 comprising SEQ ID NO: 126;

(g) a HCDR1 comprising SEQ ID NO: 127 (Kabat), 128 (Chothia), or 129 (extended); a HCDR2 comprising SEQ ID NO: 130 (Kabat), or 131 (Chothia); a HCDR3 comprising SEQ ID NO: 132; a LCDR1 comprising SEQ ID NO: 133; a LCDR2 comprising SEQ ID NO: 134; and a LCDR3 comprising SEQ ID NO: 135;

(h) a HCDR1 comprising SEQ ID NO: 136 (Kabat), 137 (Chothia), or 138 (extended); a HCDR2 comprising SEQ ID NO: 139 (Kabat), or 140 (Chothia); a HCDR3 comprising SEQ ID NO: 141; a LCDR1 comprising SEQ ID NO: 142; a LCDR2 comprising SEQ ID NO: 143; and a LCDR3 comprising SEQ ID NO: 144;

(i) a HCDR1 comprising SEQ ID NO: 145 (Kabat), 146 (Chothia), or 147 (extended); a HCDR2 comprising SEQ ID NO: 148 (Kabat), or 149 (Chothia); a HCDR3 comprising SEQ ID NO: 150; a LCDR1 comprising SEQ ID NO: 151; a LCDR2 comprising SEQ ID NO: 152; and a LCDR3 comprising SEQ ID NO: 153;

(j) a HCDR1 comprising SEQ ID NO: 154 (Kabat), 155 (Chothia), or 156 (extended); a HCDR2 comprising SEQ ID NO: 157 (Kabat), or 158 (Chothia); a HCDR3 comprising SEQ ID NO: 159; a LCDR1 comprising SEQ ID NO: 160; a LCDR2 comprising SEQ ID NO: 161; and a LCDR3 comprising SEQ ID NO: 162;

(k) a HCDR1 comprising SEQ ID NO: 163 (Kabat), 164 (Chothia), or 165 (extended); a HCDR2 comprising SEQ ID NO: 166 (Kabat), or 167 (Chothia); a HCDR3 comprising SEQ ID NO: 168; a LCDR1 comprising SEQ ID NO: 169; a LCDR2 comprising SEQ ID NO: 170; and a LCDR3 comprising SEQ ID NO: 171;

(l) a HCDR1 comprising SEQ ID NO: 172 (Kabat), 173 (Chothia), or 174 (extended); a HCDR2 comprising SEQ ID NO: 175 (Kabat), or 176 (Chothia); a HCDR3 comprising SEQ ID NO: 177; a LCDR1 comprising SEQ ID NO: 178; a LCDR2 comprising SEQ ID NO: 179; and a LCDR3 comprising SEQ ID NO: 180;

(m) a HCDR1 comprising SEQ ID NO: 181 (Kabat), 182 (Chothia), or 183 (extended); a HCDR2 comprising SEQ ID NO: 184 (Kabat), or 185 (Chothia); a HCDR3 comprising SEQ ID NO: 186; a LCDR1 comprising SEQ ID NO: 187; a LCDR2 comprising SEQ ID NO: 188; and a LCDR3 comprising SEQ ID NO: 189;

(n) a HCDR1 comprising SEQ ID NO: 190 (Kabat), 191 (Chothia), or 192 (extended); a HCDR2 comprising SEQ ID NO: 193 (Kabat), or 194 (Chothia); a HCDR3 comprising SEQ ID NO: 195; a LCDR1 comprising SEQ ID NO: 196; a LCDR2 comprising SEQ ID NO: 197; and a LCDR3 comprising SEQ ID NO: 198;

(o) a HCDR1 comprising SEQ ID NO: 199 (Kabat), 200 (Chothia), or 201 (extended); a HCDR2 comprising SEQ ID NO: 202 (Kabat), or 203 (Chothia); a HCDR3 comprising SEQ ID NO: 204; a LCDR1 comprising SEQ ID NO: 205; a LCDR2 comprising SEQ ID NO: 206; and a LCDR3 comprising SEQ ID NO: 207;

(p) a HCDR1 comprising SEQ ID NO: 208 (Kabat), 209 (Chothia), or 210 (extended); a HCDR2 comprising SEQ ID NO: 211 (Kabat), or 212 (Chothia); a HCDR3 comprising SEQ ID NO: 213; a LCDR1 comprising SEQ ID NO: 214; a LCDR2 comprising SEQ ID NO: 215; and a LCDR3 comprising SEQ ID NO: 216; or (q) a HCDR1 comprising SEQ ID NO: 217; a HCDR2 comprising SEQ ID NO: 218; a HCDR3 comprising SEQ ID NO: 219; a LCDR1 comprising SEQ ID NO: 220; a LCDR2 comprising SEQ ID NO: 221; and a LCDR3 comprising SEQ ID NO: 222.

In some embodiments, the antibody or antigen-binding portion comprises a heavy chain variable domain ($V_H$) comprising: a) a heavy chain complementarity determining region (HCDR) 3 in SEQ ID NO: 1, 3, 5, 7, 9, 11, 13, 15, 17, 19, 21, 23, 25, 27, 29 or 71 as shown in Table 7; or b) HCDR1-3 in SEQ ID NO: 1, 3, 5, 7, 9, 11, 13, 15, 17, 19, 21, 23, 25, 27, 29 or 71 as shown in Table 7.

In some embodiments, the antibody or antigen-binding portion of the disclosure comprises a light chain variable domain ($V_L$) comprising: a) a light chain complemetarity determining region (LCDR) 3 in SEQ ID NO: 2, 4, 6, 8, 10, 12, 14, 16, 18, 20, 22, 24, 26, 28, 30, or 72 as shown in Table 7; or b) LCDR1-3 in SEQ ID NO: 2, 4, 6, 8, 10, 12, 14, 16, 18, 20, 22, 24, 26, 28, 30, or 72 as shown in Table 7.

In some of the above embodiments, the antibody or antigen-binding portion comprises: a) HCDR1-3 in SEQ ID NO: 1, 3, 5, 7, 9, 11, 13, 15, 17, 19, 21, 23, 25, 27, 29, 31, or 71 as shown in Table 7; and/or b) LCDR1-3 in SEQ ID NO: 2, 4, 6, 8, 10, 12, 14, 16, 18, 20, 22, 24, 26, 28, 30, 32, or 72 as shown in Table 7.

In certain aspects, the disclosure relates to an isolated antibody or an antigen-binding portion thereof that specifically binds human interleukin-2 (hIL-2), comprising a heavy chain variable domain ($V_H$) comprising: a) an HCDR3 in SEQ ID NO: 1, 3, 5, 7, 9, 11, 13, 15, 17, 19, 21, 23, 25, 27, 29, 31, or 71 as shown in Table 7; b) HCDR1-3 in SEQ ID NO: 1, 3, 5, 7, 9, 11, 13, 15, 17, 19, 21, 23, 25, 27, 29, 31, or 71, as shown in Table 7; or c) the amino acid sequence of SEQ ID NO: 1, 3, 5, 7, 9, 11, 13, 15, 17, 19, 21, 23, 25, 27, 29, 31, or 71.

In certain aspects, the disclosure relates to an isolated antibody or an antigen-binding portion thereof that specifically binds hIL-2, comprising a light chain variable domain ($V_L$) comprising: a) an LCDR3 in SEQ ID NO: 2, 4, 6, 8, 10, 12, 14, 16, 18, 20, 22, 24, 26, 28, 30, 32, or 72 as shown in Table 7; b) LCDR1-3 in SEQ ID NO: 2, 4, 6, 8, 10, 12, 14, 16, 18, 20, 22, 24, 26, 28, 30, 32, or 72 as shown in Table 7; or c) the amino acid sequence of SEQ ID NO: 2, 4, 6, 8, 10, 12, 14, 16, 18, 20, 22, 24, 26, 28, 30, 32, or 72.

In some embodiments, the disclosure relates to an isolated antibody or antigen-binding portion whose $V_H$ comprises a) an HCDR3 in SEQ ID NO: 1, 3, 5, 7, 9, 11, 13, 15, 17, 19, 21, 23, 25, 27, 29, 31, or 71, as shown in Table 7; b) HCDR1-3 in SEQ ID NO: 1, 3, 5, 7, 9, 11, 13, 15, 17, 19, 21, 23, 25, 27, 29, 31, or 71, as shown in Table 7; or c) the amino acid sequence of SEQ ID NO: 1, 3, 5, 7, 9, 11, 13, 15, 17, 19, 21, 23, 25, 27, 29, 31, or 71; and whose $V_L$ comprises a) an LCDR3 in SEQ ID NO: 2, 4, 6, 8, 10, 12, 14, 16, 18, 20, 22, 24, 26, 28, 30, 32, or 72 as shown in Table 7; b) LCDR1-3 in SEQ ID NO: 2, 4, 6, 8, 10, 12, 14, 16, 18, 20, 22, 24, 26, 28, 30, 32, or 72 as shown in Table 7; or c) the amino acid sequence of SEQ ID NO: 2, 4, 6, 8, 10, 12, 14, 16, 18, 20, 22, 24, 26, 28, 30, 32, or 72.

In certain aspects, the disclosure relates to an isolated antibody or an antigen-binding portion thereof that specifically binds hIL-2, wherein the antibody comprises the HCDR1-3 and LCDR1-3 amino acid sequences in:

SEQ ID NOs: 1 and 2,
SEQ ID NOs: 3 and 4,
SEQ ID NOs: 5 and 6,

SEQ ID NOs: 7 and 8,
SEQ ID NOs: 9 and 10,
SEQ ID NOs: 11 and 12,
SEQ ID NOs: 13 and 14,
SEQ ID NOs: 15 and 16,
SEQ ID NOs: 17 and 18,
SEQ ID NOs: 19 and 20,
SEQ ID NOs: 21 and 22,
SEQ ID NOs: 23 and 24,
SEQ ID NOs: 25 and 26,
SEQ ID NOs: 27 and 28,
SEQ ID NOs: 29 and 30,
SEQ ID NOs: 31 and 32, or
SEQ ID NOs: 71 and 72,
respectively, as shown in Table 7.

In certain aspects, the disclosure relates to an isolated antibody or antigen-binding portion thereof whose $V_H$ and $V_L$ comprises the amino acid sequences of
SEQ ID NOs: 1 and 2,
SEQ ID NOs: 3 and 4,
SEQ ID NOs: 5 and 6,
SEQ ID NOs: 7 and 8,
SEQ ID NOs: 9 and 10,
SEQ ID NOs: 11 and 12,
SEQ ID NOs: 13 and 14,
SEQ ID NOs: 15 and 16,
SEQ ID NOs: 17 and 18,
SEQ ID NOs: 19 and 20,
SEQ ID NOs: 21 and 22,
SEQ ID NOs: 23 and 24,
SEQ ID NOs: 25 and 26,
SEQ ID NOs: 27 and 28,
SEQ ID NOs: 29 and 30,
SEQ ID NOs: 31 and 32, or
SEQ ID NOs: 71 and 72, respectively.

In some embodiments of the disclosure, the isolated antibody is an IgG (e.g., $IgG_1$, $IgG_2$, $IgG_3$, or $IgG_4$). The antibody may comprise a heavy chain constant region comprising the amino acid sequence of SEQ ID NO: 33, and/or a light chain constant region comprising the amino acid sequence of SEQ ID NO: 34 or 35. In some of these embodiments, the heavy chain C-terminal lysine is absent.

In certain aspects, the disclosure relates to an isolated antibody or an antigen-binding portion thereof that specifically binds hIL-2, wherein the antibody binds to the same epitope as, or competes for binding to IL-2Rα and IL-2Rβ with, any of the above-described antibodies.

In certain aspects, the disclosure relates to an antibody or antigen-binding portion whose $V_H$ and $V_L$ amino acid sequences are at least 90% (e.g., 95%, 98%, or 99%) identical to the following amino acid sequences, respectively:
SEQ ID NOs: 1 and 2,
SEQ ID NOs: 3 and 4,
SEQ ID NOs: 5 and 6,
SEQ ID NOs: 7 and 8,
SEQ ID NOs: 9 and 10,
SEQ ID NOs: 11 and 12,
SEQ ID NOs: 13 and 14,
SEQ ID NOs: 15 and 16,
SEQ ID NOs: 17 and 18,
SEQ ID NOs: 19 and 20,
SEQ ID NOs: 21 and 22,
SEQ ID NOs: 23 and 24,
SEQ ID NOs: 25 and 26,
SEQ ID NOs: 27 and 28,
SEQ ID NOs: 29 and 30, or
SEQ ID NOs: 31 and 32.

In some of the above-described embodiments of the disclosure, the antibody is a human antibody.

This disclosure also provides an isolated nucleic acid encoding the heavy chain, the light chain, or both, of an antibody or antigen-binding portion of the disclosure. In certain aspects, the isolated nucleic acid comprises: a) the nucleotide sequence of SEQ ID NO: 36, 38, 40, 42, 44, 46, 48, 50, 52, 54, 56, 58, 60, 62, 64, or 66; b) the nucleotide sequence of SEQ ID NO: 37, 39, 41, 43, 45, 47, 49, 51, 53, 55, 57, 59, 61, 63, 65, or 67; or c) both a) and b). For example, the isolated nucleic acid may comprise the nucleotide sequences of:
SEQ ID NOs: 36 and 37,
SEQ ID NOs: 38 and 39,
SEQ ID NOs: 40 and 41,
SEQ ID NOs: 42 and 43,
SEQ ID NOs: 44 and 45,
SEQ ID NOs: 46 and 47,
SEQ ID NOs: 48 and 49,
SEQ ID NOs: 50 and 51,
SEQ ID NOs: 52 and 53,
SEQ ID NOs: 54 and 55,
SEQ ID NOs: 56 and 57,
SEQ ID NOs: 58 and 59,
SEQ ID NOs: 60 and 61,
SEQ ID NOs: 62 and 63,
SEQ ID NOs: 64 and 65, or
SEQ ID NOs: 66 and 67.

In certain aspects, the disclosure relates to a vector comprising one or more of the above isolated nucleic acids. In other aspects, the disclosure provides a host cell (e.g., mammalian cells such as NS0 cells and CHO cells) comprising an isolated nucleic acid or vector encoding the heavy chain, the light chain, or both, of an antibody or antigen-binding portion of the disclosure. The disclosure also provides a method of producing an antibody or an antigen-binding portion thereof that specifically binds hIL-2, comprising: a) culturing a host cell under conditions that allow said antibody or antigen-binding portion to be expressed, wherein the host cell comprises nucleotide sequences coding the heavy chain and light chain of the antibody or antigen-binding portion, and b) isolating said antibody or antigen-binding portion from the culture.

In certain aspects, the disclosure relates to a pharmaceutical composition comprising an antibody or antigen-binding portion of the disclosure and a pharmaceutically acceptable carrier or excipient.

In certain aspects, the disclosure relates to a method for treating an inflammatory condition such as an autoimmune disease or inducing immunosuppression in a human subject in need thereof, comprising administering to the subject an effective amount of an antibody or antigen-binding portion of the disclosure or a pharmaceutical composition of the disclosure. In some embodiments, the antibody is administered in complex with IL-2. In related aspects, the disclosure provides an antibody or antigen-binding portion of the disclosure or a pharmaceutical composition of the disclosure for use in treating a human subject having an inflammatory condition such as an autoimmune disease or in need of immunosuppression, wherein the antibody or portion is optionally administered in complex with IL-2; and the use of an antibody or antigen-binding portion of the disclosure in the manufacture of a medicament for treating an inflammatory condition such as an autoimmune disease or inducing immunosuppression, wherein the antibody or portion is optionally administered in complex with IL-2.

The conditions that can be treated with the present compositions (including but not limited to antibody or antibody/IL-2 complexes described herein) and methods include, but are not limited to: inflammatory skin diseases including psoriasis and dermatitis (e.g., atopic dermatitis); dermatomyositis; systemic scleroderma and sclerosis; conditions associated with inflammatory bowel disease (such as Crohn's disease and ulcerative colitis); colitis; gastritis; respiratory distress syndrome (including adult respiratory distress syndrome and ARDS); dermatitis; meningitis; encephalitis; uveitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; Wegener's disease; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; vitiligo; Reiter's disease; stiff-man syndrome; Behcet's disease; giant cell arteritis; immune complex nephritis; IgA nephropathy; IgM polyneuropathies; immune thrombocytopenic purpura (ITP) or autoimmune thrombocytopenia and autoimmune hemolytic diseases; Hashimoto's thyroiditis; autoimmune hepatitis; autoimmune hemophilia; autoimmune lymphoproliferative syndrome (ALPS); autoimmune uveoretinitis; Guillain-Barre syndrome; Goodpasture's syndrome; mixed connective tissue disease; autoimmune-associated infertility; polyarteritis nodosa; alopecia areata; idiopathic myxedema; graft versus host disease; and muscular dystrophy (Duchenne, Becker, Myotonic, Limb-girdle, Facioscapulohumeral, Congenital, Oculopharyngeal, Distal, and Emery-Dreifuss). In some embodiments, the condition that can be treated with the present compositions (including but not limited to antibody or antibody/IL-2 complexes described herein) and methods is diabetes mellitus (e.g., Type I diabetes mellitus). In some embodiments, the condition that can be treated with the present compositions (including but not limited to antibody or antibody/IL-2 complexes described herein) and methods is Type I diabetes mellitus. In some embodiments, the condition that can be treated with the present compositions (including but not limited to antibody or antibody/IL-2 complexes described herein) and methods is juvenile onset diabetes.

Other features and advantages of the disclosure will be apparent from the following detailed description, and from the Exemplary Embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A-C depict 16C3 (25 µg) and F5.1.11.02 (1, 5, and 25 µg) in complex with hIL-2 increased Treg/CD4, Treg/CD8 and Treg/NK cell ratios. FIGS. 4D-F depict 16C3 (25 µg) and F5.1.11.02 (1 µg, 5 µg, and 25 µg) in complex with hIL-2 increased Treg/CD4, Treg/CD8 and Treg/NK cell ratios.

FIGS. 5A-C depict that 16C3 (25 µg) and F5.1.11.02 (1, 5, and 25 µg) in complex with hIL-2 increased the total number of CD4$^+$, CD8$^+$ cells and Tregs in the spleen. FIGS. 5D-F depict that 16C3 (25 µg) and F5.1.11.02 (1 µg, 5 µg, and 25 µg) in complex with hIL-2 increased the total number of CD4$^+$, CD8$^+$ cells and Tregs in the spleen.

FIGS. 6A-C depict CD25, Icos and FoxP3 mean fluorescence intensity (MFI) on Tregs after antibody treatment.

FIGS. 7A-V depict pSTAT5 signaling in CD8$^+$ effector T cells and Treg cells after antibody treatment. Curves represent treatment with 0.2 ng/mL hIL-2, 10 ng/mL hIL-2, or 500 ng/mL hIL-2.

FIGS. 8A-F depict pSTAT5 signaling in CD8$^+$ effector T cells and Treg cells after antibody treatment. Curves represent treatment with 0.5 ng/mL hIL-2, 5 ng/mL hIL-2, 50 ng/mL hIL-2, or 500 ng/mL hIL-2.

FIGS. 9A-D depict pSTAT5 signaling in CD8$^+$/CD25 high T cells, CD8$^+$/CD25 low T cells and Treg cells after antibody treatment. The x-axis is nM antibody. Curves represent treatment with 0.8 ng/mL hIL-2, 20 ng/mL hIL-2, or 500 ng/mL hIL-2.

FIGS. 10A-B depict pSTAT5 signaling in CD8$^+$/CD25 high T cells, CD8$^+$/CD25 low T cells and Treg cells with varying concentrations of IL-2.

FIGS. 11A-H depict pSTAT5 signaling in CD8$^+$ effector T cells and Treg cells after antibody F5.1.9, F5.1.9.5, and F5.1.11.04 treatment. The x-axis is nM antibody. Curves represent treatment with 0.8 ng/mL hIL-2, 20 ng/mL hIL-2, or 500 ng/mL hIL-2.

FIGS. 12A-B depict production of IL-2 after in vitro stimulation of mouse splenocytes with PMA/Ionomycin.

FIGS. 13A-B depict the percentage of activated (CD44$^+$ CD62L$^-$) CD4$^+$ or CD8$^+$ T cells in hIL-2Tg, NOD, or NOD mIL-2+/− mice.

FIG. 32 depicts the structure-based library design for non-human primate cross-reactivity. Alignment of the human (SEQ ID NO: 224; NCBI accession number NP_000577.2) and cyno (SEQ ID NO: 225; predicted from reference genome NCBI accession number NC_022276.1) IL-2 amino acid sequences shows the IL-2 variable loop corresponds to the F5.1.11 Fab binding interface.

FIGS. 33A-B depict a comparison between the effects of F5.1.11.02 and F5.1.11 on splenocyte and hCD45$^+$ cellularity.

FIGS. 34A-B depict a comparison between the effects of F5.1.11.02 and F5.1.11 on Treg and CD8 cell CD25 expression.

FIGS. 36A-B depict F5.1.11.02 antibody:IL-2 complex effects on Treg/CD4 and Treg/CD8 cell ratios five days after treatment.

FIGS. 37A-B depict the effects of treatment with F5.1.11.02 antibody:IL-2 complex on CD25 mean fluorescent intensity (MFI) on Treg and CD8 populations compared to isotype control.

FIG. 42 depicts the effects of F5.1.11.02 antibody:IL-2 complex effect on Treg numbers and characteristics in the pancreas.

DETAILED DESCRIPTION OF THE DISCLOSURE

Figure 1:
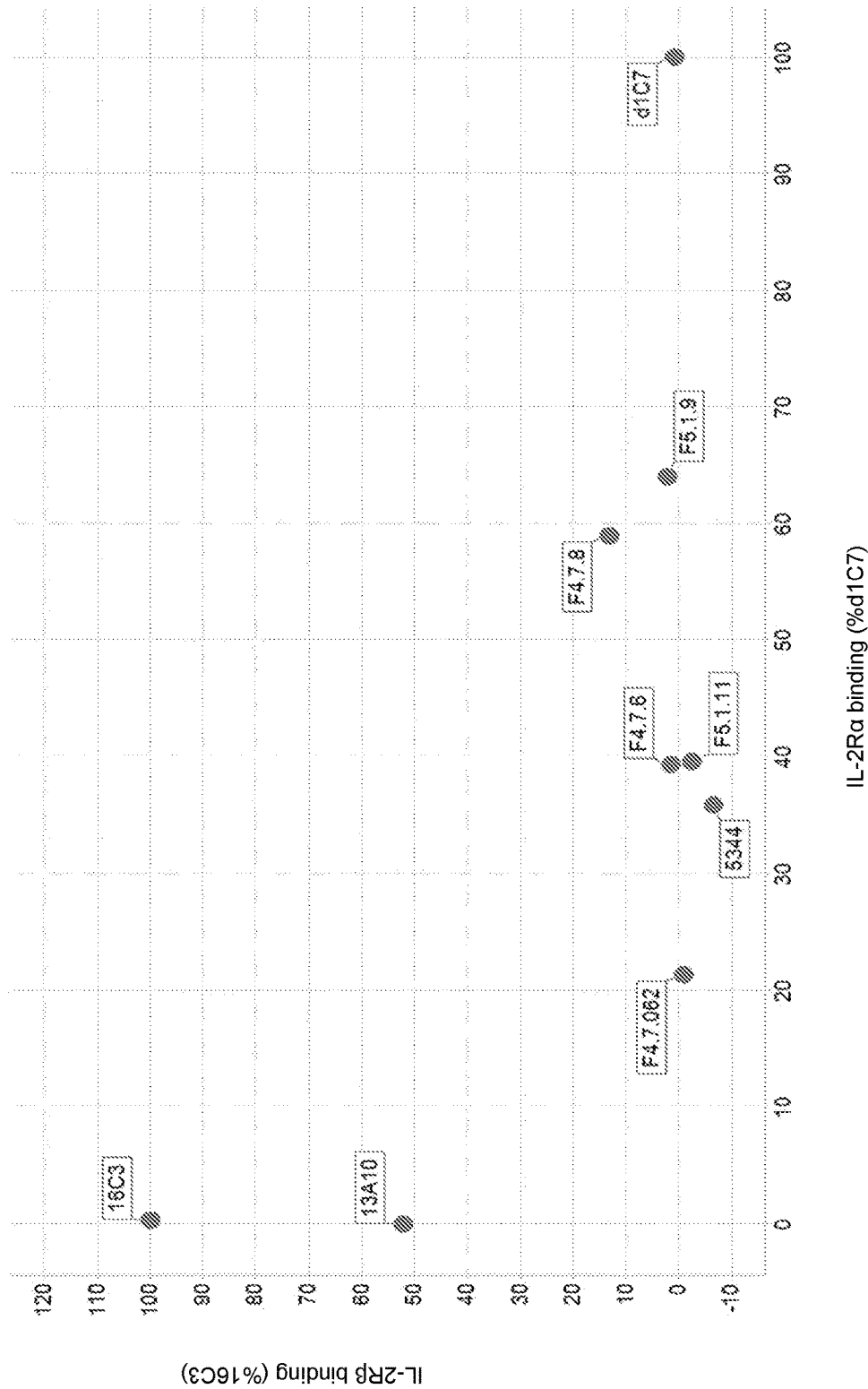
FIG. 1 depicts antibody/IL-2 affinity and IL-2Rα and IL-2Rβ binding. The response is reported as the binding to IL-2α and IL-2Rβ after 60 seconds as a percentage of the binding of two representative clones, d1C7 and 16C3 in complex with IL-2, to IL-2Rα and IL-2Rβ respectively.

The inventors have invented new and advantageous anti-IL-2 antibodies or antigen-binding portions thereof that specifically bind to hIL-2 and reduce hIL-2 binding to IL-2Rα and IL-2Rβ. These antibodies and portions can inhibit proliferation of non-Treg cells (including effector CD8$^+$, non-Treg CD4$^+$ and NK cells) more than they inhibit proliferation of Treg cells; increase Treg proliferation compared to an isotype control antibody; and/or increase the ratio of Treg cells to non-Treg cells or maintain Treg markers. The present antibodies are distinct from the IL-2Rα blocking antibodies described in International Application PCT/US2015/011794 (now published as International Publication Number WO 2015/109212 on Jul. 23, 2015), incorporated by reference in its entirety, as the present antibodies reduce, but do not abrogate, hIL-2 binding to IL-2Rα and block hIL-2 binding to IL-2Rβ.

The anti-IL-2 antibodies or antigen-binding portions thereof can be used in the prevention, treatment, and/or amelioration of diseases, disorders or conditions caused by and/or associated with IL-2 activity. Such diseases, disorders or conditions include, but are not limited to, type 1 diabetes, autoimmune diseases, Graft versus Host Disease and other immunologic diseases where Tregs mediate inflammation, among others, as would be appreciated by one skilled in the art provided with the teachings disclosed herein.

General Techniques

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Sambrook and Russell, Molecular Cloning: A Laboratory Manual, 3rd. ed., Cold Spring Harbor Laboratory Press, Cold Spring Harbor, N.Y. (2001); Ausubel et al., Current Protocols in Molecular Biology, John Wiley & Sons, N Y (2002); Harlow and Lane Using Antibodies: A Laboratory Manual, Cold Spring Harbor Laboratory Press, Cold Spring Harbor, N.Y. (1998); Coligan et al., Short Protocols in Protein Science, John Wiley & Sons, N Y (2003); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); and The Antibodies (M. Zanetti and J. D. Capra, eds., Harwood Academic Publishers, 1995).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Definitions

The following terms, unless otherwise indicated, shall be understood to have the following meanings: the term "isolated molecule" (where the molecule is, for example, a polypeptide, a polynucleotide, or an antibody or portion thereof) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, "substantially pure" means an object species is the predominant species present (i.e., on a molar basis it is more abundant than any other individual species in the composition), and in some embodiments, a substantially purified fraction is a composition wherein the object species (e.g., a glycoprotein, including an antibody or receptor) comprises at least about 50 percent (on a molar basis) of all macromolecular species present. Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species. In certain embodiments a substantially pure material is at least 50% pure (i.e., free from contaminants), in some embodiments, at least 90% pure, in some embodiments, at least 95% pure, yet in some embodiments, at least 98% pure, and in some embodiments, at least 99% pure. These amounts are not meant to be limiting, and increments between the recited percentages are specifically envisioned as part of the disclosure.

An "antibody" is an immunoglobulin molecule capable of specific binding to a target, such as a carbohydrate, polynucleotide, lipid, polypeptide, etc., through at least one antigen recognition site, located in the variable domain of the immunoglobulin molecule. As used herein, the term encompasses not only intact polyclonal or monoclonal antibodies, but also, unless otherwise specified, any antigen-binding portion thereof that competes with the intact antibody for specific binding, fusion proteins comprising an antigen-binding portion, and any other modified configuration of the immunoglobulin molecule that comprises an antigen recognition site. Antigen-binding portions include, for example, Fab, Fab', $F(ab')_2$, Fd, Fv, domain antibodies (dAbs, e.g., shark and camelid antibodies), portions including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. Depending on the antibody amino acid sequence of the constant region of its heavy chains, immunoglobulins can be assigned to different classes. There are five major classes (i.e., isotypes) of immunoglobulins: IgA, IgD, IgE, IgG, and IgM, and several of these may be further divided into subclasses (subtypes), e.g., $IgG_1$, $IgG_2$, $IgG_3$, $IgG_4$, $IgA_1$ and $IgA_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

The terms "antigen-binding portion" or "antigen-binding fragment" of an antibody (or simply "antibody portion"), as used interchangeably herein, refers to one or more portions of an antibody that retain the ability to specifically bind to an antigen (e.g., IL-2). It has been shown that the antigen-binding function of an antibody can be performed by portions of a full-length antibody. Examples of binding portions encompassed within the term "antigen-binding portion" of an antibody include (i) a Fab portion, a monovalent portion consisting of the $V_L$, $V_H$, CL and $CH_1$ domains; (ii) a F(ab')2 portion, a bivalent portion comprising two Fab portions linked by a disulfide bridge at the hinge region; (iii) a Fd portion consisting of the $V_H$ and $CH_1$ domains; (iv) a Fv portion consisting of the $V_L$ and $V_H$ domains of a single arm of an antibody, (v) a dAb portion (Ward et al., (1989) Nature 341:544-546), which consists of a $V_H$ domain; and (vi) an isolated complementarity determining region (CDR), disulfide-linked Fvs (dsFv), and anti-idiotypic (anti-Id) antibodies and intrabodies. Furthermore, although the two domains of the Fv portion, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)); see e.g., Bird et al. Science 242:423-426 (1988) and Huston et al. Proc. Natl. Acad. Sci. USA 85:5879-5883 (1988)). Such single chain antibodies are also intended to be encompassed within the term "antigen-binding portion" of an antibody. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. Proc. Natl. Acad. Sci. USA 90:6444-6448 (1993); Poljak et al., 1994, Structure 2:1121-1123).

A "variable domain" of an antibody refers to the variable domain of the antibody light chain ($V_L$) or the variable domain of the antibody heavy chain ($V_H$), either alone or in combination. As known in the art, the variable domains of the heavy and light chains each consist of four framework regions (FRs) connected by three complementarity determining regions (CDRs) also known as hypervariable regions, and contribute to the formation of the antigen-binding site of antibodies. If variants of a subject variable domain are desired, particularly with substitution in amino acid residues outside a CDR (i.e., in the framework region), appropriate amino acid substitution, in some embodiments, conservative amino acid substitution, can be identified by comparing the subject variable domain to the variable domains of other antibodies which contain CDR1 and CDR2 sequences in the same canonical class as the subject variable domain (see, e.g., Chothia and Lesk, J. Mol. Biol. 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDRs. In certain embodiments, various methods of analysis can be employed to identify or approximate the CDRs. Examples of such methods include, but are not limited to, the Kabat definition, the Chothia definition, the AbM definition, the contact definition, the conformational definition and the IMGT definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions. In certain embodiments, the extended CDR refers to all of the amino acid residues identified by the Kabat and Chothia methods.

"Contact residue" as used herein with respect to an antibody or the antigen specifically bound thereby, refers to an amino acid residue present on an antibody/antigen comprising at least one heavy atom (i.e., not hydrogen) that is within 4 Å or less of a heavy atom of an amino acid residue present on the cognate antibody/antigen.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g., murine) antibodies that are chimeric immunoglobulins, immunoglobulin chains, or portions thereof (such as Fv, Fab, Fab', F(ab')2 or other antigen-binding subsequences of antibodies) that contain minimal sequence derived from non-human immunoglobulin. In some embodiments, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable domain sequences are derived from one species and the constant region sequences are derived from another species, such as an antibody in which the variable domain sequences are derived from a mouse antibody and the constant region sequences are derived from a human antibody or vice versa. The term also encompasses an antibody comprising a V region from one individual from one species (e.g., a first mouse) and a constant region from another individual from the same species (e.g., a second mouse).

The term "antigen (Ag)" refers to the molecular entity used for immunization of an immunocompetent vertebrate to produce the antibody (Ab) that recognizes the Ag or to screen an expression library (e.g., phage, yeast or ribosome display library, among others). Herein, Ag is termed more broadly and is generally intended to include target molecules that are specifically recognized by the Ab, thus including portions or mimics of the molecule used in an immunization process for raising the Ab or in library screening for selecting the Ab. Thus, for antibodies of the disclosure binding to IL-2, full-length IL-2 from mammalian species (e.g., human, monkey, mouse and rat IL-2), including monomers and multimers, such as dimers, trimers, etc. thereof, as well as truncated and other variants of IL-2, are referred to as an antigen.

Generally, the term "epitope" refers to the area or region of an antigen to which an antibody specifically binds, i.e., an area or region in physical contact with the antibody. Thus, the term "epitope" refers to that portion of a molecule capable of being recognized by and bound by an antibody at one or more of the antibody's antigen-binding regions. Typically, an epitope is defined in the context of a molecular interaction between an "antibody, or antigen-binding portion thereof" (Ab), and its corresponding antigen. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to IL-2, e.g., the antibodies compete for binding to the antigen.

As used herein, the terms "wild-type amino acid," "wild-type IgG," "wild-type antibody," or "wild-type mAb," refer to a sequence of amino or nucleic acids that occurs naturally within a certain population (e.g., human, mouse, rats, cell, etc.).

As outlined elsewhere herein, certain positions of the antibody molecule can be altered. By "position" as used herein is meant a location in the sequence of a protein. Positions may be numbered sequentially, or according to an established format, for example the EU index and Kabat index can be used to number amino acid residues of an antibody. For example, position 297 is a position in the human antibody IgG1. Corresponding positions are determined as outlined above, generally through alignment with other parent sequences.

By "residue" as used herein is meant a position in a protein and its associated amino acid identity. For example, Asparagine 297 (also referred to as Asn297, also referred to as N297) is a residue in the human antibody IgG1.

The term "T regulatory cell" or "Treg" refers to a type of T cell that may be characterized by function or biological markers that are known to one of skill in the art (see Schmetterer et al., FASEB Vol. 26 (2012)). In certain embodiments, a Treg cell expresses one or more of the following markers: TCR/CD3, CD4, CD25 and stabilized FOXP3 based on demethylation of critical genomic elements of the FOXP3 locus.

The term "Treg sparing antibody" refers to an antibody that binds to IL-2 and detectably shifts the ratio of Treg: $CD8^+$ cells in favor of Treg cells. In some embodiments, the Treg sparing antibody inhibits proliferation of $CD8^+$ cells to a greater extent than it inhibits the proliferation of Tregs. In some embodiments, the Treg sparing antibody increases the Treg:$CD8^+$ cells ratio by at least two-fold.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. Also, an antibody "specifically binds" or "preferentially binds" to a target if it binds with greater affinity, avidity, more readily, and/or with greater duration to that target in a sample than it binds to other substances present in the sample. For example, an antibody that specifically or preferentially binds to an IL-2 epitope is an antibody that binds this epitope with greater affinity, avidity, more readily, and/or with greater duration than it binds to other IL-2 epitopes or non-IL-2 epitopes. It is also understood by reading this definition, for example, that an antibody (or moiety or epitope) which specifically or preferentially binds to a first target may or may not specifically or preferentially bind to a second target. As such, "specific binding" or "preferential binding" does not necessarily require (although it can include) exclusive binding.

A variety of assay formats may be used to select an antibody or peptide that specifically binds a molecule of interest. For example, solid-phase ELISA immunoassay, immunoprecipitation, Biacore™ (GE Healthcare, Piscataway, N.J.), KinExA, fluorescence-activated cell sorting (FACS), Octet™ (FortéBio, Inc., Menlo Park, Calif.) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice the background signal or noise, more typically more than 10 times background, even more typically, more than 50 times background, more typically, more than 100 times background, yet more typically, more than 500 times background, even more typically, more than 1000 times background, and even more typically, more than 10,000 times background. Also, an antibody is said to "specifically bind" an antigen when the equilibrium dissociation constant ($K_D$) is ≤7 nM.

The term "binding affinity" is herein used as a measure of the strength of a non-covalent interaction between two molecules, e.g., an antibody or portion thereof and an antigen. The term "binding affinity" is used to describe monovalent interactions (intrinsic activity). Binding affinity between two molecules may be quantified by determination of the dissociation constant ($K_D$). In turn, $K_D$ can be determined by measurement of the kinetics of complex formation and dissociation using, e.g., the surface plasmon resonance (SPR) method (Biacore). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D = k_d/k_a$. The value of the dissociation constant can be determined directly by well-known methods, and can be computed even for complex mixtures by methods such as those set forth in Caceci et al. (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of antibodies towards target antigens are known in the art, including for example, ELISAs, Western blots, RIAs, and flow cytometry analysis, and other assays exemplified elsewhere herein. The binding kinetics and binding affinity of the antibody also can be assessed by standard assays known in the art, such as Surface Plasmon Resonance (SPR), e.g. by using a Biacore™ system, or KinExA.

In some embodiments, the antibody may bind to hIL-2 with a $K_D$ of about $1.14 \times 10^{-10}$ M or greater. For example, the antibody may bind to hIL-2 with a $K_D$ of about $9 \times 10^{-11}$ M or greater. In some embodiments, the antibody may bind to hIL-2 with a $K_D$ of about $8 \times 10^{-11}$ M or greater. In some embodiments, the antibody may bind to hIL-2 with a $K_D$ of about $7 \times 10^{-11}$ M or greater. In some embodiments, the antibody may bind to hIL-2 with a $K_D$ of about $6 \times 10^{-11}$ M or greater. In some embodiments, the antibody may bind to hIL-2 with a $K_D$ of about $5.00 \times 10^{-11}$ M or greater. These amounts are not meant to be limiting, and increments between the recited values are specifically envisioned as part of the disclosure. In some embodiments, the antibody may bind to hIL-2 with a $k_d$ of about the same as the $K_D$ of an antibody as shown in Table 3.

In some embodiments, the antibody may bind to hIL-2 with a $k_d$ of about $4.53 \times 10^{-4}$ s$^{-1}$ or greater. For example, the antibody may bind to hIL-2 with a $k_d$ of about $3 \times 10^{-4}$ s$^{-1}$ or greater. In some embodiments, the antibody may bind to hIL-2 with a $k_d$ of about $1 \times 10^{-4}$ s$^{-1}$ or greater. In some embodiments, the antibody may bind to hIL-2 with a $k_d$ of about $9 \times 10^{-5}$ s$^{-1}$ or greater. In some embodiments, the antibody may bind to hIL-2 with a $k_d$ of about $7 \times 10^{-5}$ s$^{-1}$ or greater. In some embodiments, the antibody may bind to hIL-2 with a $k_d$ of about $5.00 \times 10^{-5}$ s$^{-1}$ or greater. These amounts are not meant to be limiting, and increments between the recited values are specifically envisioned as part of the disclosure. In some embodiments, the antibody may bind to hIL-2 with a $k_d$ of about the same as the $k_d$ of an antibody as shown in Table 3.

A competitive binding assay can be conducted in which the binding of the antibody to the target antigen is compared to the binding of the target by another ligand of that target, such as another antibody or a soluble receptor that otherwise binds the target. The concentration at which 50% inhibition occurs is known as the $K_i$. Under ideal conditions, the $K_i$ is equivalent to $K_D$. The $K_i$ value will never be less than the $K_D$, so measurement of $K_i$ can conveniently be substituted to provide an upper limit for $K_D$.

Following the above definition, binding affinities associated with different molecular interactions, e.g., comparison of the binding affinity of different antibodies for a given antigen, may be compared by comparison of the $K_D$ values for the individual antibody/antigen complexes. Similarly, the specificity of an interaction may be assessed by determination and comparison of the $K_D$ value for the interaction of interest, e.g., a specific interaction between an antibody and an antigen, with the $K_D$ value of an interaction not of interest, e.g., a control antibody known not to bind IL-2.

An antibody that specifically binds its target may bind its target with a high affinity, that is, exhibiting a low $K_D$ as discussed above, and may bind to other, non-target molecules with a lower affinity. For example, the antibody may bind to non-target molecules with a $K_D$ of $1 \times 10^{-6}$ M or more, in some embodiments, $1 \times 10^{-5}$ M or more, in some embodiments, $1 \times 10^{-4}$ M or more, in some embodiments, $1 \times 10^{-3}$ M or more, in some embodiments, $1 \times 10^{-2}$ M or more. An antibody of the disclosure is in some embodiments capable of binding to its target with an affinity that is at least two-fold, 10-fold, 50-fold, 100-fold 200-fold, 500-fold, 1,000-fold or 10,000-fold or greater than its affinity for binding to another non-IL-2 molecule. These amounts are not meant to be limiting, and increments between the recited values are specifically envisioned as part of the disclosure.

An antibody:IL-2 "complex" as the term is used herein, refers to a complex comprising at least one antibody, or antigen-binding portion thereof, of the present disclosure that specifically binds IL-2 and at least one IL-2 cytokine molecule. The complex comprises an antibody and an IL-2 molecule that are associated by covalent, non-covalent, or any other force. Preferably, the antibody and IL-2 may remain associated as a complex even after the complex is administered. It is understood that the antibody and IL-2 will form a complex based on, among other variables, the $K_D$ value for the binding interaction between them.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected and/or transformed in vivo with a polynucleotide of this disclosure.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain may vary, the human IgG heavy chain Fc region is usually defined to stretch from an amino acid residue at position Cys226, or from Pro230, to the carboxyl-terminus thereof. The numbering of the residues in the Fc region is that of the EU index as described in Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g., B cell receptor), etc. Such effector functions generally require the Fc region to be combined with a binding domain (e.g., an antibody variable domain or antigen-binding portion thereof) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, e.g., from about one to about ten amino acid substitutions, and in some embodiments, from about one to about five amino acid substitutions in a native sequence Fc region or in the Fc region of the parent polypeptide. The variant Fc region herein will in some embodiments possess at least about 80% sequence identity with a native sequence Fc region and/or with an Fc region of a parent polypeptide, and in some embodiments, at least about 90% sequence identity therewith, in some embodiments, at least about 95%, at least about 96%, at least about 97%, at least about 98%, at least about 99% sequence identity therewith. These amounts are not meant to be limiting, and increments between the recited percentages are specifically envisioned as part of the disclosure.

As used in the art, "Fc receptor" and "FcR" describe a receptor that binds to the Fc region of an antibody. In some embodiments, the FcR is a native sequence human FcR. Moreover, in some embodiments, FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

As used herein, a first antibody is said to compete with a second antibody for binding to an antigen (or an epitope) when the first antibody's presence detectably decreases the binding of the second antibody to the antigen (or the second antibody's epitope). The converse, where the binding of the first antibody to the antigen (or its epitope) is also detectably decreased in the presence of the second antibody, can, but need not, be true. However, where each antibody detectably inhibits the binding of the other antibody to a common antigen, whether to the same or a different extent, the antibodies are said to "cross-compete" with each other for binding of that antigen. Both competing and cross-competing antibodies are encompassed by the present disclosure. Regardless of the mechanism by which such competition or cross-competition occurs (e.g., steric hindrance, conformational change, or binding to a common epitope or portion(s) thereof), the skilled artisan would appreciate, based upon the teachings provided herein, that such competing and/or cross-competing antibodies are encompassed and can be useful for the methods disclosed herein.

As used herein, "treatment" is an approach for obtaining beneficial or desired clinical results. For purposes of this disclosure, beneficial or desired clinical results include, but are not limited to, one or more of the following: improved survival rate (reduced mortality), reduction in inflammation, reduction in the amount of tissue fibrosis, improvement in the appearance of the disease lesions, limitation of the pathological lesions to focal sites, decreased extent of damage from the disease, decreased duration of the disease, and/or reduction in the number, extent, or duration of symptoms related to the disease. The term includes the administration of the compounds or agents of the present disclosure to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

"Ameliorating" means a lessening or improvement of one or more symptoms as compared to not administering an IL-2 antibody. "Ameliorating" also includes shortening or reduction in duration of a symptom.

As used herein, an "effective dosage" or "effective amount" of drug, compound, or pharmaceutical composition is an amount sufficient to affect any one or more beneficial or desired results. In more specific aspects, an effective amount prevents, alleviates or ameliorates symptoms of disease or infection, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of an IL-2 mediated disease, disorder or condition or an IL-2 deficiency disease, disorder or condition, decreasing the dose of other medications required to treat the disease, enhancing the effect of another medication, and/or delaying the progression of the disease of patients. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "vector" means a construct, which is capable of delivering, and, in some embodiments, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. In some embodiments, diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

Reference to "about" a value or parameter herein includes (and describes) embodiments that are directed to that value or parameter per se. For example, description referring to "about X" includes description of "X." Numeric ranges are inclusive of the numbers defining the range.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

Unless otherwise defined, all technical and scientific terms used herein have the same meaning as commonly understood by one of ordinary skill in the art to which this disclosure belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

It is understood that wherever embodiments are described herein with the language "comprising," otherwise analogous embodiments described in terms of "consisting of" and/or "consisting essentially of" are also provided.

Where aspects or embodiments of the disclosure are described in terms of a Markush group or other grouping of alternatives, the present disclosure encompasses not only the entire group listed as a whole, but each member of the group individually and all possible subgroups of the main group, but also the main group absent one or more of the group members. The present disclosure also envisages the explicit exclusion of one or more of any of the group members in the claimed disclosure.

Exemplary methods and materials are described herein, although methods and materials similar or equivalent to those described herein can also be used in the practice or testing of the present disclosure. The materials, methods, and examples are illustrative only and not intended to be limiting.

Overview

Interleukin-2 (IL-2) is a four-helix bundle, type I cytokine that functions as a growth factor for a wide range of leukocytes, including T cells and natural killer (NK) cells. Considerable effort has been invested in the study of IL-2 as a therapeutic target for a variety of immune disorders ranging from AIDS to cancer. Recombinant human IL-2 (Proleukin®) is used at high doses to treat metastatic melanoma and renal cell carcinoma. However, only a small subset of patients (5-10%) experience long-term survival from such treatment. Adverse effects of high-dose IL-2 therapy, ranging from flu-like symptoms to life-threatening vascular leak syndrome and pulmonary edema, have greatly limited its use. Importantly, IL-2 treatment has unpredictable biologic effects.

IL-2 mediates its effects by binding to a complex receptor comprised of 3 chains CD25 (IL-2Rα), CD122 (IL-2Rβ), and common gamma chain ($\gamma_c$) such that the receptor is termed IL-2Rαβγ. The three chains are differentially expressed with the receptor trimer exhibiting the highest affinity. Individually, each of the three receptor chains in the quaternary complex bind to hIL-2 with low affinity, with hIL-2Rα having the strongest relative affinity ($K_D$~10 nM). Expression of hIL-2Rα increases the on-rate of hIL-2 for T cells and the three receptors cooperatively bind to hIL-2 with $K_D$ ~10 pM. Upon capture by IL-2Rα, IL-2 is presented to IL-2Rβ, and then $\gamma_c$, possibly in a pre-formed receptor dimer, to form the quaternary signaling complex. While hIL-2 alone binds hIL-2Rβ with low affinity ($K_D$ ~150-300 nM), the hIL-2/hIL-2Rα complex binds to hIL-2Rβ with higher affinity ($K_D$ ~60 nM), yet there is no direct contact between IL-2Rα and IL-2Rβ in the quaternary receptor complex. Recent studies suggest that wild-type IL-2 exists in a "quiescent" form that is induced into a structurally-altered conformation that represents the high affinity form which engages IL-2Rα.

Attempts have been made to engineer or modify IL-2 to improve its therapeutic potential by modifying its ability to selectively target either T effector cells (Teff) or T regulatory cells (Treg). Interestingly, there have been a number of approaches to more effective and directive IL-2s. In mouse models, which are not directly analogous to humans, Boyman and colleagues have demonstrated that, in some circumstances, a rat anti-mouse IL-2 mAb (JES6-1) can be complexed with wild type IL-2 and used to preferentially enhance $T_{REG}$ populations (Boyman et al., 2006, Science 311:1924-1927; and International Patent Publication No. WO 2007/095643). Although the mechanistic basis for this effect has not been elucidated, it may be, without wishing to be bound by any particular theory, that IL-2 in complex with certain antibodies is "fixed" in a conformation that selectively triggers discriminatory signals resulting in selective expansion of individual $T_{REG}$ or $T_{EFF}$ cell subsets. In addition, several efforts have been focused on developing IL-2 mutant proteins which enhance activation of CD25+ T cells and minimize activation of CD25− NK cells by increasing IL-2 binding to the trimolecular IL-2R complex CD25. In this regard, a mutant IL-2 has been made by Bayer with a significantly lower affinity for the IL-2Rβ$\gamma_c$ with the expectation that treatment with this variant IL-2 may not activate NK or memory CD8+ T cells. However, both the IL-2 mutant and IL-2/anti-IL-2 antibody complex approaches described above do not take into account the potential inability of a drug to alter endogenous wild type IL-2 that is being produced during the inflammatory T cell response. Moreover, any therapy with IL-2 variants that induce endogenous IL-2 (a demonstrated feedback mechanism) can result in wild type IL-2 effects in vivo that may not have been observed in vitro.

Therefore, although IL-2 was originally developed as an immune stimulatory agent due to its ability to enhance effector T cell ($T_{EFF}$) and NK function, it is now believed that the primary function of IL-2 is NOT activation of immunity but rather the generation and survival of $T_{REG}$, which function to inhibit immune responses and prevent autoimmune disease. There has been an increased understanding using animal models, including IL-2 and IL-2 receptor (IL-2R)-deficient mice, that IL-2 plays a crucial role in peripheral immune tolerance mediated by $T_{REG}$ cells. Studies have shown that low dose IL-2 therapy preferentially activates $T_{REG}$ due to its constitutive expression of the high affinity IL-2R. More specifically, an increasing number of animal studies have demonstrated that $T_{REG}$ can suppress GVHD and autoimmunity. Further, this potential suppressive role has been demonstrated in humans in two recent studies, one in GVHD and the other in autoimmune vasculitis, where short term low dose therapy led to amelioration of disease in some individuals. Thus, there is a long-felt need for IL-2-based therapeutics to selectively activate the tolerogenic versus effector immune response, i.e., therapies designed to tip the $T_{REG}$: $T_{EFF}$ balance towards $T_{REG}$, thereby treating a wide range of diseases. The present disclosure meets that need.

IL-2 Antibodies

The present invention relates to antibodies that specifically bind to IL-2, i.e., they bind to IL-2 but they do not detectably bind, or bind at a lower affinity, to other molecules. In some embodiments, the antibodies specifically bind to human IL-2. In some embodiments, the antibodies specifically bind helices A and C and the B-C loop of hIL-2. In some embodiments, the antibodies specifically bind helix A of hIL-2. In some embodiments, the antibodies specifically bind helix C of hIL-2. In some embodiments, the antibodies specifically bind helices A and C of hIL-2. In some embodiments, the antibodies specifically bind the B-C loop of hIL-2. In some embodiments, the antibodies compete for binding to human IL-2 (hIL-2), with, or bind the same epitope of hIL-2 as, an antibody comprising the amino acid sequences of SEQ ID NOs: 13, 14, 126, 127, 128, 129, 130, 131, 132, 133, and 134. In some embodiments, the antibodies specifically bind human IL-2 (hIL-2), and reduce the binding affinity of hIL-2 to IL-2Rα by about 1 fold to about 199 fold. In some embodiments, the antibodies reduce the binding affinity of hIL-2 to IL-2Rα by about 10 fold. In some embodiments, the antibodies reduce the binding affinity of hIL-2 to IL-2Rα by about 2, 10, 25, 50, 75, 100, 125, 150, or 175 fold.

In some embodiments, the IL-2 antibody reduces IL-2 binding to IL-2Rα and IL-2Rβ, and does not inhibit the activity of regulatory T (Treg) cells. For example, in some embodiments, the IL-2 antibody blocks IL-2 binding to IL-2Rβ, and reduces the affinity of hIL-2 binding to IL-2Rα. In some embodiments, the IL-2 antibody reduces IL-2 binding to IL-2Rα by about 5, 10, 15, 20, 25, 30, 35, 40, 45, 50, 55, 60, 65, 70, 75, 80, 85, 90, 95, or 99%. In some embodiments, the IL-2 antibody reduces IL-2 binding to IL-2Rβ by at least 50, 55, 60, 65, 70, 75, 80, 85, 90, 95, or 99%. In some embodiments, the IL-2 antibody completely blocks IL-2 binding to IL-2Rβ. In particular, the disclosure relates to antibodies that specifically bind to IL-2 and further, antibodies that inhibit proliferation of non-Treg cells (including effector $CD8^+$, non-Treg $CD4^+$ and NK cells) more than they inhibit proliferation of Treg cells or increase Treg proliferation compared to an isotype control antibody or increase the ratio of Treg cells to non-Treg cells or maintain Treg markers or a combination thereof. In some embodiments, the antibodies inhibit proliferation of $CD8^+$, non-Treg $CD4^+$ or NK cells at least 2-fold more than said antibody inhibits the proliferation of Tregs. In some embodiments, the antibodies inhibit proliferation of $CD8^+$, non-Treg $CD4^+$ or NK cells at least 2, 3, 4, 5, 6, 7, 8, 9, 10, 11, 12, 13, 14, 15, 16, 17, 18, 19, 20-fold more than said antibody inhibits the proliferation of Tregs. In some embodiments, the antibodies reduce IL-2 binding to IL-2Rα and IL-2Rβ and increase the ratio of T regulatory cells (Tregs) to $CD8^+$, non-Treg $CD4^+$ or NK cells in a peripheral blood mononuclear cell (PBMC) culture or reconstitution assay. In some embodiments, the ratio is increased at least 2, 3, 4, 5, 6, 7, 8, 9, 10, 11, 12, 13, 14, 15, 16, 17, 18, 19, 20-fold or greater. In some embodiments, the antibody increases Tregs: $CD8^+$ cells ratio by two (2) fold or greater, and may reflect increased Treg proliferation. In some embodiments, the antibodies enhance T regulatory cell (Treg) proliferation greater than an isotype control when IL-2 is limiting, for example, at a concentration of less than 1 nM in vitro. In some embodiments, the antibodies inhibit proliferation of $CD8^+$ cells. In some embodiments, the antibodies reduce IL-2 binding to IL-2Rα and IL-2Rβ and maintain expression of one or more FOXP3, CD25, and Icos in Treg cells. In some embodiments, the antibodies reduce IL-2 binding to IL-2Rα and IL-2Rβ and increase expression of one or more FOXP3, CD25, and Icos in Treg cells. In some embodiments, an IL-2 antibody of the disclosure has at least one of these features, and in some embodiments, the antibody has two or more of these features. In some embodiments, the antibodies have all of the features.

In some embodiments, the antibody, or antigen-binding portion thereof, that specifically binds IL-2, reduces IL-2 binding to IL-2Rα and IL-2Rβ, and inhibits STAT5 phosphorylation in $CD8^+$ T cells to a higher degree than in regulatory T (Treg) cells. In some embodiments, the IL-2 antibody, or antigen-binding portion maintains STAT5 phosphorylation in Tregs by greater than 50%. In some embodiments, the IL-2 antibody, or antigen-binding portion maintains STAT5 phosphorylation in Tregs by greater than 60%. In some embodiments, the IL-2 antibody, or antigen-binding portion maintains STAT5 phosphorylation in Tregs by greater than 70%. In some embodiments, the IL-2 antibody, or antigen-binding portion maintains STAT5 phosphorylation in Tregs by greater than 80%. In some embodiments, the IL-2 antibody, or antigen-binding portion maintains STAT5 phosphorylation in Tregs by greater than 90%. In some embodiments, the antibodies specifically bind to hIL-2. These amounts are not meant to be limiting, and increments between the recited percentages are specifically envisioned as part of the disclosure.

The disclosure also relates to compositions comprising such antibodies as well as uses for such antibodies, including therapeutic and pharmaceutical uses.

By the term "IL-2" is meant any naturally occurring form of IL-2, whether monomeric or multimeric, including dimers, trimers, etc., which may be derived from any suitable organism. As used herein, "IL-2" refers to a mammalian IL-2, such as human, rat or mouse, as well as non-human primate, bovine, ovine, or porcine IL-2. In some embodiments, the IL-2 is human (see, e.g., Genbank Accession Number P60568) or "hIL-2." The IL-2 can also be cynomolgus monkey IL-2 (see, e.g., Genbank Accession Number Q29615). The term "IL-2" also encompasses portions, variants, isoforms, and other homologs of such IL-2 molecules. Variant IL-2 molecules will generally be characterized by having the same type of activity as naturally occurring IL-2, such as the ability to bind IL-2 receptor, and the ability to induce receptor-mediated activity.

The IL-2 may comprise one or more, two or more, three or more, four or more, five or more, six or more, seven or more, eight or more, nine or more, ten or more, twelve or more or fifteen or more surface accessible residues of IL-2. Where the IL-2 comprises a homomultimeric form of IL-2, the target may comprise one or more, two or more, three or more, four or more, five or more, six or more, seven or more, eight or more, nine or more, ten or more, twelve or more, or fifteen or more surface accessible residues of a first subunit of IL-2, and one or more, two or more, three or more, four or more, five or more, six or more, seven or more, eight or more, nine or more, ten or more, twelve or more, or fifteen or more surface accessible residues of a second subunit of IL-2.

The target molecule may comprise a known epitope from IL-2. The target molecule may comprise a known epitope from hIL-2. In some embodiments, the target may comprise helix A of hIL-2. In some embodiments, the target may comprise helix C of hIL-2. In some embodiments, the target may comprise helices A and C of hIL-2. In some embodiments, the target may comprise the B-C loop of hIL-2. In some embodiments, the target may comprise helices A and C and the B-C loop of hIL-2.

In one embodiment, the disclosure provides any of the following, or compositions (including pharmaceutical compositions) comprising, an antibody having a light chain sequence, or a portion thereof, and a heavy chain, or a portion thereof, derived from any of the following antibodies: F4.7.6, F4.7.8, F5.1.11, F5.1.9, F4.7.062, F5.11.1.01, F5.1.11.02, F5.1.11.03, F5.1.11.04, F5.1.11.05, F5.1.11.06, F5.1.11.07, F5.1.11.08, F5.1.11.09, F5.1.9.5, or d1C7. Antibody F5.1.11 is also referred to as antibody F5111, 5.1.11, 5111. These terms are interchangeable. Variants of this parental antibody may be referred to by this nomenclature with an additional number, e.g., antibody F5111.2, 5.1.11.2, F5.1.11.02, or 5111.2; or antibody F5.1.11.01, F5111.1, 5.1.11.1, or 5111.1.

The antibodies useful in the present disclosure can encompass monoclonal antibodies, polyclonal antibodies, antibody portions (e.g., Fab, Fab', $F(ab')_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the IL-2 antibody is a monoclonal antibody. In some embodiments, the antibody is a human or humanized antibody.

The IL-2 antibodies of the disclosure may be made by any method known in the art. General techniques for production of human and mouse antibodies are known in the art and/or are described herein.

IL-2 antibodies can be identified or characterized using methods known in the art, whereby reduction, amelioration, or neutralization of IL-2 activity is detected and/or measured, for example, pAKT and/or pSTAT5. In some embodiments, an IL-2 antibody is identified by incubating a candidate agent (e.g., IL-2) with IL-2 receptor and monitoring binding and/or attendant reduction or inhibition of a biological activity of IL-2. In some embodiments, hIL-2 antibodies can be identified or characterized using methods known in the art, whereby reduction, amelioration, or neutralization of hIL-2 activity is detected and/or measured, for example, pAKT and/or pSTAT5. In some embodiments, a hIL-2 antibody is identified by incubating a candidate agent (e.g., hIL-2) with hIL-2 receptor and monitoring binding and/or attendant reduction or inhibition of a biological activity of hIL-2. The binding assay may be performed with, e.g., purified IL-2 polypeptide(s), or with cells naturally expressing various receptors, or transfected to express, IL-2 receptor. In one embodiment, the binding assay is a competitive binding assay, where the ability of a candidate antibody to compete with a known IL-2 antibody for IL-2 binding is evaluated. The assay may be performed in various formats, including the ELISA format. In some embodiments, an IL-2 antibody is identified by incubating a candidate antibody with IL-2 and monitoring binding.

Following initial identification, the activity of a candidate IL-2 antibody can be further confirmed and refined by bioassays, known to test the targeted biological activities. In some embodiments, an in vitro cell assay is used to further characterize a candidate IL-2 antibody. For example, bioassays can be used to screen candidates directly. Some of the methods for identifying and characterizing IL-2 antibody are described in detail in the Examples.

IL-2 antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an IL-2 antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with IL-2 antibody. In another example, the epitope to which the IL-2 antibody binds can be determined in a systematic screening by using overlapping peptides derived from the IL-2 sequence and determining binding by the antibody. According to the gene fragment expression assays, the open reading frame encoding IL-2 can be fragmented either randomly or by specific genetic constructions and the reactivity of the expressed fragments of IL-2 with the antibody to be tested is determined. The gene fragments may, for example, be produced by PCR and then transcribed and translated into protein in vitro, in the presence of radioactive amino acids. The binding of the antibody to the radioactively labeled IL-2 fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant IL-2 in which various residues of the IL-2 polypeptide have been replaced with alanine. By assessing binding of the antibody to the mutant IL-2, the importance of the particular IL-2 residues to antibody binding can be assessed.

Yet another method which can be used to characterize an IL-2 antibody is to use competition assays with other antibodies known to bind to the same antigen, i.e., various fragments on IL-2, to determine if the IL-2 antibody binds to the same epitope as other antibodies. Competition assays are well known to those of skill in the art.

Further, the epitope for a given antibody/antigen binding pair can be defined and characterized at different levels of detail using a variety of experimental and computational epitope mapping methods. The experimental methods include mutagenesis, X-ray crystallography, Nuclear Magnetic Resonance (NMR) spectroscopy, hydrogen/deuterium exchange Mass Spectrometry (H/D-MS) and various competition binding methods well-known in the art. As each method relies on a unique principle, the description of an epitope is intimately linked to the method by which it has been determined. Thus, the epitope for a given antibody/antigen pair will be defined differently depending on the epitope mapping method employed.

At its most detailed level, the epitope for the interaction between the Ag and the Ab can be defined by the spatial coordinates defining the atomic contacts present in the Ag-Ab interaction, as well as information about their relative contributions to the binding thermodynamics. At a less detailed level the epitope can be characterized by the spatial coordinates defining the atomic contacts between the Ag and Ab. At a further less detailed level the epitope can be characterized by the amino acid residues that it comprises as defined by a specific criterion, e.g., by distance between atoms (e.g., heavy, i.e., non-hydrogen atoms) in the Ab and the Ag. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag (e.g. using alanine scanning).

From the fact that descriptions and definitions of epitopes, dependent on the epitope mapping method used, are obtained at different levels of detail, it follows that comparison of epitopes for different Abs on the same Ag can similarly be conducted at different levels of detail.

Epitopes described at the amino acid level, e.g., determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

Epitopes characterized by competition binding are said to be overlapping if the binding of the corresponding antibodies are mutually exclusive, i.e., binding of one antibody excludes simultaneous or consecutive binding of the other antibody. The epitopes are said to be separate (unique) if the antigen is able to accommodate binding of both corresponding antibodies simultaneously.

The definition of the term "paratope" is derived from the above definition of "epitope" by reversing the perspective. Thus, the term "paratope" refers to the area or region on the antibody which specifically binds an antigen, i.e., the amino acid residues on the antibody which make contact with the antigen (IL-2) as "contact" is defined elsewhere herein.

The epitope and paratope for a given antibody/antigen pair may be identified by routine methods. For example, the general location of an epitope may be determined by assessing the ability of an antibody to bind to different fragments or variant IL-2 polypeptides. The specific amino acids within IL-2 that make contact with an antibody (epitope) and the specific amino acids in an antibody that make contact with IL-2 (paratope) may also be determined using routine methods, such as those described in the examples. For example, the antibody and target molecule may be combined and the antibody/antigen complex may be crystallized. The crystal structure of the complex may be determined and used to identify specific sites of interaction between the antibody and its target.

An antibody according to the current disclosure may bind to the same epitope or domain of IL-2 as the antibodies of the disclosure that are specifically disclosed herein. For example, other yet unidentified antibodies of the disclosure may be identified by comparing their binding to IL-2 with that of any of the following monoclonal antibodies: F4.7.6, F4.7.8, F5.1.11, F5.1.9, F4.7.062, F5.11.1.01, F5.1.11.02, F5.1.11.03, F5.1.11.04, F5.1.11.05, F5.1.11.06, F5.1.11.07, F5.1.11.08, F5.1.11.09, F5.1.9.5, or d1C7, and variants thereof; or by comparing the function of yet unidentified antibodies with that of the antibodies described herein; and/or by comparing the epitope/contact residues on IL-2 of yet unidentified antibodies with those of the antibodies of the disclosure. Analyses and assays that may be used for the purpose of such identification include assays assessing the competition for binding of IL-2 between the antibody of interest and IL-2 receptor, in biological activity assays as described in Examples 1-5, and in analysis of the crystal structure of the antibody.

An antibody of the disclosure may have the ability to compete or cross-compete with another antibody of the disclosure for binding to IL-2 as described herein. For example, an antibody of the disclosure may compete or cross-compete with antibodies described herein for binding to IL-2, or to a suitable fragment or variant of IL-2 that is bound by the antibodies disclosed herein.

That is, if a first antibody competes with a second antibody for binding to IL-2, but it does not compete where the second antibody is first bound to IL-2, it is deemed to "compete" with the second antibody (also referred to as unidirectional competition). Where an antibody competes with another antibody regardless of which antibody is first bound to IL-2, then the antibody "cross-competes" for binding to IL-2 with the other antibody. Such competing or cross-competing antibodies can be identified based on their ability to compete/cross-compete with a known antibody of the disclosure in standard binding assays. For example, SPR e.g. by using a Biacore™ system, ELISA assays or flow cytometry may be used to demonstrate competition/cross-competition. Such competition/cross-competition may suggest that the two antibodies bind to identical, overlapping or similar epitopes.

An antibody of the disclosure may therefore be identified by a method that comprises a binding assay which assesses whether or not a test antibody is able to compete/cross-compete with a reference antibody of the disclosure (e.g., F4.7.6, F4.7.8, F5.1.11, F5.1.9, F4.7.062, F5.11.1.01, F5.1.11.02, F5.1.11.03, F5.1.11.04, F5.1.11.05, F5.1.11.06, F5.1.11.07, F5.1.11.08, F5.1.11.09, F5.1.9.5, or d1C7) for a binding site on the target molecule. Methods for carrying out competitive binding assays are disclosed herein and/or are well known in the art. For example they may involve binding a reference antibody of the disclosure to a target molecule using conditions under which the antibody can bind to the target molecule. The antibody/target complex may then be exposed to a test/second antibody and the extent to which the test antibody is able to displace the reference antibody of the disclosure from antibody/target complexes may be assessed. An alternative method may involve contacting a test antibody with a target molecule under conditions that allow for antibody binding, then adding a reference antibody of the disclosure that is capable of binding that target molecule and assessing the extent to which the reference antibody of the disclosure is able to displace the test antibody from antibody/target complexes or to simultaneously bind to the target (i.e., non-competing antibody).

The ability of a test antibody to inhibit the binding of a reference antibody of the disclosure to the target demonstrates that the test antibody can compete with a reference antibody of the disclosure for binding to the target and thus that the test antibody binds to the same, or substantially the same, epitope or region on the IL-2 protein as the reference antibody of the disclosure. A test antibody that is identified as competing with a reference antibody of the disclosure in such a method is also an antibody of the present disclosure. The fact that the test antibody can bind IL-2 in the same region as a reference antibody of the disclosure and can compete with the reference antibody of the disclosure suggests that the test antibody may act as a ligand at the same binding site as the antibody of the disclosure and that the test antibody may therefore mimic the action of the reference antibody and is, thus, an antibody of the disclosure. This can be confirmed by comparing the activity of IL-2 in the presence of the test antibody with the activity of IL-2 in the presence of the reference antibody under otherwise identical conditions, using an assay as more fully described elsewhere herein.

The reference antibody of the disclosure may be an antibody as described herein, such as F4.7.6, F4.7.8, F5.1.11, F5.1.9, F4.7.062, F5.11.1.01, F5.1.11.02, F5.1.11.03, F5.1.11.04, F5.1.11.05, F5.1.11.06, F5.1.11.07, F5.1.11.08, F5.1.11.09, F5.1.9.5, or d1C7, or any variant, or portion thereof, as described herein that retains the ability to bind to IL-2. An antibody of the disclosure may bind to the same epitope as the reference antibodies described herein or any variant or portion thereof as described herein that retains the ability to bind to IL-2.

As stated previously elsewhere herein, specific binding may be assessed with reference to binding of the antibody to a molecule that is not the target. This comparison may be made by comparing the ability of an antibody to bind to the target and to another molecule. This comparison may be made as described above in an assessment of $K_D$ or $K_i$. The other molecule used in such a comparison may be any molecule that is not the target molecule. In some embodiments, the other molecule is not identical to the target molecule. In some embodiments, the target molecule is not a fragment of the target molecule.

The other molecule used to determine specific binding may be unrelated in structure or function to the target. For example, the other molecule may be an unrelated material or accompanying material in the environment.

The other molecule used to determine specific binding may be another molecule involved in the same in vivo pathway as the target molecule, i.e., IL-2. By ensuring that the antibody of the disclosure has specificity for IL-2 over another such molecule, unwanted in vivo cross-reactivity may be avoided.

The antibody of the disclosure may retain the ability to bind to some molecules that are related to the target molecule.

Alternatively, the antibody of the disclosure may have specificity for a particular target molecule. For example, it may bind to one target molecule as described herein, but may not bind, or may bind with significantly reduced affinity to a different target molecule as described herein. For example, a full length mature human IL-2 may be used as the target, but the antibody that binds to that target may be unable to bind to or may bind with lesser affinity to, e.g. other IL-2 proteins from other species, such as other mammalian IL-2. In some embodiments, the antibody binds to both human and mouse IL-2.

Polypeptide or antibody "fragments" or "portions" according to the disclosure may be made by truncation, e.g., by removal of one or more amino acids from the N and/or C-terminal ends of a polypeptide. Up to 10, up to 20, up to 30, up to 40 or more amino acids may be removed from the N and/or C terminal in this way. Portions may also be generated by one or more internal deletions.

An antibody of the disclosure may be, or may comprise, a portion of, any one of antibodies F4.7.6, F4.7.8, F5.1.11, F5.1.9, F4.7.062, F5.11.1.01, F5.1.11.02, F5.1.11.03, F5.1.11.04, F5.1.11.05, F5.1.11.06, F5.1.11.07, F5.1.11.08, F5.1.11.09, F5.1.9.5, or d1C7, or a variant thereof. The antibody of the disclosure may be or may comprise an antigen-binding portion of this antibody or a variant thereof. For example, the antibody of the disclosure may be a Fab portion of this antibody or a variant thereof or may be a single chain antibody derived from this antibody or a variant thereof.

A variant antibody may comprise 1, 2, 3, 4, 5, up to 10, up to 20, up to 30 or more amino acid substitutions and/or deletions and/or insertions from the specific sequences and portions discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 2, 3, 4 or 5 amino acids, or insertion of larger amino acid regions, such as the insertion of specific amino acid domains or other features. "Substitution" variants in some embodiments involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as described below.

Substitution variants have at least one amino acid residue in the antibody molecule removed and a different residue inserted in its place. The sites of greatest interest for substitutional mutagenesis include the hypervariable domains, but framework alterations are also contemplated. Conservative substitutions are shown in Table 1 under the heading of "conservative substitutions." If such substitutions result in a change in biological activity, then more substantial changes, denominated "exemplary substitutions" shown below, or as further described below in reference to amino acid classes, may be introduced and the products screened.

TABLE 1

Amino Acid Substitutions

| Original Residue | Conservative Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gin;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody portion such as an Fv portion.

The disclosure also provides methods of generating, selecting, and making IL-2 antibodies. The antibodies of this disclosure can be made by procedures known in the art. In some embodiments, antibodies may be made recombinantly and expressed using any method known in the art. The disclosure also provides methods of generating, selecting, and making hIL-2 antibodies. The antibodies of this disclosure can be made by procedures known in the art. In some embodiments, antibodies may be made recombinantly and expressed using any method known in the art.

In some embodiments, antibodies may be prepared and selected by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348:552-553, 1990) can be used to produce human antibodies and antibody portions in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody portions on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from human donors can be constructed and antibodies to a diverse array of antigens (including self-antigens) can be isolated essentially following the techniques described by Mark et al., 1991, J. Mol. Biol. 222:581-597, or Griffith et al., 1993, EMBO J. 12:725-734. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., 1992, Bio/Technol. 10:779-783). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody portions with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable domains capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

In some embodiments, antibodies may be made using hybridoma technology. It is contemplated that any mammalian subject including humans or antibody producing cells therefrom can be manipulated to serve as the basis for production of mammalian, including human, hybridoma cell lines. The route and schedule of immunization of the host animal are generally in keeping with established and conventional techniques for antibody stimulation and production, as further described herein. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the IL-2 monoclonal antibodies of the subject disclosure. The hybridomas or other immortalized B-cells are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for IL-2, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with an IL-2 polypeptide, or a portion containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N$=$C$=$NR$, where R and $R^1$ are different alkyl groups, can yield a population of antibodies (e.g., monoclonal antibodies).

If desired, the IL-2 antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

The plasmids indicated in Table 2 are being deposited under terms in accordance with the Budapest Treaty with the American Type Culture Collection (ATCC), 10801 University Blvd., Manassas, Va. 20110-2209. The plasmids have been assigned the following accession numbers:

TABLE 2

| ATCC No. | Antibody | Strain Designation | Deposit Date |
| --- | --- | --- | --- |
| PTA-123497 | F5.1.11.02 VH | F5.1.11.02-VH | 8 Sep. 2016 |
| PTA-123498 | F5.1.11.02 VL | F5.1.11.02-VL | 8 Sep. 2016 |

In some embodiments, the polynucleotide sequence may be used for genetic manipulation to "humanize" the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., domain, single chain, etc. are known in the art.

Immunoassays and flow cytometry sorting techniques such as fluorescence activated cell sorting (FACS) can also be employed to isolate antibodies that are specific for IL-2.

DNA encoding the monoclonal antibodies is readily isolated and sequenced using conventional procedures (e.g., by using oligonucleotide probes that are capable of binding specifically to genes encoding the heavy and light chains of the monoclonal antibodies). In some embodiments, the hybridoma cells serve as a source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a, IL-2 antibody herein.

Antibody portions can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In some embodiments, a polynucleotide comprises a sequence encoding the heavy chain and/or the light chain variable domains of IL-2 antibody of the present disclosure. The sequence encoding the antibody of interest may be maintained in a vector in a host cell and the host cell can then be expanded and frozen for future use. Vectors (including expression vectors) and host cells are further described herein.

The disclosure includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a $K_D$ of about 10 nM or lower.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position). In some embodiments, every amino acid position in a CDR is replaced (in some embodiments, one at a time) with all 20 natural amino acids except cysteine using art recognized mutagenesis methods In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18.

The CDR may be heavy chain variable domain (VH) CDR3 and/or light chain variable domain (VL) CDR3. The CDR may be one or more of VH CDR1, VH CDR2, VH CDR3, VL CDR1, VL CDR2, and/or VL CDR3. The CDR may be a Kabat CDR, a Chothia CDR, an extended CDR, an AbM CDR, a contact CDR, or a conformational CDR.

In some embodiments, the library is made according to SEQ ID NOs: 71 and 72.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore, Kinexa™ biosensor analysis, and selection using any method known in the art for selection, including phage display, yeast display, and ribosome display.

To express the IL-2 antibodies of the present disclosure, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The disclosure encompasses modifications to the variable domains and the CDRs indicated in Table 7. For example, the disclosure includes antibodies comprising functionally equivalent variable domains and CDRs which do not significantly affect their properties as well as variants which have enhanced or decreased activity and/or affinity. For example, the amino acid sequence may be mutated to obtain an antibody with the desired binding affinity to IL-2. In some embodiments, the amino acid sequence may be mutated to obtain an antibody with the desired binding affinity to IL-2. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

The antibodies may also be modified, e.g., in the variable domains of the heavy and/or light chains, e.g., to alter a binding property of the antibody. Changes in the variable domain can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody for IL-2, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of an IL-2 antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the disclosure, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments, the antibody comprises a modified constant region that has increased or decreased binding affinity to a human Fc gamma receptor, is immunologically inert or partially inert, e.g., does not trigger complement mediated lysis, does not stimulate antibody-dependent cell mediated cytotoxicity (ADCC), or does not activate microglia; or has reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., Immunology 86:319-324, 1995; Lund et al., J. Immunology 157: 4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Application No. PCT/GB99/ 01441; and/or UK Patent Application No. 9809951.8.

In some embodiments, an antibody constant region can be modified to avoid interaction with Fc gamma receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In some embodiments, the constant region is modified as described in Eur. J. Immunol., 1999, 29:2613-2624; PCT Application No. PCT/GB99/01441; and/or UK Patent Application No. 9809951.8. In such embodiments, the Fc can be human $IgG_2$ or human $IgG_4$. The Fc can be human $IgG_2$ containing the mutation A330P331 to S330S331 ($IgG_{2\Delta a}$), in which the amino acid residues are numbered with reference to the wild type $IgG_2$ sequence. Eur. J. Immunol., 1999, 29:2613-2624. In some embodiments, the antibody comprises a constant region of $IgG_4$ comprising the following mutations (Armour et al., 2003, Molecular Immunology 40 585-593): E233F234L235 to P233V234A235 ($IgG_{4\Delta c}$), in which the numbering is with reference to wild type $IgG_4$. In yet another embodiment, the Fc is human $IgG_4$ E233F234L235 to P233V234A235 with deletion G236 ($IgG_{4\Delta b}$). In another embodiment, the Fc is any human $IgG_4$ Fc ($IgG_4$, $IgG_{4\Delta b}$ or $IgG_{4\Delta c}$) containing hinge stabilizing mutation S228 to P228 (Aalberse et al., 2002, Immunology 105, 9-19).

In some embodiments, the antibody comprises a human heavy chain $IgG_2$ constant region comprising the following mutations: A330P331 to S330S331 (amino acid numbering with reference to the wild type $IgG_2$ sequence). Eur. J. Immunol., 1999, 29:2613-2624. In still other embodiments, the constant region is aglycosylated for N-linked glycosylation. In some embodiments, the constant region is aglycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

The disclosure also provides an antibody constant domain that may be further modified. It is known that variants of the Fc region, e.g., amino acid substitutions, insertions, and/or additions and/or deletions, enhance or diminish effector function. See, e.g., Presta et al, 2002, Biochem. Soc. Trans. 30:487-490; Strohl, 2009, Curr. Opin. Biotechnol. 20(6): 685-691; U.S. Pat. Nos. 5,624,821, 5,648,260, 5,885,573, 6,737,056, 7,317,091; PCT publication Nos. WO 99/58572, WO 00/42072, WO 04/029207, WO 2006/105338, WO 2008/022152, WO 2008/150494, WO 2010/033736; U.S. Patent Application Publication Nos. 2004/0132101, 2006/0024298, 2006/0121032, 2006/0235208, 2007/0148170; Armour et al., 1999, Eur. J. Immunol. 29(8):2613-2624 (reduced ADCC and CDC); Shields et al., 2001, J. Biol. Chem. 276(9):6591-6604 (reduced ADCC and CDC); Idusogie et al., 2000, J. Immunol. 164(8):4178-4184 (increased ADCC and CDC); Steurer et al., 1995, J. Immunol. 155(3): 1165-1174 (reduced ADCC and CDC); Idusogie et al., 2001, J. Immunol. 166(4):2571-2575 (increased ADCC and CDC); Lazar et al., 2006, Proc. Natl. Acad. Sci. USA 103(11): 4005-4010 (increased ADCC); Ryan et al., 2007, Mol. Cancer. Ther., 6: 3009-3018 (increased ADCC); Richards et al., 2008, Mol. Cancer Ther. 7(8):2517-2527.

In some embodiments, the antibody comprises a modified constant region that has increased binding affinity for FcRn and/or an increased serum half-life as compared with the unmodified antibody.

In a process known as "germlining", certain amino acids in the VH and VL sequences can be mutated to match those found naturally in germ line VH and VL sequences. In particular, the amino acid sequences of the framework regions in the VH and VL sequences can be mutated to match the germline sequences to reduce the risk of immunogenicity when the antibody is administered. Germline DNA sequences for human VH and VL genes are known in the art (see e.g., the "Vbase" human germ line sequence database; see also Kabat, E. A., et al., 1991, Sequences of Proteins of Immunological Interest, Fifth Edition, U.S. Department of Health and Human Services, NIH Publication No. 91-3242; Tomlinson et al., 1992, J. Mol. Biol. 227:776-798; and Cox et al., 1994, Eur. J. Immunol. 24:827-836).

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an IL-2 antibody of the disclosure can be cleaved or otherwise removed. In various embodiments of the disclosure, the heavy and light chains of the antibodies may optionally include a signal sequence.

Once DNA fragments encoding the VH and VL segments of the present disclosure are obtained, these DNA fragments can be further manipulated by standard recombinant DNA techniques, for example to convert the variable domain genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in some embodiments, is an $IgG_1$ or $IgG_2$ constant region. The IgG constant region sequence can be any of the various alleles or allotypes known to occur among different individuals, such as Gm(1), Gm(2), Gm(3), and Gm(17). These allotypes represent naturally occurring amino acid substitution in the $IgG_1$ constant regions. For a Fab fragment heavy chain gene, the $V_H$-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. Linkers of other sequences have been designed and used (Bird et al., 1988, supra). Linkers can in turn be modified for additional functions, such as attachment of drugs or attachment to solid supports. The single chain antibody may be monovalent, if only a single VH and VL are used, bivalent, if two VH and VL are used, or polyvalent, if more than two VH and VL are used. Bispecific or polyvalent antibodies may be generated that bind specifically to IL-2 and to another molecule. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies, are also encompassed. Diabodies are bivalent, bispecific antibodies in which VH and VL are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad Sci. USA 90:6444-6448; and Poljak, R. J., et al., 1994, Structure 2:1121-1123).

Heteroconjugate antibodies, comprising two covalently joined antibodies, are also within the scope of the disclosure. Such antibodies have been used to target immune system cells to unwanted cells (U.S. Pat. No. 4,676,980), and for treatment of HIV infection (PCT Publication Nos. WO 91/00360 and WO 92/200373; and EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

The disclosure also encompasses fusion proteins comprising one or more portions or regions from the antibodies disclosed herein. In some embodiments, a fusion antibody may be made that comprises all or a portion of an IL-2 antibody of the disclosure linked to another polypeptide. In another embodiment, only the variable domains of the IL-2 antibody are linked to the polypeptide. In another embodiment, the VH domain of an IL-2 antibody is linked to a first polypeptide, while the VL domain of an IL-2 antibody is linked to a second polypeptide that associates with the first polypeptide in a manner such that the VH and VL domains can interact with one another to form an antigen binding site. In another embodiment, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In some embodiments, a fusion polypeptide is provided that comprises at least 10 contiguous amino acids of the variable light chain region shown in SEQ ID NOs: 2, 4, 6, 8, 10, 12, 14, 16, 18, 20, 22, 24, 26, 28, 30, 32, or 72 and/or at least 10 amino acids of the variable heavy chain region shown in SEQ ID NOs: 1, 3, 5, 7, 9, 11, 13, 15, 17, 19, 21, 23, 25, 27, 29, 31, or 71. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises one or more CDR(s). In still other embodiments, the fusion polypeptide comprises VH CDR3 and/or VL CDR3. For purposes of this disclosure, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag (SEQ ID NO: 223). Tags are well known in the art.

A fusion polypeptide can be created by methods known in the art, for example, synthetically or recombinantly. Typically, the fusion proteins of this disclosure are made by preparing and expressing a polynucleotide encoding them using recombinant methods described herein, although they may also be prepared by other means known in the art, including, for example, chemical synthesis.

In other embodiments, other modified antibodies may be prepared using nucleic acid molecules encoding an IL-2 antibody. For instance, "Kappa bodies" (Ill et al., 1997, Protein Eng. 10:949-57), "Minibodies" (Martin et al., 1994, EMBO J. 13:5303-9), "Diabodies" (Holliger et al., supra), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121:210). For example, bispecific antibodies or antigen-binding portions can be produced by fusion of hybridomas or linking of Fab' portions. See, e.g., Songsivilai & Lachmann, 1990, Clin. Exp. Immunol. 79:315-321, and Kostelny et al., 1992, J. Immunol. 148:1547-1553. Traditionally, the recombinant production of bispecific antibodies was based on the coexpression of two immunoglobulin heavy chain-light chain pairs, with the two heavy chains having different specificities (Millstein and Cuello, 1983, Nature 305, 537-539). In addition, bispecific antibodies may be formed as "diabodies" or "Janusins." In some embodiments, the bispecific antibody binds to two different epitopes of IL-2. In some embodiments, the modified antibodies described above are prepared using one or more of the variable domains or CDR regions from an IL-2 antibody provided herein.

According to one approach to making bispecific antibodies, antibody variable domains with the desired binding specificities (antibody-antigen combining sites) are fused to immunoglobulin constant region sequences. In some embodiments, the fusion is with an immunoglobulin heavy chain constant region, comprising at least part of the hinge, CH2 and CH3 regions. In some embodiments, the first heavy chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide portions in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

This disclosure also provides compositions comprising antibodies conjugated (for example, linked) to an agent that facilitate coupling to a solid support (such as biotin or avidin). For simplicity, reference will be made generally to antibodies with the understanding that these methods apply to any of the IL-2 binding embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the disclosure. Those skilled in the art will know of other suitable carriers for binding antibodies, or will be able to ascertain such, using routine experimentation.

An antibody or polypeptide of this disclosure may be linked to a labeling agent such as a fluorescent molecule, a radioactive molecule or any others labels known in the art. Labels are known in the art which generally provide (either directly or indirectly) a signal.

The amino acid sequences of the light chain variable domain (VL) and heavy chain variable domains (VH) of the IL-2 antibodies disclosed herein are summarized in Table 7 by sequence identification number.

An antibody of the disclosure may comprise both:
a) a VH comprising the amino acid sequence of SEQ ID NO:1, and a VL comprising the amino acid sequence of SEQ ID NO:2,
b) a VH comprising the amino acid sequence of SEQ ID NO:3, and a VL comprising the amino acid sequence of SEQ ID NO:4,
c) a VH comprising the amino acid sequence of SEQ ID NO:5, and a VL comprising the amino acid sequence of SEQ ID NO:6,
d) a VH comprising the amino acid sequence of SEQ ID NO:7, and a VL comprising the amino acid sequence of SEQ ID NO:8,
e) a VH comprising the amino acid sequence of SEQ ID NO:9, and a VL comprising the amino acid sequence of SEQ ID NO:10,
f) a VH comprising the amino acid sequence of SEQ ID NO:11, and a VL comprising the amino acid sequence of SEQ ID NO:12,
g) a VH comprising the amino acid sequence of SEQ ID NO:13, and a VL comprising the amino acid sequence of SEQ ID NO:14,
h) a VH comprising the amino acid sequence of SEQ ID NO:15, and a VL comprising the amino acid sequence of SEQ ID NO:16,
i) a VH comprising the amino acid sequence of SEQ ID NO:17, and a VL comprising the amino acid sequence of SEQ ID NO:18,
j) a VH comprising the amino acid sequence of SEQ ID NO:19, and a VL comprising the amino acid sequence of SEQ ID NO:20,
k) a VH comprising the amino acid sequence of SEQ ID NO:21, and a VL comprising the amino acid sequence of SEQ ID NO:22, l) a VH comprising the amino acid sequence of SEQ ID NO:23, and a VL comprising the amino acid sequence of SEQ ID NO:24, m) a VH comprising the amino acid sequence of SEQ ID NO:25, and a VL comprising the amino acid sequence of SEQ ID NO:26, n) a VH comprising the amino acid sequence of SEQ ID NO:27, and a VL comprising the amino acid sequence of SEQ ID NO:28, o) a VH comprising the amino acid sequence of SEQ ID NO:29, and a VL comprising the amino acid sequence of SEQ ID NO:30, p) a VH comprising the amino acid sequence of SEQ ID NO:31, and a VL comprising the amino acid sequence of SEQ ID NO:32 or q) a VH comprising the amino acid sequence of SEQ ID NO:71, and a VL comprising the amino acid sequence of SEQ ID NO:72.

In another aspect, the antibody comprises a variant of these sequences, wherein such variants can include both conservative and non-conservative substitutions, deletions, and/or additions, and typically include peptides that share at least 60%, at least 65%, at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific sequences disclosed herein.

For example, in one aspect, the disclosure provides an isolated antibody or antigen-binding portion thereof that comprises a $V_L$ chain amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, or SEQ ID NO:72, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, or SEQ ID NO:72. In a further aspect, said variant shares at least 65%, at least 75%, at least 85%, at least 90%, at least 95%, at least 96%, at least 97%, at least 98%, or at least 99% sequence identity with SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, or SEQ ID NO:72, and wherein said antibody or antigen-binding portion specifically binds IL-2. In some embodiments, said antibody or antigen-binding portion specifically binds hIL-2.

In a further aspect, the disclosure provides an isolated antibody or antigen-binding portion thereof that comprises a $V_H$ chain amino acid sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, or SEQ ID NO:71, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, or SEQ ID NO:71. In a further aspect, said variant shares at least 65%, at least 75%, at least 85%, at least 90%, at least 95%, at least 96%, at least 97%, at least 98%, or at least 99% sequence identity with SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, or SEQ ID NO:71, and wherein said antibody or antigen-binding portion specifically binds IL-2. In some embodiments, said antibody or antigen-binding portion specifically binds hIL-2.

An antibody of the disclosure may comprise a heavy chain comprising a VH comprising the amino acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, or SEQ ID NO:71, wherein the antibody further comprises a heavy chain constant domain. As more fully set forth elsewhere herein, the antibody heavy chain constant domain can be selected from an $IgG_1$, $IgG_2$, $IgG_3$, $IgG_4$, IgA, IgE, IgM or IgD constant region, but in some embodiments, is an $IgG_1$ or $IgG_2$ constant region. The IgG constant region sequence can be any of the various alleles or allotypes known to occur among different individuals, such as Gm(1), Gm(2), Gm(3), and Gm(17). For a Fab portion heavy chain gene, the VH-encoding DNA can be operatively linked to another DNA molecule encoding only the heavy chain CH1 constant region. The CH1 heavy chain constant region may be derived from any of the heavy chain genes.

In one aspect, the antibody may comprise a heavy chain comprising a VH selected from a VH comprising the amino acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, or SEQ ID NO:71, and further comprising the IgG1 constant domain comprising a triple mutation decreasing or abolishing Fc effector function (hIgG1-3m; SEQ ID NO:2). In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the full length heavy chain. In a further aspect, said variant shares at least 65%, at least 75%, at least 85%, at least 90%, at least 95%, at least 96%, at least 97%, at least 98%, or at least 99% sequence identity with the full length heavy chain, and wherein said antibody or antigen-binding portion specifically binds IL-2.

An antibody of the disclosure may comprise a light chain comprising a VL comprising the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, or SEQ ID NO:72, wherein the antibody further comprises a light chain constant domain. As more fully set forth elsewhere herein, the antibody light chain constant domain can be selected from a Cκ or Cλ constant region, for example the Cλ constant region of SEQ ID NO:1. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the full length light chain. In a further aspect, said variant shares at least 65%, at least 75%, at least 85%, at least 90%, at least 95%, at least 96%, at least 97%, at least 98%, or at least 99% sequence identity with the full length light chain, and wherein said antibody or antigen-binding portion specifically binds IL-2.

An antibody of the disclosure may comprise a portion of one of the VL or VH amino acid sequences shown in Table 7. For example, an antibody of the disclosure may comprise a portion of at least 7, at least 8, at least 9, at least 10, at least 12, at least 15, at least 18, at least 20 or at least 25 consecutive amino acids from a VH comprising SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, or SEQ ID NO:71, or from a VL comprising SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, or SEQ ID NO:72. Such a portion will preferably retain one or more of the functions discussed above, such as the ability to bind to IL-2. In some embodiments, such a portion will preferably retain one or more of the functions discussed above, such as the ability to bind to hIL-2.

In some embodiments, the antibody of the disclosure comprises the VH CDR1, CDR2, and CDR3 in accordance with Kabat, Chothia, or extended sequences and/or VL CDR1, CDR2, and CDR3 in accordance with Kabat and/or Chothia amino acid sequences as shown in Table 7. In some embodiments, the antibody of the disclosure comprises a VH CDR1 in accordance with the following Kabat amino acid sequences: SEQ ID NO:73, SEQ ID NO:82, SEQ ID NO:91, SEQ ID NO:100, SEQ ID NO:109, SEQ ID NO:118, SEQ ID NO:127, SEQ ID NO:136, SEQ ID NO:145, SEQ ID NO:154, SEQ ID NO:163, SEQ ID NO:172, SEQ ID NO:181, SEQ ID NO:190, SEQ ID NO:199, or SEQ ID NO:208. In some embodiments, the antibody of the disclosure comprises a VH CDR1 in accordance with the following Chothia amino acid sequences: SEQ ID NO:74, SEQ ID NO:83, SEQ ID NO:92, SEQ ID NO:101, SEQ ID NO:110, SEQ ID NO:119, SEQ ID NO:128, SEQ ID NO:137, SEQ ID NO:146, SEQ ID NO:155, SEQ ID NO:164, SEQ ID NO:173, SEQ ID NO:182, SEQ ID NO:191, SEQ ID NO:200, or SEQ ID NO:209. In some embodiments, the antibody of the disclosure comprises a VH CDR1 in accordance with the following combination amino acid sequences: SEQ ID NO:75, SEQ ID NO:84, SEQ ID NO:93, SEQ ID NO:102, SEQ ID NO:111, SEQ ID NO:120, SEQ ID NO:129, SEQ ID NO:138, SEQ ID NO:147, SEQ ID NO:156, SEQ ID NO:165, SEQ ID NO:174, SEQ ID NO:183, SEQ ID NO:192, SEQ ID NO:201, or SEQ ID NO:210. In some embodiments, the antibody of the disclosure comprises a VH CDR2 in accordance with the following Kabat amino acid sequences: SEQ ID NO:76, SEQ ID NO:85, SEQ ID NO:94, SEQ ID NO:103, SEQ ID NO:112, SEQ ID NO:121, SEQ ID NO:130, SEQ ID NO:139, SEQ ID NO:148, SEQ ID NO:157, SEQ ID NO:166, SEQ ID NO:175, SEQ ID NO:184, SEQ ID NO:193, SEQ ID NO:202, or SEQ ID NO:211. In some embodiments, the antibody of the disclosure comprises a VH CDR2 in accordance with the following Chothia amino acid sequences: SEQ ID NO:77, SEQ ID NO:86, SEQ ID NO:95, SEQ ID NO:104, SEQ ID NO:113, SEQ ID NO:122, SEQ ID NO:131, SEQ ID NO:140, SEQ ID NO:149, SEQ ID NO:158, SEQ ID NO:167, SEQ ID NO:176, SEQ ID NO:185, SEQ ID NO:194, SEQ ID NO:203, or SEQ ID NO:212. In some embodiments, the antibody of the disclosure comprises a VH CDR3 in accordance with the following amino acid sequences: SEQ ID NO:78, SEQ ID NO:87, SEQ ID NO:96, SEQ ID NO:105, SEQ ID NO:114, SEQ ID NO:123, SEQ ID NO:132, SEQ ID NO:141, SEQ ID NO:150, SEQ ID NO:159, SEQ ID NO:168, SEQ ID NO:177, SEQ ID NO:186, SEQ ID NO:195, SEQ ID NO:204, or SEQ ID NO:213. In some embodiments, the antibody of the disclosure comprises a VL CDR1 in accordance with the following amino acid sequences: SEQ ID NO:79, SEQ ID NO:88, SEQ ID NO:97, SEQ ID NO:106, SEQ ID NO:115, SEQ ID NO:124, SEQ ID NO:133, SEQ ID NO:142, SEQ ID NO:151, SEQ ID NO:160, SEQ ID NO:169, SEQ ID NO:178, SEQ ID NO:187, SEQ ID NO:196, SEQ ID NO:205, SEQ ID NO:214, or SEQ ID NO:220. In some embodiments, the antibody of the disclosure comprises a VL CDR2 in accordance with the following amino acid sequences: SEQ ID NO:80, SEQ ID NO:89, SEQ ID NO:98, SEQ ID NO:107, SEQ ID NO:116, SEQ ID NO:125, SEQ ID NO:134, SEQ ID NO:143, SEQ ID NO:152, SEQ ID NO:161, SEQ ID NO:170, SEQ ID NO:179, SEQ ID NO:188, SEQ ID NO:197, SEQ ID NO:206, SEQ ID NO:215, or SEQ ID NO:221. In some embodiments, the antibody of the disclosure comprises a VL CDR3 in accordance with the following amino acid sequences: SEQ ID NO:81, SEQ ID NO:90, SEQ ID NO:99, SEQ ID NO:108, SEQ ID NO:117, SEQ ID NO:126, SEQ ID NO:135, SEQ ID NO:144, SEQ ID NO:153, SEQ ID NO:162, SEQ ID NO:171, SEQ ID NO:180, SEQ ID NO:189, SEQ ID NO:198, SEQ ID NO:207, SEQ ID NO:216, or SEQ ID NO:222. In some embodiments, the antibody of the disclosure comprises the VH CDR1 in accordance with SEQ ID NO:217. In some embodiments, the antibody of the disclosure comprises the VH CDR2 in accordance with SEQ ID NO:218. In some embodiments, the antibody of the disclosure comprises the VH CDR3 in accordance with SEQ ID NO:219. In certain embodiments, the antibody of the disclosure comprises the VH CDR1, CDR2, and CDR3 in accordance with Kabat, Chothia, or extended sequences and/or VL CDR1, CDR2, and CDR3 in accordance with Kabat and/or Chothia amino acid sequences of an antibody selected from: F4.7.6 VH, F4.7.8 VH, F5.1.11 VH, F5.1.9 VH, F4.7.062 VH, F5.1.11.01 VH, F5.1.11.02 VH, F5.1.11.03 VH, F5.1.11.04 VH, F5.1.11.05 VH, F5.1.11.06 VH, F5.1.11.07 VH, F5.1.11.08 VH, F5.1.11.09 VH, F5.1.9.5 VH, d1C7 VH, F4.7.6 VL, F4.7.8 VL, F5.1.11 VL, F5.1.9 VL, F4.7.062 VL, F5.1.11.01 VL, F5.1.11.02 VL, F5.1.11.03 VL, F5.1.11.04 VL, F5.1.11.05 VL, F5.1.11.06 VL, F5.1.11.07 VL, F5.1.11.08 VL, F5.1.11.09 VL, F5.1.9.5 VL, or d1C7 VL as shown in Table 7. In certain embodiments, the antibody of the disclosure comprises the VH CDR1, CDR2, and CDR3 in accordance with Kabat, Chothia, or extended sequences and/or VL CDR1, CDR2, and CDR3 in accordance with Kabat and/or Chothia amino acid sequences of antibody F5.1.11.02 as shown in Table 7.

A suitable portion or variant of any of these VH or VL sequences will retain the ability to bind to IL-2. In some embodiments, it will preferably retain the ability to specifically bind to IL-2. In some embodiments, it will preferably retain the ability to specifically bind to the same or similar epitope or region of the IL-2 molecule as the antibody from which it is derived. In some embodiments, it will preferably retain one or more additional functions of the antibody from which it is derived, such as binding hIL-2, reducing hIL-2 binding to IL-2Rα and IL-2Rβ, and being Treg sparing, among others.

In some embodiments, a suitable portion or variant of any of these VH or VL sequences will retain the ability to bind to hIL-2. In some embodiments, it will retain the ability to specifically bind to hIL-2. In some embodiments, it will retain the ability to specifically bind to the same or similar epitope or region of the hIL-2 molecule as the antibody from which it is derived. In some embodiments, it will retain one or more additional functions of the antibody from which it is derived, such as binding hIL-2, reducing hIL-2 binding to IL-2Rα and IL-2Rβ, and being Treg sparing, among others.

An antibody of the disclosure may comprise a CDR region from the specific antibody identified herein such as a CDR region from within SEQ ID NO:1-32. In some embodiments, such an antibody will preferably retain the ability to bind to IL-2 as described herein. In some embodiments, such an antibody will preferably retain the ability to bind to hIL-2 as described herein. For example, the CDR sequences of the antibodies of the disclosure are shown in the Sequence Listing Table (Table 7) and the SEQ ID NOs. are shown in Table 6. In certain embodiments, an antibody of the disclosure comprises 1, 2, 3, 4, 5 or 6 CDRs from within an antibody of the disclosure.

In one aspect, the disclosure provides an antibody variant comprising 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to one or more of the CDRs listed above. In a further aspect, the variant shares at least 65%, at least 75%, at least 85%, at least 90%, at least 95%, at least 96%, at least 97%, at least 98%, or at least 99% sequence identity with one or more of the CDR sequences listed above, and wherein the antibody or antigen-binding portion specifically binds IL-2. In some embodiments, the antibody or antigen-binding portion specifically binds hIL-2.

Polynucleotides, Vectors, and Host Cells

The disclosure also provides polynucleotides encoding any of the antibodies, including antibody portions and modified antibodies described herein, such as, e.g., antibodies having impaired effector function. In another aspect, the disclosure provides a method of making any of the polynucleotides described herein. Polynucleotides can be made and expressed by procedures known in the art. Accordingly, the disclosure provides polynucleotides or compositions, including pharmaceutical compositions, comprising polynucleotides, encoding any of the following IL-2 antibodies and antigen-binding portions thereof: F4.7.6 VH, F4.7.8 VH, F5.1.11 VH, F5.1.9 VH, F4.7.062 VH, F5.1.11.01 VH, F5.1.11.02 VH, F5.1.11.03 VH, F5.1.11.04 VH, F5.1.11.05 VH, F5.1.11.06 VH, F5.1.11.07 VH, F5.1.11.08 VH, F5.1.11.09 VH, F5.1.9.5 VH, d1C7 VH, F4.7.6 VL, F4.7.8 VL, F5.1.11 VL, F5.1.9 VL, F4.7.062 VL, F5.1.11.01 VL, F5.1.11.02 VL, F5.1.11.03 VL, F5.1.11.04 VL, F5.1.11.05 VL, F5.1.11.06 VL, F5.1.11.07 VL, F5.1.11.08 VL, F5.1.11.09 VL, F5.1.9.5 VL, or d1C7 VL or any portion or part thereof having the ability to bind IL-2.

In one embodiment, the VH and VL domains, or antigen-binding portion thereof, or full length HC or LC, are encoded by separate polynucleotides. Alternatively, both VH and VL, or antigen-binding portion thereof, or HC and LC, are encoded by a single polynucleotide.

In another aspect, the disclosure provides polynucleotides and variants thereof encoding an IL-2 antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid disclosed herein. These amounts are not meant to be limiting, and increments between the recited percentages are specifically envisioned as part of the disclosure.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. In some embodiments, variants exhibit at least about 70% identity, in some embodiments, at least about 80% identity, in some embodiments, at least about 90% identity, and in some embodiments, at least about 95% identity to a polynucleotide sequence that encodes a native antibody or a portion thereof. These amounts are not meant to be limiting, and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

In some embodiments, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen.

Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The disclosure also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). In some embodiments, the host cells express the cDNAs at a level of about 5 fold higher, in some embodiments, 10 fold higher, and in some embodiments, 20 fold higher than that of the corresponding endogenous antibody or protein of interest, if present, in the host cells. Screening the host cells for a specific binding to IL-2 is effected by an immunoassay or FACS. A cell over-expressing the antibody or protein of interest can be identified.

An expression vector can be used to direct expression of an IL-2 antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

Therapeutic Methods

Therapeutic methods involve administering to a subject in need of treatment a therapeutically effective amount, or "effective amount", of an IL-2 antibody, an antigen-binding portion, or an antibody:IL-2 complex comprising the IL-2 antibody as described herein are contemplated by the present disclosure. As used herein, a "therapeutically effective", or "effective", amount refers to an amount of an antibody or portion thereof that is of sufficient quantity to result in a decrease in severity of disease symptoms, an increase in frequency and duration of disease symptom-free periods, or a prevention of impairment or disability due to the disease affliction—either as a single dose or according to a multiple dose regimen, alone or in combination with other agents. One of ordinary skill in the art would be able to determine such amounts based on such factors as the subject's size, the severity of the subject's symptoms, and the particular composition or route of administration selected. The subject may be a human or non-human animal (e.g., rabbit, rat, mouse, monkey or other lower-order primate).

An antibody, antigen-binding portion, or antibody:IL-2 complex comprising the IL-2 antibody of the disclosure might be co-administered with known medicaments, and in some instances the antibody might itself be modified. For example, an antibody could be conjugated to an immunotoxin or radioisotope to potentially further increase efficacy. Regarding co-administration with additional therapeutic agents, such agents can include a cytotoxic agent, a radiotoxic agent or an immunosuppressive agent. The antibody can be linked to the agent (as an immunocomplex) or can be administered separately from the agent. In the latter case (separate administration), the antibody can be administered before, after or concurrently with the agent or can be co-administered with other known therapies, e.g., an anti-cancer therapy, e.g., radiation. Co-administration of the IL-2 antibodies, antigen-binding portions thereof, or antibody: IL-2 complexes comprising the IL-2 antibodies of the present disclosure with a therapeutic agent provides two agents which operate via different mechanisms may provide a therapeutic and perhaps synergistic effect to human disease.

The antibodies, antigen-binding portions, and antibody: IL-2 complexes comprising the IL-2 antibodies disclosed herein can be used as therapeutics or diagnostic tools in a variety of situations where IL-2 is undesirably active, such as inflammatory conditions such as an autoimmune disease, or situations where immunosuppression is desired. In certain embodiments, immunosuppression therapy may be in preparation for organ or bone marrow transplantation. Given the involvement of IL-2 in inflammatory pathways and in numerous diseases, disorders and conditions, many such diseases, disorders or conditions are particularly suitable for treatment with an antibody, antigen-binding portion, or an antibody:IL-2 complex comprising the IL-2 antibody of the present disclosure. Accordingly, the IL-2 antibodies, antigen-binding portions thereof, or antibody:IL-2 complexes comprising the IL-2 antibodies of this disclosure can be used in the treatment or prevention of IL-2-mediated disorders or IL-2-deficiency disorders. In addition, the disclosure provides for use of the IL-2 antibodies, antigen-binding portions thereof, or antibody:IL-2 complexes comprising the IL-2 antibodies of this disclosure in the manufacture of a medicament for use in treatment or prevention of IL-2-mediated disorders or IL-2-deficiency disorders. In another embodiment, this application discloses IL-2 antibodies, antigen-binding portions thereof, or antibody:IL-2 complexes comprising the IL-2 antibodies of this disclosure for use in treatment of IL-2-mediated disorders or IL-2-deficiency disorders. In a further embodiment, this application discloses pharmaceutical compositions comprising the IL-2 antibodies, antigen-binding portions thereof, or antibody: IL-2 complexes comprising the IL-2 antibodies of this disclosure for use in treating or preventing IL-2-mediated diseases or IL-2-deficiency disorders. In certain embodiments, the antibody specifically binds hIL-2.

In certain embodiments, these diseases include immunologic diseases, such as Graft vs Host disease. In certain embodiments, the disease may be any disease associated with IL-2, such as muscular dystrophy and obesity. Exemplary autoimmune diseases and disorders that may be treated with the antibodies, antigen-binding portions thereof, or antibody:IL-2 complexes comprising the IL-2 antibodies provided herein include, for example, inflammatory responses such as inflammatory skin diseases including psoriasis and dermatitis (e. g. atopic dermatitis); dermatomyositis; systemic scleroderma and sclerosis; responses associated with inflammatory bowel disease (such as Crohn's disease and ulcerative colitis); respiratory distress syndrome (including adult respiratory distress syndrome; and ARDS); dermatitis; meningitis; encephalitis; uveitis; colitis; gastritis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; Wegener's disease; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; vitiligo; Reiter's disease; stiff-man syndrome; Behcet's disease; giant cell arteritis; immune complex nephritis; IgA nephropathy; IgM polyneuropathies; immune thrombocytopenic purpura (ITP) or autoimmune thrombocytopenia and autoimmune hemolytic diseases; Hashimoto's thyroiditis; autoimmune hepatitis; autoimmune hemophilia; autoimmune lymphoproliferative syndrome (ALPS); autoimmune uveoretinitis; Guillain-Barre syndrome; Goodpasture's syndrome; mixed connective tissue disease; autoimmune-associated infertility; polyarteritis nodosa; alopecia areata; and idiopathic myxedema. In some embodiments, the condition that can be treated with the present compositions and methods is diabetes mellitus (e.g., Type I diabetes mellitus). In some embodiments, the disease is Type I diabetes mellitus. In some embodiments, the disease is juvenile onset diabetes.

To treat any of the foregoing disorders, pharmaceutical compositions for use in accordance with the present disclosure may be formulated in a conventional manner using one or more pharmaceutically acceptable carriers or excipients and administered as more fully discussed below.

Determining a therapeutically effective amount of an antibody, antigen-binding portion thereof, or antibody:IL-2 complex comprising the IL-2 antibody of this disclosure according to the present disclosure will largely depend on particular patient characteristics, route of administration, and the nature of the disorder being treated and is more fully discussed below.

Administration and dosing of the antibody, antigen-binding portion thereof, or antibody:IL-2 complex comprising the IL-2 antibody of this disclosure are more fully discussed elsewhere below.

Diagnostic Methods

The IL-2 antibodies, or antigen-binding portions thereof disclosed herein can be used for diagnostic testing and imaging. For example, the IL-2 antibodies or antigen-binding portions thereof can be used in an ELISA assay. The antibodies or antigen-binding portions thereof can also be used as a radiolabeled monoclonal antibody. See, for example, Srivastava (ed.), Radiolabeled Monoclonal Antibodies For Imaging And Therapy, Plenum Press (1988); Chase, "Medical Applications of Radioisotopes," in Remington's Pharmaceutical Sciences, 18th Edition, Gennaro et al. (eds.), Mack Publishing Co., pp. 624-652 (1990); and Brown, "Clinical Use of Monoclonal Antibodies," in Biotechnology and Pharmacy, Pezzuto et al. (eds.), Chapman and Hall, pp. 227-249 (1993); Grossman, 1986, Urol. Clin. North Amer. 13:465-474; Unger et al., 1985, Invest. Radiol. 20:693-700; and Khaw et al., 1980, Science 209:295-297. This technique, also known as immunoscintigraphy, uses a gamma camera to detect the location of gamma-emitting radioisotopes conjugated to monoclonal antibodies. Diagnostic imaging can be used to diagnose cancer, autoimmune disease, infectious disease and/or cardiovascular disease. (See, e.g., Brown, supra.)

In one embodiment, the IL-2 antibodies or antigen-binding portions thereof can be used to diagnose IL-2-related diseases, disorders, or conditions, including immune-related diseases. For example, the antibodies, or antigen-binding portions thereof, can be used to detect IL-2 levels in patients, among other uses.

In addition to diagnosis, the IL-2 antibodies or antigen-binding portions thereof can be used to monitor therapeutic responses, detect recurrences of a disease, and guide subsequent clinical decisions.

In some embodiments, for diagnostic and monitoring purposes, radioisotopes may be bound to antibody portions either directly or indirectly by using an intermediary functional group. Such intermediary functional groups include, for example, DTPA (diethylenetriaminepentaacetic acid) and EDTA (ethylene diamine tetraacetic acid). The radiation dose delivered to the patient is typically maintained at as low a level as possible. This may be accomplished through the choice of isotope for the best combination of minimum half-life, minimum retention in the body, and minimum quantity of isotope which will permit detection and accurate measurement. Examples of radioisotopes which can be bound to antibodies and are appropriate for diagnostic imaging include $^{99}$mTc and $^{111}$In.

Studies indicate that antibody portions, particularly Fab and Fab', provide suitable tumor/background ratios. (See, e.g., Brown, supra.)

The IL-2 antibody or antigen-binding portions thereof also can be labeled with paramagnetic ions for purposes of in vivo diagnosis. Elements which are particularly useful for Magnetic Resonance Imaging include Gd, Mn, Dy, and Fe ions.

The IL-2 antibody or antigen-binding portions thereof can also detect the presence of IL-2 in vitro. In such immunoassays, the antibody or antigen-binding portions thereof may be utilized in liquid phase or bound to a solid-phase carrier. For example, an intact antibody, or antigen-binding portion thereof, can be attached to a polymer, such as aminodextran, in order to link the antibody component to an insoluble support such as a polymer-coated bead, plate, or tube. In some embodiments, the IL-2 for detection is human IL-2 (hIL-2). In some embodiments, the hIL-2 for detection is present at a concentration of between 0.1 ng/mL and 1000 ng/mL in vitro. In some embodiments, the hIL-2 for detection is present at a concentration of between 0.1 ng/mL and 750 ng/mL in vitro. In some embodiments, the hIL-2 for detection is present at a concentration of between 0.5 ng/mL and 500 ng/mL in vitro. In some embodiments, the hIL-2 for detection is present at a concentration of between 0.5 ng/mL and 250 ng/mL in vitro. In some embodiments, the hIL-2 for detection is present at a concentration of between 0.5 ng/mL and 100 ng/mL in vitro. In some embodiments, the hIL-2 for detection is present at a concentration of between 0.5 ng/mL and 50 ng/mL in vitro. In some embodiments, the hIL-2 for detection is present at a concentration of between 0.5 ng/mL and 25 ng/mL in vitro. In some embodiments, the hIL-2 for detection is present at a concentration of between 0.5 ng/mL and 10 ng/mL in vitro. In some embodiments, the hIL-2 for detection is present at a concentration of between 0.5 ng/mL and 5 ng/mL in vitro. In some embodiments, the hIL-2 for detection is present at a concentration of between 0.5 ng/mL and 1 ng/mL in vitro. In some embodiments, the hIL-2 for detection is present at a concentration of between 0.1 ng/mL and 5 ng/mL in vitro. In some embodiments, the hIL-2 for detection is present at a concentration of between 0.1 ng/mL and 1 ng/mL in vitro. In some embodiments, the hIL-2 for detection is present at a concentration of between 0.8 ng/mL and 500 ng/mL in vitro. In some embodiments, the hIL-2 for detection is present at a concentration of between 1 ng/mL and 500 ng/mL in vitro. In some embodiments, the hIL-2 for detection is present at a concentration of between 1 ng/mL and 250 ng/mL in vitro. In some embodiments, the hIL-2 for detection is present at a concentration of between 1 ng/mL and 100 ng/mL in vitro. In some embodiments, the hIL-2 for detection is present at a concentration of between 1 ng/mL and 50 ng/mL in vitro. In some embodiments, the hIL-2 for detection is present at a concentration of between 1 ng/mL and 25 ng/mL in vitro. In some embodiments, the hIL-2 for detection is present at a concentration of between 1 ng/mL and 10 ng/mL in vitro. In some embodiments, the hIL-2 for detection is present at a concentration of between 50 ng/mL and 500 ng/mL in vitro. In some embodiments, the hIL-2 for detection is present at a concentration of between 100 ng/mL and 500 ng/mL in vitro. In some embodiments, the hIL-2 for detection is present at a concentration of between 250 ng/mL and 500 ng/mL in vitro. In some embodiments, the hIL-2 for detection is present at a concentration of between 400 ng/mL and 500 ng/mL in vitro. In some embodiments, the hIL-2 for detection is present at a concentration of between 500 ng/mL and 1000 ng/mL in vitro. In some embodiments, the hIL-2 for detection is present at a concentration of between 750 ng/mL and 1000 ng/mL in vitro. In some embodiments, the hIL-2 for detection is present at a concentration of 0.8 ng/mL in vitro. In some embodiments, the hIL-2 for detection is present at a concentration of 500 ng/mL in vitro. These amounts are not meant to be limiting, and increments between the recited values are specifically envisioned as part of the disclosure.

Alternatively, the IL-2 antibody or antigen-binding portions thereof can be used to detect the presence of particular antigens in tissue sections prepared from a histological specimen. Such in situ detection can be accomplished, for example, by applying a detectably-labeled IL-2 antibody or antigen-binding portion thereof to the tissue sections. In situ detection can be used to determine the presence of a particular antigen and to determine the distribution of the antigen in the examined tissue. General techniques of in situ detection are well known to those of ordinary skill. (See, e.g., Ponder, "Cell Marking Techniques and Their Application," in Mammalian Development: A Practical Approach, Monk (ed.), IRL Press, pp. 115-138 (1987); Coligan et al., supra.)

Detectable labels such as enzymes, fluorescent compounds, electron transfer agents, and the like can be linked to a carrier by conventional methods well known to the art. These labeled carriers and the antibody conjugates prepared from them can be used for in vitro immunoassays and for in situ detection, much as an antibody conjugate can be prepared by direct attachment of the labels to antibody. The loading of the antibody conjugates with a plurality of labels can increase the sensitivity of immunoassays or histological procedures, where only a low extent of binding of the antibody, or antibody portion, to target antigen is achieved.

Compositions

The disclosure also provides pharmaceutical compositions comprising an effective amount of an IL-2 antibody described herein. Examples of such compositions, as well as how to formulate, are also described herein. In some embodiments, the composition comprises one or more IL-2 antibodies. In other embodiments, the IL-2 antibody recognizes IL-2. In other embodiments, the IL-2 antibody is a human antibody. In other embodiments, the IL-2 antibody is a humanized antibody. In some embodiments, the IL-2 antibody comprises a constant region that is capable of triggering a desired immune response, such as antibody-mediated lysis or ADCC. In other embodiments, the IL-2 antibody comprises a constant region that does not trigger an unwanted or undesirable immune response, such as antibody-mediated lysis or ADCC. In other embodiments, the IL-2 antibody comprises one or more CDR(s) of the antibody (such as one, two, three, four, five, or, in some embodiments, all six CDRs).

It is understood that the compositions can comprise more than one IL-2 antibody (e.g., a mixture of IL-2 antibodies that recognize different epitopes of IL-2). Other exemplary compositions comprise more than one IL-2 antibody that recognize the same epitope(s), or different species of IL-2 antibodies that bind to different epitopes of IL-2. In some embodiments, the compositions comprise a mixture of IL-2 antibodies that recognize different variants of IL-2.

The composition used in the present disclosure can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

The IL-2 antibody and compositions thereof can also be used in conjunction with other agents that serve to enhance and/or complement the effectiveness of the agents.

In certain embodiments, the IL-2 antibody is complexed with IL-2 before administration. In certain embodiments, the IL-2 antibody is not complexed with IL-2 before administration.

The disclosure also provides compositions, including pharmaceutical compositions, comprising any of the polynucleotides of the disclosure. In some embodiments, the composition comprises an expression vector comprising a polynucleotide encoding the antibody as described herein. In other embodiments, the composition comprises an expression vector comprising a polynucleotide encoding any of the antibodies described herein. In still other embodiments, the composition comprises either or both of the polynucleotides encoding the sequence shown in SEQ ID NO: 1 and SEQ ID NO: 2, either or both of the polynucleotides encoding the sequence shown in SEQ ID NO: 3 and SEQ ID NO: 4, either or both of the polynucleotides encoding the sequence shown in SEQ ID NO:5 and SEQ ID NO:6, either or both of the polynucleotides encoding the sequence shown in SEQ ID NO:7 and SEQ ID NO:8, either or both of the polynucleotides encoding the sequence shown in SEQ ID NO:9 and SEQ ID NO:10, either or both of the polynucleotides encoding the sequence shown in SEQ ID NO:11 and SEQ ID NO:12, either or both of the polynucleotides encoding the sequence shown in SEQ ID NO:13 and SEQ ID NO:14, either or both of the polynucleotides encoding the sequence shown in SEQ ID NO:15 and SEQ ID NO:16, either or both of the polynucleotides encoding the sequence shown in SEQ ID NO:17 and SEQ ID NO:18, either or both of the polynucleotides encoding the sequence shown in SEQ ID NO:19 and SEQ ID NO:20, either or both of the polynucleotides encoding the sequence shown in SEQ ID NO:21 and SEQ ID NO:22, either or both of the polynucleotides encoding the sequence shown in SEQ ID NO:23 and SEQ ID NO:24, either or both of the polynucleotides encoding the sequence shown in SEQ ID NO:25 and SEQ ID NO:26, either or both of the polynucleotides encoding the sequence shown in SEQ ID NO:27 and SEQ ID NO:28, either or both of the polynucleotides encoding the sequence shown in SEQ ID NO:29 and SEQ ID NO:30, or either or both of the polynucleotides encoding the sequence shown in SEQ ID NO:31 and SEQ ID NO:32. In still other embodiments, the composition comprises either or both of the polynucleotides comprising the sequence shown in SEQ ID NO: 36 and SEQ ID NO: 37, either or both of the polynucleotides comprising the sequence shown in SEQ ID NO: 38 and SEQ ID NO: 39, either or both of the polynucleotides comprising the sequence shown in SEQ ID NO: 40 and SEQ ID NO: 41, either or both of the polynucleotides comprising the sequence shown in SEQ ID NO: 42 and SEQ ID NO: 43, either or both of the polynucleotides comprising the sequence shown in SEQ ID NO: 44 and SEQ ID NO: 45, either or both of the polynucleotides comprising the sequence shown in SEQ ID NO: 46 and SEQ ID NO: 47, either or both of the polynucleotides comprising the sequence shown in SEQ ID NO: 48 and SEQ ID NO: 49, either or both of the polynucleotides comprising the sequence shown in SEQ ID NO: 50 and SEQ ID NO: 51, either or both of the polynucleotides comprising the sequence shown in SEQ ID NO: 52 and SEQ ID NO: 53, either or both of the polynucleotides comprising the sequence shown in SEQ ID NO: 54 and SEQ ID NO: 55, either or both of the polynucleotides comprising the sequence shown in SEQ ID NO: 56 and SEQ ID NO: 57, either or both of the polynucleotides comprising the sequence shown in SEQ ID NO: 58 and SEQ ID NO: 59, either or both of the polynucleotides comprising the sequence shown in SEQ ID NO: 60 and SEQ ID NO: 61, either or both of the polynucleotides comprising the sequence shown in SEQ ID NO: 62 and SEQ ID NO: 63, either or both of the polynucleotides comprising the sequence shown in SEQ ID NO: 64 and SEQ ID NO: 65, or either or both of the polynucleotides comprising the sequence shown in SEQ ID NO: 66 and SEQ ID NO: 67.

In another aspect, the polynucleotide can encode the VH, VL and/or both VH and VL of the antibody of the disclosure. That is, the composition comprises a single polynucleotide or more than one polynucleotide encoding the antibody, or antigen-binding portion thereof, or the disclosure.

Pharmaceutical compositions of the disclosure also can be administered in combination therapy, such as, combined with other agents. For example, the combination therapy can include IL-2 antibody, or antigen-binding portion thereof, of the present disclosure combined with at least one other therapy wherein the therapy may be surgery, immunotherapy, or drug therapy.

The pharmaceutical compounds of the disclosure may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A pharmaceutical composition of the present disclosure may be prepared, packaged, or sold in a formulation suitable for ophthalmic administration. Such formulations may, for example, be in the form of eye drops including, for example, a 0.1%-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Remington's Pharmaceutical Sciences, Genaro, ed., Mack Publishing Co., Easton, Pa. (1985), which is incorporated herein by reference.

In one embodiment, the IL-2 antibody, or antigen-binding portion thereof, is administered in an intravenous formulation as a sterile aqueous solution containing 5 mg/mL, or in some embodiments, about 10 mg/mL, or in some embodiments, about 15 mg/mL, or in some embodiments, about 20 mg/mL of antibody, with sodium acetate, polysorbate 80, and sodium chloride at a pH ranging from about 5 to 6. In some embodiments, the intravenous formulation is a sterile aqueous solution containing 5 or 10 mg/mL of antibody, with 20 mM sodium acetate, 0.2 mg/mL polysorbate 80, and 140 mM sodium chloride at pH 5.5. Further, a solution comprising an antibody, or antigen-binding portion thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 100 mg IL-2 antibody or antigen-binding portion of the present disclosure, 10 mM histidine, 5% sucrose, and 0.01% polysorbate 80 at pH 5.8. This composition may be provided as a lyophilized powder. When the powder is reconstituted at full volume, the composition retains the same formulation. Alternatively, the powder may be reconstituted at half volume, in which case the composition comprises 100 mg IL-2 antibody or antigen-binding portion thereof of the present disclosure, 20 mM histidine, 10% sucrose, and 0.02% polysorbate 80 at pH 5.8.

In one embodiment, part of the dose is administered by an intravenous bolus and the rest by infusion of the antibody formulation. For example, a 0.01 mg/kg intravenous injection of the IL-2 antibody, or antigen-binding portion thereof, may be given as a bolus, and the rest of the antibody dose may be administered by intravenous injection. A predetermined dose of the IL-2 antibody, or antigen-binding portion thereof, may be administered, for example, over a period of an hour and a half to two hours to five hours.

With regard to a therapeutic agent, where the agent is, e.g., a small molecule, it can be present in a pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment the compositions of the disclosure are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food and Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In another embodiment, endotoxin and pyrogen levels in the composition are less than about 10 EU/mg, or less than about 5 EU/mg, or less than about 1 EU/mg, or less than about 0.1 EU/mg, or less than about 0.01 EU/mg, or less than about 0.001 EU/mg.

In one embodiment, the disclosure comprises administering a composition wherein said administration is oral, parenteral, intramuscular, intranasal, vaginal, rectal, lingual, sublingual, buccal, intrabuccal, intravenous, cutaneous, subcutaneous or transdermal.

In another embodiment the disclosure further comprises administering a composition in combination with other therapies, such as surgery, chemotherapy, hormonal therapy, biological therapy, immunotherapy or radiation therapy.

Dosing/Administration

To prepare pharmaceutical or sterile compositions including an IL-2 antibody, or antigen-binding portion thereof of the disclosure, the antibody is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.), 1993, Monoclonal Antibodies and Peptide Therapy in Autoimmune Diseases, Marcel Dekker, New York, N.Y.; Baert, et al., 2003, New Engl. J. Med. 348:601-608; Milgrom, et al., 1999, New Engl. J. Med. 341:1966-1973; Slamon, et al., 2001, New Engl. J. Med. 344:783-792; Beniaminovitz, et al., 2000, New Engl. J. Med. 342:613-619; Ghosh, et al., 2003, New Engl. J. Med. 348:24-32; Lipsky, et al., 2000, New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Compositions comprising IL-2 antibodies or antigen-binding portions thereof, of the disclosure can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 15 mg/kg, at least 20 mg/kg, at least 25 mg/kg, or at least 50 mg/kg (see, e.g., Yang, et al., 2003, New Engl. J. Med. 349:427-434; Herold, et al., 2002, New Engl. J. Med. 346:1692-1698; Liu, et al., 1999, J. Neurol. Neurosurg. Psych. 67:451-456; Portielji, et al., 2003, Cancer. Immunol. Immunother. 52: 133-144). The dose may be at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For IL-2 antibodies or antigen-binding portions thereof of the disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the IL-2 antibody or antigen-binding portion thereof may be calculated using the patient's weight in kilograms (kg) multiplied by the dose to be administered in mg/kg. The dosage of the antibodies of the disclosure may be 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.1 µg/kg or less of a patient's body weight.

Unit dose of the IL-2 antibodies or antigen-binding portions thereof of the disclosure may be 0.1 mg to 200 mg, 0.1 mg to 175 mg, 0.1 mg to 150 mg, 0.1 mg to 125 mg, 0.1 mg to 100 mg, 0.1 mg to 75 mg, 0.1 mg to 50 mg, 0.1 mg to 30 mg, 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the IL-2 antibodies or antigen-binding portions thereof of the disclosure may achieve a serum titer of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL in a subject. Alternatively, the dosage of the antibodies of the disclosure may achieve a serum titer of at least 0.1 µg/mL, at least 0.5 µg/mL, at least 1 µg/mL, at least, 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL in the subject.

Doses of IL-2 antibodies, or antigen-binding portions thereof of the disclosure may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side effects (see, e.g., Maynard, et al., 1996, A Handbook of SOPs for Good Clinical Practice, Interpharm Press, Boca Raton, Fla.; Dent, 2001, Good Laboratory and Good Clinical Practice, Urch Publ, London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., 1983, Biopolymers 22:547-556; Langer, et al., 1981, J. Biomed. Mater. Res. 15: 167-277; Langer, 1982, Chem. Tech. 12:98-105; Epstein, et al., 1985, Proc. Natl. Acad. Sci. USA 82:3688-3692; Hwang, et al., 1980, Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985, 320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, the IL-2 antibody, or antigen-binding portion thereof, or a composition of the disclosure is administered using Alkermes AIR™ pulmonary drug delivery technology (Alkermes, Inc., Cambridge, Mass.).

A composition of the present disclosure may also be administered via one or more routes of administration using one or more of a variety of methods known in the art. As will be appreciated by the skilled artisan, the route and/or mode of administration will vary depending upon the desired results. Selected routes of administration for antibodies of the disclosure include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-parenteral route, such as a topical, epidermal or mucosal route of administration, for example, intranasally, orally, vaginally, rectally, sublingually or topically.

If the IL-2 antibodies, or antigen-binding portions thereof, of the disclosure are administered in a controlled release or sustained release system, a pump may be used to achieve controlled or sustained release (see, Langer, supra; Sefton, 1987, CRC Crit. Ref Biomed. Eng. 14:20; Buchwald et al., 1980, Surgery 88:501; Saudek et al., 1989, N. Engl. J. Med. 321:514).

Polymeric materials can be used to achieve controlled or sustained release of the therapies of the disclosure (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. ScL Rev. Macromol. Chem. 23:61; see also Levy et al, 1985, Science 11 225:190; During et al., 19Z9, Ann. Neurol. 25:351; Howard et al, 1989, J. Neurosurg. 71: 105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), polyvinyl alcohol), polyacrylamide, polyethylene glycol), polylactides (PLA), polyoeactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer, 1990, Science 249:1527-1533. Any technique known to one of skill in the art can be used to produce sustained release formulations comprising one or more antibodies of the disclosure or conjugates thereof. See, e.g., U.S. Pat. No. 4,526,938, International Patent Publication Nos. WO 91/05548, WO 96/20698, Ning et al., 1996, "Intratumoral Radioimmunotheraphy of a Human Colon Cancer Xenograft Using a Sustained-Release Gel," Radiotherapy and Oncology 59:179-189, Song et al., 1995, "Antibody Mediated Lung Targeting of Long-Circulating Emulsions," PDA Journal of Pharmaceutical Science and Technology 50:372-397, Cleek et ah, 1997, "Biodegradable Polymeric Carriers for a bFGF Antibody for Cardiovascular Application," Pro. MI. Symp. Control. Rel. Bioact. Mater. 24:853-854, and Lam et al., 1997, "Microencapsulation of Recombinant Humanized Monoclonal Antibody for Local Delivery," Proc. MI. Symp. Control Rel. Bioact. Mater. 24:759-160, each of which is incorporated herein by reference in their entirety.

If the IL-2 antibody, or antigen-binding portion thereof, of the disclosure is administered topically, it can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising IL-2 antibodies, or antigen-binding portions thereof, are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams and Wilkins, Phila., Pa.; Chabner and Longo (eds.) (2001) Cancer Chemotherapy and Biotherapy, Lippincott, Williams and Wilkins, Phila., Pa.). An effective amount of therapeutic may decrease the symptoms by at least 10 percent; by at least 20 percent; at least about 30 percent; at least 40 percent, or at least 50 percent.

Additional therapies (e.g., prophylactic or therapeutic agents), which can be administered in combination with the IL-2 antibodies, or antigen-binding portions of the disclosure, may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies of the disclosure. The two or more therapies may be administered within one same patient visit.

The IL-2 antibodies, or antigen-binding portions thereof, of the disclosure and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In one embodiment, the IL-2 antibodies of the disclosure can be co-administered with compositions for treating autoimmune diseases and disorders, including, but not limited to, adriamycin, azathiopurine, busulfan, cyclophosphamide, cyclosporine A, Cytoxan, fludarabine, 5-fluorouracil, methotrexate, mycophenolate mofetil, 6-mercaptopurine, a corticosteroid, a nonsteroidal anti-inflammatory, sirolimus (rapamycin), and tacrolimus (FK-506). In alternative embodiments, the immunomodulatory or immunosuppressive agent is an antibody selected from the group consisting of muromonab-CD3, alemtuzumab (Campath®), basiliximab, daclizumab, muromonab (OKT3®), rituximab, antithymocyte globulin and IVIg, and others, which are known to persons skilled in the art.

In one embodiment, the IL-2 antibodies of the disclosure can be co-administered with compositions for treating diabetes, including, but not limited to, biguanides (e.g., buformin, metformin, and phenform), hormones and analogs thereof (amylin, insulin, insulin aspart, insulin detemir, insulin glargine, insulin glulisine, insulin lispro, liraglutide, and pramlintide), sulfonylurea derivatives (acetohexamide, carbutamide, chlorpropamide, glibornuride, gliclazide, glimepiride, glipizide, gliquidone, glisoxepid, glyburide, glybuthiazole, glybuzole, glyhexamide, glymidine, tolazamide, tolbutamide, and tolcyclamide), thiazolidinediones (pioglitazone, rosiglitazone, and troglitazone), acarbose, exenatide, miglitol, mitiglinide, muraglitazar, nateglinide, repaglinide, sitagliptin, tesaglitazar, vildagliptin, and voglibose.

In certain embodiments, the IL-2 antibodies, or antigen-binding portions thereof of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522, 811; 5,374,548; and 5,399,331. The liposomes may comprise one or more moieties which are selectively transported into specific cells or organs, thus enhance targeted drug delivery (see, e.g., V. V. Ranade, 1989, J. Clin. Pharmacol. 29:685). Exemplary targeting moieties include folate or biotin (see, e.g., U.S. Pat. No. 5,416,016); mannosides (Umezawa et al., Biochem. Biophys. Res. Commun. 153: 1038); antibodies (P. G. Bloeman et al., 1995, FEBS Lett. 357: 140; M. Owais et al., 1995, Antimicrob. Agents Chemother. 39: 180); surfactant protein A receptor (Briscoe et al. (1995) Am. J. Physiol. 1233: 134); pl20 (Schreier et al. (1994) J. Biol. Chem. 269:9090); see also K. Keinanen; M. L. Laukkanen, 1994, FEBS Lett. 346:123; Killion; Fidler, 1994; Immunomethods 4:273.

The disclosure provides protocols for the administration of pharmaceutical composition comprising IL-2 antibodies, or antigen-binding portions thereof, of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising IL-2 antibodies, or antigen-binding portions thereof, of the disclosure are administered to a subject in a sequence and within a time interval such that the antibodies of the disclosure or conjugates thereof can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Kits

The disclosure also provides kits comprising any or all of the antibodies described herein. Kits of the disclosure include one or more containers comprising an IL-2 antibody described herein and instructions for use in accordance with any of the methods of the disclosure described herein. Generally, these instructions comprise a description of administration of the antibody for the above described therapeutic treatments. In some embodiments, kits are provided for producing a single-dose administration unit. In certain embodiments, the kit can contain both a first container having a dried protein and a second container having an aqueous formulation. In certain embodiments, kits containing an applicator, e.g., single and multi-chambered prefilled syringes (e.g., liquid syringes and lyosyringes), are included.

The instructions relating to the use of an IL-2 antibody generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an IL-2 antibody of the disclosure. The container may further comprise a second pharmaceutically active agent.

Kits may optionally provide additional components such as buffers and interpretive information. Normally, the kit comprises a container and a label or package insert(s) on or associated with the container.

The disclosure also provides diagnostic kits comprising any or all of the antibodies described herein. The diagnostic kits are useful for, for example, detecting the presence of IL-2 in a sample. In some embodiments, a diagnostic kit can be used to identify an individual with a latent disease, disorder or condition that may put them at risk of developing IL-2-mediated disease, disorder or condition or an IL-2 deficiency disease, disorder or condition. In some embodiments, a diagnostic kit can be used to detect the presence and/or level of IL-2 in an individual suspected of having an IL-2 mediated disease or an IL-2 deficiency disease, disorder or condition.

Diagnostic kits of the disclosure include one or more containers comprising an IL-2 antibody described herein and instructions for use in accordance with any of the methods of the disclosure described herein. Generally, these instructions comprise a description of use of the IL-2 antibody to detect the presence of IL-2 in individuals at risk for, or suspected of having, an IL-2 mediated disease or an IL-2 deficiency disease, disorder or condition. In some embodiments, an exemplary diagnostic kit can be configured to contain reagents such as, for example, an IL-2 antibody, a negative control sample, a positive control sample, and directions for using the kit.

EQUIVALENTS

The foregoing description and following Examples detail certain specific embodiments of the disclosure and describes the best mode contemplated by the inventors. It will be appreciated, however, that no matter how detailed the foregoing may appear in text, the disclosure may be practiced in many ways and the disclosure should be construed in accordance with the appended claims and any equivalents thereof.

Although the disclosed teachings have been described with reference to various applications, methods, kits, and compositions, it will be appreciated that various changes and modifications can be made without departing from the teachings herein and the claimed disclosure below. The following examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

EXEMPLARY EMBODIMENTS

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

EXAMPLES

Example 1. IL-2 Antibody Binding Kinetics and Affinity

The affinity of the antibodies for IL-2 was determined by surface plasmon resonance using a Biacore T200 instrument (GE Healthcare, Piscataway, N.J.). Anti-IL-2 IgGs were captured on a CM5 sensor chip by an anti-human IgG prepared using the Biacore Human Antibody Capture Kit according to the manufactures directions (GE Healthcare). The mouse anti-human IL-2 clone 5344 (clone 5344.111, BD Biosciences) was captured on an anti-mouse IgG capture surface prepared using the Biacore Mouse Antibody Capture Kit according to the manufactures directions (GE Healthcare). Experiments were performed at 25° C. using a 30 µL/minute flow rate in 0.01 M HEPES pH 7.4, 0.15 M NaCl and 0.005% v/v surfactant P20 (HBS-P) buffer. After each cycle, the chip surface was regenerated with 3 M $MgCl_2$ and new antibody captured. Recombinant IL-2 (Humanzyme, Chicago, Ill.) was injected over the surface for 3 minutes and the association monitored for a further 20 minutes. Data were analyzed using the Biacore T200 Evaluation software, the signal from the adjacent control flow cell with only the capture antibody immobilized was background subtracted along with buffer only injections for each antibody. A 1:1 Langmuir binding model was used to fit all binding curves.
Results The human antibodies tested bind to IL-2 with affinities ranging from 536 pM to 13.4 nM (Table 3). The antibodies identified for their ability to inhibit IL-2Rβ binding and decrease binding to IL-2Rα relative to the d1C7/IL-2 complex, have weaker affinities for IL-2 compared to the comparator clones 16C3 and d1C7. The 5344 antibody was found to have a very stable off-rate beyond the detection limits of the Biacore instrument, the calculated affinity is assumed to be 50 pM or less, with a significantly slower off-rate compared to the human antibody clones tested. The significantly slower off-rate of 5344 may contribute to the antibody not having the desired Treg sparing properties exhibited by other hIL-2 antibodies described in this application below (Example 5).

TABLE 3

| Clone | $k_a$ (M$^{-1}$s$^{-1}$) | $k_d$ (s$^{-1}$) | $K_D$ (M) |
|---|---|---|---|
| F4.7.062 | 3.77E+06 | 5.80E−03 | 1.54E−09 |
| F4.7.6 | 2.44E+06 | 7.38E−03 | 3.03E−09 |
| F5.1.11 | 2.21E+06 | 6.88E−03 | 3.12E−09 |
| F4.7.8 | 2.31E+05 | 3.10E−03 | 1.34E−08 |
| F5.1.9 | 2.48E+05 | 3.28E−03 | 1.33E−08 |
| 16C3 | 9.89E+05 | 6.19E−04 | 6.37E−10 |
| d1C7 | 1.13E+06 | 6.07E−04 | 5.36E−10 |
| 5344 | 1.02E+06 | <=5.00E−05* | <=5.00E−11 |

*off-rate was outside the specifications of the instrument, an off-rate of 5.0E−05 or less has been assumed The mIL-2 and hIL-2 binding studies with antibodies F5.1.11, d1C7, 13A10, and 16C3 indicate that F5.1.11 and d1C7 do not bind to mIL-2 and that 13A10 and 16C3 bind mIL-2 with reduced affinity compared to hIL-2 (data not shown).

Example 2. IL-2/Antibody Complex Receptor Binding

The ability of the antibodies to modify IL-2 binding to the IL-2 receptors IL-2Rα and IL-2Rβ was assessed using a Biacore T200 Instrument (GE Healthcare, Piscataway, N.J.). Recombinant IL-2α and IL-2Rβ protein was biotin labeled and captured on a Biacore Streptavidin chip (GE Healthcare). Experiments were performed at 25° C. using a 10 μL/minute flow rate in 10 mM HEPES (pH 7.4), 150 mM NaCl and 0.005% v/v Surfactant P20 buffer. IL-2 (333 nM) was pre-incubated with IgGs (1000 nM) for at least 20 minutes. IL-2/antibody complexes were injected over the receptor coupled chip surface for 60 seconds and allowed to dissociate for 20 minutes. Data was background subtracted using the adjacent control flow cell and buffer only injections. The response is reported as the binding to IL-2α and IL-2Rβ after 60 seconds as a percentage of the binding of two representative clones, d1C7 and 16C3 in complex with IL-2, to IL-2Rα and IL-2Rβ respectively.
Results The clone 16C3/IL-2 complex bound IL-2Rβ but not IL-2Rα whereas the d1C7/IL-2 complex bound to IL-2Rα but not IL-2Rβ. These two antibody/IL-2 complexes were used as representative clones to normalize for IL-2Rα and IL-2Rβ binding. Each of the tested antibody/IL-2 complexes is reported as their relative binding to each of the receptors. Clone 4.7.062, F5.1.11, F4.7.6, F4.7.8, F5.1.9 and the commercially available 5344 (Clone 5344.111, BD Biosciences) all inhibited IL-2 from binding to IL-2Rβ similar to the d1C7/IL-2 complex and showed reduced binding to IL-2Rα compared to the d1C7/IL-2 complex. Thus these antibodies were identified for their ability to block IL-2 binding to IL-2Rβ and reduce the rate of binding to IL-2Rα (FIG. 1).

Figure 2:
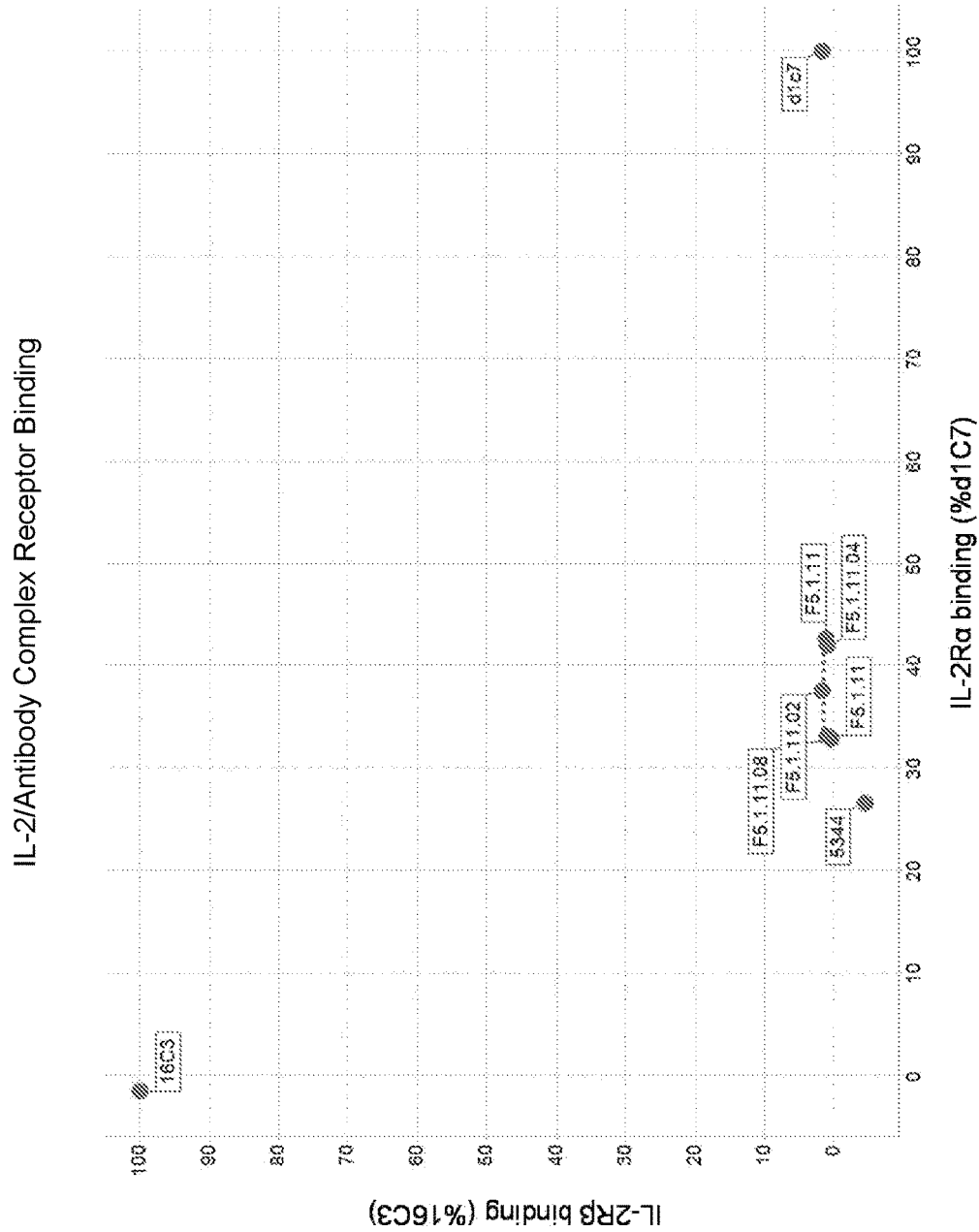
FIG. 2 depicts antibody/IL-2 affinity and IL-2Rα and IL-2Rβ binding. Both the parental and affinity matured clones showed complete inhibition of the antibody/IL-2 complex binding to IL-2Rβ and a reduction in the binding to IL-2Rα compared to the clone d1C7/IL-2 complex.

Example 3. Antibody/IL-2 Affinity and Receptor Binding for Affinity Matured Clones The binding kinetics and receptor binding profile of the affinity-matured F5.1.11 antibody/IL-2 complexes was measured using surface plasmon resonance as described for the parental antibody (Example 1).
Results The affinity maturation campaign increased the apparent binding affinity of clone F5.1.11 for IL-2 up to 16-fold. The three affinity-matured variants, F5.1.11.02, F5.1.11.04 and F5.1.11.08, were measured to have binding affinities for IL-2 of 114, 624 and 205 pM respectively. Characterization of the antibody/IL-2 complex binding to IL-2Rα and IL-2Rβ found that the receptor binding profile of the higher affinity variants was maintained compared to the parental molecule. Both the parental and affinity matured clones showed complete inhibition of the antibody/IL-2 complex binding to IL-2Rβ and a reduction in the binding to IL-2Rα compared to the clone d1C7/IL-2 complex. Some variation in the parental F5.1.11/IL-2 binding to IL-2Rα was observed over the course of the experiment, this is represented by a dotted line on the graph to depict the potential range. The three higher affinity variants, F5.1.11.02, F5.1.11.04 and F5.1.11.08, all fall within this range (Table 4 and FIG. 2).

TABLE 4

| clone | $k_a$ (M$^{-1}$s$^{-1}$) | $k_d$ (s$^{-1}$) | $K_D$ (M) |
|---|---|---|---|
| F5.1.11 | 3.78E+06 | 7.11E−03 | 1.88E−09 |
| F5.1.11.02 | 5.05E+06 | 5.74E−04 | 1.14E−10 |
| F5.1.11.04 | 7.34E+05 | 4.58E−04 | 6.24E−10 |
| F5.1.11.08 | 2.21E+06 | 4.53E−04 | 2.05E−10 |

Example 4. Phenotype of Tregs after IL-2:Anti-IL-2 mAb Treatment

IL-2-Anti-IL-2 Complex Treatment

Figure 3:
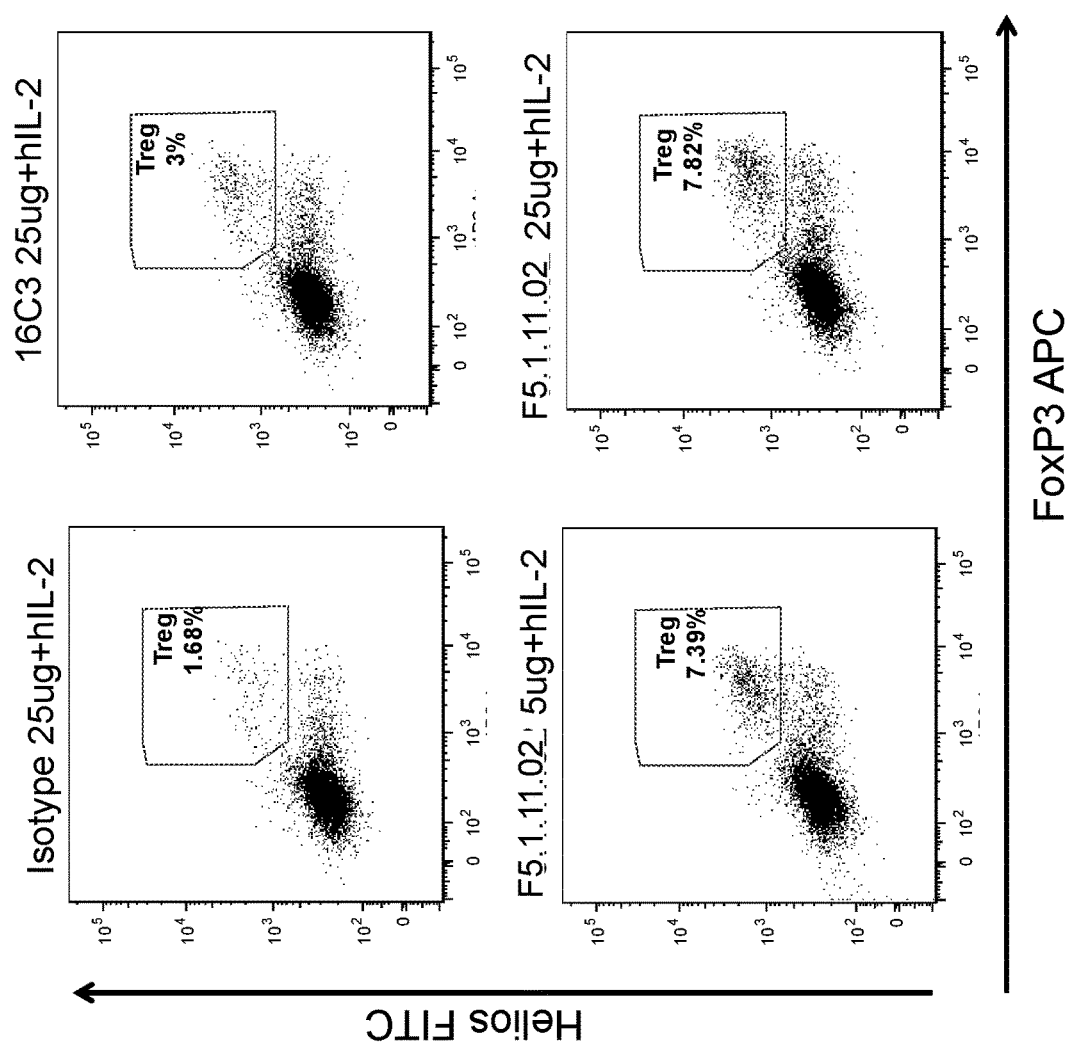
FIG. 3 depicts the phenotype of Tregs after IL-2:anti-IL-2 mAb treatment. Treg population was gated on hCD45$^+$ CD3$^+$ CD4$^+$ Helios$^+$ FoxP3$^+$ cells.

PBMCs were isolated from healthy donors by ficoll and activated overnight with 12.5 ng/mL antiCD3 and 25 ng/mL antiCD28. After an over night incubation, cells were harvested and extensively washed in PBS and resuspended at the concentration of 30×10$^6$ cells in 200 μL of PBS. PBMCs were injected i.v. in the NSG recipients. The NSG mice injected with human PBMCs received an intraperitoneal injection for 5 days of 8,000 U hIL-2 (Proleukin) complexed with 25 μg of Isotype, 25 μg of 16C3, 1 μg, 5 μg or 25 μg of Ab F5.1.11.02 for 30 minutes at 37° C.
Isolation of Splenocytes and Cell Staining Mice were sacrificed with CO$_2$ and splenocytes were harvested and stained extracellularly with anti human CD45 Pacific Orange, CD4 PercPCy 5.5, CD3 PeCy7/Pacific Blue/PercP, CD25 APC-Cy7/Pe, CD238 Pe, CD39 PeCy7, CD8 APC-H7, Ki67 Pe, NKG2D PeCy7, CD44 V450 and intracellularly with anti human Helios FITC and FoxP3 APC. Labeled antibodies were purchased from BD PharMingen or Ebioscience. Stained single cells suspensions were analyzed with a Fortessa flow cytometer running FACSDiva (BD Biosciences) and FSC 3.0 files analyzed and presented with FLOWJO Software.
Results The antibody 16C3 in complex with hIL-2 increased Treg percentage in the spleen. An incremental increase in Treg percentage was also observed in response to treatment with two different doses (5 μg and 25 μg) of the antibody F5.1.11.02. Treg population was gated on hCD45$^+$ CD3$^+$ CD4+ Helios+ FoxP3+ cells (FIG. 3). Both 16C3 and F5.1.11.02 in complex with hIL-2 increase Treg/Teff and Treg/NK cell ratios.

16C3 (25 µg) in complex with hIL-2 increased Treg/CD4, Treg/CD8 and Treg/NK cell ratios. The treatment with F5.1.11.02 at the lowest dose (1 µg) in the first experiment did not show an increase in the ratio. Instead a significant increase in Treg/CD4, Treg/CD8 and Treg/NK cell ratios in response to 5 µg and 25 µg of F5.1.11.02 in complex with hIL-2 was observed (FIGS. 4A-C). In the second experiment, the same results for 16C3 and 5 µg and 25 µg of F5.1.11.02 were observed, and, in addition, an increase in the ratio was also evident with the low dose of F5.1.11.02 (1 µg) (FIGS. 4D-F). Both 16C3 and F5.1.11.02 in complex with hIL-2 increase Teff and Treg total cell numbers. 16C3 (25 µg) in complex with hIL-2 increased the total number of CD4+, CD8+ cells and Tregs in the spleen in the two experiments.

F5.1.11.02 in complex with hIL-2 also showed an increase in CD4+, CD8+, and Tregs total cell numbers. The effect was more evident at the doses of 5 µg and 25 µg of F5.1.11.02 in the first experiment (FIGS. 5A-C). The second experiment showed an increase in total numbers of CD4+, CD8+ cells and Tregs in response to F5.1.11.02 in a dose dependent manner (FIGS. 5D-F). The treatment with F5.1.11.02 also induced an increase of CD25, Icos and FoxP3 mean fluorescence intensity (MFI) on Tregs that was not observed in presence of 16C3 (FIGS. 6A-C).

Example 5. Anti-IL-2 Antibodies Inhibit pSTAT5

Splenocytes from C57Bl6 expressing GFP under control of the Foxp3 promoter were harvested, processed to a single cell suspension, and re-suspended in RPMI 0.1% BSA. Cells were rested at 37° C. in tissue culture incubator until time of assay (1-2 hours).

PBMCs were purified from human Trima residuals (Blood Centers of the Pacific) and re-suspended in RPMI 0.1% BSA. Cells were rested at 37° C. in tissue culture incubator until time of assay (1-2 hours).

IL-2-Induced pSTAT5 Assay

PBMCs or splenocytes were plated in a 96 well V-bottom plate, such that 1 million cells were in each well, in a volume of 50 µL (RPMI, 0.1% BSA). The plate was returned to 37° C. incubator to maintain temperature. Antibody (JES6-1 (JES6-1A12 eBioscience) or anti-human IL-2) was titrated, and IL-2 was tested at 4 concentrations: 500 ng/mL, 50 ng/mL, 5 ng/mL, and 0.5 ng/mL.

Commercially available mouse IL-2 monoclonal antibody JES6-1 blocks both the IL2Rα and IL2Rβ interfaces of IL-2 (León et al. 2013, "Mathematical models of the impact of IL2 modulation therapies on T cell dynamics," Frontiers in Immunology, 4:439, incorporated in its entirety herein by reference). JES6-1 binds mIL-2 and not hIL-2 because the epitope is not conserved in hIL-2. Key amino acid residues for binding of JES6-1 to IL-2 including mIL-2 residues Q36 and E37, which correspond to hIL-2 residues Q22 and M23, are detailed in FIGS. 3, 4, S2, S3, and S4 of Spangler et al. 2015, "Antibodies to Interleukin-2 Elicit Selective T Cell Subset Production through Distinct Conformational Mechanisms," Immunity, 42: 815, incorporated in its entirety herein by reference. The KD of mIL-2/mIL-2Rβ is reported by Spangler et al. as >7 µM, and for mIL-2/mIL-2Rα the KD is 2-4 fold weaker than in hIL-2. A comparison of the mouse and human IL-2 amino acid sequences is available in FIG. 6 of Yokota et al. 1985, "Use of a cDNA expression vector for isolation of mouse interleukin 2 cDNA clones: Expression of T-cell growth-factor activity after transfection of monkey cells," Proc. Natl. Acad. Sci. USA, 82: 68, incorporated in its entirety herein by reference.

Equal volume (50 µL) of 2× IL2:antibody complex (prepared for 1 hr at 37° C.) was added to wells, and cells were cultured in 37° C. incubator for 40 minutes. Cells were fixed by addition of 100 µL of IC fix buffer (eBioscience). After 15 minutes fixation, cells were washed and stored in FACs buffer (PBS+0.2% BSA) until staining.

Assay plates were centrifuged to pellet cells, and permeabilization buffer III (BD Biosciences) was used to re-suspend cells, followed by 30 minutes incubation on ice. Cells were washed 2× in FACs buffer, and stained with the following Abs for PBMCs: from eBioscience, anti-human CD3 APC e780, CD4 Percp e710, and CD127 (PE). CD8 FITC, CD25 (PeCy7), FoxP3 (e660), and pSTAT5 (Pacific blue) were purchased from BD Biosciences. For splenocytes, the following anti-mouse antibodies were used: from eBioscience CD4 e660 and CD8a PeCy7. pSTAT5 Pacific Blue (BD Biosciences) was used for both mouse and human cells.

Data were collected on LSR Fortessa, and analyzed using FlowJo software. Data are plotted as background subtracted MFI, normalized to max signal for each cell type (IL2 500 ng/mL+Isotype). Background is defined as non-stimulated, but stained, pSTAT5. Human Tregs are defined as CD3+CD8-CD4+CD25hiCD127lo. Mouse Tregs are defined as CD8-CD4+Foxp3.GFP+ cells.

Results

Inhibition of pSTAT5 in PBMCs: F5.1.11 Affinity Variants

Affinity variants of F5.1.11 demonstrated that antibodies with increased affinity for IL-2, such as F5.1.11.02 and F5.1.11.08, were more effective at inhibiting pSTAT5 signaling in CD8+ effector T cells, and non-Treg CD4+ T cells. Treg pSTAT5 was maintained greater than 50% at IL-2 concentrations of 5-500 ng/mL. At the lowest concentration of IL-2 tested (0.5 ng/mL) pSTAT5 levels in Tregs were inhibited below 50% of max signal, however pSTAT5 was still detectable across all Ab concentrations (FIGS. 7A-V). The 5344 antibody was also tested in the pSTAT5 signaling assay, and in Tregs pSTAT5 was no longer detectable at low concentrations of IL-2 (data not shown).

Comparison of JES6-1 and Antibody F5.1.11.02

Mouse IL-2 antibody JES6-1 spared Treg pSTAT5 signaling at most IL-2 concentrations tested, similar to isotype control (FIGS. 8A-F). In contrast, IL-2 induced pSTAT5 signaling was strongly inhibited by JES6-1 in mouse CD8+ T cells, at all IL-2 concentrations tested. This data agrees with published observations that JES6-1 in complex with IL-2 promotes the growth of Treg cells in vivo.

Anti-human IL-2 antibody F5.1.11.02 largely spared human Treg pSTAT5 signaling at most IL-2 concentrations tested. CD8+ T cell pSTAT5 was inhibited by IL-2 antibody F5.1.11.02 at all IL-2 concentrations tested. Overall, the pattern of pSTAT5 inhibition of IL-2 antibody F5.1.11.02 in CD8 and Tregs is similar to that observed with mouse IL-2 antibody JES6-1.

In Table 5, pSTAT5% max values from FIGS. 8A-F were used to generate area under the curve values for either Tregs or CD8 cells, treated with either Isotype or anti-IL-2 antibody. The ratio of Treg/CD8 AUC for each concentration of IL-2 was listed. In isotype treated samples, decreasing amounts of IL-2 resulted in an increased AUC ratio, reflecting more pSTAT5 signaling in the Tregs than in the CD8+ effector cells. Although the absolute numbers differ, this observation was consistent between mouse and human cells.

JES6-1 treatment shifted the ratio to be in favor of Tregs at higher concentrations of IL-2. A similar change in AUC ratio occurred in the human cells treated with F5.1.11.02 antibody.

Overall, F5.1.11.02 appeared to have a similar pSTAT5 signaling profile to JES6-1.

TABLE 5

| | Ratio Treg/CD8 AUC | | |
|---|---|---|---|
| | IL-2 (ng/ml) | Isotype | JES6 |
| Mouse | 5 | 21.5 | 30.0 |
| | 50 | 2.5 | 40.7 |
| | 500 | 1.0 | 18.3 |
| | | Isotype | F5.1.11.02 |
| Human | 5 | 6.0 | 6.2 |
| | 50 | 1.8 | 12.0 |
| | 500 | 1.0 | 4.4 |

Impact of Antibody Epitope on pSTAT5 Inhibition of CD25hi CD8$^+$ T Cells

Some peripheral CD8$^+$ T cells express CD25 (IL-2Rα). As shown in FIGS. 10A-B, if cells were gated based on CD25 expression, CD25hi CD8 cells were more sensitive to low levels of IL-2. IL-2 antibodies' blocking of CD25 binding, all or in part, may therefore be required to inhibit pSTAT5 signaling in CD25hi CD8$^+$ T cells.

As shown in FIG. 9, pSTAT5 induced by low doses of IL-2 (0.8 ng/mL) was best inhibited by IL-2 antibodies that blocked IL-2Rα binding to IL-2, such as 13A10 or F5.1.11.02. Conversely, high concentrations of IL-2 (500 ng/mL), presumably not requiring the presence of IL-2Rα to enable signaling, were best inhibited by antibodies that block binding of IL-2 to IL-2Rβ, such as d1C7 or F5.1.11.02. Antibody F5.1.11.02 was best able to inhibit pSTAT5 signaling in CD8$^+$ effector T cells across a range of IL-2 concentrations pSTAT5 Inhibition by IL-2 Antibody F5.1.9

IL-2 antibody F5.1.9 and variant F5.1.9.5 were assessed for inhibition of pSTAT5 (FIGS. 11A-H). Affinity variant F5.1.9.5 of F5.1.9 was effective at inhibiting pSTAT5 signaling in CD8$^+$ effector T cells to a greater extent than it inhibited pSTAT5 signaling in Tregs. F5.1.9.5 $k_a$ (M$^{-1}$ s$^{-1}$) was 1.23E+06, $k_d$ (s$^{-1}$) was 8.18E−04, and $K_D$ (M) 6.63E−10.

Example 6. Generation of NOD mIL-2−/− hIL-2+/− Mice

A mouse IL-2-containing bacterial artificial chromosome (BAC) (clone RP23-290D8) was engineered to express human IL-2 coding sequence. The following modifications were made in the BAC: the mouse IL-2 promoter, 5' and 3' UTRs and introns were left intact; the mouse signal peptide was replaced with the human one; the 3' half of exon 1 downstream of signal peptide, exons 2 and 3 were replaced with human sequence; the 5' half of exon 4 was replaced with human coding sequence.

The engineered BAC was subsequently transferred through a pronuclear injection in fertilized oocytes of an FVB/NJ (Friend Virus B) female mouse (Jackson). The fertilized oocytes were then implanted in an FVB female mouse to generate FVB mIL-2+/+hIL-2 BAC+ mice. In order to generate mice in NOD background who were lacking the expression of mIL2, the FVB mIL-2+/+hIL-2 BAC+ mice were backcrossed with a NOD mIL-2−/− mouse. The NOD mIL-2−/−hIL-2 BAC+/− mice generated from this initial breeding, were backcrossed with a NOD mIL-2−/− mouse for 8 generations in order to generate mice with type I diabetes. The mice obtained were used for experiments.

Methods

Whole blood (100 μL), after ACK lysis, was stimulated overnight with PMA/Ionomycin, the supernatant (125 μL) was collected and the ELISA performed for both the mIL-2 (50 μL) and hIL-2 (50 μL) (ELISA: ebioscience).

The female NOD mIL2−/−hIL2+/− mice were injected at the age of 14 weeks and they received an intraperitoneal injection for 5 days of 8,000 IU hIL-2 (Proleukin) in complex with 25 μg of isotype, or 5 μg or 25 μg of F5.1.11.02 antibody. IL2:antibody complexes were formed by incubating IL-2 and antibody together for 30 minutes at 37° C.

Isolation of Different Organs and Cell Staining

Mice were sacrificed with CO$_2$ and immediately perfused through the left ventricle with PBS until the effluent ran clear. Splenocytes and pancreatic lymph nodes (pLN) were harvested and extracellular staining with CD25 PeCy7, CD4 BV605, CD8 PercP-Cy5.5, CD44 Pe, CD62L Al647 and intracellular staining with FoxP3 FITC was performed.

Whole pancreas was prepared by digesting for 30 minutes at 37° C. with 0.8 mg/mL Collagenase P and 20 μg/mL DNase (Roche) followed by mincing. After digestion, the homogenate was filtered twice by using a 40 μm cell strainer and extracellular staining with CD45 PercP Cy5.5, CD25 Pe, CD4 PeCy7, CD8 Al647, Thy1.2 BV605, and intracellular staining with FoxP3 FITC, was performed. Labeled antibodies were purchased from BD Pharmingen or Ebioscience. Stained single cell suspensions were analyzed and presented with FLOWJO software.

Results

Phenotype of Human IL-2 Transgenic (hIL-2 Tg) Mice

Figure 14:
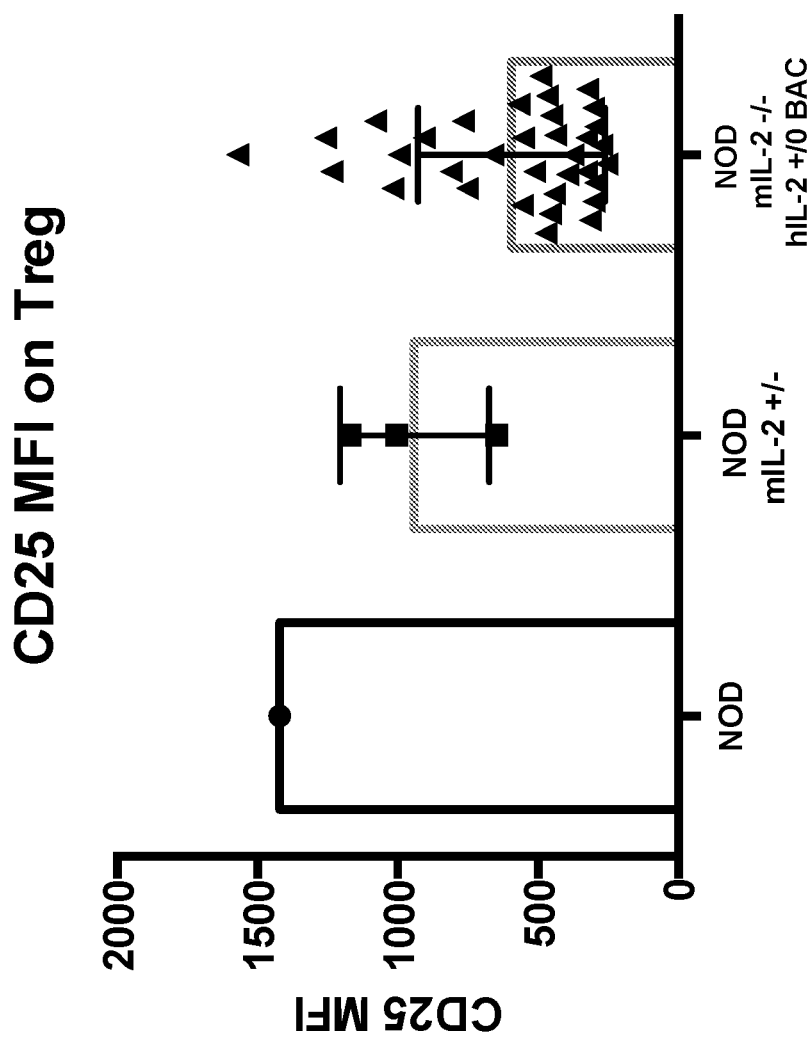
FIG. 14 depicts the cell surface expression of CD25 on Tregs from hIL-2 Tg, NOD, or NOD mIL-2+/− mice.

In vitro stimulation of mouse splenocytes (FIGS. 12A-B) with PMA/Ionomycin confirmed the production of human IL-2 from transgenic mice, although human IL-2 was produced at lower levels than mouse IL2 from wildtype mice. hIL-2 Tg/mIL-2−/− mice appeared healthy and viable. However, hIL-2Tg mice had an increased percentage of activated (CD44$^+$CD62L−) CD4$^+$ or CD8$^+$ T cells, as compared to NOD or NOD mIL-2+/− mice (FIGS. 13A-B). Although Treg frequency was similar to NOD or NOD mIL-2+/− mice, Tregs from hIL-2 Tg mice had a decreased cell surface expression of CD25 (FIG. 14).

Figure 15:
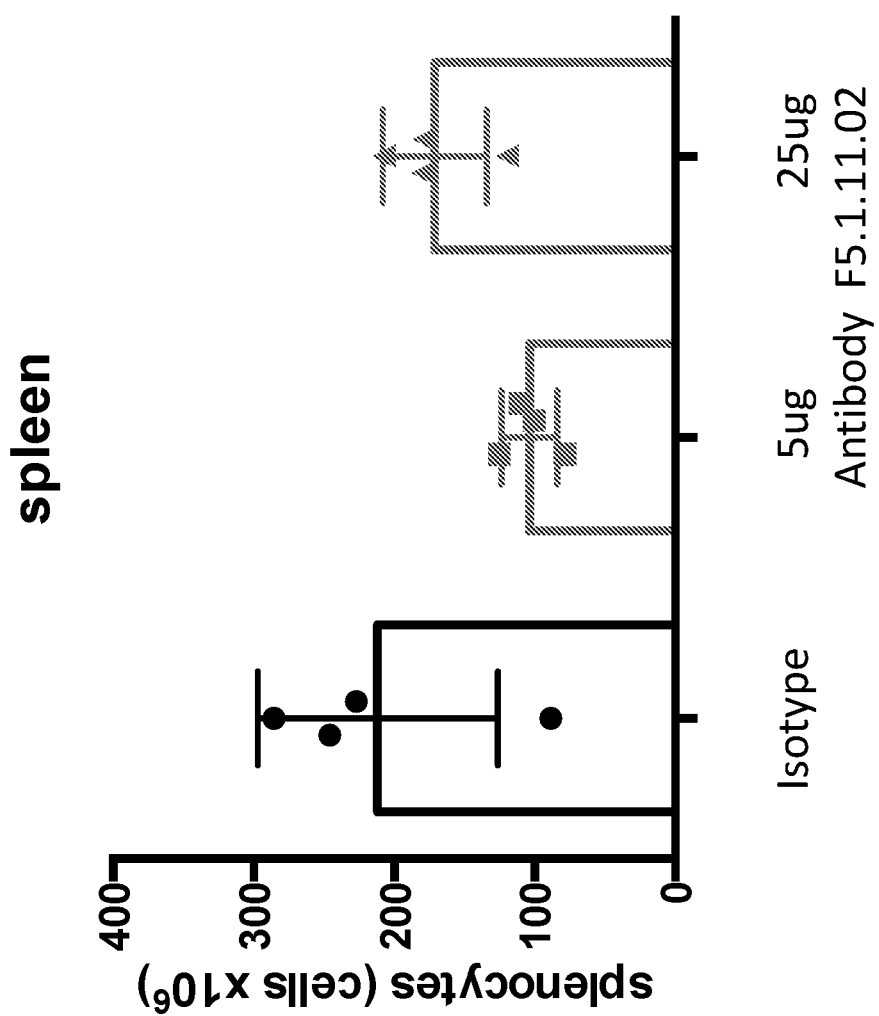
FIG. 15 depicts the effect of F5.1.11.02:IL-2 complex on overall cellularity of the spleen at day 7.
Figure 16:
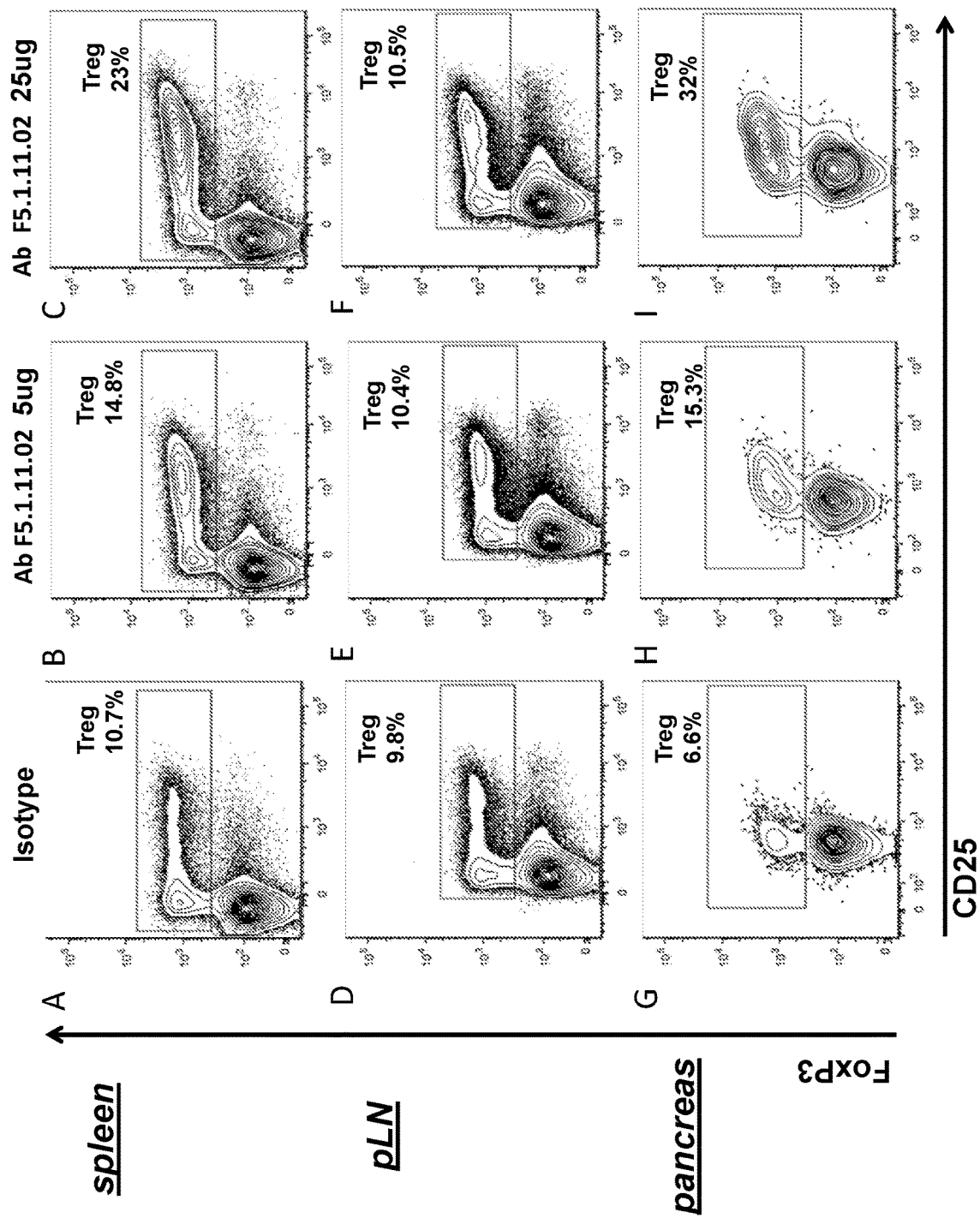
FIGS. 16A-I depict the effect of F5.1.11.02:IL-2 complex on Treg percentage in spleen, pLN and pancreas.
Figure 17:
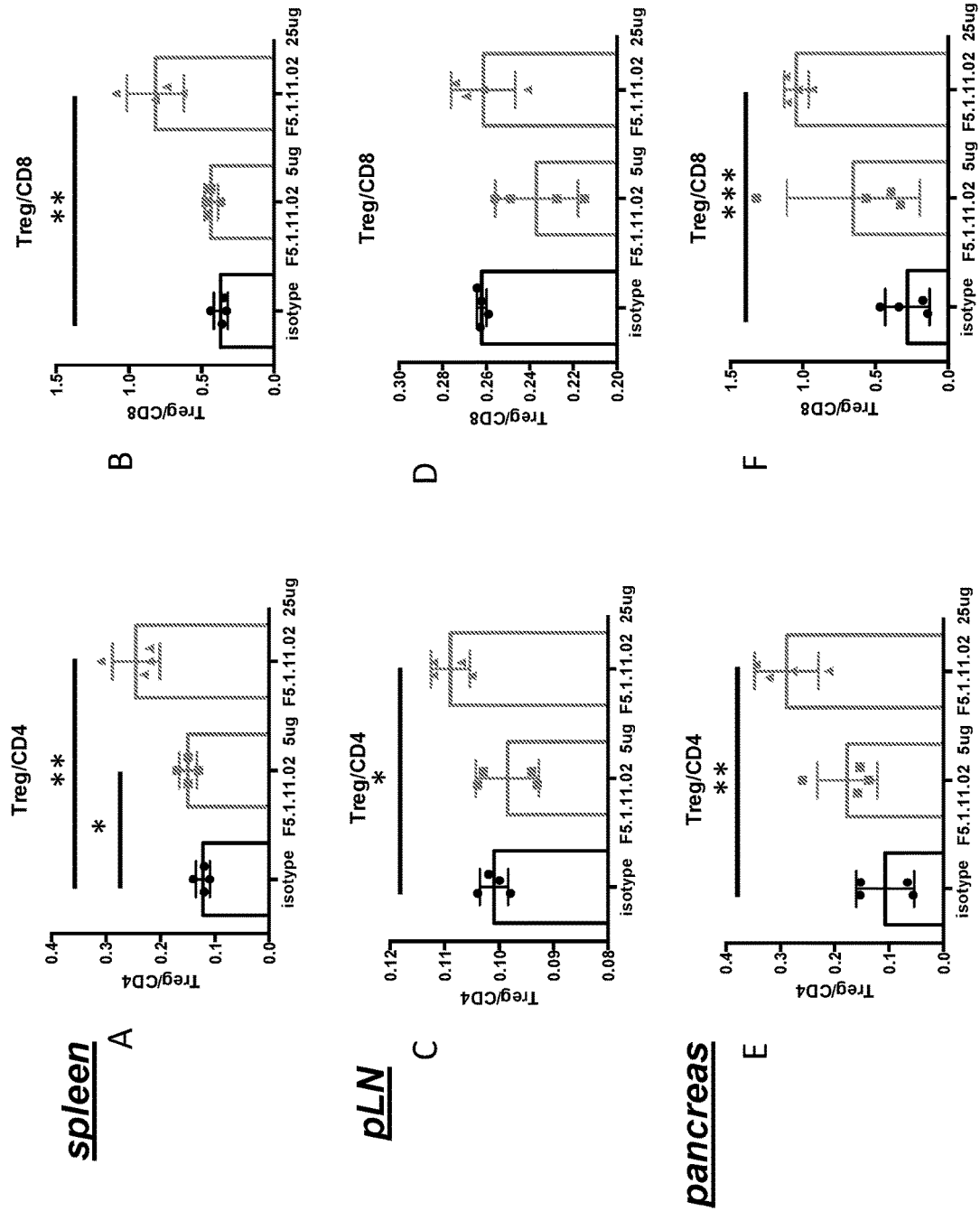
FIGS. 17A-F depict the effect of F5.1.11.02 (25 µg) in complex with hIL-2 on Treg/CD4 and Treg/CD8 ratios in spleen, pLN and pancreas.

Treatment of hIL-2 Tg Mice with F5.1.11.02:hIL-2 Complex hIL-2 Tg mice were treated with F5.1.11.02:IL-2 complex, as described above (methods). Treatment did not increase overall cellularity of the spleen at day 7, and a slight decrease in total splenocytes was observed in the 5 μg treatment group (FIG. 15). An increase in Treg percentage was observed in response to treatment with both doses of F5.1.11.02 in complex with hIL-2 compared to the isotype control in all organs except pLNs, with a more significant increase in the pancreas (FIGS. 16A-I). In the spleen and pLNs, the Treg population was gated on CD4$^+$ CD25$^+$ FoxP3$^+$ cells and in the pancreas Treg cells were identified by gating on CD45$^+$ Thy1.2$^+$ CD4$^+$ CD25$^+$ FoxP3$^+$ cells.

After treatment with the complex, a decrease of CD4, CD8 and Treg total cell numbers was observed in the spleen and pLN. However, in the pancreas, F5.1.11.02 complex treatment induced a slight increase in Treg total cell number in response to the 25 µg dose of F5.1.11.02. No differences in CD4 and CD8 total cell numbers were observed in the pancreas (data not shown).

Treatment of hIL-2 Tg mice with F5.1.11.02 (25 µg) in complex with hIL-2 induced a significant increase in Treg/CD4 and Treg/CD8 cell ratios in the spleen (FIGS. 17A-F). The same results were observed in the pancreas, with a significant increase in ratio for both Treg/CD4 and Treg/CD8 observed with 5 µg and 25 µg of F5.1.11.02. F5.1.11.02:IL2 complex treatment had little effect on cell ratios in the pancreatic lymph node.

Figure 18:
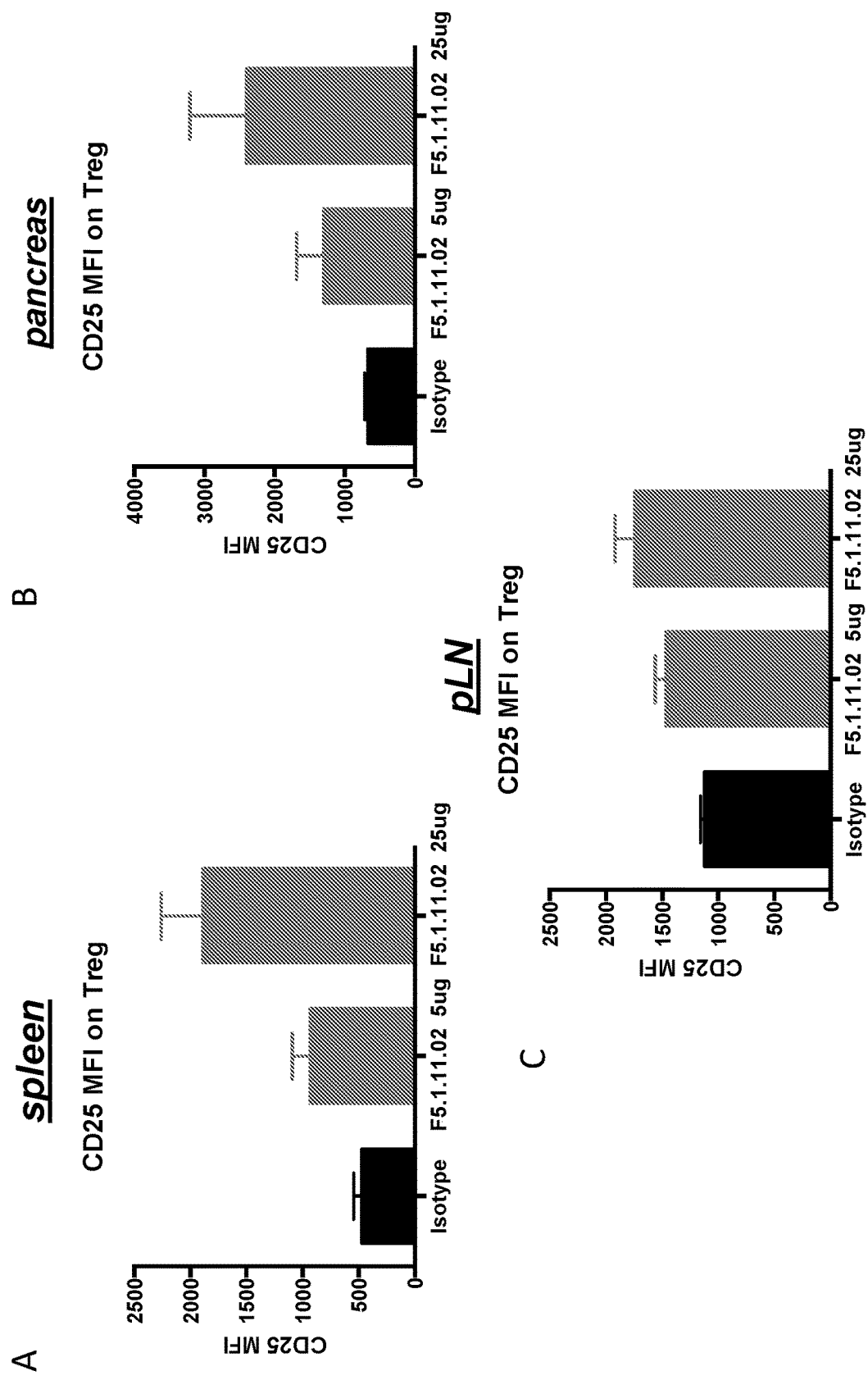
FIGS. 18A-C depict the effect of F5.1.11.02:IL-2 complex (5 µg and 25 µg F5.1.11.02) on CD25 mean fluorescence intensity (MFI) on Tregs in spleen, pLN and pancreas.

Lastly, treatment of huIL2 Tg mice with F5.1.11.02:IL-2 complex (5 µg and 25 µg F5.1.11.02) induced an increase of CD25 mean fluorescence intensity (MFI) on Tregs in all organs (FIGS. 18A-C). This increase was particularly significant in the pancreas, where Treg CD25 MFI was very low prior to treatment.

NSG Experiment with CTV

PBMCs were isolated from healthy donors by ficoll and activated overnight with 12.5 ng/mL antiCD3 and 25 ng/mL antiCD28. After an over night activation, cells were harvested and labeled with CellTrace Violet (Life technology) at the concentration of 1 µL CTV/10×10$^6$ cells. After the staining, the cells were extensively washed in PBS and resuspended at the concentration of 30×10$^6$ cells in 200 µL of PBS. PBMCs were injected i.v. in the NSG recipients. The NSG mice injected with human PBMCs received an intraperitoneal injection daily for 5 days of 8,000 U hIL-2 (Proleukin) in complex with isotype or antibody, in the amounts indicated, for 30 minutes at 37° C.

Isolation of Splenocytes and Cell Staining

Mice were sacrificed with CO$_2$ at day 3 and day 5 and splenocytes were harvested and stained extracellularly with anti human CD45 Pacific Orange, CD4 PercPCy5.5, CD25Pe, CD8 APC-H7, NKG2D PeCy7 and intracellularly with anti human Helios FITC and FoxP3 APC. Labeled antibodies were purchased from BD PharMingen or Ebioscience. Stained single cells suspensions were analyzed with a Fortessa flow cytometer running FACSDiva (BD Biosciences) and FSC 3.0 files analyzed and presented with FLOWJO Software.

Results

Figure 19:
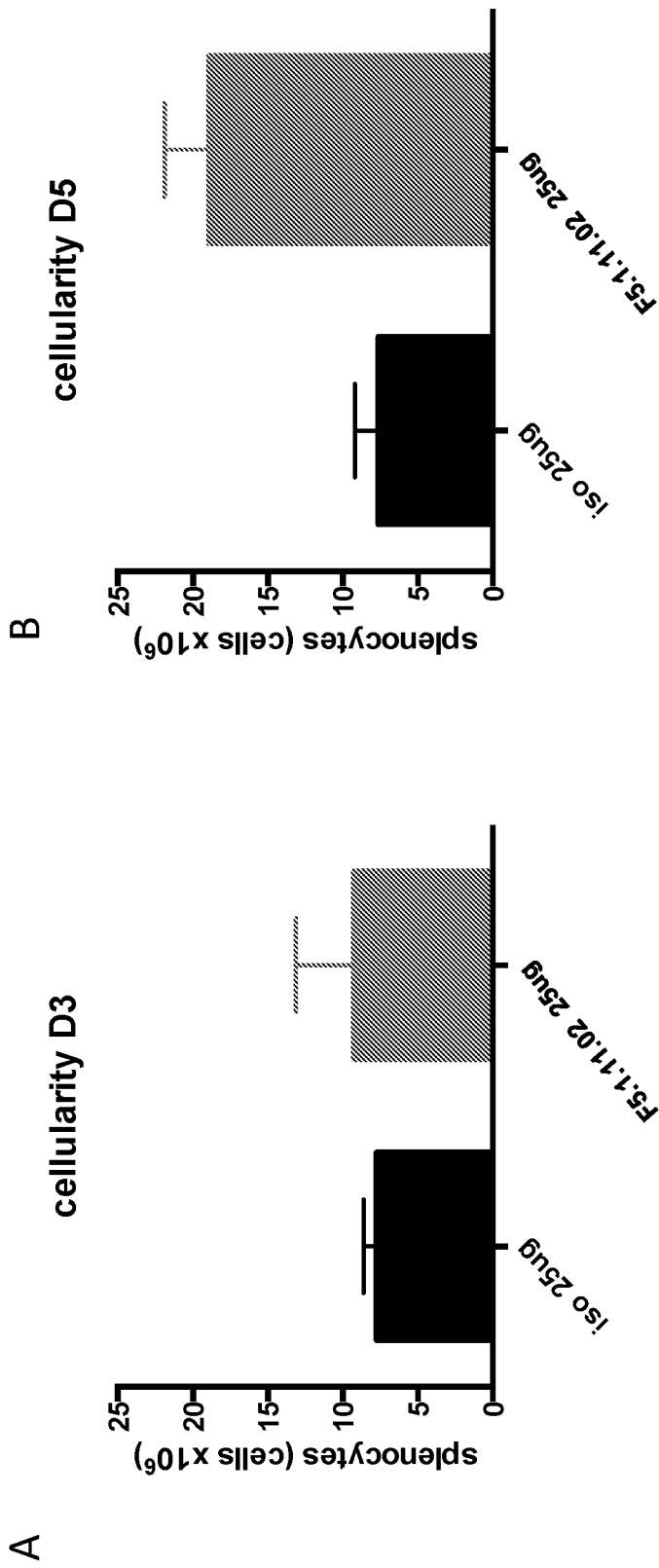
FIGS. 19A-B depict the effect of 25 µg of F5.1.11.02 in complex with hIL-2 on the number of total splenocytes.
Figure 20:
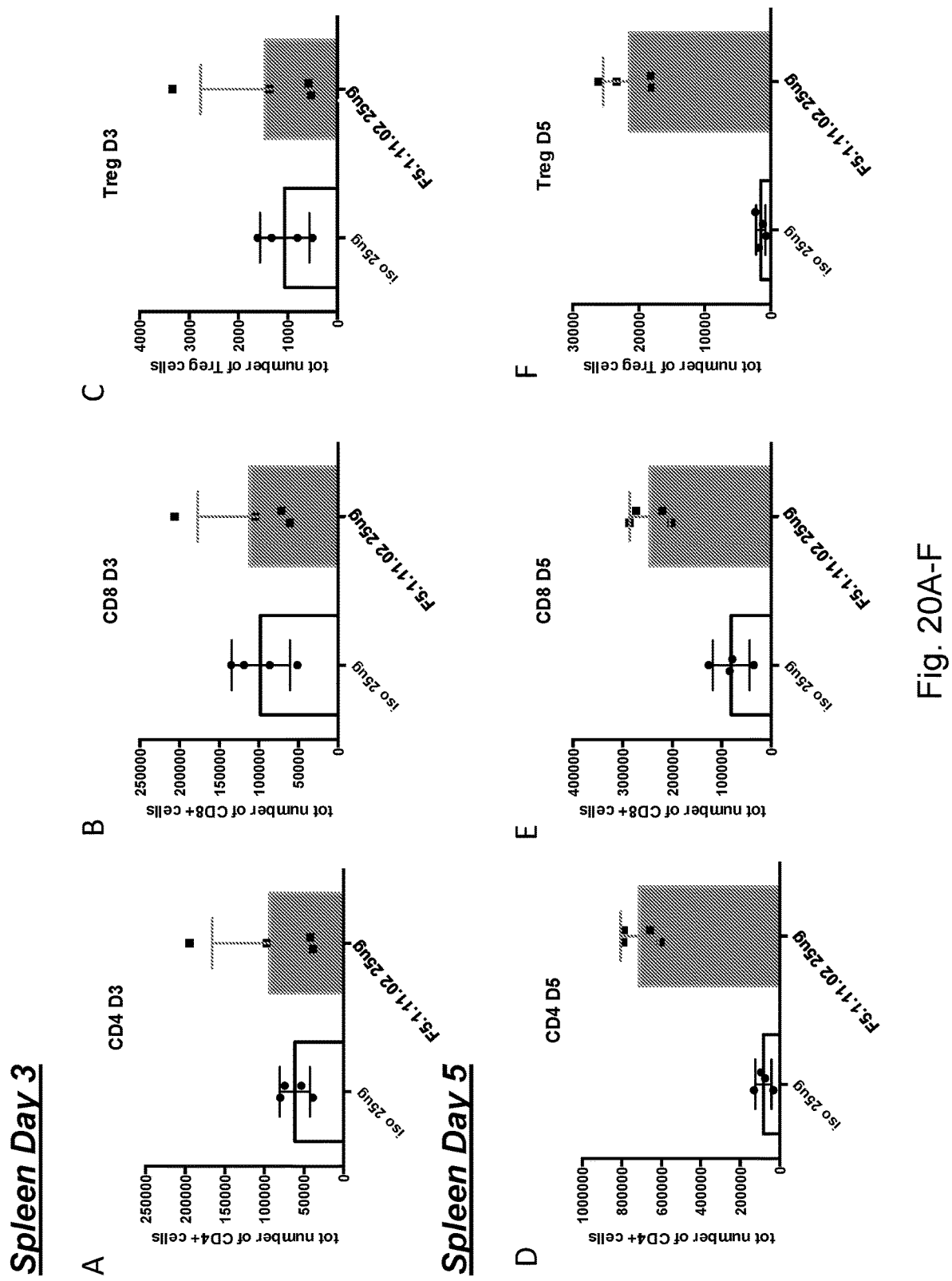
FIGS. 20A-F depict the effect of F5.1.11.02 antibody:IL-2 complex on Teff and Treg total cell number in the spleen. Treg population was gated on hCD45$^+$ CD3$^+$ CD4$^+$ Helios$^+$ FoxP3$^+$ cells.
Figure 21:
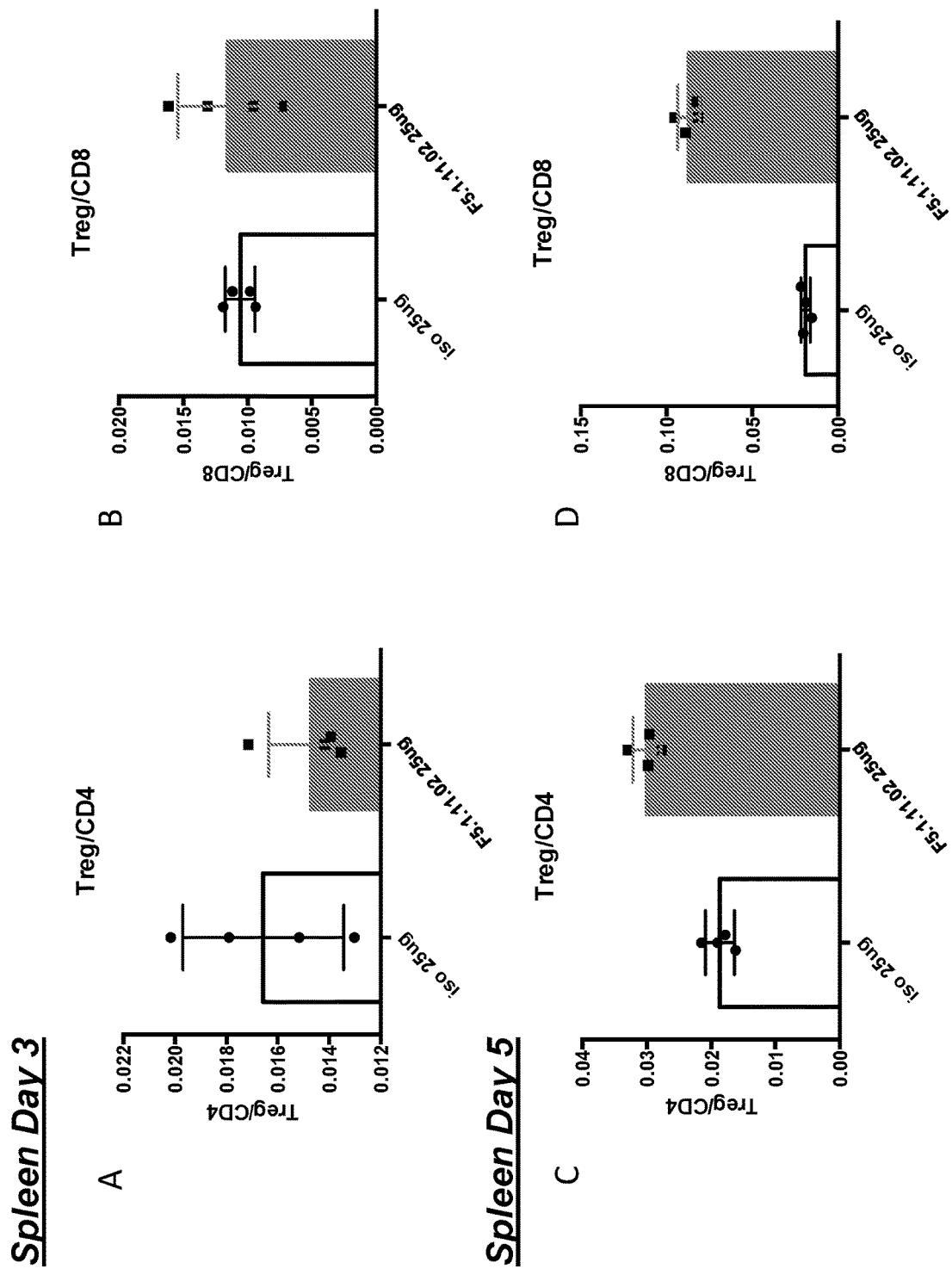
FIGS. 21A-D depict the effect of F5.1.11.02 antibody: IL-2 complex on Treg/CD4 and Treg/CD8 ratios in the spleen. Treg population was gated on hCD45$^+$ CD3$^+$ CD4$^+$ Helios$^+$ FoxP3$^+$ cells.
Figure 22:
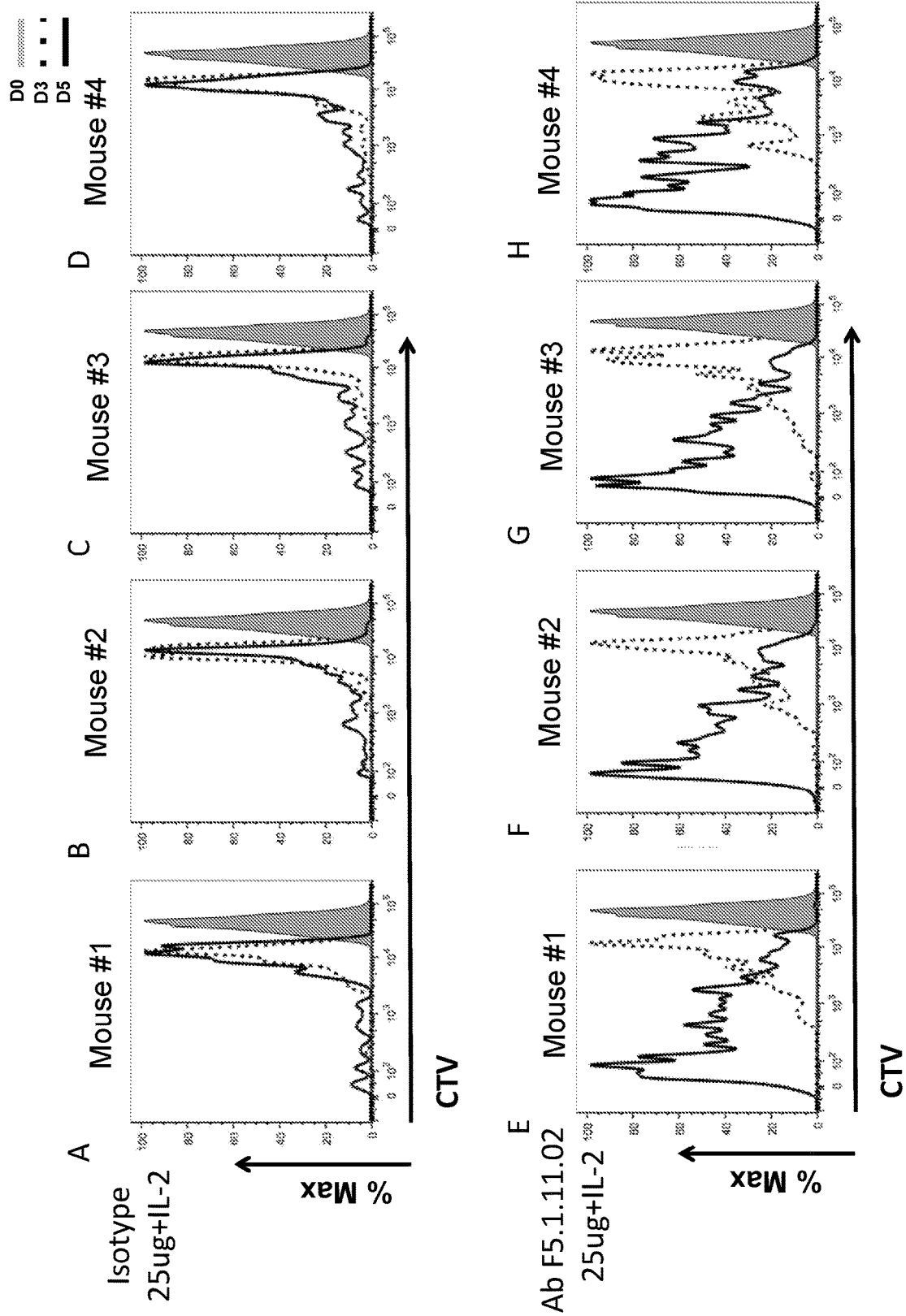
FIGS. 22A-H depict the effect of F5.1.11.02 antibody: IL-2 complex treatment on the proliferation of Tregs.
Figure 23:
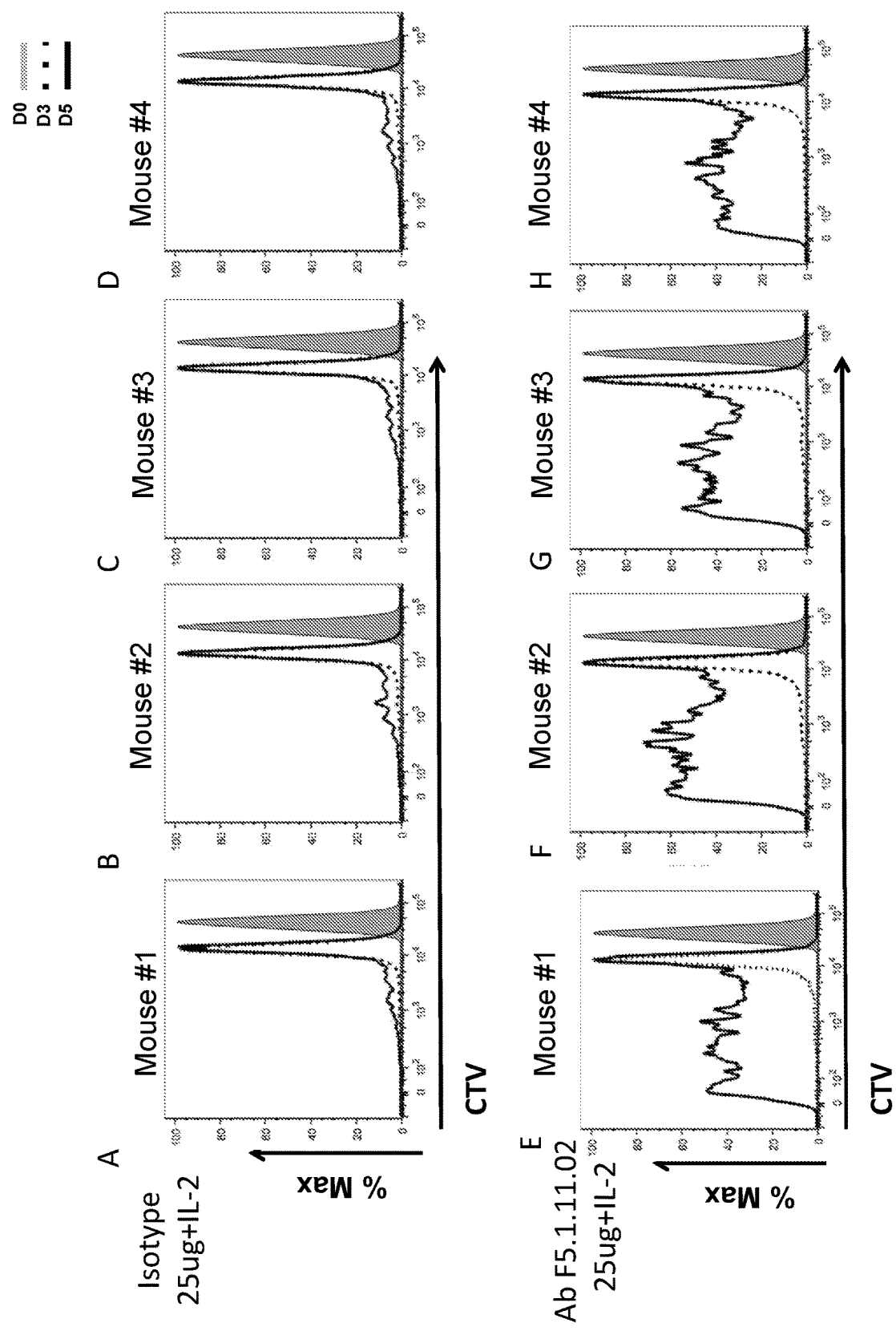
FIGS. 23A-H depict the effect of F5.1.11.02 antibody: IL-2 complex treatment on the proliferation of CD8 T cells.

The treatment with 25 µg of F5.1.11.02 in complex with hIL-2 induced an increase in the number of total splenocytes at day 5 but not at day 3 (FIGS. 19A-B).

F5.1.11.02 antibody:IL-2 complex was also able to increase Teff and Treg total cell number (FIGS. 20A-F) and Treg/CD4 and Treg/CD8 ratios (FIGS. 21A-D) in the spleen at day 5, a result that was not observed at day 3. Treg population was gated on hCD45$^+$ CD3$^+$ CD4$^+$ Helios$^+$ FoxP3$^+$ cells.

By including CTV labeling prior to transfer and treatment, we observed that treatment with F5.1.11.02 antibody:IL-2 complex induced proliferation of Tregs compared to isotype, an effect already evident at day 3 and resulting in a low number of undivided cells by day 5 (FIGS. 22A-H). Proliferation of CD8 T cells was also increased by treatment with F5.1.11.02 antibody:IL-2 complex, however this was only significant at day 5 and greater numbers of undivided cells remained than in the Treg population (FIGS. 23A-H). Overall, this CTV data supports an increase in Treg proliferation as underlying the shift in Treg/CD8 ratio observed.

Figure 24:
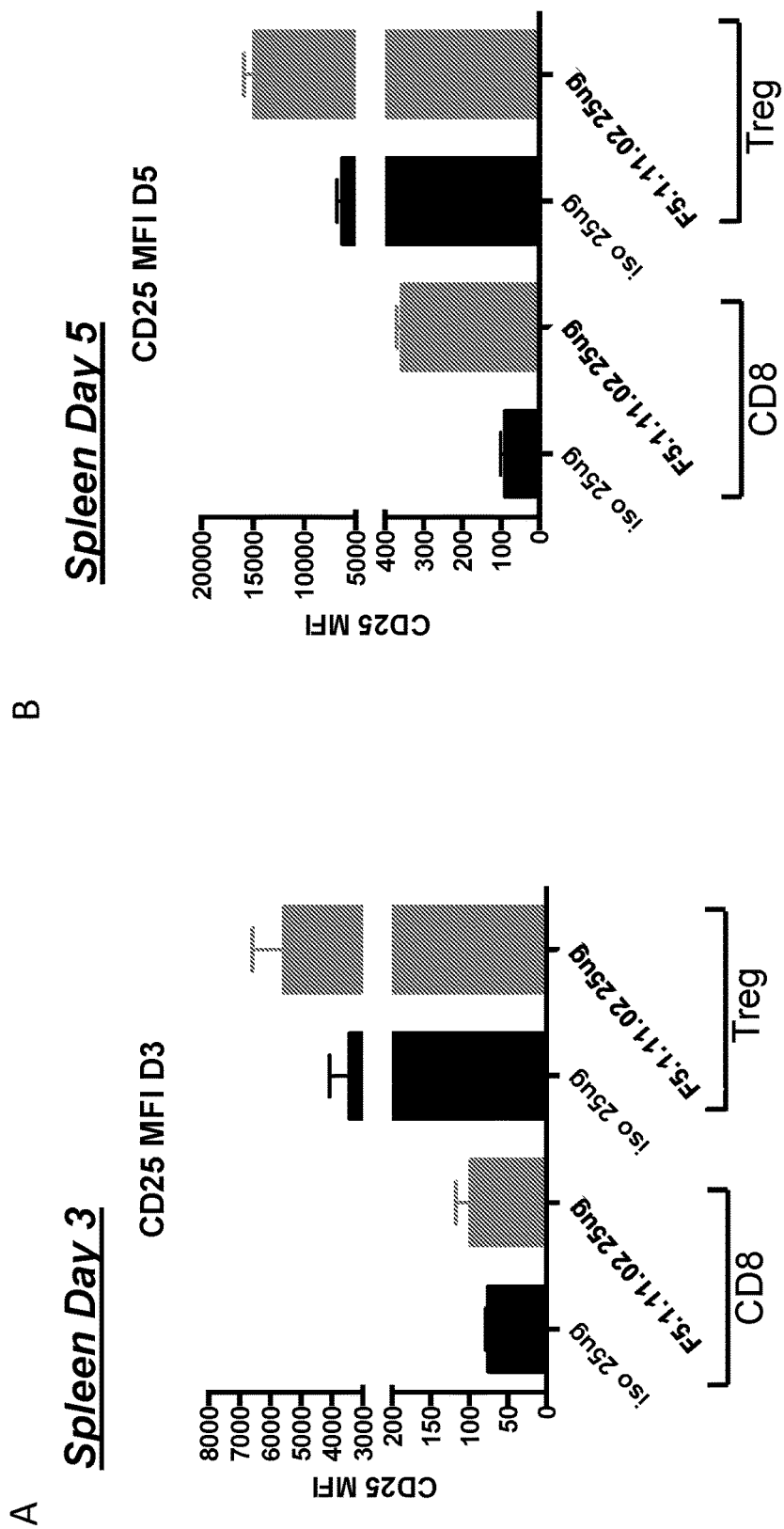
FIGS. 24A-B depict treatment with both doses of the F5.1.11.02 antibody:IL-2 complex induced an increase of CD25 mean fluorescence intensity (MFI) on Tregs and on the CD8 population in the spleen compared to the isotype control.
Figure 25:
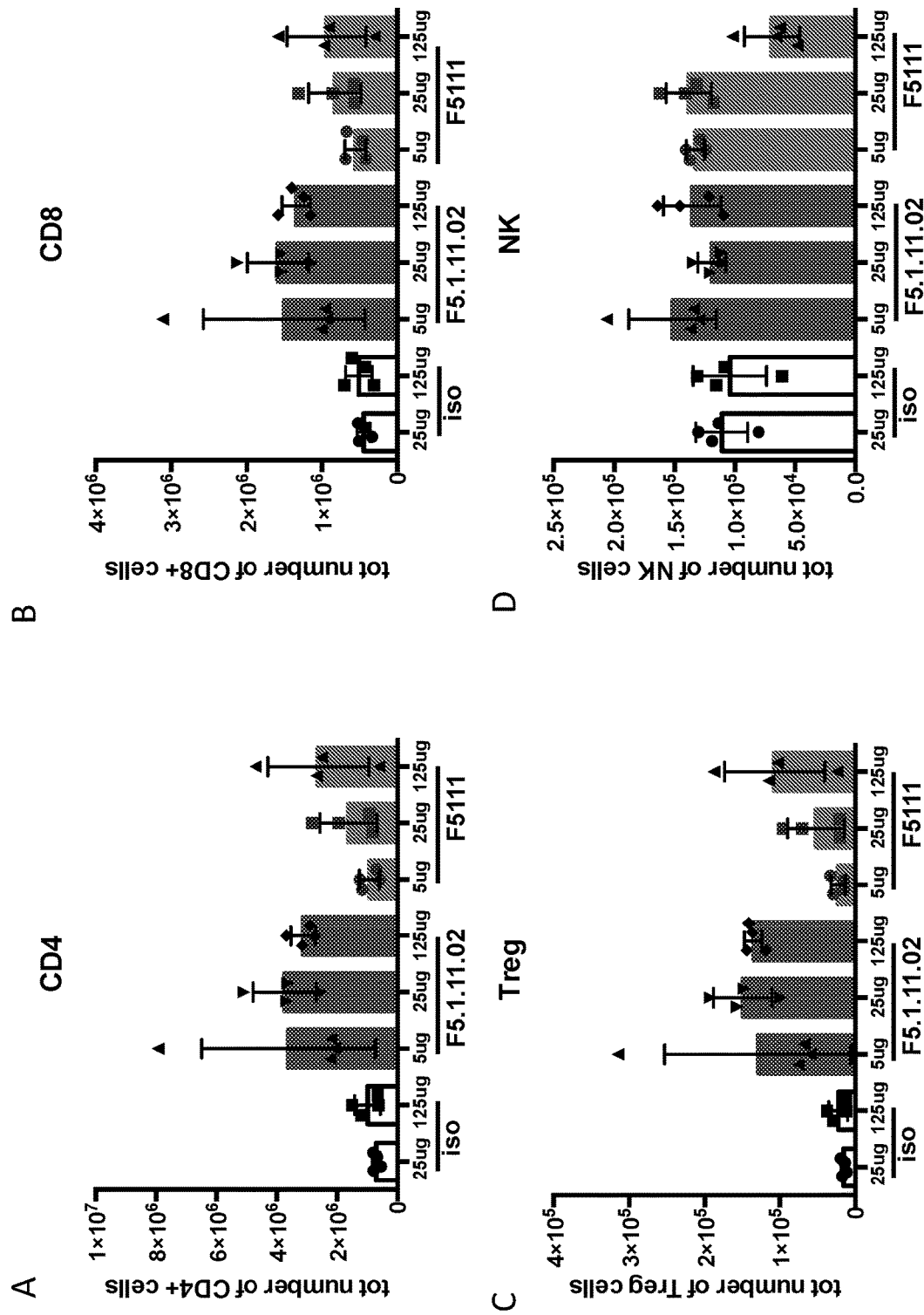
FIGS. 25A-D depict a comparison between the effects of F5.1.11.02 and F5.1.11 on Treg and CD8 cell number.
Figure 26:
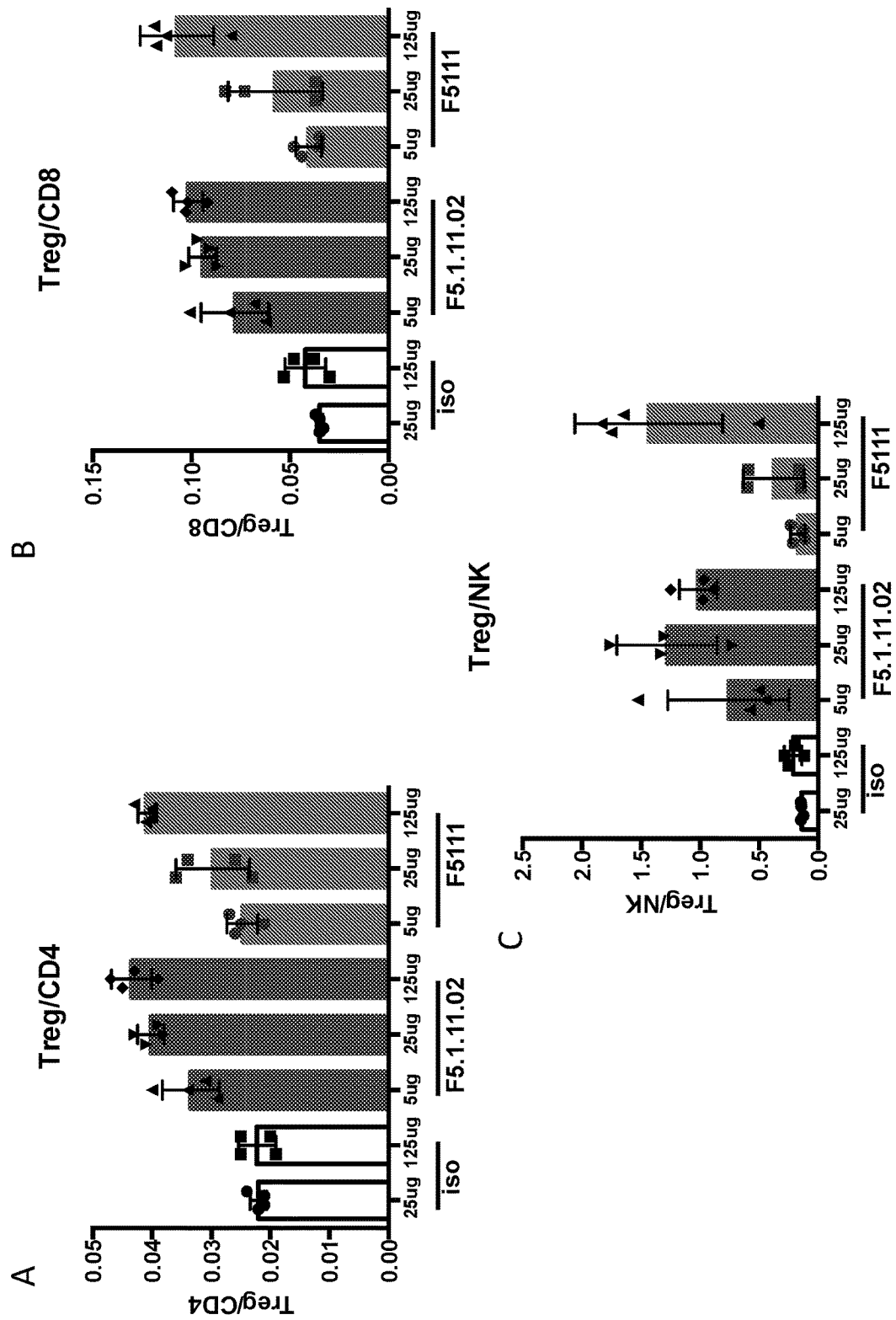
FIGS. 26A-C depict a comparison between the effects of F5.1.11.02 and F5.1.11 on Treg/CD8 ratio.
Figure 27:
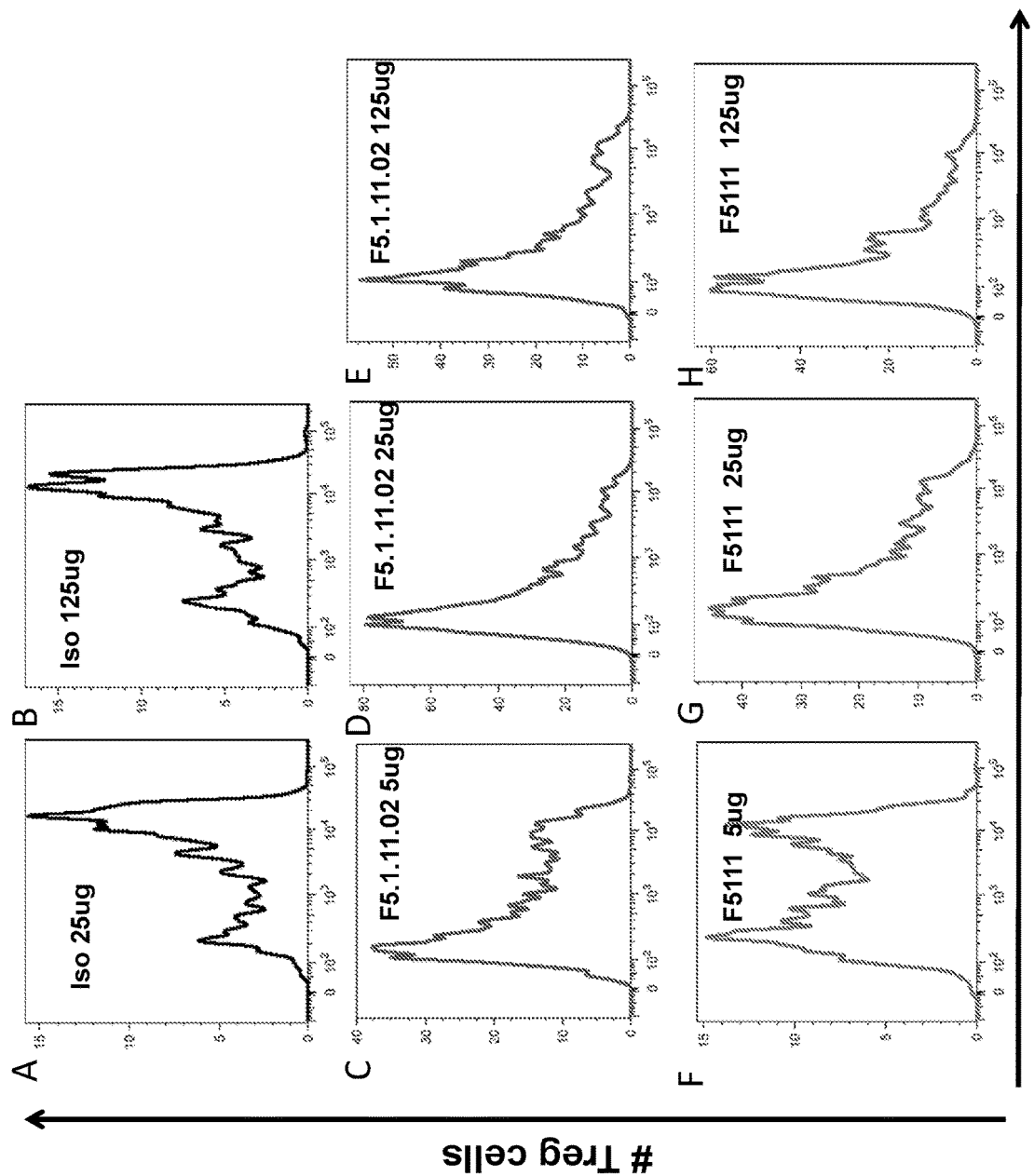
FIGS. 27A-H depict the effect of antibodies on Treg proliferation at various doses.
Figure 28:
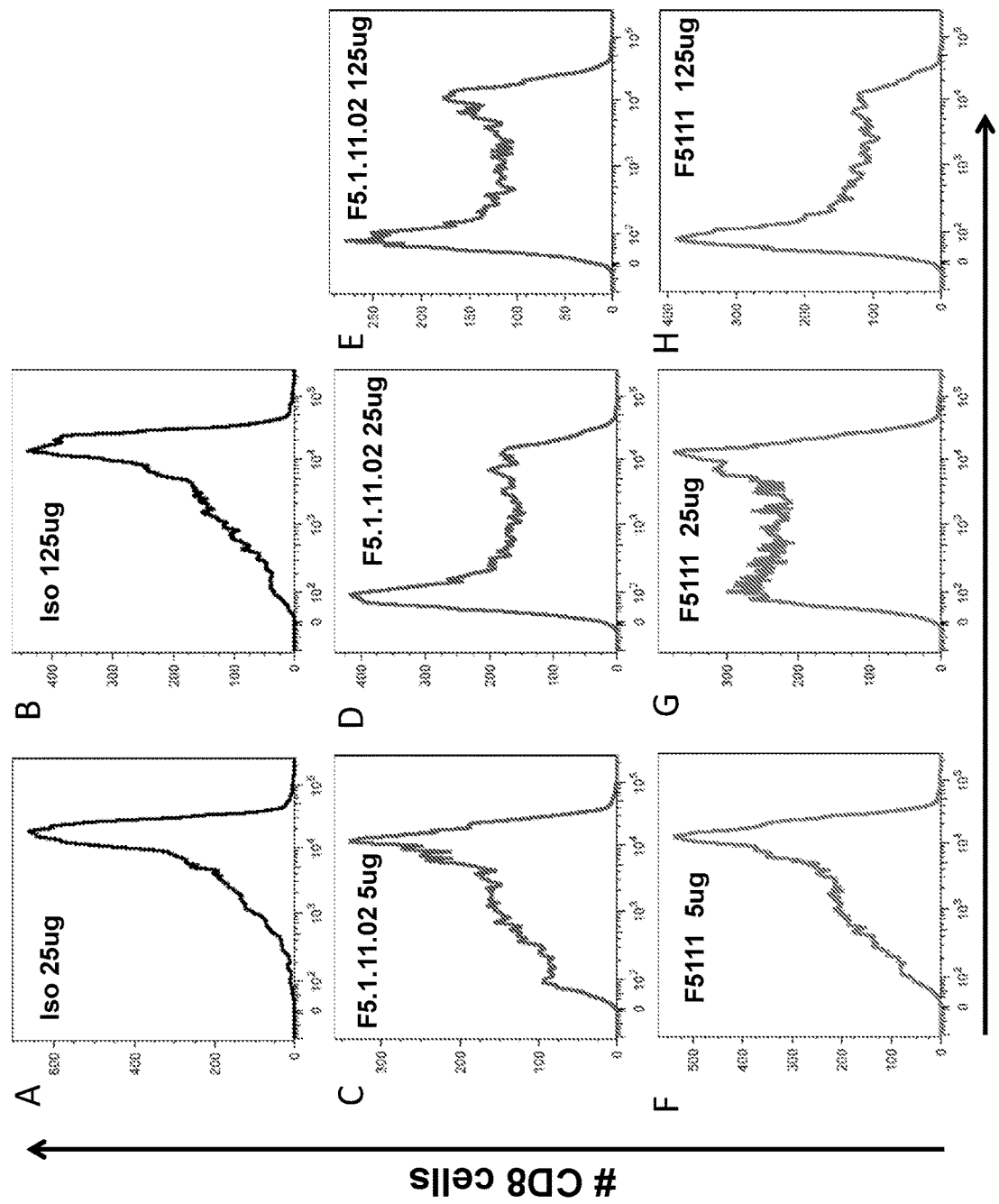
FIGS. 28A-H depict the effect of antibodies on CD8 cell proliferation at various doses.

Lastly, in the spleen the treatment with both doses of the complex induced an increase of CD25 mean fluorescence intensity (MFI) on Tregs and on the CD8 population compared to the isotype control (FIGS. 24A-B). However, the absolute expression of CD25 on Tregs was many fold higher than on CD8 cells.

In a follow-on experiment, we compared F5.1.11.02 with a lower affinity, 'parental' antibody, F5.1.11. We extended the dose range to 125 µg of antibody, in complex with hIL2, to assess if a higher dose of a lower affinity antibody would have a comparable effect in vivo. At 125 µg, F5.1.11 had comparable effects on Treg and CD8 cell number, increased Treg/CD8 ratio, and cellularity, equivalent to 25 µg of F5.1.11.02 (FIGS. 25A-D, 26A-C, and 33A-B). This was again supported by increased Treg proliferation, as observed in the CTV dilution (FIGS. 27A-H, 28A-H, and 38A-B). We predict that in vitro, F5.1.11.02 will similarly increase Foxp3 and CD25 protein levels on human Tregs.

Example 7. IL-2 Antibody Binding Affinity for Cynomolgus Monkey IL-2

Recombinant cynomolgus monkey (*Macaca fascicularis*) IL-2 was expressed in mammalian cells and purified using immobilized metal ion affinity chromatography (IMAC). The affinity of the antibodies for cynomolgus monkey IL-2 (1-100 nM) was measured using surface plasmon resonance as described for the human IL-2 (Example 1). A 1:1 Langmuir binding model was used to fit binding curves or the steady-state affinity constant calculated from a concentration-response curve. Clones were designated as "very weak" in cases where the concentration-response relationship observed for 1-100 nM IL-2 was insufficient to calculate the apparent binding affinity.

Results

The human antibody clones tested bind to cynomolgus monkey IL-2 with affinities ranging from 516 pM through to very weak associations that could not be quantified in this assay (Table 6). The majority of clones tested where selected based on their ability to inhibit IL-2Rβ binding (Examples 2 and 3), these clones showed a significant loss of affinity for the cynomolgus monkey IL-2 when compared to human IL-2. 16C3, which has been observed to inhibit IL-2Rα binding (Example 2), showed equivalent binding to both human and cynomolgus monkey IL-2. These results are consistent with our structural analysis which found the divergent region between human and cynomolgus monkey IL-2 to fall within both the IL-2Rβ binding site and the epitope of the F5.1.11 antibody clone (Example 9).

TABLE 6

| Clone | Human IL-2 KD (M) | Cyno IL-2 KD (M) |
| --- | --- | --- |
| F5.1.11 | 3.12E−09 | very weak |
| F4.7.8 | 1.34E−08 | 9.24E−08 |
| F5.1.9 | 1.33E−08 | very weak |
| 16C3 | 6.37E−10 | 5.16E−10 |
| d1C7 | 5.36E−10 | >=1.08E−07 |
| 5344 | <=5.00E−11* | >=5.0E−08 |
| F5.1.11.02 | 1.14E−10 | ~2.11E−07 |

*off-rate was outside the specifications of the instrument, an off-rate of 5.0E−05 or less has been assumed.

Example 8. IL-2/Fab Complex Receptor Binding Affinity

Figure 29:
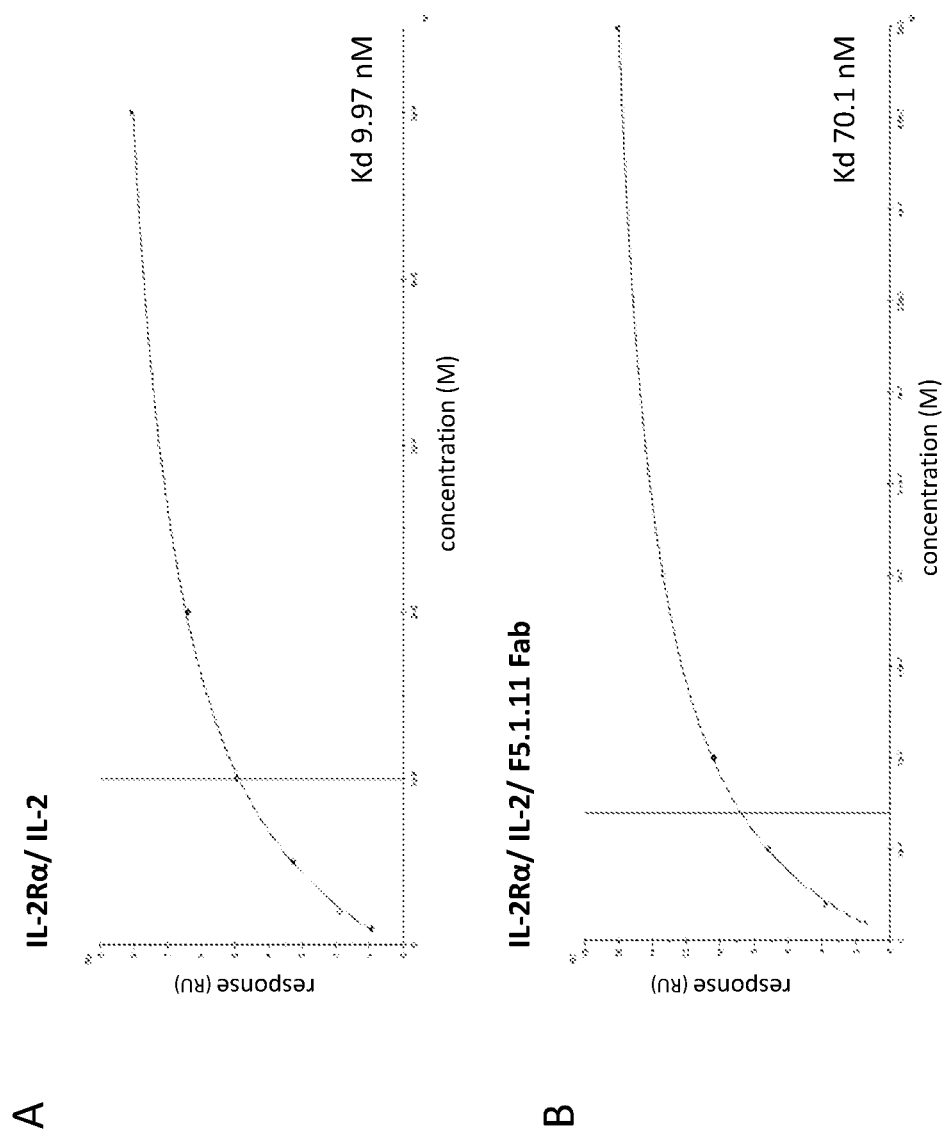
FIGS. 29A-B depict an equilibrium binding analysis for IL-2Rα binding to increasing concentrations of IL-2 (A) and IL-2/F5.1.11 Fab (B).

The affinity of IL-2Rα for IL-2 or the IL-2/F5.1.11 Fab complex was measured using a Biacore T200 Instrument (GE Healthcare, Piscataway, N.J.). Recombinant IL-2α was biotin labeled and captured on a Biacore Streptavidin chip (GE Healthcare). Experiments were performed at 25° C. using a 10 µL/minute flow rate in 10 mM HEPES (pH7.4), 150 mM NaCl and 0.005% v/v Surfactant P20 buffer. IL-2 (1-50 nM) or IL-2/F5.1.11 Fab (1-500 nM IL-2 with excess Fab pre-complexed) was were injected over the receptor coupled chip surface for 120 seconds at 30 µL/minute and allowed to dissociate for 5 minutes. Data was background subtracted using the adjacent control flow cell and buffer only injections. The affinity of the interaction was calculated from concentration-response relationship at equilibrium.
Results
The IL-2/F5.1.11 Fab complex binds to IL-2Rα with a lower affinity compared to unliganded IL-2. Equilibrium binding analysis of the complex and unliganded IL-2 found the F5.1.11 Fab bound IL-2 has an approximately 7-fold weaker affinity for IL-2Rα (9.97 nM compared to 70.1 nM) (FIGS. 29A-B). This result is consistent with the reduced binding observed in the IL-2/antibody complex receptor binding assay (Example 2) and the analysis of the IL-2/F5.1.11 Fab crystal structure (Example 9).

Example 9. Crystal Structure of the F5.1.11 Fab Bound to Human IL-2

Figure 30:
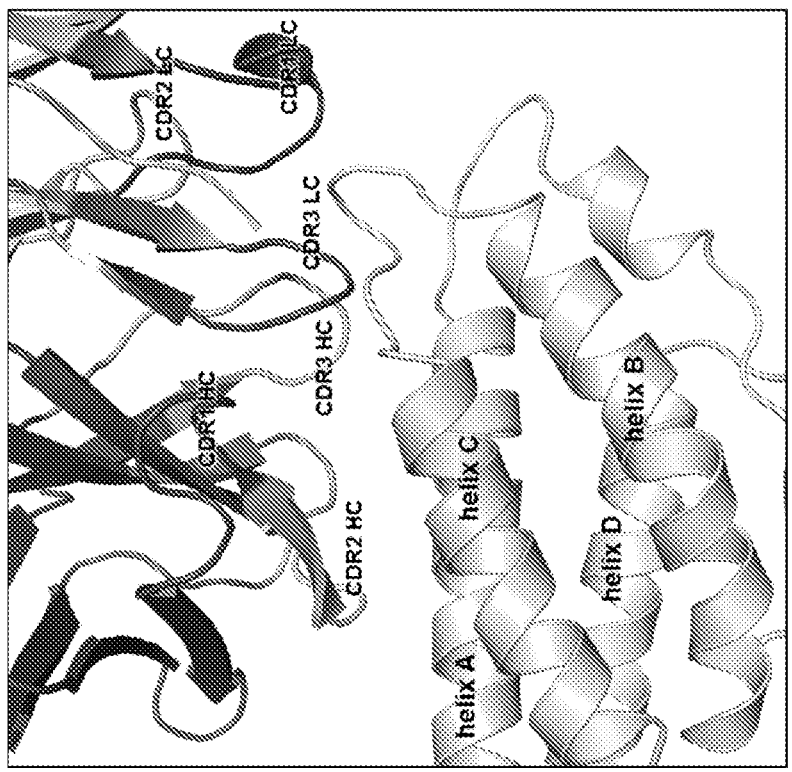
FIG. 30 depicts the F5.1.11 Fab interaction with IL-2 via the light chain (LC) CDR1 and CDR3 loops and the heavy chain (HC) CDR2 and CDR3 loops.
Figure 31:
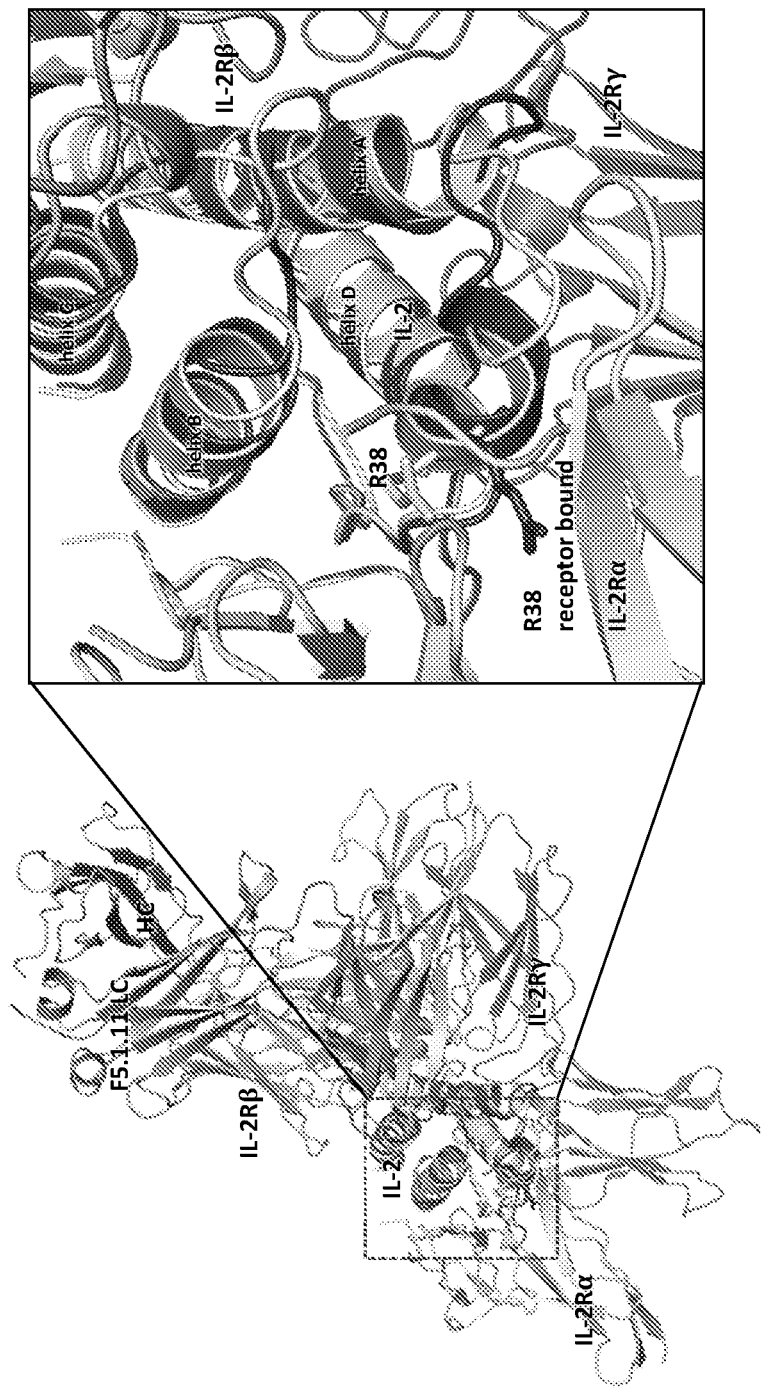
FIG. 31 depicts the F5.1.11 Fab/IL-2 complex overlaid with the IL-2-receptor quaternary complex showing the binding sites of the F5.1.11 Fab and IL-2Rβ are overlapping (left hand panel). The IL-2 conformation when bound to the F5.1.11 Fab shows a conformational change relative to the receptor bound IL-2 resulting in an allosteric modulation of the IL-2Rα binding site (right hand panel).

Interleukin-2 Expression and Purification
Full-length IL-2 (residues 1-133) was purified as described (Rickert et al., 2004). Briefly, the gene was cloned into the pAcgp67A vector in-frame with the gp67A signal sequence of the vector and followed by a C-terminal hexa-histidine tag (SEQ ID NO: 223). *Spodoptera frugiperda* (Sf9) cells were used to generate high-titer recombinant virus. Trichopulsia ni (High-Five) cells grown in Insect Xpress medium (Lonza) were infected with the virus and allowed to express protein for 48 hours at 28° C. The protein was purified by Ni-NTA and digested overnight with carboxypeptidases A and B at 4° C., then purified on a Superdex 200 gel filtration column (GE Healthcare).
Crystallization of 5.1.11 Fab Complex with Interleukin-2
F5.1.11 Fab was mixed with a 1.5-fold excess of IL-2 and the complex was purified by FPLC on a Superdex 200 column (GE Healthcare). The purified Fab/IL-2 complex was concentrated to 10 mg/mL as measured at 280 nm using an extinction coefficient of 1.49 mL*mg$^{-1}$*cm$^{-1}$. The complex was mixed with an equal volume of precipitant solution (100 mM sodium citrate, pH 5.0; 20% polyethylene glycol 6000) and crystallized by sitting drop vapor diffusion over a reservoir of precipitant solution. Prismatic crystals formed within one week. Crystals were cryoprotected by addition of glycerol to 30% (v/v), harvested, and rapidly cooled by plunging into liquid nitrogen.
Crystallographic Data Collection and Refinement
Diffraction data were collected at the Advanced Light Source Beam line 8.2.1 (Berkeley, Calif.). The crystals were indexed in space group P2$_1$ with unit cell dimensions a=86.01 Å, b=145.73 Å, c=107.32 Å, β=95.38°. A maximum resolution of 2.75 Å was used for structure solution and refinement. The structure was solved by molecular replacement using the program Phaser (McCoy et al., 2007). Search models included the heavy chain constant domain from PDB entry 3U1S, the heavy chain variable domain from 4NPY, the light chain constant domain from 3N9G, the light chain variable domain from 4HP0, and interleukin-2 from 2B5I (Wang et al., 2005; McLellan et al., 2011; Ogata et al., 2013; Sok et al., 2013; Kaufmann et al.). Four copies of the Fab/IL-2 complex were modeled in the asymmetric unit. The structure was built by iterative cycles of manual rebuilding and refinement using the programs Coot (Emsley et al., 2010) and PHENIX (Adams et al., 2010). Protein-protein interactions were analyzed by visual inspection in Coot and with PISA (Krissinel and Henrick, 2005; 2007). A homology model of cynomologus monkey (*Macaca fascicularis*) IL-2 was prepared with I-TASSER (Roy et al., 2010; Yang et al., 2015), using the human apo-IL-2 (PDB ID 1M47 (Arkin et al., 2003)) as a template.
Results
F5.1.11 interacts with the IL-2 at helices A and C and the B-C loop via the light chain CDR1 and CDR3 loops and the heavy chain CDR2 and CDR3 loops (FIG. 30). Comparison to the IL-2/IL-2Rβ/γ$_c$/CD25 quaternary structure (PDB ID 2B5I) reveals that F5.1.11 occludes the IL-2Rβ binding site of IL-2 but not the CD25 or γ$_c$ binding sites. The overall structure of IL-2 is similar to the apo structure (RMSD 0.359 Å over 95 Cα atoms). A significant perturbation occurs where F5.1.11 binds the B-C loop of IL-2; this perturbation is propagated to the adjacent IL-2 A-B loop (FIG. 31). Since the A-B loop forms part of the CD25 binding site in the quaternary complex, this movement may explain the decreased affinity of F5.1.11/IL-2 for CD25.
To explain the weak cross-reactivity of F5.1.11 to cynomolgus monkey IL-2, we generated a homology model of cynomolgus monkey IL-2 based on the apo human IL-2 structure. Although the sequences are 95% identical, an insertion in the B-C loop of cyno IL-2 appears likely to disrupt the interaction with the light chain CDR1 residues (Ala30, Ser31, Asn32, and Tyr33) and heavy chain CDR3 residues (Gly105 and Asp106) (FIG. 32).
In order to improve binding of mAb F5.1.11.02 to non-human primate IL-2, target mAb residues whose side chains contact the IL-2 loop that varies between human and cyno IL-2 were chosen based on the F5.1.11 Fab/hIL-2 crystal structure. Codons corresponding to residues Gly105, Asp106 of CDRH3 in the heavy chain and Ala30, Ser31, Asn32, Tyr33 of CDRL1 in the light chain were randomized combinatorially by PCR with degenerate oligonucleotides encoding 19 amino acids (excluding cysteine). The resulting library in scFv format was screened by surface display methods for binding to both cyno and human IL-2.

Example 10. Diabetes Remission by IL-2 Complex Anti-IL-2:IL-2 Complex Treatment

PBMCs were isolated from healthy donors by ficoll and activated overnight with 12.5 ng/mL antiCD3 and 25 ng/mL antiCD28. After an over night incubation, cells were harvested and labeled with CellTrace Violet (Life technology) at the concentration of 1 µL CTV/10×10$^6$ cells. After the staining, the cells were extensively washed in PBS and resuspended at the concentration of 30×10$^6$ cells in 200 µL of PBS. PBMCs were injected i.v. in NSG recipients. Antibody:IL-2 complexes were formed by incubating isotype or anti-IL-2 antibody, at concentrations indicated, with 8000 U human IL2 (Proleukin) for 30 minutes at 37° C. The NSG mice injected with human PBMCs received an intraperitoneal injection daily for 5 days of antibody:IL-2 complex.
Isolation of Splenocytes and Cell Staining
Mice were sacrificed with CO$_2$ and splenocytes were harvested and stained extracellularly with anti human CD45 Pacific Orange, CD4 PercPCy 5.5, CD3 PeCy7/Pacific Blue/PercP, CD25 APC-Cy7/Pe, CD238 Pe, CD39 PeCy7, CD8 APC-H7, Ki67 Pe, NKG2D PeCy7, CD44 V450 and intracellularly with anti human Helios FITC and FoxP3 APC. FoxP3 buffer kit (eBioscience) was used for fixation and permeabilization, as per manufacturer's instructions, prior to intracellular staining. Labeled antibodies were purchased from BD PharMingen or Ebioscience. Stained single cells suspensions were analyzed with a Fortessa flow cytometer running FACSDiva (BD Biosciences) and FSC 3.0 files analyzed and presented with FLOWJO Software.

Diabetes Remission by IL2 Complex

Spontaneous new-onset diabetic NOD mice (one blood glucose concentration between 250 mg/dl and 350 mg/dl) were treated for 5 days with 8,000 U hIL-2 (Proleukin) complexed with 125 µg of Isotype or 125 µg of F5.1.11.02 and 0.5 µg mIL2 (Ebioscience) complexed with 5 µg of JES6-1 (Ebioscience). Blood glucose concentrations were monitored over time.

After 1 week of remission, some mice were sacrificed and the pancreas was analyzed. Whole pancreas was prepared by digesting for 30 minutes at 37° C. with 0.8 mg/mL Collagenase P and 20 µg/mL DNase (Roche) followed by mincing. After digestion, the homogenate was filtered twice by using a 40 µm cell strainer and stained extracellularly with CD45 PercP Cy5.5, CD25 Pe, CD4 PeCy7, CD8 Al647, Thy1.2 BV605 and intracellularly with FoxP3 FITC. Labeled antibodies were purchased from BD Pharmingen or Ebioscience. Stained single cell suspensions were analyzed and presented with FLOWJO software.

Results

Figure 35A:
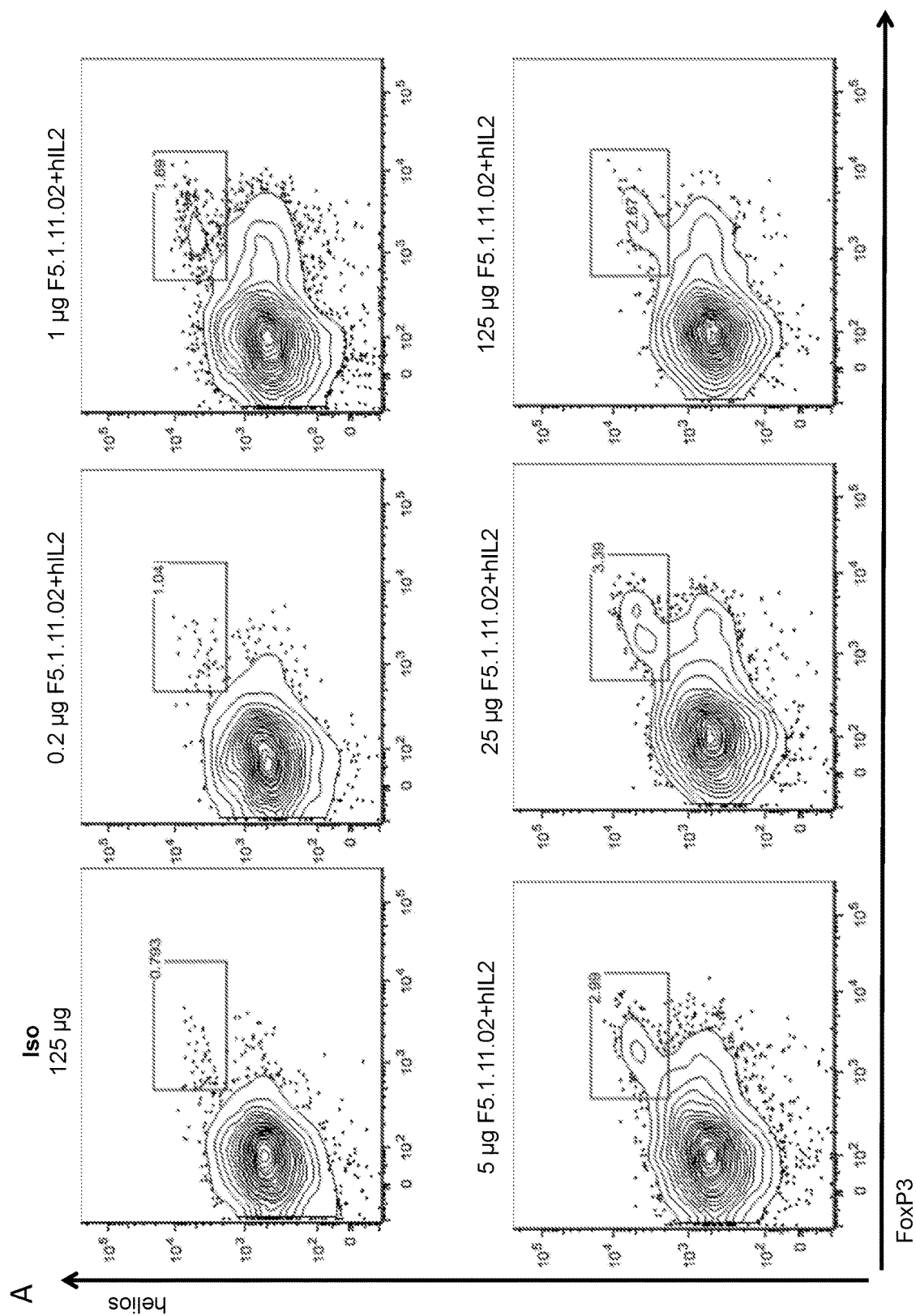
FIGS. 35A-B depict F5.1.11.02 antibody:IL-2 complex effects on Treg, CD4, and CD8 total cell numbers five days after treatment.
Figure 35B:
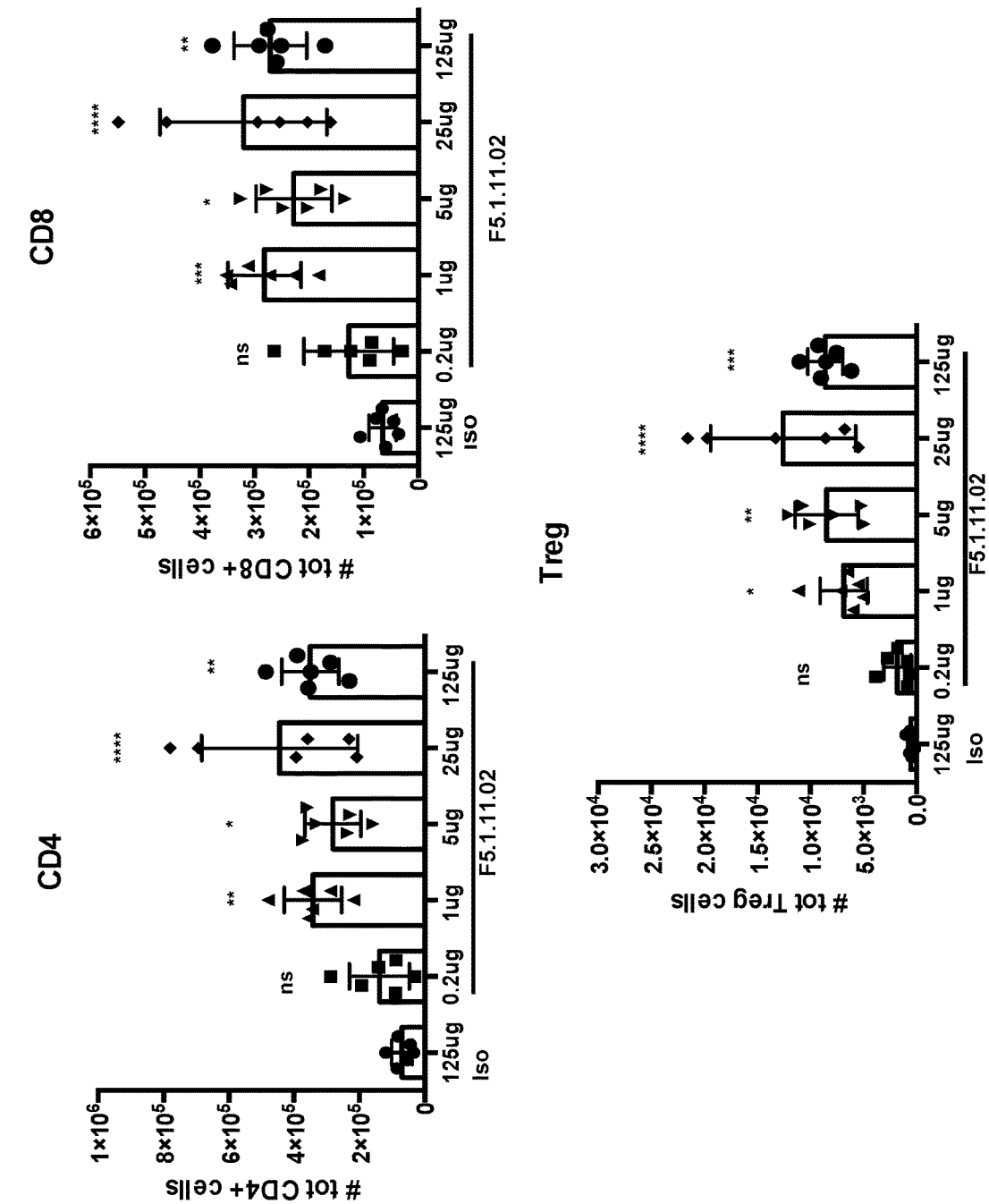

The treatment with F5.1.11.02 in complex with hIL2 (F5.1.11.02:IL2 complex) induced an increase in the percent of Tregs in the spleen. Treg population was gated on hCD45$^+$ CD3$^+$ CD4$^+$ Helios$^+$ FoxP3$^+$ cells. F5.1.11.02 antibody:IL-2 complex increased Tregs total cell number, although an increase in total CD4 and CD8 cell number was also observed (FIGS. 35 A-B). Overall, the ratios of Treg/CD4 and Treg/CD8 (FIG. 36A) were increased in a dose dependent manner. The effect was significant starting at the dose of 1 µg.

By including CTV labeling prior to transfer and treatment, we observed that treatment with F5.1.11.02 antibody:IL-2 complex induced increased proliferation of Tregs compared to isotype. Proliferation of CD8 T cells was also increased by treatment with F5.1.11.02 antibody:IL-2 complex, however greater numbers of undivided cells remained in the CD8 population than in Treg population (FIG. 36B). Overall, this CTV data supports an increase in Treg proliferation as underlying the shift in Treg/CD8 ratio observed.

Figure 38:
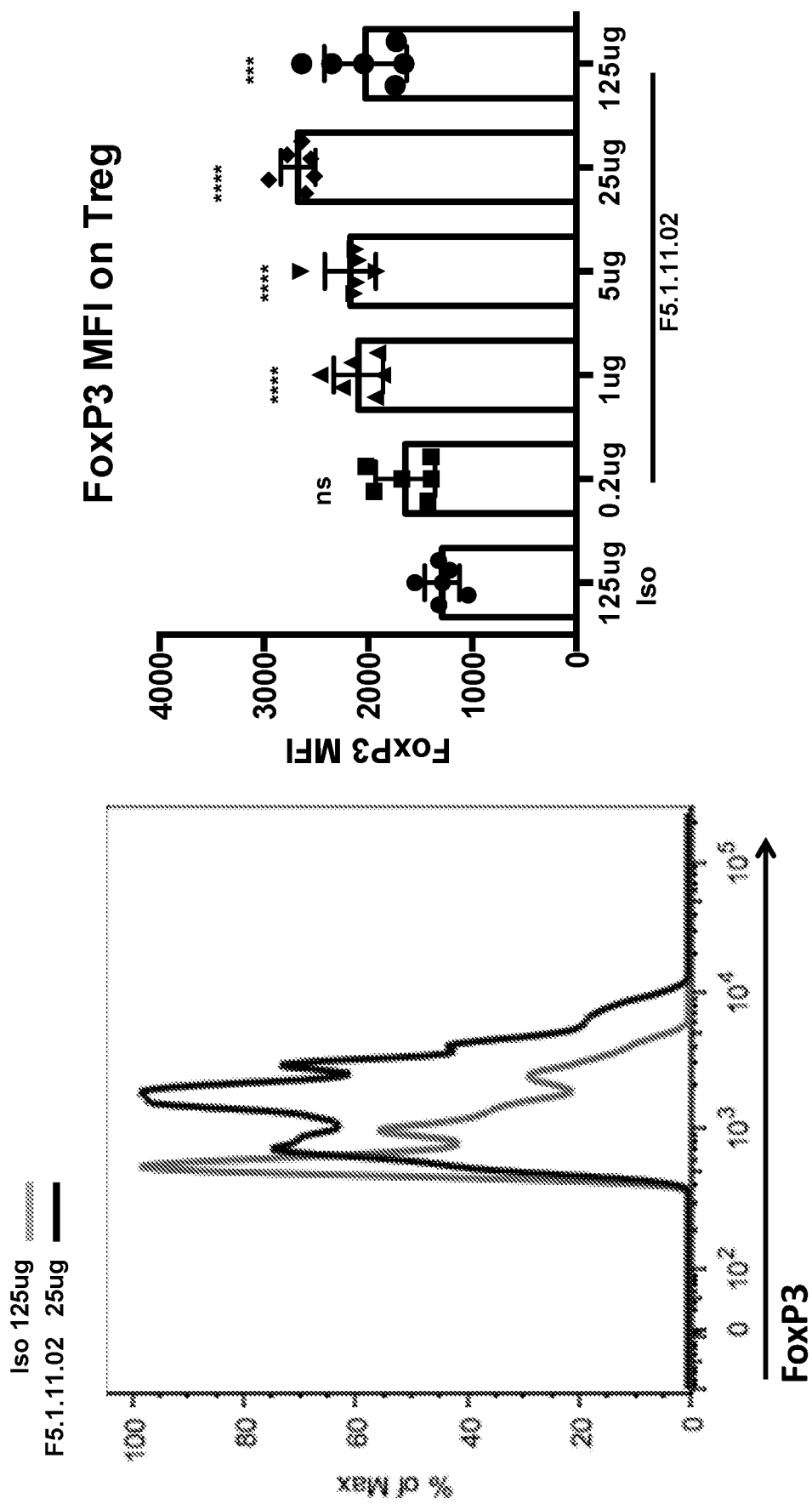
FIG. 38 depicts the effects of treatment with F5.1.11.02 antibody:IL-2 complex on FoxP3 mean fluorescent intensity (MFI) on Tregs.

In the spleen the treatment with all doses of the complex induced an increase of CD25 mean fluorescent intensity (MFI) on Tregs and CD8 population compared to isotype control. However, the absolute expression of CD25 on Tregs was many folds higher than on CD8 cells (FIGS. 37A-B). In addition, after treatment with F5.1.11.02:IL-2 complex, an increase in FoxP3 MFI on Tregs was also observed (FIG. 38). Together, these data suggest that the expanded Tregs maintain phenotype and function.

In vitro data have suggested that anti-IL2 antibodies that block the binding of IL2Rb to IL-2 will be better able to promote differential Treg expansion. In order to directly test this hypothesis, we compared antibodies that blocked different receptor epitopes on IL-2: an IL-2Rα blocker (16C3.4), an IL2Rβ blocker (d1C7), and an IL2Rβ blocker that also reduced IL2's binding to IL-2Rα (F5.1.11.02). All three antibodies in complex with hIL2 increased Treg cell number, and to a lesser extent CD4 and CD8 cell numbers also increased. The increase in CD8 cell number was much greater in response to 16C3.4 than to either of the IL-2Rb blocking antibodies (d1C7 or F5.1.11.02) (FIG. 39A).

Figure 39:
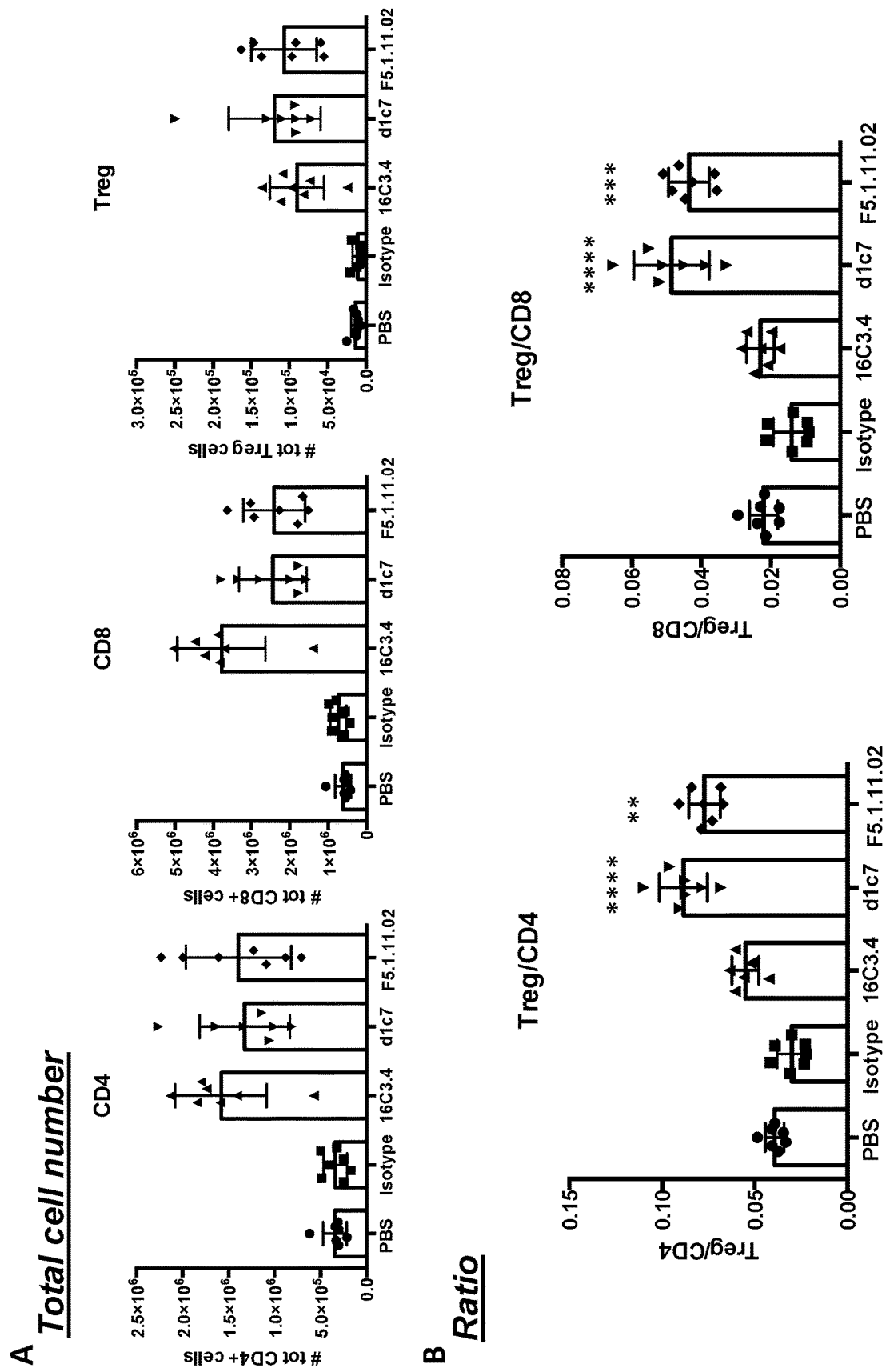
FIGS. 39A-B depict promotion of differential Treg expansion using antibodies that bind different epitopes on IL-2 thereby inhibiting binding to different receptor epitopes/binding domains: an IL-2Rα blocker (16C3.4), an IL2Rβ blocker (d1C7), and an IL2Rβ blocker that also reduced IL2's binding to IL-2Rα (F5.1.11.02). Statistical one-way ANOVA 16C3.4 vs d1c7 or 16C3.4 vs F5.1.11.02.
Figure 40:
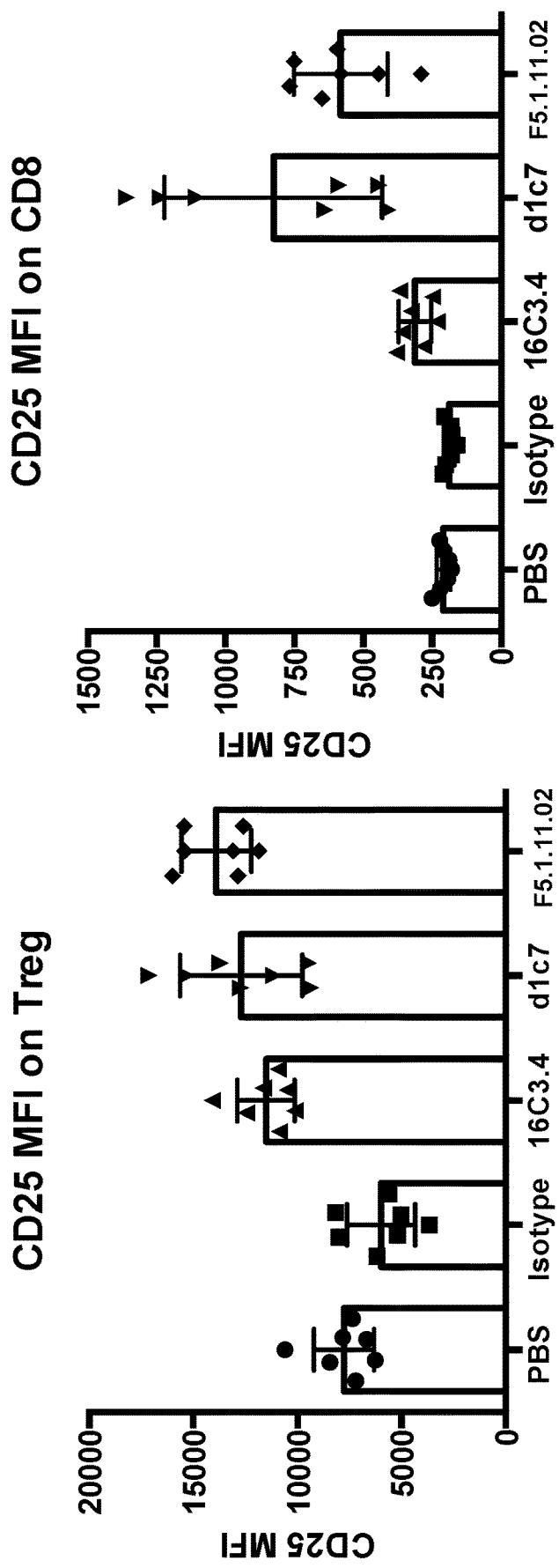
FIG. 40 depicts the effects of treatment with 16C3.4, d1C7, and F5.1.11.02 on CD25 mean fluorescent intensity (MFI) on Treg and CD8 populations compared to isotype control.

Consistent with the altered cell numbers, d1C7 and F5.1.11.02:IL-2 complex showed an increase in Treg/CD4 and Treg/CD8 ratios, which was not observed with 16C3.4 (FIG. 39B). The treatment with d1C7 and F5.1.11.02 in complex increased CD25 MFI on Treg and CD8, however the CD25 expression on CD8 was higher with d1C7, suggesting that F5.1.11.02 might be more selective for Tregs (FIG. 40).

Figure 41:
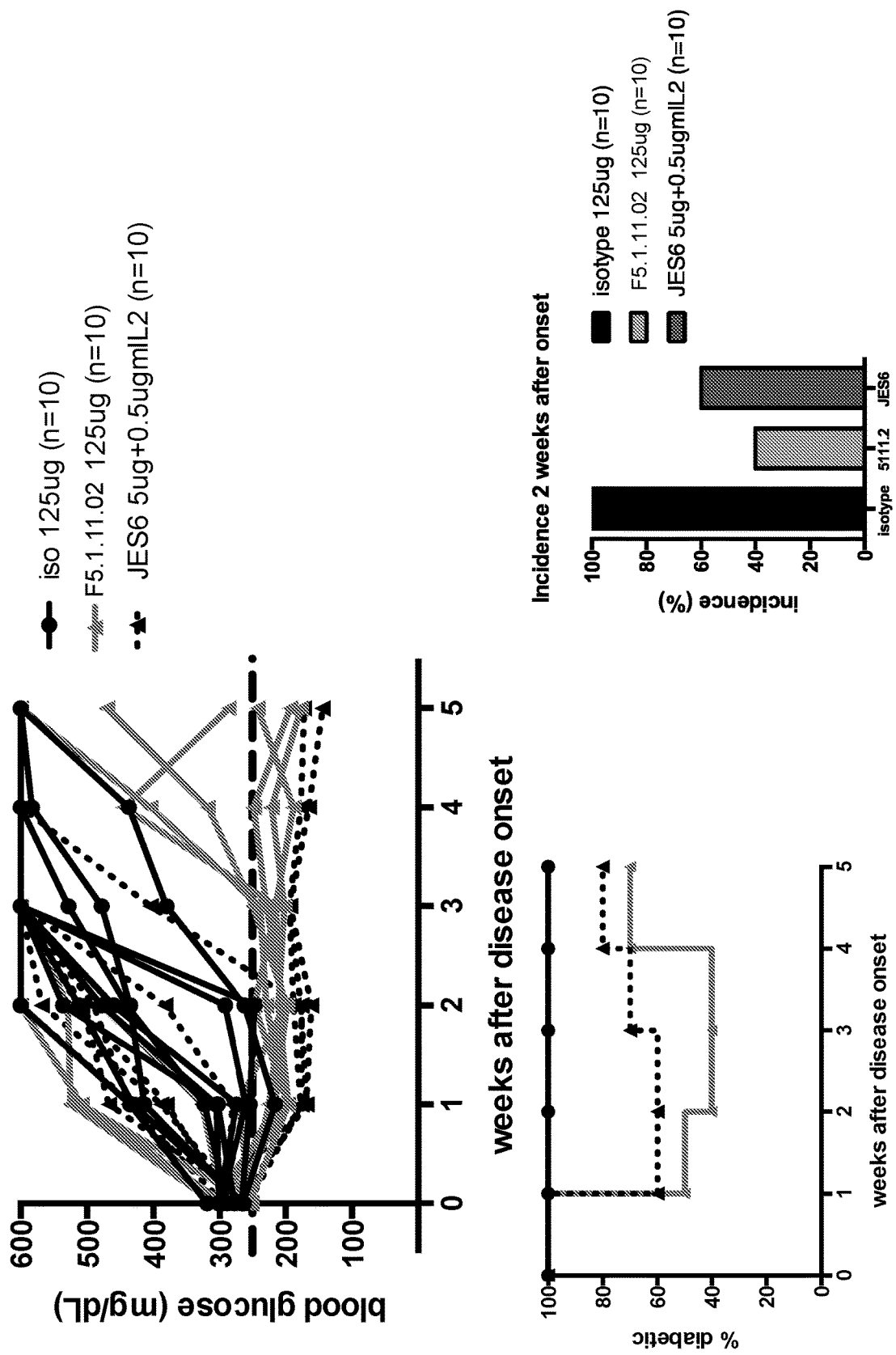
FIG. 41 depicts diabetes remission by F5.1.11.02 antibody:IL-2 complex.

Lastly, we assessed if 5 days of F5.1.11.02:IL-2 complex administration could be effective to cure clinical diabetes in NOD mice. Remarkably, this treatment induced diabetes remission in 50% of the mice within 1 week and most of them remained normoglycemic over the 4 week duration of the experiment. JES6-1:mouse IL-2 complex provided a less curative effect than F5.1.11.02 and no effect was observed in response to isotype (FIG. 41).

To establish whether the F5.1.11.02 antibody:IL-2 complex effect was related to a modification of Treg numbers and characteristics in the pancreas, we quantified their proportion in the pancreas after 1 week of remission. We observed that the percentage of pancreatic Treg was significantly increased after treatment with F5.1.11.02 in complex. We also observed that the treatment with the complex was associated with a rise in the expression of markers associated with Treg cell function, such as CD25 and FoxP3, which was not observed with isotype control (FIG. 42). Overall these data suggest that Treg increase in the pancreas after treatment might control the progression to destructive insulitis in diabetic mice.

REFERENCES

Adams P D, Afonine P V, Bunkoczi G, Chen V B, Davis I W, Echols N, et al. PHENIX: a comprehensive Python-based system for macromolecular structure solution. Acta Cryst (2010). D66, 213-221 [doi:10.1107/S0907444909052925]. International Union of Crystallography; 2010 Jan. 22; 1-9.

Arkin M R, Randal M, DeLano W L, Hyde J, Luong T N, Oslob J D, et al. Binding of small molecules to an adaptive protein-protein interface. Proc Natl Acad Sci USA. 2003 Feb. 18; 100(4):1603-8. PMCID: PMC149879

Emsley P, Lohkamp B, Scott W G, Cowtan K. research papers. Acta Cryst (2010). D66, 486-501 [doi:10.1107/50907444910007493]. International Union of Crystallography; 2010 Mar. 24; 1-16.

Kaufmann B, Vogt M R, Goudsmit J, Holdaway H A, Aksyuk A A, Chipman P R, et al. Neutralization of West Nile virus by cross-linking of its surface proteins with Fab fragments of the human monoclonal antibody CR4354. pnas.org.

Krissinel E, Henrick K. Detection of protein assemblies in crystals. Berthold M R, Glen R C, Diederichs K, Kohlbacher O, Fischer I, editors. Computational Life Sciences. Berlin: Springer; 2005. p. 163-74.

Krissinel E, Henrick K. Inference of Macromolecular Assemblies from Crystalline State. J Mol Biol. 2007 September; 372(3):774-97.

McCoy A J, Grosse-Kunstleve R W, Adams P D, Winn M D, Storoni L C, Read R J. research papers. J. Appl. Cryst (2007). 40, 658-674 [doi:10.1107/S0021889807021206]. International Union of Crystallography; 2007 Jul. 13; 1-17.

McLellan J S, Pancera M, Carrico C, Gorman J, Julien J-P, Khayat R, et al. Structure of HIV-1 gp120 V1/V2 domain with broadly neutralizing antibody PG9. Nature. Nature Publishing Group; 2011 Dec. 15; 480(7377):336-43.

Ogata M, Umemoto N, Ohnuma T, Numata T, Suzuki A, Usui T, et al. A Novel Transition-state Analogue for Lysozyme, 4-O-Tri-N-acetylchitotriosyl Moranoline, Provided Evidence Supporting the Covalent Glycosyl-enzyme Intermediate. Journal of Biological Chemistry. 2013 Mar. 1; 288(9):6072-82.

Rickert M, Boulanger M J, Goriatcheva N, Garcia K C. Compensatory energetic mechanisms mediating the assembly of signaling complexes between interleukin-2 and its alpha, beta, and gamma(c) receptors. J Mol Biol. 2004 Jun. 18; 339(5):1115-28.

Roy A, Kucukural A, Zhang Y. I-TASSER: a unified platform for automated protein structure and function prediction. Nat Protoc. 2010 April; 5(4):725-38. PMCID: PMC2849174

Sok D, Laserson U, Laserson J, Liu Y, Vigneault F, Julien J-P, et al. The Effects of Somatic Hypermutation on Neutralization and Binding in the PGT121 Family of Broadly Neutralizing HIV Antibodies. PLOS Pathog. Public Library of Science; 2013 Nov. 21; 9(11):e1003754.

Wang X, Rickert M, Garcia K C. Structure of the quaternary complex of interleukin-2 with its alpha, beta, and gammac receptors. Science. 2005 Nov. 18; 310(5751):1159-63.

Yang J, Yan R, Roy A, Xu D, Poisson J, Zhang Y. The I-TASSER Suite: protein structure and function prediction. Nat Methods. 2015; 12:7-8.

Particular embodiments of the invention are set forth in the following numbered paragraphs:

1. An isolated antibody or an antigen-binding portion thereof that specifically binds human IL-2 (hIL-2), wherein the antibody binds helices A and C and the B-C loop of hIL-2.
2. An isolated antibody or an antigen-binding portion thereof that competes for binding to human IL-2 (hIL-2) with, or binds the same epitope of hIL-2 as, an antibody comprising the amino acid sequences of SEQ ID NOs: 13 and 14.
3. An isolated antibody or an antigen-binding portion thereof that specifically binds human IL-2 (hIL-2), wherein the antibody reduces the binding affinity of hIL-2 to IL-2Rα by 1 to 199 fold.
4. The antibody or antigen-binding portion of paragraph 3, wherein the antibody reduces the binding affinity of hIL-2 to IL-2Rα by 10 fold.
5. An isolated antibody or an antigen-binding portion thereof that specifically binds human IL-2 (hIL-2), wherein the antibody reduces hIL-2 binding to IL-2Rα and IL-2Rβ, and inhibits an activity in CD8$^+$ T cells to a higher degree than in regulatory T (Treg) cells.
6. An isolated antibody or an antigen-binding portion thereof that specifically binds human interleukin-2 (hIL-2), wherein the antibody reduces hIL-2 binding to IL-2Rα and IL-2Rβ, and inhibits STAT5 phosphorylation in CD8$^+$ T cells to a higher degree than in regulatory T (Treg) cells.
7. An isolated antibody or an antigen-binding portion thereof that specifically binds human interleukin-2 (hIL-2), wherein the antibody reduces hIL-2 binding to IL-2Rα and IL-2Rβ, and increases the ratio of regulatory T (Treg) cells to CD8$^+$ or CD4$^+$ T cells or to NK cells as measured in a peripheral blood mononuclear cell (PBMC) culture or reconstitution assay.
8. An isolated antibody or an antigen-binding portion thereof that specifically binds human interleukin-2 (hIL-2), wherein the antibody reduces hIL-2 binding to IL-2Rα and IL-2Rβ, and increases expression of one or more of FOXP3, CD25, and Icos in regulatory T (Treg) cells.
9. The isolated antibody or antigen-binding portion of any one of paragraphs 1-8, wherein the antibody or antigen-binding portion has at least one of the following properties:
   a) binding to hIL-2 with an off-rate greater than about $4.53 \times 10^{-4}$ s$^{-1}$; and
   b) binding to hIL-2 with a K$_D$ greater than about $1.14 \times 10^{-10}$ M.
10. The antibody or antigen-binding portion of any one of paragraphs 1-9, wherein the antibody is a human antibody.
11. The antibody or antigen-binding portion of any one of paragraphs 1-10, comprising:
   (a) a HCDR1 comprising SEQ ID NO: 73 (Kabat), 74 (Chothia), or 75 (extended); a HCDR2 comprising SEQ ID NO: 76 (Kabat), or 77 (Chothia); a HCDR3 comprising SEQ ID NO: 78; a LCDR1 comprising SEQ ID NO: 79; a LCDR2 comprising SEQ ID NO: 80; and a LCDR3 comprising SEQ ID NO: 81;
   (b) a HCDR1 comprising SEQ ID NO: 82 (Kabat), 83 (Chothia), or 84 (extended); a HCDR2 comprising SEQ ID NO: 85 (Kabat), or 86 (Chothia); a HCDR3 comprising SEQ ID NO: 87; a LCDR1 comprising SEQ ID NO: 88; a LCDR2 comprising SEQ ID NO: 89; and a LCDR3 comprising SEQ ID NO: 90;
   (c) a HCDR1 comprising SEQ ID NO: 91 (Kabat), 92 (Chothia), or 93 (extended); a HCDR2 comprising SEQ ID NO: 94 (Kabat), or 95 (Chothia); a HCDR3 comprising SEQ ID NO: 96; a LCDR1 comprising SEQ ID NO: 97; a LCDR2 comprising SEQ ID NO: 98; and a LCDR3 comprising SEQ ID NO: 99;
   (d) a HCDR1 comprising SEQ ID NO: 100 (Kabat), 101 (Chothia), or 102 (extended); a HCDR2 comprising SEQ ID NO: 103 (Kabat), or 104 (Chothia); a HCDR3 comprising SEQ ID NO: 105; a LCDR1 comprising SEQ ID NO: 106; a LCDR2 comprising SEQ ID NO: 107; and a LCDR3 comprising SEQ ID NO: 108;
   (e) a HCDR1 comprising SEQ ID NO: 109 (Kabat), 110 (Chothia), or 111 (extended); a HCDR2 comprising SEQ ID NO: 112 (Kabat), or 113 (Chothia); a HCDR3 comprising SEQ ID NO: 114; a LCDR1 comprising SEQ ID NO: 115; a LCDR2 comprising SEQ ID NO: 116; and a LCDR3 comprising SEQ ID NO: 117;
   (f) a HCDR1 comprising SEQ ID NO: 118 (Kabat), 119 (Chothia), or 120 (extended); a HCDR2 comprising SEQ ID NO: 121 (Kabat), or 122 (Chothia); a HCDR3 comprising SEQ ID NO: 123; a LCDR1 comprising SEQ ID NO: 124; a LCDR2 comprising SEQ ID NO: 125; and a LCDR3 comprising SEQ ID NO: 126;
   (g) a HCDR1 comprising SEQ ID NO: 127 (Kabat), 128 (Chothia), or 129 (extended); a HCDR2 comprising SEQ ID NO: 130 (Kabat), or 131 (Chothia); a HCDR3 comprising SEQ ID NO: 132; a LCDR1 comprising SEQ ID NO: 133; a LCDR2 comprising SEQ ID NO: 134; and a LCDR3 comprising SEQ ID NO: 135;
   (h) a HCDR1 comprising SEQ ID NO: 136 (Kabat), 137 (Chothia), or 138 (extended); a HCDR2 comprising SEQ ID NO: 139 (Kabat), or 140 (Chothia); a HCDR3 comprising SEQ ID NO: 141; a LCDR1 comprising SEQ ID NO: 142; a LCDR2 comprising SEQ ID NO: 143; and a LCDR3 comprising SEQ ID NO: 144;
   (i) a HCDR1 comprising SEQ ID NO: 145 (Kabat), 146 (Chothia), or 147 (extended); a HCDR2 comprising SEQ ID NO: 148 (Kabat), or 149 (Chothia); a HCDR3 comprising SEQ ID NO: 150; a LCDR1 comprising SEQ ID NO: 151; a LCDR2 comprising SEQ ID NO: 152; and a LCDR3 comprising SEQ ID NO: 153;
   (j) a HCDR1 comprising SEQ ID NO: 154 (Kabat), 155 (Chothia), or 156 (extended); a HCDR2 comprising SEQ ID NO: 157 (Kabat), or 158 (Chothia); a HCDR3 comprising SEQ ID NO: 159; a LCDR1 comprising SEQ ID NO: 160; a LCDR2 comprising SEQ ID NO: 161; and a LCDR3 comprising SEQ ID NO: 162;
(k) a HCDR1 comprising SEQ ID NO: 163 (Kabat), 164 (Chothia), or 165 (extended); a HCDR2 comprising SEQ ID NO: 166 (Kabat), or 167 (Chothia); a HCDR3 comprising SEQ ID NO: 168; a LCDR1 comprising SEQ ID NO: 169; a LCDR2 comprising SEQ ID NO: 170; and a LCDR3 comprising SEQ ID NO: 171;
(l) a HCDR1 comprising SEQ ID NO: 172 (Kabat), 173 (Chothia), or 174 (extended); a HCDR2 comprising SEQ ID NO: 175 (Kabat), or 176 (Chothia); a HCDR3 comprising SEQ ID NO: 177; a LCDR1 comprising SEQ ID NO: 178; a LCDR2 comprising SEQ ID NO: 179; and a LCDR3 comprising SEQ ID NO: 180;
(m) a HCDR1 comprising SEQ ID NO: 181 (Kabat), 182 (Chothia), or 183 (extended); a HCDR2 comprising SEQ ID NO: 184 (Kabat), or 185 (Chothia); a HCDR3 comprising SEQ ID NO: 186; a LCDR1 comprising SEQ ID NO: 187; a LCDR2 comprising SEQ ID NO: 188; and a LCDR3 comprising SEQ ID NO: 189;
(n) a HCDR1 comprising SEQ ID NO: 190 (Kabat), 191 (Chothia), or 192 (extended); a HCDR2 comprising SEQ ID NO: 193 (Kabat), or 194 (Chothia); a HCDR3 comprising SEQ ID NO: 195; a LCDR1 comprising SEQ ID NO: 196; a LCDR2 comprising SEQ ID NO: 197; and a LCDR3 comprising SEQ ID NO: 198;
(o) a HCDR1 comprising SEQ ID NO: 199 (Kabat), 200 (Chothia), or 201 (extended); a HCDR2 comprising SEQ ID NO: 202 (Kabat), or 203 (Chothia); a HCDR3 comprising SEQ ID NO: 204; a LCDR1 comprising SEQ ID NO: 205; a LCDR2 comprising SEQ ID NO: 206; and a LCDR3 comprising SEQ ID NO: 207;
(p) a HCDR1 comprising SEQ ID NO: 208 (Kabat), 209 (Chothia), or 210 (extended); a HCDR2 comprising SEQ ID NO: 211 (Kabat), or 212 (Chothia); a HCDR3 comprising SEQ ID NO: 213; a LCDR1 comprising SEQ ID NO: 214; a LCDR2 comprising SEQ ID NO: 215; and a LCDR3 comprising SEQ ID NO: 216; or
(q) a HCDR1 comprising SEQ ID NO: 217; a HCDR2 comprising SEQ ID NO: 218; a HCDR3 comprising SEQ ID NO: 219; a LCDR1 comprising SEQ ID NO: 220; a LCDR2 comprising SEQ ID NO: 221; and a LCDR3 comprising SEQ ID NO: 222.

12. The antibody or antigen-binding portion of any one of paragraphs 1-10, comprising:
(a) a heavy chain variable domain ($V_H$) comprising:
  i) an HCDR3 in SEQ ID NO: 1, 3, 5, 7, 9, 11, 13, 15, 17, 19, 21, 23, 25, 27, 29, or 71 as shown in Table 7; or
  ii) HCDR1-3 in SEQ ID NO: 1, 3, 5, 7, 9, 11, 13, 15, 17, 19, 21, 23, 25, 27, 29, or 71 as shown in Table 7; or
(b) a light chain variable domain ($V_L$) comprising:
  i) an LCDR3 in SEQ ID NO: 2, 4, 6, 8, 10, 12, 14, 16, 18, 20, 22, 24, 26, 28, 30, or 72 as shown in Table 7; or
  ii) LCDR1-3 in SEQ ID NO: 2, 4, 6, 8, 10, 12, 14, 16, 18, 20, 22, 24, 26, 28, 30, or 72 as shown in Table 7.

13. An isolated antibody or an antigen-binding portion thereof that specifically binds human interleukin-2 (hIL-2), comprising a heavy chain variable domain ($V_H$) comprising:
a) an HCDR3 in SEQ ID NO: 1, 3, 5, 7, 9, 11, 13, 15, 17, 19, 21, 23, 25, 27, 29, 31, or 71 as shown in Table 7;
b) HCDR1-3 in SEQ ID NO: 1, 3, 5, 7, 9, 11, 13, 15, 17, 19, 21, 23, 25, 27, 29, 31, or 71 as shown in Table 7; or
c) the amino acid sequence of SEQ ID NO: 1, 3, 5, 7, 9, 11, 13, 15, 17, 19, 21, 23, 25, 27, 29, 31, or 71.

14. An isolated antibody or an antigen-binding portion thereof that specifically binds human interleukin-2 (hIL-2), comprising a light chain variable domain ($V_L$) comprising:
a) an LCDR3 in SEQ ID NO: 2, 4, 6, 8, 10, 12, 14, 16, 18, 20, 22, 24, 26, 28, 30, 32, or 72 as shown in Table 7;
b) LCDR1-3 in SEQ ID NO: 2, 4, 6, 8, 10, 12, 14, 16, 18, 20, 22, 24, 26, 28, 30, 32, or 72 as shown in Table 7; or
c) the amino acid sequence of SEQ ID NO: 2, 4, 6, 8, 10, 12, 14, 16, 18, 20, 22, 24, 26, 28, 30, 32, or 72.

15. An isolated antibody or an antigen-binding portion thereof that specifically binds human IL-2 (hIL-2), wherein the antibody comprises the HCDR1-3 and LCDR1-3 amino acid sequences in:
SEQ ID NOs: 1 and 2,
SEQ ID NOs: 3 and 4,
SEQ ID NOs: 5 and 6,
SEQ ID NOs: 7 and 8,
SEQ ID NOs: 9 and 10,
SEQ ID NOs: 11 and 12,
SEQ ID NOs: 13 and 14,
SEQ ID NOs: 15 and 16,
SEQ ID NOs: 17 and 18,
SEQ ID NOs: 19 and 20,
SEQ ID NOs: 21 and 22,
SEQ ID NOs: 23 and 24,
SEQ ID NOs: 25 and 26,
SEQ ID NOs: 27 and 28,
SEQ ID NOs: 29 and 30,
SEQ ID NOs: 31 and 32, or
SEQ ID NOs: 71 and 72,
respectively, as shown in Table 7.

16. The isolated antibody or antigen-binding portion of paragraph 15, wherein the antibody comprises the amino acid sequences of
SEQ ID NOs: 1 and 2,
SEQ ID NOs: 3 and 4,
SEQ ID NOs: 5 and 6,
SEQ ID NOs: 7 and 8,
SEQ ID NOs: 9 and 10,
SEQ ID NOs: 11 and 12,
SEQ ID NOs: 13 and 14,
SEQ ID NOs: 15 and 16,
SEQ ID NOs: 17 and 18,
SEQ ID NOs: 19 and 20,
SEQ ID NOs: 21 and 22,
SEQ ID NOs: 23 and 24,
SEQ ID NOs: 25 and 26,
SEQ ID NOs: 27 and 28,
SEQ ID NOs: 29 and 30,
SEQ ID NOs: 31 and 32, or
SEQ ID NOs: 71 and 72.

17. The antibody or antigen-binding portion of paragraph 15 or 16, wherein the antibody is an IgG antibody.

18. The antibody or antigen-binding portion of paragraph 17, further comprising a heavy chain constant region comprising the amino acid sequence of SEQ ID NO: 33.

19. The antibody or antigen-binding portion of paragraph 17, further comprising a heavy chain constant region comprising the amino acid sequence of SEQ ID NO: 33 without the C-terminal lysine.

20. The antibody or antigen-binding portion of paragraph 18 or 19, further comprising a light chain constant region comprising the amino acid sequence of SEQ ID NO: 34 or 35.

21. An isolated nucleic acid encoding the heavy chain, the light chain, or both, of the antibody or antigen-binding portion of any one of paragraphs 11-20.
22. An isolated nucleic acid encoding the heavy chain, the light chain, or both, of an antibody or an antigen-binding portion thereof that specifically binds human interleukin-2 (hIL-2), wherein said nucleic acid comprises:
   a) the nucleotide sequence of SEQ ID NO: 36, 38, 40, 42, 44, 46, 48, 50, 52, 54, 56, 58, 60, 62, 64, or 66;
   b) the nucleotide sequence of SEQ ID NO: 37, 39, 41, 43, 45, 47, 49, 51, 53, 55, 57, 59, 61, 63, 65, or 67; or
   c) one of the following nucleotide sequence pairs:
     SEQ ID NOs: 36 and 37,
     SEQ ID NOs: 38 and 39,
     SEQ ID NOs: 40 and 41,
     SEQ ID NOs: 42 and 43,
     SEQ ID NOs: 44 and 45,
     SEQ ID NOs: 46 and 47,
     SEQ ID NOs: 48 and 49,
     SEQ ID NOs: 50 and 51,
     SEQ ID NOs: 52 and 53,
     SEQ ID NOs: 54 and 55,
     SEQ ID NOs: 56 and 57,
     SEQ ID NOs: 58 and 59,
     SEQ ID NOs: 60 and 61,
     SEQ ID NOs: 62 and 63,
     SEQ ID NOs: 64 and 65, or
     SEQ ID NOs: 66 and 67.
23. A vector comprising the nucleic acid of paragraph 21 or 22.
24. A host cell comprising the nucleic acid of paragraph 21 or 22 or the vector of paragraph 23.
25. The host cell of paragraph 24, wherein the cell is a mammalian cell.
26. A method of producing an antibody or an antigen-binding portion thereof that specifically binds human interleukin-2 (hIL-2), said method comprising:
   a) culturing the host cell of paragraph 24 or 25 under conditions that allow said antibody or antigen-binding portion to be expressed, wherein the host cell comprises nucleotide sequences coding the heavy chain and light chain of the antibody or antigen-binding portion, and
   b) isolating said antibody or antigen-binding portion from the culture.
27. An isolated antibody or an antigen-binding portion thereof that specifically binds human interleukin-2 (hIL-2), wherein the antibody competes for binding to hIL-2 with, or binds to the same epitope as, the antibody or antigen-binding portion of paragraph 16.
28. The antibody or antigen-binding portion of paragraph 27, wherein the antibody comprises a $V_H$ amino acid sequence and a $V_L$ amino acid sequence that are at least 95% identical to the following amino acid sequences, respectively:
   SEQ ID NOs: 1 and 2,
   SEQ ID NOs: 3 and 4,
   SEQ ID NOs: 5 and 6,
   SEQ ID NOs: 7 and 8,
   SEQ ID NOs: 9 and 10,
   SEQ ID NOs: 11 and 12,
   SEQ ID NOs: 13 and 14,
   SEQ ID NOs: 15 and 16,
   SEQ ID NOs: 17 and 18,
   SEQ ID NOs: 19 and 20,
   SEQ ID NOs: 21 and 22,
   SEQ ID NOs: 23 and 24,
   SEQ ID NOs: 25 and 26,
   SEQ ID NOs: 27 and 28,
   SEQ ID NOs: 29 and 30, or
   SEQ ID NOs: 31 and 32.
29. A pharmaceutical composition comprising the antibody or antigen-binding portion of any one of paragraphs 1-20, 27, and 28, and a pharmaceutically acceptable carrier or excipient.
30. A method for treating an inflammatory condition in a human subject, comprising administering to the subject an effective amount of the antibody or antigen-binding portion of any one of paragraphs 1-20, 27, and 28, or the pharmaceutical composition of paragraph 29.
31. A method for inducing immunosuppression in a human subject in need thereof, comprising administering to the subject an effective amount of the antibody or antigen-binding portion of any one of paragraphs 1-20, 27, and 28, or the pharmaceutical composition of paragraph 29.
32. An antibody or antigen-binding portion of any one of paragraphs 1-20, 27, and 28, or a pharmaceutical composition of paragraph 29, for use in treating a human subject having an inflammatory condition or in need of immunosuppression.
33. Use of an antibody or antigen-binding portion of any one of paragraphs 1-20, 27, and 28 in the manufacture of a medicament for treating an inflammatory condition or inducing immunosuppression in a human subject in need thereof.
34. The method of paragraph 30 or 31, the antibody, portion or pharmaceutical composition of paragraph 32, or the use of paragraph 33, wherein the subject has an autoimmune disease or graft versus host disease.
35. The method of paragraph 30 or 31, the antibody, portion or pharmaceutical composition of paragraph 32, or the use of paragraph 33, wherein the antibody or portion is administered in complex with IL-2.
36. The method of paragraph 30 or 31, the antibody, portion or pharmaceutical composition of paragraph 32, or the use of paragraph 33, wherein the subject has diabetes mellitus.
37. The method of paragraph 30 or 31, the antibody, portion or pharmaceutical composition of paragraph 32, or the use of paragraph 33, wherein the subject has Type I diabetes mellitus.
38. A composition comprising the antibody or antigen-binding portion of any one of paragraphs 1-20, 27, and 27 complexed with human IL-2.
39. A pharmaceutical composition comprising the antibody or antigen-binding portion of any one of paragraphs 1-20, 27, and 28, complexed with human IL-2, and a pharmaceutically acceptable carrier or excipient.
40. A method for treating an inflammatory condition in a human subject, comprising administering to the subject an effective amount of the antibody or antigen-binding portion of any one of paragraphs 1-20, 27, and 28 complexed with human IL-2, the pharmaceutical composition of paragraph 29, the composition of paragraph 38, or the pharmaceutical composition of paragraph 39.
41. An isolated antibody F5.1.11.02 or an antigen-binding portion thereof that specifically binds human interleukin-2 (hIL-2), wherein the antibody comprises: a heavy chain variable domain (VH) comprising the amino acid sequence encoded by the cDNA insert of the plasmid deposited under ATCC accession number PTA-123497 and/or a light chain variable domain (VL) comprising the amino acid sequence encoded by the cDNA insert of the plasmid deposited under ATCC accession number PTA-123498.

TABLE 7

Sequence Listing Table
Kabat CDR amino acid sequences are in bold. Chothia CDR amino acid
sequences are underlined. Extended CDR amino acid sequences include both
underlined and bold amino acid residues.

| | | |
|---|---|---|
| F4.7.6 VH | SEQ ID NO: 1 | EVQLQESGPGLVKPSQTLSLTCTVSGGS<u>IS</u>SGGYYWSWIRQ HPGKGLEWIG<u>YIYYSGSTY</u>YNPSLKSRVTISVDTSKNQFSLK LSSVTAADTAVYYCARTPTVTGDWFDPWGQGTLVTVSS |
| F4.7.6 VL | SEQ ID NO: 2 | NFMLTQPHSVSESPGKTVTISCTRSSGSIASNYVQWYQQRP GSSPTTVIYEDNQRPSGVPDRFSGSIDSSSNSASLTISGLKT EDEADYYCQSYDSSTVVFGGGTKLTVL |
| F4.7.8 VH | SEQ ID NO: 3 | QVQLVQSGAEVKKPGASVKVSCKASG<u>YTFTGYYMH</u>WVRQ APGQGLEWMGWINPNSGGTNYAQKFQGRVTMTRDTSISTA YMELSRLRSDDTAVYYCARDLTFDYWGQGTLVTVSS |
| F4.7.8 VL | SEQ ID NO: 4 | AIQLTQSPSSLSASVGDRVTITCQASQDIFNLLNWYRQKPGK APDLLVYRASNLETGVPSRFSGSGSGTDFTFTISSLQPEDV GTYYCQQSANLPLTFGGGTKVEIK |
| F5.1.11 VH | SEQ ID NO: 5 | QLQLQESGPGLVKPSQTLSLTCTVSGGS<u>IS</u>SGGYYWSWIRQ HPGKGLEWIG<u>YIYYSGSTY</u>YNPSLKSRVTISVDTSKNQFSLK LSSVTAADTAVYYCARTPTVTGDWFDPWGRGTLVTVSS |
| F5.1.11 VL | SEQ ID NO: 6 | NFMLTQPHSVSESPGKTVTISCTRSSGSIASNYVQWYQQRP GSSPTTVIYEDNQRPSGVPDRFSGSIDSSSNSASLTISGLKT EDEADYYCQSYDSSNVVFGGGTKLTVL |
| F5.1.9 VH | SEQ ID NO: 7 | EVQLVESGPGLVKPSETLSLTCAVSG<u>YSISSGGYYWG</u>WIRQP PGKGLEWIGSIYHSGSTYYNPSLKSRVTISVDTSKNQFSLKL SSVTAADTAVYYCAREAYSDRAFDIWGQGTMVTVSS |
| F5.1.9 VL | SEQ ID NO: 8 | NFMLTQPHSVSESPGKTITISCTRSSGSIASDYVQWYQQRP GSSPSTVIYADNQRPSEVPDRFSGSIDSSSNSASLTISGLMT EDEADYYCQSYDSNIVIFGGGTKLTVL |
| F4.7.062 VH | SEQ ID NO: 9 | QVQLQESGPGLVKPSQTLSLTCTVSGGS<u>IS</u>SGGYYWSWIRQ HPGKGLEWIG<u>YIYYSGSTY</u>YNPSLKSRVTISVDTSKNQFSLK LSSVTAADTAVYYCARTPTVTGDWFDPWGQGTLVTVSS |
| F4.7.062 VL | SEQ ID NO: 10 | NFMLTQPHSVSESPGKTVTISCTRSSGSIASNYVQWYQQRP GSSPTTVIYEDNQRPSGVPDRFSGSIDSSSNSASLTISGLKT EDEADYYCQSYDSSNVVFGGGTKLTVL |
| F5.1.11.01 VH | SEQ ID NO: 11 | QLQLQESGPGLVKPSQTLSLTCTVSGGS<u>IS</u>SGGYYWS WIRQHPGKGLEWIG<u>YIYKSGSAY</u>YSPSLKSRVTISVDTSKNQ FSLKLSSVTAADTAVYYCARTPTVTGDWFDPWGRGTLVTVS S |
| F5.1.11.01 VL | SEQ ID NO: 12 | NFMLTQPHSVSESPGKTVTISCTRSSGSIASNYVQWYQQRP GSSPTTVIYEDNQRPSGVPDRFSGSIDSSSNSASLTISGLKT EDEADYYCQSYDTRDVVFGGGTKLTVL |
| F5.1.11.02 VH | SEQ ID NO: 13 | QLQLQESGPGLVKPSQTLSLTCTVSGGS<u>IS</u>SGGYYWS WIRQHPGKGLEWIG<u>YIYKSGSAY</u>YSPSLKSRVTISVDTSKNQ FSLKLSSVTAADTAVYYCARTPTVTGDWFDPWGRGTLVTVS S |
| F5.1.11.02 VL | SEQ ID NO: 14 | NFMLTQPHSVSESPGKTVTISCTRSSGSIASNYVQWYQQRP GSSPTTVIYEDNQRPSGVPDRFSGSidSSSNSASLTISGLKTE DEADYYCQTYDSIDVYFGGGTKLTVL |
| F5.1.11.03 VH | SEQ ID NO: 15 | QLQLQESGPGLVKPSQTLSLTCTVSGGS<u>IS</u>SGGYYWSWIRQ HPGKGLEWIG<u>YIYKSGSAY</u>YSPSLKSRVTISVDTSKNQFSLK LSSVTAADTAVYYCARTPTVTGDWFDPWGRGTLVTVSS |
| F5.1.11.03 VL | SEQ ID NO: 16 | NFMLTQPHSVSESPGKTVTISCTRSSGSIASNYVQWYQQRP GSSPTTVIYEDNQRPSGVPDRFSGSIDSSSNSASTISGLKTE DEADYYCQSYDTLNVYFGGGTKLTVL |
| F5.1.11.04 VH | SEQ ID NO: 17 | QLQLQESGPGLVKPSQTLSLTCTVSGGS<u>IS</u>SGGYYWS WIRQHPGKGLEWIG<u>YIYYSGSNY</u>WNPSLKSRVTISVDTSKN QFSLKLSSVTAADTAVYYCARTPTVTGDWFDPWGRGTLVTV SS |
| F5.1.11.04 VL | SEQ ID NO: 18 | NFMLTQPHSVSESPGKTVTISCTRSSGSIASNYVQWYQQRP GSSPTTVIYEDNQRPSGVPDRFSGSIDSSSNSASLTISGLKT EDEADYYCQSYDTRDVVFGGGTKLTVL |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| F5.1.11.05 VH | SEQ ID NO: 19 | QLQLQESGPGLVKPSQTLSLTCTVSGGSISSGGYYWSWIRQHPGKGLEWIGIYYSGSNYWNPSLKSRVTISVDTSKNQFSLKLSSVTAADTAVYYCARTPTVTGDWFDPWGRGTLVTVSS |
| F5.1.11.05 VL | SEQ ID NO: 20 | NFMLTQPHSVSESPGKTVTISCTRSSGSIASNYVQWYQQRPGSSPTTVIYEDNQRPSGVPDRFSGSIDSSSNSASLTISGLKTEDEADYYCQTYDSIDVYFGGGTKLTVL |
| F5.1.11.06 VH | SEQ ID NO: 21 | QLQLQESGPGLVKPSQTLSLTCTVSGGSISSGGYYWSWIRQHPGKGLEWIGIYYSGSNYWNPSLKSRVTISVDTSKNQFSLKLSSVTAADTAVYYCARTPTVTGDWFDPWGRGTLVTVSS |
| F5.1.11.06 VL | SEQ ID NO: 22 | NFMLTQPHSVSESPGKTVTISCTRSSGSIASNYVQWYQQRPGSSPTTVIYEDNQRPSGVPDRFSGSIDSSSNSASLTISGLKTEDEADYYCQSYDTLNVYFGGGTKLTVL |
| F5.1.11.07 VH | SEQ ID NO: 23 | QLQLQESGPGLVKPSQTLSLTCTVSGGSISSGGYYWSWIRQHPGKGLEWIGIYKSGSNYWNPSLKSRVTISVDTSKNQFSLKLSSVTAADTAVYYCARTPTVTGDWFDPWGRGTLVTVSS |
| F5.1.11.07 VL | SEQ ID NO: 24 | NFMLTQPHSVSESPGKTVTISCTRSSGSIASNYVQWYQQRPGSSPTTVIYEDNQRPSGVPDRFSGSIDSSSNSASLTISGLKTEDEADYYCQSYDTRDVVFGGGTKLTVL |
| F5.1.11.08 VH | SEQ ID NO: 25 | QLQLQESGPGLVKPSQTLSLTCTVSGGSISSGGYYWSWIRQHPGKGLEWIGIYKSGSNYWNPSLKSRVTISVDTSKNQFSLKLSSVTAADTAVYYCARTPTVTGDWFDPWGRGTLVTVSS |
| F5.1.11.08 VL | SEQ ID NO: 26 | NFMLTQPHSVSESPGKTVTISCTRSSGSIASNYVQWYQQRPGSSPTTVIYEDNQRPSGVPDRFSGSIDSSSNSASLTISGLKTEDEADYYCQTYDSIDVYFGGGTKLTVL |
| F5.1.11.09 VH | SEQ ID NO: 27 | QLQLQESGPGLVKPSQTLSLTCTVSGGSISSGGYYWSWIRQHPGKGLEWIGIYKSGSNYWNPSLKSRVTISVDTSKNQFSLKLSSVTAADTAVYYCARTPTVTGDWFDPWGRGTLVTVSS |
| F5.1.11.09 VL | SEQ ID NO: 28 | NFMLTQPHSVSESPGKTVTISCTRSSGSIASNYVQWYQQRPGSSPTTVIYEDNQRPSGVPDRFSGSIDSSSNSASLTISGLKTEDEADYYCQSYDTLNVYFGGGTKLTVL |
| F5.1.9.5 VH | SEQ ID NO: 29 | EVQLVESGPGLVKPSETLSLTCAVSGYSISSGYYWGWIRQPPGKGLEWIGLSYHTRSTYYDPSLKSRVTISVDTSKNQFSLKLSSVTAADTAVYYCAREAYSDRAFDIWGQGTMVTVSS |
| F5.1.9.5 VL | SEQ ID NO: 30 | NFMLTQPHSVSESPGKTITISCTRSSGSIASDYVQWYQQRPGSSPSTVIYADNQRPSEVPDRFSGSIDSSSNSASLTISGLMTEDEADYYCQSYDSNIVIFGGGTKLTVL |
| d1C7 VH | SEQ ID NO: 31 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARVDRYYNWNYFLGSFDYWGQGTLVTVSS |
| d1C7 VL | SEQ ID NO: 32 | SYVLTQPPSVSVAPGKTARITCGGNNIRSKSVHWYQQKPGQAPVVVIYYDSDRPSGIPERISGSNSGNTATLTISRVEAGDEADYFCQVWDSSSDHHVFGGGTKLTVL |
| HEAVY C | SEQ ID NO: 33 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| LIGHT C KAPPA | SEQ ID NO: 34 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| LIGHT C LAMBDA | SEQ ID NO: 35 | GQPKAAPSVTLFPPSSEELQANKATLVCLISDFYPGAVTVAW KADSSPVKAGVETTTPSKQSNNKYAASSYLSLTPEQWKSHR SYSCQVTHEGSTVEKTVAPTECS |
| F4.7.6 VH | SEQ ID NO: 36 | GAGGTCCAGCTGCAGGAGTCGGGCCCAGGACTGGTGAA GCCTTCACAGACCCTGTCCCTCACCTGCACTGTCTCTGGT GGCTCCATCAGCAGTGGTGGTTACTACTGGAGCTGGATC CGCCAGCACCCAGGGAAGGGCCTGGAGTGGATTGGGTA CATCTATTACAGTGGGAGCACCTACTACAACCCGTCCCTC AAGAGTCGAGTTACCATATCAGTAGACACGTCTAAGAACC AGTTCTCCCTGAAGCTGAGCTCTGTGACTGCCGCGGACA CGGCCGTGTATTACTGTGCGAGGACTCCTACGGTGACCG GGGACTGGTTCGACCCCTGGGGCCAGGGAACCCTGGTC ACCGTCTCGAGC |
| F4.7.6 VL | SEQ ID NO: 37 | AATTTTATGCTGACTCAGCCCCACTCTGTGTCGGAGTCTC CGGGGAAGACGGTAACCATCTCCTGCACCCGCAGCAGTG GCAGCATTGCCAGCAACTATGTGCAGTGGTACCAGCAGC GCCCGGGCAGTTCCCCCACCACTGTGATCTATGAGGATA ACCAAAGACCCTCTGGGGTCCCTGATCGGTTCTCTGGCT CCATCGACAGCTCCTCCAACTCTGCCTCCCTCACCATCTC TGGACTGAAGACTGAGGACGAGGCTGACTACTACTGTCA GTCTTATGATAGCAGCACCGTGGTATTCGGCGGAGGGAC CAAGCTGACCGTCCTA |
| F4.7.8 VH | SEQ ID NO: 38 | CAGGTCCAGCTGGTGCAGTCTGGGGCTGAGGTGAAGAA GCCTGGGGCCTCAGTGAAGGTCTCCTGCAAGGCTTCTGG ATACACCTTCACCGGCTACTATATGCACTGGGTGCGACAG GCCCCTGGACAAGGGCTTGAGTGGATGGGATGGATCAAC CCTAACAGTGGTGGCACAAACTATGCACAGAAGTTTCAGG GCAGGGTCACCATGACCAGGGACACGTCCATCAGCACAG CCTACATGGAGCTGAGCAGGCTGAGATCTGACGACACGG CCGTGTATTACTGTGCGAGAGACCTAACGTTTGACTACTG GGGCCAGGGAACCCTGGTCACCGTCTCGAGC |
| F4.7.8 VL | SEQ ID NO: 39 | GCCATCCAGTTGACCCAGTCTCCATCCTCCCTGTCTGCGT CTGTAGGAGACAGGGTCACCATCACTTGCCAGGCGAGTC AGGACATTTTCAACCTCTTAAATTGGTATAGGCAGAAACC AGGGAAAGCCCCTGACCTCCTGGTCTACCGCGCTTCCAA TTTGGAGACAGGGGTCCCATCCAGGTTCAGTGGAAGTGG GTCTGGGACAGACTTTACTTTCACCATTAGTAGCCTGCAG CCTGAAGATGTTGGAACCTATTATTGTCAACAGAGTGCTA ATCTCCCCCTCACTTTCGGCGGAGGGACCAAGGTGGAGA TCAAA |
| F5.1.11 VH | SEQ ID NO: 40 | CAGCTGCAGCTGCAGGAGTCGGGCCCAGGACTGGTGAA GCCTTCACAGACCCTGTCCCTCACCTGCACTGTCTCTGGT GGCTCCATCAGCAGTGGTGGTTACTACTGGAGCTGGATC CGCCAGCACCCAGGGAAGGGCCTGGAGTGGATTGGGTA CATCTATTACAGTGGGAGCACCTACTACAACCCGTCCCTC AAGAGTCGAGTTACCATATCAGTAGACACGTCTAAGAACC AGTTCTCCCTGAAGCTGAGCTCTGTGACTGCCGCGGACA CGGCCGTGTATTACTGTGCGAGGACTCCTACGGTGACCG GGGACTGGTTCGACCCCTGGGGCCGTGGCACCCTGGTC ACCGTCTCGAGC |
| F5.1.11 VL | SEQ ID NO: 41 | AATTTTATGCTGACTCAGCCCCACTCTGTGTCGGAGTCTC CGGGGAAGACGGTAACCATCTCCTGCACCCGCAGCAGTG GCAGCATTGCCAGCAACTATGTGCAGTGGTACCAGCAGC GCCCGGGCAGTTCCCCCACCACTGTGATCTATGAGGATA ACCAAAGACCCTCTGGGGTCCCTGATCGGTTCTCTGGCT CCATCGACAGCTCCTCCAACTCTGCCTCCCTCACCATCTC TGGACTGAAGACTGAGGACGAGGCTGACTACTACTGTCA GTCTTATGATAGCAGCAATGTGGTATTCGGCGGAGGGAC CAAGCTGACCGTCCTA |
| F5.1.9 VH | SEQ ID NO: 42 | GAGGTGCAGCTGGTGGAGTCGGGCCCAGGACTGGTGAA GCCTTCGGAGACCCTGTCCCTCACCTGCGCTGTCTCTGG TTACTCCATCAGCAGTGGTTACTACTGGGGCTGGATCCG GCAGCCCCCAGGGAAGGGGCTGGAGTGGATTGGGAGTA TCTATCATAGTGGGAGCACCTACTACAACCCGTCCCTCAA GAGTCGAGTCACCATATCAGTAGACACGTCCAAGAACCA GTTCTCCCTGAAGCTGAGCTCTGTGACCGCCGCAGACAC GGCCGTGTATTACTGTGCGAGAGAGGCCTACTCCGATCG |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| | | GGCTTTTGATATCTGGGGCCAAGGGACAATGGTCACCGT<br>CTCGAGC |
| F5.1.9 VL | SEQ ID NO: 43 | AATTTTATGCTGACTCAGCCCCACTCTGTGTCGGAGTCTC<br>CGGGGAAGACGATAACCATCTCCTGCACCCGCAGCAGTG<br>GCAGCATTGCCAGCGACTATGTGCAGTGGTACCAGCAGC<br>GCCCGGGCAGTTCCCCCAGCACTGTGATCTATGCGGATA<br>ACCAAAGACCCTCTGAAGTCCCTGATCGGTTCTCTGGCTC<br>CATCGACAGCTCCTCCAACTCTGCCTCCCTCACCATCTCT<br>GGACTGATGACTGAGGACGAGGCTGACTACTACTGTCAG<br>TCTTATGATAGCAACATCGTGATATTCGGCGGAGGGACCA<br>AGCTGACCGTCCTA |
| F4.7.062<br>VH | SEQ ID NO: 44 | CAGGTGCAGCTACAGGAGTCGGGCCCAGGACTGGTGAA<br>GCCTTCACAGACCCTGTCCCTCACCTGCACTGTCTCTGGT<br>GGCTCCATCAGCAGTGGTGGTTACTACTGGAGCTGGATC<br>CGCCAGCACCCAGGGAAGGGCCTGGAGTGGATTGGGTA<br>CATCTATTACAGTGGGAGCACCTACTACAACCCGTCCCTC<br>AAGAGTCGAGTTACCATATCAGTAGACACGTCTAAGAACC<br>AGTTCTCCCTGAAGCTGAGCTCTGTGACTGCCGCGGACA<br>CGGCCGTGTATTACTGTGCGAGGACTCCTACGGTGACCG<br>GGGACTGGTTCGACCCCTGGGGCCAGGGAACCCTGGTC<br>ACCGTCTCGAGC |
| F4.7.062<br>VL | SEQ ID NO: 45 | AATTTTATGCTGACTCAGCCCCACTCTGTGTCGGAGTCTC<br>CGGGGAAGACGGTAACCATCTCCTGCACCCGCAGCAGTG<br>GCAGCATTGCCAGCAACTATGTGCAGTGGTACCAGCAGC<br>GCCCGGGCAGTTCCCCCACCACTGTGATCTATGAGGATA<br>ACCAAAGACCCTCTGGGGTCCCTGATCGGTTCTCTGGCT<br>CCATCGACAGCTCCTCCAACTCTGCCTCCCTCACCATCTC<br>TGGACTGAAGACTGAGGACGAGGCTGACTACTACTGTCA<br>GTCTTATGATAGCAGCAATGTGGTATTCGGCGGAGGGAC<br>CAAGCTGACCGTCCTA |
| F5.1.11.01<br>VH | SEQ ID NO: 46 | CAGCTGCAGCTGCAGGAGTCGGGCCCAGGACTGGTGAA<br>GCCTTCACAGACCCTGTCCCTCACCTGCACTGTCTCTGGT<br>GGCTCCATCAGCAGTGGTGGTTACTACTGGAGCTGGATC<br>CGCCAGCACCCAGGGAAGGGCCTGGAGTGGATTGGATAT<br>ATCTATAAGAGTGGGAGCGCGTACTACAGCCCGTCCCTC<br>AAGAGTCGAGTTACCATATCAGTAGACACGTCTAAGAACC<br>AGTTCTCCCTGAAGCTGAGCTCTGTGACTGCCGCGGACA<br>CGGCCGTGTATTACTGTGCGAGGACTCCTACGGTGACCG<br>GGGACTGGTTCGACCCCTGGGGCCGTGGCACCCTGGTC<br>ACCGTCTCCTCA |
| F5.1.11.01<br>VL | SEQ ID NO: 47 | AATTTTATGCTGACTCAGCCCCACTCTGTGTCGGAGTCTC<br>CGGGGAAGACGGTAACCATCTCCTGCACCCGCAGCAGTG<br>GCAGCATTGCCAGCAACTATGTGCAGTGGTACCAGCAGC<br>GCCCGGGCAGTTCCCCCACCACTGTGATCTATGAGGATA<br>ACCAAAGACCCTCTGGGGTCCCTGATCGGTTCTCTGGCT<br>CCATCGACAGCTCCTCCAACTCTGCCTCCCTCACCATCTC<br>TGGACTGAAGACTGAGGACGAGGCTGACTACTACTGTCA<br>GTCTTATGATACCAGGGATGTCGTATTCGGCGGAGGGAC<br>CAAGCTGACCGTCCTA |
| F5.1.11.02<br>VH | SEQ ID NO: 48 | CAGCTGCAGCTGCAGGAGTCGGGCCCAGGACTGGTGAA<br>GCCTTCACAGACCCTGTCCCTCACCTGCACTGTCTCTGGT<br>GGCTCCATCAGCAGTGGTGGTTACTACTGGAGCTGGATC<br>CGCCAGCACCCAGGGAAGGGCCTGGAGTGGATTGGATAT<br>ATCTATAAGAGTGGGAGCGCGTACTACAGCCCGTCCCTC<br>AAGAGTCGAGTTACCATATCAGTAGACACGTCTAAGAACC<br>AGTTCTCCCTGAAGCTGAGCTCTGTGACTGCCGCGGACA<br>CGGCCGTGTATTACTGTGCGAGGACTCCTACGGTGACCG<br>GGGACTGGTTCGACCCCTGGGGCCGTGGCACCCTGGTC<br>ACCGTCTCCTCA |
| F5.1.11.02<br>VL | SEQ ID NO: 49 | AATTTTATGCTGACTCAGCCCCACTCTGTGTCGGAGTCTC<br>CGGGGAAGACGGTAACCATCTCCTGCACCCGCAGCAGTG<br>GCAGCATTGCCAGCAACTATGTGCAGTGGTACCAGCAGC<br>GCCCGGGCAGTTCCCCCACCACTGTGATCTATGAGGATA<br>ACCAAAGACCCTCTGGGGTCCCTGATCGGTTCTCTGGCT<br>CCATCGACAGCTCCTCCAACTCTGCCTCCCTCACCATCTC |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| | | TGGACTGAAGACTGAGGACGAGGCTGACTACTACTGTCA GACTTATGACAGCATCGATGTGTATTTCGGCGGAGGGAC CAAGCTGACCGTCCTA |
| F5.1.11.03 VH | SEQ ID NO: 50 | CAGCTGCAGCTGCAGGAGTCGGGCCCAGGACTGGTGAA GCCTTCACAGACCCTGTCCCTCACCTGCACTGTCTCTGGT GGCTCCATCAGCAGTGGTGGTTACTACTGGAGCTGGATC CGCCAGCACCCAGGGAAGGGCCTGGAGTGGATTGGATAT ATCTATAAGAGTGGGAGCGCGTACTACAGCCCGTCCCTC AAGAGTCGAGTTACCATATCAGTAGACACGTCTAAGAACC AGTTCTCCCTGAAGCTGAGCTCTGTGACTGCCGCGGACA CGGCCGTGTATTACTGTGCGAGGACTCCTACGGTGACCG GGGACTGGTTCGACCCCTGGGGCCGTGGCACCCTGGTC ACCGTCTCCTCA |
| F5.1.11.03 VL | SEQ ID NO: 51 | AATTTTATGCTGACTCAGCCCCACTCTGTGTCGGAGTCTC CGGGGAAGACGGTAACCATCTCCTGCACCCGCAGCAGTG GCAGCATTGCCAGCAACTATGTGCAGTGGTACCAGCAGC GCCCGGGCAGTTCCCCCACCACTGTGATCTATGAGGATA ACCAAAGACCCTCTGGGGTCCCTGATCGGTTCTCTGGCT CCATCGACAGCTCCTCCAACTCTGCCTCCCTCACCATCTC TGGACTGAAGACTGAGGACGAGGCTGACTACTACTGTCA GTCTTATGATACCCTTAATGTGTATTTCGGCGGAGGGACC AAGCTGACCGTCCTA |
| F5.1.11.04 VH | SEQ ID NO: 52 | CAGCTGCAGCTGCAGGAGTCGGGCCCAGGACTGGTGAA GCCTTCACAGACCCTGTCCCTCACCTGCACTGTCTCTGGT GGCTCCATCAGCAGTGGTGGTTACTACTGGAGCTGGATC CGCCAGCACCCAGGGAAGGGCCTGGAGTGGATTGGATA CATTTATTACAGCGGGAGCAACTACTGGAATCCGTCCCTC AAGAGTCGAGTTACCATATCAGTAGACACGTCTAAGAACC AGTTCTCCCTGAAGCTGAGCTCTGTGACTGCCGCGGACA CGGCCGTGTATTACTGTGCGAGGACTCCTACGGTGACCG GGGACTGGTTCGACCCCTGGGGCCGTGGCACCCTGGTC ACCGTCTCCTCA |
| F5.1.11.04 VL | SEQ ID NO: 53 | AATTTTATGCTGACTCAGCCCCACTCTGTGTCGGAGTCTC CGGGGAAGACGGTAACCATCTCCTGCACCCGCAGCAGTG GCAGCATTGCCAGCAACTATGTGCAGTGGTACCAGCAGC GCCCGGGCAGTTCCCCCACCACTGTGATCTATGAGGATA ACCAAAGACCCTCTGGGGTCCCTGATCGGTTCTCTGGCT CCATCGACAGCTCCTCCAACTCTGCCTCCCTCACCATCTC TGGACTGAAGACTGAGGACGAGGCTGACTACTACTGTCA GTCTTATGATACCAGGGATGTCGTATTCGGCGGAGGGAC CAAGCTGACCGTCCTA |
| F5.1.11.05 VH | SEQ ID NO: 54 | CAGCTGCAGCTGCAGGAGTCGGGCCCAGGACTGGTGAA GCCTTCACAGACCCTGTCCCTCACCTGCACTGTCTCTGGT GGCTCCATCAGCAGTGGTGGTTACTACTGGAGCTGGATC CGCCAGCACCCAGGGAAGGGCCTGGAGTGGATTGGATA CATTTATTACAGCGGGAGCAACTACTGGAATCCGTCCCTC AAGAGTCGAGTTACCATATCAGTAGACACGTCTAAGAACC AGTTCTCCCTGAAGCTGAGCTCTGTGACTGCCGCGGACA CGGCCGTGTATTACTGTGCGAGGACTCCTACGGTGACCG GGGACTGGTTCGACCCCTGGGGCCGTGGCACCCTGGTC ACCGTCTCCTCA |
| F5.1.11.05 VL | SEQ ID NO: 55 | AATTTTATGCTGACTCAGCCCCACTCTGTGTCGGAGTCTC CGGGGAAGACGGTAACCATCTCCTGCACCCGCAGCAGTG GCAGCATTGCCAGCAACTATGTGCAGTGGTACCAGCAGC GCCCGGGCAGTTCCCCCACCACTGTGATCTATGAGGATA ACCAAAGACCCTCTGGGGTCCCTGATCGGTTCTCTGGCT CCATCGACAGCTCCTCCAACTCTGCCTCCCTCACCATCTC TGGACTGAAGACTGAGGACGAGGCTGACTACTACTGTCA GACTTATGACAGCATCGATGTGTATTTCGGCGGAGGGAC CAAGCTGACCGTCCTA |
| F5.1.11.06 VH | SEQ ID NO: 56 | CAGCTGCAGCTGCAGGAGTCGGGCCCAGGACTGGTGAA GCCTTCACAGACCCTGTCCCTCACCTGCACTGTCTCTGGT GGCTCCATCAGCAGTGGTGGTTACTACTGGAGCTGGATC CGCCAGCACCCAGGGAAGGGCCTGGAGTGGATTGGATA CATTTATTACAGCGGGAGCAACTACTGGAATCCGTCCCTC AAGAGTCGAGTTACCATATCAGTAGACACGTCTAAGAACC AGTTCTCCCTGAAGCTGAGCTCTGTGACTGCCGCGGACA CGGCCGTGTATTACTGTGCGAGGACTCCTACGGTGACCG |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| | | GGGACTGGTTCGACCCCTGGGGCCGTGGCACCCTGGTC<br>ACCGTCTCCTCA |
| F5.1.11.06<br>VL | SEQ ID NO: 57 | AATTTTATGCTGACTCAGCCCCACTCTGTGTCGGAGTCTC<br>CGGGGAAGACGGTAACCATCTCCTGCACCCGCAGCAGTG<br>GCAGCATTGCCAGCAACTATGTGCAGTGGTACCAGCAGC<br>GCCCGGGCAGTTCCCCCACCACTGTGATCTATGAGGATA<br>ACCAAAGACCCTCTGGGGTCCCTGATCGGTTCTCTGGCT<br>CCATCGACAGCTCCTCCAACTCTGCCTCCCTCACCATCTC<br>TGGACTGAAGACTGAGGACGAGGCTGACTACTACTGTCA<br>GTCTTATGATACCCTTAATGTGTATTTCGGCGGAGGGACC<br>AAGCTGACCGTCCTA |
| F5.1.11.07<br>VH | SEQ ID NO: 58 | CAGCTGCAGCTGCAGGAGTCGGGCCCAGGACTGGTGAA<br>GCCTTCACAGACCCTGTCCCTCACCTGCACTGTCTCTGGT<br>GGCTCCATCAGCAGTGGTGGTTACTACTGGAGCTGGATC<br>CGCCAGCACCCAGGGAAGGGCCTGGAGTGGATTGGGTA<br>CATCTATAAGAGCGGGAGCAACTACTGGAACCCGTCCCT<br>CAAGAGTCGAGTTACCATATCAGTAGACACGTCTAAGAAC<br>CAGTTCTCCCTGAAGCTGAGCTCTGTGACTGCCGCGGAC<br>ACGGCCGTGTATTACTGTGCGAGGACTCCTACGGTGACC<br>GGGGACTGGTTCGACCCCTGGGGCCGTGGCACCCTGGT<br>CACCGTCTCCTCA |
| F5.1.11.07<br>VL | SEQ ID NO: 59 | AATTTTATGCTGACTCAGCCCCACTCTGTGTCGGAGTCTC<br>CGGGGAAGACGGTAACCATCTCCTGCACCCGCAGCAGTG<br>GCAGCATTGCCAGCAACTATGTGCAGTGGTACCAGCAGC<br>GCCCGGGCAGTTCCCCCACCACTGTGATCTATGAGGATA<br>ACCAAAGACCCTCTGGGGTCCCTGATCGGTTCTCTGGCT<br>CCATCGACAGCTCCTCCAACTCTGCCTCCCTCACCATCTC<br>TGGACTGAAGACTGAGGACGAGGCTGACTACTACTGTCA<br>GTCTTATGATACCAGGGATGTCGTATTCGGCGGAGGGAC<br>CAAGCTGACCGTCCTA |
| F5.1.11.08<br>VH | SEQ ID NO: 60 | CAGCTGCAGCTGCAGGAGTCGGGCCCAGGACTGGTGAA<br>GCCTTCACAGACCCTGTCCCTCACCTGCACTGTCTCTGGT<br>GGCTCCATCAGCAGTGGTGGTTACTACTGGAGCTGGATC<br>CGCCAGCACCCAGGGAAGGGCCTGGAGTGGATTGGGTA<br>CATCTATAAGAGCGGGAGCAACTACTGGAACCCGTCCCT<br>CAAGAGTCGAGTTACCATATCAGTAGACACGTCTAAGAAC<br>CAGTTCTCCCTGAAGCTGAGCTCTGTGACTGCCGCGGAC<br>ACGGCCGTGTATTACTGTGCGAGGACTCCTACGGTGACC<br>GGGGACTGGTTCGACCCCTGGGGCCGTGGCACCCTGGT<br>CACCGTCTCCTCA |
| F5.1.11.08<br>VL | SEQ ID NO: 61 | AATTTTATGCTGACTCAGCCCCACTCTGTGTCGGAGTCTC<br>CGGGGAAGACGGTAACCATCTCCTGCACCCGCAGCAGTG<br>GCAGCATTGCCAGCAACTATGTGCAGTGGTACCAGCAGC<br>GCCCGGGCAGTTCCCCCACCACTGTGATCTATGAGGATA<br>ACCAAAGACCCTCTGGGGTCCCTGATCGGTTCTCTGGCT<br>CCATCGACAGCTCCTCCAACTCTGCCTCCCTCACCATCTC<br>TGGACTGAAGACTGAGGACGAGGCTGACTACTACTGTCA<br>GACTTATGACAGCATCGATGTGTATTTCGGCGGAGGGAC<br>CAAGCTGACCGTCCTA |
| F5.1.11.09<br>VH | SEQ ID NO: 62 | CAGCTGCAGCTGCAGGAGTCGGGCCCAGGACTGGTGAA<br>GCCTTCACAGACCCTGTCCCTCACCTGCACTGTCTCTGGT<br>GGCTCCATCAGCAGTGGTGGTTACTACTGGAGCTGGATC<br>CGCCAGCACCCAGGGAAGGGCCTGGAGTGGATTGGGTA<br>CATCTATAAGAGCGGGAGCAACTACTGGAACCCGTCCCT<br>CAAGAGTCGAGTTACCATATCAGTAGACACGTCTAAGAAC<br>CAGTTCTCCCTGAAGCTGAGCTCTGTGACTGCCGCGGAC<br>ACGGCCGTGTATTACTGTGCGAGGACTCCTACGGTGACC<br>GGGGACTGGTTCGACCCCTGGGGCCGTGGCACCCTGGT<br>CACCGTCTCCTCA |
| F5.1.11.09<br>VL | SEQ ID NO: 63 | AATTTTATGCTGACTCAGCCCCACTCTGTGTCGGAGTCTC<br>CGGGGAAGACGGTAACCATCTCCTGCACCCGCAGCAGTG<br>GCAGCATTGCCAGCAACTATGTGCAGTGGTACCAGCAGC<br>GCCCGGGCAGTTCCCCCACCACTGTGATCTATGAGGATA<br>ACCAAAGACCCTCTGGGGTCCCTGATCGGTTCTCTGGCT<br>CCATCGACAGCTCCTCCAACTCTGCCTCCCTCACCATCTC<br>TGGACTGAAGACTGAGGACGAGGCTGACTACTACTGTCA<br>GTCTTATGATACCCTTAATGTGTATTTCGGCGGAGGGACC<br>AAGCTGACCGTCCTA |

TABLE 7-continued

Sequence Listing Table
Kabat CDR amino acid sequences are in bold. Chothia CDR amino acid
sequences are underlined. Extended CDR amino acid sequences include both
underlined and bold amino acid residues.

| | | |
|---|---|---|
| F5.1.9.5 VH | SEQ ID NO: 64 | GAGGTGCAGCTGGTGGAGTCGGGCCCAGGACTGGTGAA
GCCTTCGGAGACCCTGTCCCTCACCTGCGCTGTCTCTGG
TTACTCCATCAGCAGTGGTTACTACTGGGGCTGGATCCG
GCAGCCCCCAGGGAAGGGGCTGGAGTGGATTGGTTTGA
GCTACCACACTCGTTCTACCTACTACGATCCGTCCCTCAA
GAGTCGAGTCACCATATCAGTAGACACGTCCAAGAACCA
GTTCTCCCTGAAGCTGAGCTCTGTGACCGCCGCAGACAC
GGCCGTGTATTACTGTGCGAGAGAGGCCTACTCCGATCG
GGCTTTTGATATCTGGGGCCAAGGGACAATGGTCACCGT
CTCCTCA |
| F5.1.9.5 VL | SEQ ID NO: 65 | AATTTTATGCTGACTCAGCCCCACTCTGTGTCGGAGTCTC
CGGGGAAGACGATAACCATCTCCTGCACCCGCAGCAGTG
GCAGCATTGCCAGCGACTATGTGCAGTGGTACCAGCAGC
GCCCGGGCAGTTCCCCCAGCACTGTGATCTATGCGGATA
ACCAAAGACCCTCTGAAGTCCCTGATCGGTTCTCTGGCTC
CATCGACAGCTCCTCCAACTCTGCCTCCCTCACCATCTCT
GGACTGATGACTGAGGACGAGGCTGACTACTACTGTCAG
TCTTATGATAGCAACATCGTGATATTCGGCGGAGGGACCA
AGCTGACCGTCCTA |
| d1C7 VH | SEQ ID NO: 66 | CAGGTCCAGCTGGTGCAGTCTGGGGCTGAGGTGAAGAA
GCCTGGGTCCTCGGTGAAGGTCTCCTGCAAGGCTTCTGG
AGGCACCTTCAGCAGCTATGCTATCAGCTGGGTGCGACA
GGCCCCTGGACAAGGGCTTGAGTGGATGGGAGGGATCA
TCCCTATCTTTGGTACAGCAAACTACGCACAGAAGTTCCA
GGGCAGAGTCACGATTACCGCGGACGAATCCACGAGCAC
AGCCTACATGGAGCTGAGCAGCCTGAGATCTGAGGACAC
GGCCGTGTATTACTGTGCGAGAGTGGACCGGTATTATAA
CTGGAACTACTTTTTAGGCTCCTTTGACTACTGGGGCCAG
GGAACCCTGGTCACCGTCTCGAGC |
| d1C7 VL | SEQ ID NO: 67 | AGCTATGTGCTGACTCAGCCACCCTCAGTGTCAGTGGCC
CCAGGAAAGACGGCCAGGATTACCTGTGGGGGAAACAAC
ATTAGAAGTAAAAGTGTGCACTGGTACCAGCAGAAGCCC
GGCCAGGCCCCTGTGGTGGTCATCTATTATGATAGCGAC
CGGCCCTCAGGGATCCCTGAGCGAATCTCTGGGTCCAAC
TCTGGAAACACGGCCACCCTGACCATCAGCAGGGTCGAA
GCCGGGGATGAGGCCGACTATTTTTGTCAGGTGTGGGAT
AGTAGTAGTGACCATCATGTATTCGGCGGAGGGACCAAG
CTGACCGTCCTA |
| Heavy C | SEQ ID NO: 68 | GCCTCCACCAAGGGCCCATCGGTCTTCCCCCTGGCACCC
TCCTCCAAGAGCACCTCTGGGGGCACAGCGGCCCTGGG
CTGCCTGGTCAAGGACTACTTCCCCGAACCGGTGACGGT
GTCGTGGAACTCAGGCGCCCTGACCAGCGGCGTGCACA
CCTTCCCGGCTGTCCTACAGTCCTCAGGACTCTACTCCCT
CAGCAGCGTGGTGACCGTGCCCTCCAGCAGCTTGGGCA
CCCAGACCTACATCTGCAACGTGAATCACAAGCCCAGCA
ACACCAAGGTGGACAAGAAAGTTGAGCCCAAATCTTGTGA
CAAAACTCACACATGCCCACCGTGCCCAGCACCTGAAGC
CGCTGGGGCACCGTCAGTCTTCCTCTTCCCTCCAAAACC
CAAGGACACCCTCATGATCTCCCGGACCCCTGAGGTCAC
ATGCGTGGTGGTGGACGTGAGCCACGAAGACCCTGAGGT
CAAGTTCAACTGGTACGTGGACGGCGTGGAGGTGCATAA
TGCCAAGACAAAGCCGCGGGAGGAGCAGTACAACAGCAC
GTACCGTGTGGTCAGCGTCCTCACCGTCCTGCACCAGGA
CTGGCTGAATGGCAAGGAGTACAAGTGCAAGGTCTCCAA
CAAAGCCCTCCCAGCCCCCATCGAGAAAACCATCTCCAA
AGCCAAAGGGCAGCCCCGAGAACCACAGGTGTACACCCT
GCCCCCATCCCGGGAGGAGATGACCAAGAACCAGGTCA
GCCTGACCTGCCTGGTCAAAGGCTTCTATCCCAGCGACA
TCGCCGTGGAGTGGGAGAGCAATGGGCAGCCGGAGAAC
AACTACAAGACCACGCCTCCCGTGCTGGACTCCGACGGC
TCCTTCTTCCTCTATAGCAAGCTCACCGTGGACAAGAGCA
GGTGGCAGCAGGGGAACGTCTTCTCATGCTCCGTGATGC
ATGAGGCTCTGCACAACCACTACACGCAGAAGAGCCTCT
CCCTGTCTCCGGGTAAA |
| Light C Kappa | SEQ ID NO: 69 | CGAACTGTGGCTGCACCATCTGTCTTCATCTTCCCGCCAT
CTGATGAGCAGTTGAAATCTGGAACTGCCTCTGTTGTGTG
CCTGCTGAATAACTTCTATCCCAGAGAGGCCAAAGTACAG
TGGAAGGTGGATAACGCCCTCCAATCGGGTAACTCCCAG
GAGAGTGTCACAGAGCAGGACAGCAAGGACAGCACCTAC |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| | | AGCCTCAGCAGCACCCTGACGCTGAGCAAAGCAGACTAC GAGAAACACAAAGTCTACGCCTGCGAAGTCACCCATCAG GGCCTGAGCTCGCCCGTCACAAAGAGCTTCAACAGGGGA GAGTGT |
| Light C Lambda | SEQ ID NO: 70 | GGTCAGCCCAAGGCTGCCCCCTCGGTCACTCTGTTCCCA CCCTCCTCTGAGGAGCTTCAAGCCAACAAGGCCACACTG GTGTGTCTCATAAGTGACTTCTACCCGGGAGCCGTGACA GTGGCCTGGAAGGCAGATAGCAGCCCCGTCAAGGCGGG AGTGGAGACCACCACACCCTCCAAACAAAGCAACAACAA GTACGCGGCCAGCAGCTACCTGAGCCTGACGCCTGAGCA GTGGAAGTCCCACAGAAGCTACAGCTGCCAGGTCACGCA TGAAGGGAGCACCGTGGAGAAGACAGTGGCCCCTACAGA ATGTTCA |
| F5.1.11.02 library VH (ital. randomized except C) | SEQ ID NO: 71 | QLQLQESGPGLVKPSQTLSLTCTVSGGSISSGGYYWSWIRQ HPGKGLEWIGYIYKSGSAYYSPSLKSRVTISVDTSKNQFSLK LSSVTAADTAVYYCARTPTVTGDWFDPWGRGTLVTVSS |
| F5.1.11.02 library VL (ital. randomized except C) | SEQ ID NO: 72 | NFMLTQPHSVSESPGKTVTISCTRSSGSIASNYVQWYQQRP GSSPTTVIYEDNQRPSGVPDRFSGSIDSSSNSASLTISGLKT EDEADYYCQTYDSIDVYFGGGTKLTVL |
| F4.7.6 HCDR1 Kabat | SEQ ID NO: 73 | SGGYYWS |
| F4.7.6 HCDR1 Chothia | SEQ ID NO: 74 | GSISSGGY |
| F4.7.6 HCDR1 Extended | SEQ ID NO: 75 | GSISSGGYYWS |
| F4.7.6 HCDR2 Kabat | SEQ ID NO: 76 | GYIYYSGSTYYNPSLKSRV |
| F4.7.6 HCDR2 Chothia | SEQ ID NO: 77 | IYYSGSTY |
| F4.7.6 HCDR3 | SEQ ID NO: 78 | TPTVTGDWFDP |
| F4.7.6 LCDR1 | SEQ ID NO: 79 | TRSSGSIASNYVQ |
| F4.7.6 LCDR2 | SEQ ID NO: 80 | EDNQRPS |
| F4.7.6 LCDR3 | SEQ ID NO: 81 | QSYDSSTVV |
| F4.7.8 HCDR1 Kabat | SEQ ID NO: 82 | GYYMH |
| F4.7.8 HCDR1 Chothia | SEQ ID NO: 83 | YTFTGY |
| F4.7.8 HCDR1 Extended | SEQ ID NO: 84 | YTFTGYYMH |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| F4.7.8 HCDR2 Kabat | SEQ ID NO: 85 | GWINPNSGGTNYAQKFQGRV |
| F4.7.8 HCDR2 Chothia | SEQ ID NO: 86 | INPNSGGTN |
| F4.7.8 HCDR3 | SEQ ID NO: 87 | DLTFDY |
| F4.7.8 LCDR1 | SEQ ID NO: 88 | QASQDIFNLLN |
| F4.7.8 LCDR2 | SEQ ID NO: 89 | RASNLET |
| F4.7.8 LCDR3 | SEQ ID NO: 90 | QQSANLPLT |
| F5.1.11 HCDR1 Kabat | SEQ ID NO: 91 | SGGYYWS |
| F5.1.11 HCDR1 Chothia | SEQ ID NO: 92 | GSISSGGY |
| F5.1.11 HCDR1 Extended | SEQ ID NO: 93 | GSISSGGYYWS |
| F5.1.11 HCDR2 Kabat | SEQ ID NO: 94 | GYIYYSGSTYYNPSLKSRV |
| F5.1.11 HCDR2 Chothia | SEQ ID NO: 95 | IYYSGSTY |
| F5.1.11 HCDR3 | SEQ ID NO: 96 | TPTVTGDWFDP |
| F5.1.11 LCDR1 | SEQ ID NO: 97 | TRSSGSIASNYVQ |
| F5.1.11 LCDR2 | SEQ ID NO: 98 | EDNQRPS |
| F5.1.11 LCDR3 | SEQ ID NO: 99 | QSYDSSNVV |
| F5.1.9 HCDR1 Kabat | SEQ ID NO: 100 | SGYYWG |
| F5.1.9 HCDR1 Chothia | SEQ ID NO: 101 | YSISSGY |
| F5.1.9 HCDR1 Extended | SEQ ID NO: 102 | YSISSGYYWG |
| F5.1.9 HCDR2 Kabat | SEQ ID NO: 103 | GSIYHSGSTYYNPSLKSRV |
| F5.1.9 HCDR2 Chothia | SEQ ID NO: 104 | IYHSGSTY |
| F5.1.9 HCDR3 | SEQ ID NO: 105 | EAYSDRAFDI |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| F5.1.9 LCDR1 | SEQ ID NO: 106 | TRSSGSIASDYVQ |
| F5.1.9 LCDR2 | SEQ ID NO: 107 | ADNQRPS |
| F5.1.9 LCDR3 | SEQ ID NO: 108 | QSYDSNIVI |
| F4.7.062 HCDR1 Kabat | SEQ ID NO: 109 | SGGYYWS |
| F4.7.062 HCDR1 Chothia | SEQ ID NO: 110 | GSISSGGY |
| F4.7.062 HCDR1 Extended | SEQ ID NO: 111 | GSISSGGYYWS |
| F4.7.062 HCDR2 Kabat | SEQ ID NO: 112 | GYIYYSGSTYYNPSLKSRV |
| F4.7.062 HCDR2 Chothia | SEQ ID NO: 113 | IYYSGSTY |
| F4.7.062 HCDR3 | SEQ ID NO: 114 | TPTVTGDWFDP |
| F4.7.062 LCDR1 | SEQ ID NO: 115 | TRSSGSIASNYVQ |
| F4.7.062 LCDR2 | SEQ ID NO: 116 | EDNQRPS |
| F4.7.062 LCDR3 | SEQ ID NO: 117 | QSYDSSNVV |
| F5.1.11.01 HCDR1 Kabat | SEQ ID NO: 118 | SGGYYWS |
| F5.1.11.01 Chothia HCDR1 | SEQ ID NO: 119 | GSISSGGY |
| F5.1.11.01 HCDR1 Extended | SEQ ID NO: 120 | GSISSGGYYWS |
| F5.1.11.01 HCDR2 Kabat | SEQ ID NO: 121 | GYIYKSGSAYYSPSLKSRV |
| F5.1.11.01 HCDR2 Chothia | SEQ ID NO: 122 | IYKSGSAY |
| F5.1.11.01 HCDR3 | SEQ ID NO: 123 | TPTVTGDWFDP |
| F5.1.11.01 LCDR1 | SEQ ID NO: 124 | TRSSGSIASNYVQ |
| F5.1.11.01 LCDR2 | SEQ ID NO: 125 | EDNQRPS |
| F5.1.11.01 LCDR3 | SEQ ID NO: 126 | QSYDTRDVV |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| F5.1.11.02 HCDR1 Kabat | SEQ ID NO: 127 | SGGYYWS |
| F5.1.11.02 HCDR1 Chothia | SEQ ID NO: 128 | GSISSGGY |
| F5.1.11.02 HCDR1 Extended | SEQ ID NO: 129 | GSISSGGYYWS |
| F5.1.11.02 HCDR2 Kabat | SEQ ID NO: 130 | GYIYKSGSAYYSPSLKSRV |
| F5.1.11.02 HCDR2 Chothia | SEQ ID NO: 131 | IYKSGSAY |
| F5.1.11.02 HCDR3 | SEQ ID NO: 132 | TPTVTGDWFDP |
| F5.1.11.02 LCDR1 | SEQ ID NO: 133 | TRSSGSIASNYVQ |
| F5.1.11.02 LCDR2 | SEQ ID NO: 134 | EDNQRPS |
| F5.1.11.02 LCDR3 | SEQ ID NO: 135 | QTYDSIDVY |
| F5.1.11.03 HCDR1 Kabat | SEQ ID NO: 136 | SGGYYWS |
| F5.1.11.03 HCDR1 Chothia | SEQ ID NO: 137 | GSISSGGY |
| F5.1.11.03 HCDR1 Extended | SEQ ID NO: 138 | GSISSGGYYWS |
| F5.1.11.03 HCDR2 Kabat | SEQ ID NO: 139 | GYIYKSGSAYYSPSLKSRV |
| F5.1.11.03 HCDR2 Chothia | SEQ ID NO: 140 | IYKSGSAY |
| F5.1.11.03 HCDR3 | SEQ ID NO: 141 | TPTVTGDWFDP |
| F5.1.11.03 LCDR1 | SEQ ID NO: 142 | TRSSGSIASNYVQ |
| F5.1.11.03 LCDR2 | SEQ ID NO: 143 | EDNQRPS |
| F5.1.11.03 LCDR3 | SEQ ID NO: 144 | QSYDTLNVY |
| F5.1.11.04 HCDR1 Kabat | SEQ ID NO: 145 | SGGYYWS |
| F5.1.11.04 HCDR1 Chothia | SEQ ID NO: 146 | GSISSGGY |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| F5.1.11.04 HCDR1 Extended | SEQ ID NO: 147 | GSISSGGYYWS |
| F5.1.11.04 HCDR2 Kabat | SEQ ID NO: 148 | GYIYYSGSNYWNPSLKSRV |
| F5.1.11.04 HCDR2 Chothia | SEQ ID NO: 149 | IYYSGSNY |
| F5.1.11.04 HCDR3 | SEQ ID NO: 150 | TPTVTGDWFDP |
| F5.1.11.04 LCDR1 | SEQ ID NO: 151 | TRSSGSIASNYVQ |
| F5.1.11.04 LCDR2 | SEQ ID NO: 152 | EDNQRPS |
| F5.1.11.04 LCDR3 | SEQ ID NO: 153 | QSYDTRDVV |
| F5.1.11.05 HCDR1 Kabat | SEQ ID NO: 154 | SGGYYWS |
| F5.1.11.05 HCDR1 Chothia | SEQ ID NO: 155 | GSISSGGY |
| F5.1.11.05 HCDR1 Extended | SEQ ID NO: 156 | GSISSGGYYWS |
| F5.1.11.05 HCDR2 Kabat | SEQ ID NO: 157 | GYIYYSGSNYWNPSLKSRV |
| F5.1.11.05 HCDR2 Chothia | SEQ ID NO: 158 | IYYSGSNY |
| F5.1.11.05 HCDR3 | SEQ ID NO: 159 | TPTVTGDWFDP |
| F5.1.11.05 LCDR1 | SEQ ID NO: 160 | TRSSGSIASNYVQ |
| F5.1.11.05 LCDR2 | SEQ ID NO: 161 | EDNQRPS |
| F5.1.11.05 LCDR3 | SEQ ID NO: 162 | QTYDSIDVY |
| F5.1.11.06 HCDR1 Kabat | SEQ ID NO: 163 | SGGYYWS |
| F5.1.11.06 HCDR1 Chothia | SEQ ID NO: 164 | GSISSGGY |
| F5.1.11.06 HCDR1 Extended | SEQ ID NO: 165 | GSISSGGYYWS |
| F5.1.11.06 HCDR2 Kabat | SEQ ID NO: 166 | GYIYYSGSNYWNPSLKSRV |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| F5.1.11.06 HCDR2 Chothia | SEQ ID NO: 167 | IYYSGSNY |
| F5.1.11.06 HCDR3 | SEQ ID NO: 168 | TPTVTGDWFDP |
| F5.1.11.06 LCDR1 | SEQ ID NO: 169 | TRSSGSIASNYVQ |
| F5.1.11.06 LCDR2 | SEQ ID NO: 170 | EDNQRPS |
| F5.1.11.06 LCDR3 | SEQ ID NO: 171 | QSYDTLNVY |
| F5.1.11.07 HCDR1 Kabat | SEQ ID NO: 172 | SGGYYWS |
| F5.1.11.07 HCDR1 Chothia | SEQ ID NO: 173 | GSISSGGY |
| F5.1.11.07 HCDR1 Extended | SEQ ID NO: 174 | GSISSGGYYWS |
| F5.1.11.07 HCDR2 Kabat | SEQ ID NO: 175 | GYIYKSGSNYWNPSLKSRV |
| F5.1.11.07 HCDR2 Chothia | SEQ ID NO: 176 | IYKSGSNY |
| F5.1.11.07 HCDR3 | SEQ ID NO: 177 | TPTVTGDWFDP |
| F5.1.11.07 LCDR1 | SEQ ID NO: 178 | TRSSGSIASNYVQ |
| F5.1.11.07 LCDR2 | SEQ ID NO: 179 | EDNQRPS |
| F5.1.11.07 LCDR3 | SEQ ID NO: 180 | QSYDTRDVV |
| F5.1.11.08 HCDR1 Kabat | SEQ ID NO: 181 | SGGYYWS |
| F5.1.11.08 HCDR1 Chothia | SEQ ID NO: 182 | GSISSGGY |
| F5.1.11.08 HCDR1 Extended | SEQ ID NO: 183 | GSISSGGYYWS |
| F5.1.11.08 HCDR2 Kabat | SEQ ID NO: 184 | GYIYKSGSNYWNPSLKSRV |
| F5.1.11.08 HCDR2 Chothia | SEQ ID NO: 185 | IYKSGSNY |
| F5.1.11.08 HCDR3 | SEQ ID NO: 186 | TPTVTGDWFDP |
| F5.1.11.08 LCDR1 | SEQ ID NO: 187 | TRSSGSIASNYVQ |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| F5.1.11.08 LCDR2 | SEQ ID NO: 188 | EDNQRPS |
| F5.1.11.08 LCDR3 | SEQ ID NO: 189 | QTYDSIDVY |
| F5.1.11.09 HCDR1 Kabat | SEQ ID NO: 190 | SGGYYWS |
| F5.1.11.09 HCDR1 Chothia | SEQ ID NO: 191 | GSISSGGY |
| F5.1.11.09 HCDR1 Extended | SEQ ID NO: 192 | GSISSGGYYWS |
| F5.1.11.09 HCDR2 Kabat | SEQ ID NO: 193 | GYIYKSGSNYWNPSLKSRV |
| F5.1.11.09 HCDR2 Chothia | SEQ ID NO: 194 | IYKSGSNY |
| F5.1.11.09 HCDR3 | SEQ ID NO: 195 | TPTVTGDWFDP |
| F5.1.11.09 LCDR1 | SEQ ID NO: 196 | TRSSGSIASNYVQ |
| F5.1.11.09 LCDR2 | SEQ ID NO: 197 | EDNQRPS |
| F5.1.11.09 LCDR3 | SEQ ID NO: 198 | QSYDTLNVY |
| F5.1.9.5 HCDR1 Kabat | SEQ ID NO: 199 | SGYYWG |
| F5.1.9.5 HCDR1 Chothia | SEQ ID NO: 200 | YSISSGY |
| F5.1.9.5 HCDR1 Extended | SEQ ID NO: 201 | YSISSGYYWG |
| F5.1.9.5 HCDR2 Kabat | SEQ ID NO: 202 | GLSYHTRSTYYDPSLKSRV |
| F5.1.9.5 HCDR2 Chothia | SEQ ID NO: 203 | SYHTRSTY |
| F5.1.9.5 HCDR3 | SEQ ID NO: 204 | EAYSDRAFDI |
| F5.1.9.5 LCDR1 | SEQ ID NO: 205 | TRSSGSIASDYVQ |
| F5.1.9.5 LCDR2 | SEQ ID NO: 206 | ADNQRPS |
| F5.1.9.5 LCDR3 | SEQ ID NO: 207 | QSYDSNIVI |
| d1C7 HCDR1 Kabat | SEQ ID NO: 208 | SYAIS |

TABLE 7-continued

Sequence Listing Table
Kabat CDR amino acid sequences are in bold. Chothia CDR amino acid sequences are underlined. Extended CDR amino acid sequences include both underlined and bold amino acid residues.

| | | |
|---|---|---|
| d1C7 HCDR1 Chothia | SEQ ID NO: 209 | GTFSSY |
| d1C7 HCDR1 Extended | SEQ ID NO: 210 | GTFSSYAIS |
| d1C7 HCDR2 Kabat | SEQ ID NO: 211 | GGIIPIFGTANYAQKFQGRV |
| d1C7 HCDR2 Chothia | SEQ ID NO: 212 | IIPIFGTAN |
| d1C7 HCDR3 | SEQ ID NO: 213 | VDRYYNWNYFLGSFDY |
| d1C7 LCDR1 | SEQ ID NO: 214 | GGNNIRSKSVH |
| d1C7 LCDR2 | SEQ ID NO: 215 | YDSDRPS |
| d1C7 LCDR3 | SEQ ID NO: 216 | QVWDSSSDHHV |
| F5.1.11.02 library HCDR1 | SEQ ID NO: 217 | SGGYYWS |
| F5.1.11.02 library HCDR2 | SEQ ID NO: 218 | GYIYKSGSAYYSPSLKSRV |
| F5.1.11.02 library HCDR3 (ital. randomized except C) | SEQ ID NO: 219 | TPTVTGDWFDP |
| F5.1.11.02 library LCDR1 (ital. randomized except C) | SEQ ID NO: 220 | TRSSGSIASNYVQ |
| F5.1.11.02 library LCDR2 | SEQ ID NO: 221 | EDNQRPS |
| F5.1.11.02 library LCDR3 | SEQ ID NO: 222 | QTYDSIDVY |

TABLE 8

HUMAN ANTI-IL-2 ANTIBODIES

| Monoclonal Antibody | SEQUENCE IDENTIFIER (SEQ ID NO:) Variable Domains | | | |
|---|---|---|---|---|
| | Light | | Heavy | |
| | DNA | Protein | DNA | Protein |
| F4.7.6 | 37 | 2 | 36 | 1 |
| F4.7.8 | 39 | 4 | 38 | 3 |
| F5.1.11 | 41 | 6 | 40 | 5 |
| F5.1.9 | 43 | 8 | 42 | 7 |
| F4.7.062 | 45 | 10 | 44 | 9 |
| F5.1.11.01 | 47 | 12 | 46 | 11 |
| F5.1.11.02 | 49 | 14 | 48 | 13 |
| F5.1.11.03 | 51 | 16 | 50 | 15 |
| F5.1.11.04 | 53 | 18 | 52 | 17 |
| F5.1.11.05 | 55 | 20 | 54 | 19 |
| F5.1.11.06 | 57 | 22 | 56 | 21 |
| F5.1.11.07 | 59 | 24 | 58 | 23 |
| F5.1.11.08 | 61 | 26 | 60 | 25 |
| F5.1.11.09 | 63 | 28 | 62 | 27 |
| F5.1.9.5 | 65 | 30 | 64 | 29 |
| d1C7 | 67 | 32 | 66 | 31 |

What is claimed is:

1. An isolated nucleic acid encoding a heavy chain, a light chain, or both a heavy chain and a light chain of an antibody or an antigen-binding portion thereof that specifically binds human interleukin-2 (hIL-2), wherein said nucleic acid comprises:
    (a) the nucleotide sequence of SEQ ID NO: 48;
    (b) the nucleotide sequence of SEQ ID NO: 49; or
    (c) the nucleotide sequence pairs
    SEQ ID NOs: 48 and 49.

2. A vector comprising the nucleic acid of claim 1.

3. A host cell comprising the nucleic acid of claim 2.

4. The host cell of claim 3, wherein the cell is a mammalian cell.

5. A method of producing an antibody or an antigen-binding portion thereof that specifically binds human interleukin-2 (hIL-2), said method comprising:
    a) culturing the host cell of claim 4 under conditions that allow said antibody or antigen-binding portion to be expressed, wherein the host cell comprises nucleotide sequences coding the heavy chain and light chain of the antibody or antigen-binding portion, and
    b) isolating said antibody or antigen-binding portion from the culture.

6. An isolated polynucleotide that encodes a polypeptide comprising the amino acid sequence of the polypeptide encoded by the plasmid deposited with American Type Culture Collection (ATCC) under deposit number PTA-123497 or PTA-123498.

* * * * *

SEQUENCE LISTING

<160> NUMBER OF SEQ ID NOS: 225

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Thr Val Thr Gly Asp Trp Phe Asp Pro Trp Gly
            100                 105                 110

Gln Gly Thr Leu Val Thr Val Ser Ser
        115                 120

<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
            50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                85                  90                  95

Ser Thr Val Val Phe Gly Gly Gly Thr Lys Leu Thr Val Leu
            100                 105                 110

<210> SEQ ID NO 3
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Asp Leu Thr Phe Asp Tyr Trp Gly Gln Gly Thr Leu Val Thr
            100                 105                 110

Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Ile Gln Leu Thr Gln Ser Pro Ser Ser Leu Ser Ala Ser Val Gly
 1               5                  10                  15

Asp Arg Val Thr Ile Thr Cys Gln Ala Ser Gln Asp Ile Phe Asn Leu
            20                  25                  30

Leu Asn Trp Tyr Arg Gln Lys Pro Gly Lys Ala Pro Asp Leu Leu Val
        35                  40                  45

Tyr Arg Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Val Gly Thr Tyr Tyr Cys Gln Gln Ser Ala Asn Leu Pro Leu
                85                  90                  95

Thr Phe Gly Gly Gly Thr Lys Val Glu Ile Lys
            100                 105

<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Thr Val Thr Gly Asp Trp Phe Asp Pro Trp Gly
            100                 105                 110

Arg Gly Thr Leu Val Thr Val Ser Ser
        115                 120

<210> SEQ ID NO 6
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Val Val Phe Gly Gly Gly Thr Lys Leu Thr Val Leu
            100                 105                 110

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Glu Val Gln Leu Val Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Glu Ala Tyr Ser Asp Arg Ala Phe Asp Ile Trp Gly Gln Gly
        100                 105                 110

Thr Met Val Thr Val Ser Ser
        115
```

<210> SEQ ID NO 8
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Asn Phe Met Leu Thr Gln Pro His Ser Val Ser Glu Ser Pro Gly Lys
1               5                   10                  15

Thr Ile Thr Ile Ser Cys Thr Arg Ser Ser Gly Ser Ile Ala Ser Asp
            20                  25                  30

Tyr Val Gln Trp Tyr Gln Gln Arg Pro Gly Ser Ser Pro Ser Thr Val
        35                  40                  45

Ile Tyr Ala Asp Asn Gln Arg Pro Ser Glu Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Met Thr Glu Asp Glu Ala Asp Tyr Tyr Cys Gln Ser Tyr Asp Ser
            85                  90                  95

Asn Ile Val Ile Phe Gly Gly Gly Thr Lys Leu Thr Val Leu
        100                 105                 110
```

<210> SEQ ID NO 9
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60
```

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Thr Pro Thr Val Thr Gly Asp Trp Phe Asp Pro Trp Gly
            100                 105                 110

Gln Gly Thr Leu Val Thr Val Ser Ser
            115                 120
```

```
<210> SEQ ID NO 10
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
                 20                  25                  30

Tyr Val Gln Trp Tyr Gln Gln Arg Pro Gly Ser Ser Pro Thr Thr Val
             35                  40                  45

Ile Tyr Glu Asp Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Asn Val Val Phe Gly Gly Gly Thr Lys Leu Thr Val Leu
            100                 105                 110
```

```
<210> SEQ ID NO 11
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Leu Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                 20                  25                  30

Gly Tyr Tyr Trp Ser Trp Ile Arg Gln His Pro Gly Lys Gly Leu Glu
             35                  40                  45

Trp Ile Gly Tyr Ile Tyr Lys Ser Gly Ser Ala Tyr Tyr Ser Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Thr Pro Thr Val Thr Gly Asp Trp Phe Asp Pro Trp Gly
            100                 105                 110

Arg Gly Thr Leu Val Thr Val Ser Ser
            115                 120
```

```
<210> SEQ ID NO 12
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Thr
                85                  90                  95

Arg Asp Val Val Phe Gly Gly Gly Thr Lys Leu Thr Val Leu
            100                 105                 110

<210> SEQ ID NO 13
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Leu Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Lys Ser Gly Ser Ala Tyr Tyr Ser Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Thr Val Thr Gly Asp Trp Phe Asp Pro Trp Gly
            100                 105                 110

Arg Gly Thr Leu Val Thr Val Ser Ser
        115                 120

<210> SEQ ID NO 14
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asn Phe Met Leu Thr Gln Pro His Ser Val Ser Glu Ser Pro Gly Lys
```

```
            1               5                  10                 15
Thr Val Thr Ile Ser Cys Thr Arg Ser Gly Ser Ile Ala Ser Asn
                20                 25                 30

Tyr Val Gln Trp Tyr Gln Gln Arg Pro Gly Ser Ser Pro Thr Thr Val
                35                 40                 45

Ile Tyr Glu Asp Asn Gln Arg Pro Ser Gly Val Pro Asp Arg Phe Ser
        50                 55                 60

Gly Ser Ile Asp Ser Ser Ser Asn Ser Ala Ser Leu Thr Ile Ser Gly
65                  70                 75                 80

Leu Lys Thr Glu Asp Glu Ala Asp Tyr Tyr Cys Gln Thr Tyr Asp Ser
                85                 90                 95

Ile Asp Val Tyr Phe Gly Gly Gly Thr Lys Leu Thr Val Leu
                100                105                110
```

<210> SEQ ID NO 15
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Leu Gln Leu Gln Glu Ser Gly Pro Gly Leu Val Lys Pro Ser Gln
1               5                  10                 15

Thr Leu Ser Leu Thr Cys Thr Val Ser Gly Gly Ser Ile Ser Ser Gly
                20                 25                 30

Gly Tyr Tyr Trp Ser Trp Ile Arg Gln His Pro Gly Lys Gly Leu Glu
                35                 40                 45

Trp Ile Gly Tyr Ile Tyr Lys Ser Gly Ser Ala Tyr Tyr Ser Pro Ser
        50                 55                 60

Leu Lys Ser Arg Val Thr Ile Ser Val Asp Thr Ser Lys Asn Gln Phe
65                  70                 75                 80

Ser Leu Lys Leu Ser Ser Val Thr Ala Ala Asp Thr Ala Val Tyr Tyr
                85                 90                 95

Cys Ala Arg Thr Pro Thr Val Thr Gly Asp Trp Phe Asp Pro Trp Gly
                100                105                110

Arg Gly Thr Leu Val Thr Val Ser Ser
        115                120
```

<210> SEQ ID NO 16
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Asn Phe Met Leu Thr Gln Pro His Ser Val Ser Glu Ser Pro Gly Lys
1               5                  10                 15

Thr Val Thr Ile Ser Cys Thr Arg Ser Ser Gly Ser Ile Ala Ser Asn
                20                 25                 30

Tyr Val Gln Trp Tyr Gln Gln Arg Pro Gly Ser Ser Pro Thr Thr Val
                35                 40                 45

Ile Tyr Glu Asp Asn Gln Arg Pro Ser Gly Val Pro Asp Arg Phe Ser
        50                 55                 60

Gly Ser Ile Asp Ser Ser Ser Asn Ser Ala Ser Thr Ile Ser Gly Leu
```

```
                65                  70                  75                  80
Lys Thr Glu Asp Glu Ala Asp Tyr Tyr Cys Gln Ser Tyr Asp Thr Leu
                    85                  90                  95

Asn Val Tyr Phe Gly Gly Gly Thr Lys Leu Thr Val Leu
                100                 105
```

```
<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17
```

```
Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Asn Tyr Trp Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Thr Val Thr Gly Asp Trp Phe Asp Pro Trp Gly
            100                 105                 110

Arg Gly Thr Leu Val Thr Val Ser Ser
        115                 120
```

```
<210> SEQ ID NO 18
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Thr
                85                  90                  95

Arg Asp Val Val Phe Gly Gly Gly Thr Lys Leu Thr Val Leu
            100                 105                 110
```

```
<210> SEQ ID NO 19
<211> LENGTH: 121
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 19

```
Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Asn Tyr Trp Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Thr Val Thr Gly Asp Trp Phe Asp Pro Trp Gly
            100                 105                 110

Arg Gly Thr Leu Val Thr Val Ser Ser
        115                 120
```

<210> SEQ ID NO 20
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Ser
                85                  90                  95

Ile Asp Val Tyr Phe Gly Gly Gly Thr Lys Leu Thr Val Leu
            100                 105                 110
```

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30
```

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Asn Tyr Trp Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Thr Pro Thr Val Thr Gly Asp Trp Phe Asp Pro Trp Gly
            100                 105                 110

Arg Gly Thr Leu Val Thr Val Ser Ser
            115                 120

<210> SEQ ID NO 22
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Thr
            85                  90                  95

Leu Asn Val Tyr Phe Gly Gly Gly Thr Lys Leu Thr Val Leu
            100                 105                 110

<210> SEQ ID NO 23
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
            35                  40                  45

Trp Ile Gly Tyr Ile Tyr Lys Ser Gly Ser Asn Tyr Trp Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Thr Pro Thr Val Thr Gly Asp Trp Phe Asp Pro Trp Gly
            100                 105                 110

Arg Gly Thr Leu Val Thr Val Ser Ser
        115                 120

<210> SEQ ID NO 24
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Arg Pro Gly Ser Ser Pro Thr Thr Val
        35                  40                  45

Ile Tyr Glu Asp Asn Gln Arg Pro Ser Gly Val Pro Asp Arg Phe Ser
50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Thr
                85                  90                  95

Arg Asp Val Val Phe Gly Gly Gly Thr Lys Leu Thr Val Leu
            100                 105                 110

<210> SEQ ID NO 25
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Lys Ser Gly Ser Asn Tyr Trp Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Thr Val Thr Gly Asp Trp Phe Asp Pro Trp Gly
            100                 105                 110

Arg Gly Thr Leu Val Thr Val Ser Ser
        115                 120

<210> SEQ ID NO 26
<211> LENGTH: 110
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 26

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Ser
                85                  90                  95

Ile Asp Val Tyr Phe Gly Gly Gly Thr Lys Leu Thr Val Leu
            100                 105                 110

<210> SEQ ID NO 27
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Lys Ser Gly Ser Asn Tyr Trp Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Thr Val Thr Gly Asp Trp Phe Asp Pro Trp Gly
            100                 105                 110

Arg Gly Thr Leu Val Thr Val Ser Ser
        115                 120

<210> SEQ ID NO 28
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30
```

```
Tyr Val Gln Trp Tyr Gln Gln Arg Pro Gly Ser Ser Pro Thr Thr Val
             35                  40                  45

Ile Tyr Glu Asp Asn Gln Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Thr
                 85                  90                  95

Leu Asn Val Tyr Phe Gly Gly Gly Thr Lys Leu Thr Val Leu
             100                 105                 110

<210> SEQ ID NO 29
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Pro Gly Leu Val Lys Pro Ser Glu
 1               5                   10                  15

Thr Leu Ser Leu Thr Cys Ala Val Ser Gly Tyr Ser Ile Ser Ser Gly
             20                  25                  30

Tyr Tyr Trp Gly Trp Ile Arg Gln Pro Pro Gly Lys Gly Leu Glu Trp
             35                  40                  45

Ile Gly Leu Ser Tyr His Thr Arg Ser Thr Tyr Tyr Asp Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Glu Ala Tyr Ser Asp Arg Ala Phe Asp Ile Trp Gly Gln Gly
             100                 105                 110

Thr Met Val Thr Val Ser Ser
        115

<210> SEQ ID NO 30
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asn Phe Met Leu Thr Gln Pro His Ser Val Ser Glu Ser Pro Gly Lys
 1               5                   10                  15

Thr Ile Thr Ile Ser Cys Thr Arg Ser Ser Gly Ser Ile Ala Ser Asp
             20                  25                  30

Tyr Val Gln Trp Tyr Gln Gln Arg Pro Gly Ser Ser Pro Ser Thr Val
             35                  40                  45

Ile Tyr Ala Asp Asn Gln Arg Pro Ser Glu Val Pro Asp Arg Phe Ser
 50                  55                  60

Gly Ser Ile Asp Ser Ser Asn Ser Ala Ser Leu Thr Ile Ser Gly
 65                  70                  75                  80

Leu Met Thr Glu Asp Glu Ala Asp Tyr Tyr Cys Gln Ser Tyr Asp Ser
                 85                  90                  95
```

```
Asn Ile Val Ile Phe Gly Gly Gly Thr Lys Leu Thr Val Leu
                100                 105                 110
```

<210> SEQ ID NO 31
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asp Arg Tyr Tyr Asn Trp Asn Tyr Phe Leu Gly Ser Phe
            100                 105                 110

Asp Tyr Trp Gly Gln Gly Thr Leu Val Thr Val Ser Ser
        115                 120                 125
```

<210> SEQ ID NO 32
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Arg Ser Lys Ser Val
            20                  25                  30

His Trp Tyr Gln Gln Lys Pro Gly Gln Ala Pro Val Val Val Ile Tyr
        35                  40                  45

Tyr Asp Ser Asp Arg Pro Ser Gly Ile Pro Glu Arg Ile Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Phe Cys Gln Val Trp Asp Ser Ser Ser Asp His
                85                  90                  95

His Val Phe Gly Gly Gly Thr Lys Leu Thr Val Leu
            100                 105
```

<210> SEQ ID NO 33
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 35
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Ser Ser Pro
         35                  40                  45

Val Lys Ala Gly Val Glu Thr Thr Thr Pro Ser Lys Gln Ser Asn Asn
     50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 36
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gaggtccagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatt gggtacatct attacagtgg agcacctac    180 tacaacccgt ccctcaagag tcgagttacc atatcagtag acacgtctaa gaaccagttc   240
tccctgaagc tgagctctgt gactgccgcg gacacggccg tgtattactg tgcgaggact   300
cctacggtga ccggggactg gttcgacccc tggggccagg gaaccctggt caccgtctcg   360
agc                                                                363

<210> SEQ ID NO 37
<211> LENGTH: 330
<212> TYPE: DNA
```

```
<213> ORGANISM: Artificial Sequence
<220> FEATURE:
<223> OTHER INFORMATION: Description of Artificial Sequence: Synthetic
      polynucleotide

<400> SEQUENCE: 37
aattttatgc tgactcagcc ccactctgtg tcggagtctc cggggaagac ggtaaccatc      60
tcctgcaccc gcagcagtgg cagcattgcc agcaactatg tgcagtggta ccagcagcgc     120
ccgggcagtt cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgatagcag caccgtggta     300
ttcggcggag ggaccaagct gaccgtccta                                     330

<210> SEQ ID NO 38
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
caggtccagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccta acagtggtgg cacaaactat      180
gcacagaagt tcagggcag gtcaccatg accagggaca cgtccatcag cacagcctac      240
atggagctga gcaggctgag atctgacgac acggccgtgt attactgtgc gagagaccta     300
acgtttgact actggggcca gggaaccctg gtcaccgtct cgagc                     345

<210> SEQ ID NO 39
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gccatccagt tgacccagtc tccatcctcc ctgtctgcgt ctgtaggaga cagggtcacc      60
atcacttgcc aggcgagtca ggacattttc aacctcttaa attggtatag cagaaaacca     120
gggaaagccc ctgacctcct ggtctaccgc gcttccaatt tggagacagg ggtcccatcc     180
aggttcagtg gaagtgggtc tgggacagac tttactttca ccattagtag cctgcagcct     240
gaagatgttg gaacctatta ttgtcaacag agtgctaatc tccccctcac tttcggcgga     300
gggaccaagg tggagatcaa a                                              321

<210> SEQ ID NO 40
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
cagctgcagc tgcaggagtc gggcccagga ctggtgaagc cttcacagac cctgtccctc      60
acctgcactg tctctggtgg ctccatcagc agtggtggtt actactggag ctggatccgc     120
```

```
cagcacccag ggaagggcct ggagtggatt gggtacatct attacagtgg gagcacctac      180
tacaacccgt ccctcaagag tcgagttacc atatcagtag acacgtctaa gaaccagttc      240
tccctgaagc tgagctctgt gactgccgcg gacacggccg tgtattactg tgcgaggact      300
cctacggtga ccggggactg gttcgacccc tggggccgtg caccctggt caccgtctcg       360 agc                                                                    363

<210> SEQ ID NO 41
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
aattttatgc tgactcagcc ccactctgtg tcggagtctc cggggaagac ggtaaccatc       60
tcctgcaccc gcagcagtgg cagcattgcc agcaactatg tgcagtggta ccagcagcgc      120
ccgggcagtt cccccaccac tgtgatctat gaggataacc aaagaccctc tggggtccct      180
gatcggttct ctggctccat cgacagctcc tccaactctg cctccctcac catctctgga      240
ctgaagactg aggacgaggc tgactactac tgtcagtctt atgatagcag caatgtggta      300
ttcggcggag ggaccaagct gaccgtccta                                       330

<210> SEQ ID NO 42
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gaggtgcagc tggtggagtc gggcccagga ctggtgaagc cttcggagac cctgtccctc       60
acctgcgctg tctctggtta ctccatcagc agtggttact actggggctg gatccggcag      120
cccccaggga aggggctgga gtggattggg agtatctatc atagtgggag cacctactac      180
aacccgtccc tcaagagtcg agtcaccata tcagtagaca cgtccaagaa ccagttctcc      240
ctgaagctga gctctgtgac cgccgcagac acggccgtgt attactgtgc gagagaggcc      300
tactccgatc gggcttttga tatctggggc caagggacaa tggtcaccgt ctcgagc         357

<210> SEQ ID NO 43
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
aattttatgc tgactcagcc ccactctgtg tcggagtctc cggggaagac gataaccatc       60
tcctgcaccc gcagcagtgg cagcattgcc agcgactatg tgcagtggta ccagcagcgc      120
ccgggcagtt cccccagcac tgtgatctat gcggataacc aaagaccctc tgaagtccct      180
gatcggttct ctggctccat cgacagctcc tccaactctg cctccctcac catctctgga      240
ctgatgactg aggacgaggc tgactactac tgtcagtctt atgatagcaa catcgtgata      300
ttcggcggag ggaccaagct gaccgtccta                                       330
```

<210> SEQ ID NO 44
<211> LENGTH: 363
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 44

```
caggtgcagc tacaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgaggact     300
cctacggtga ccggggactg gttcgacccc tggggccagg gaaccctggt caccgtctcg     360
agc                                                                   363
```

<210> SEQ ID NO 45
<211> LENGTH: 330
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 45

```
aattttatgc tgactcagcc ccactctgtg tcggagtctc cggggaagac ggtaaccatc      60
tcctgcaccc gcagcagtgg cagcattgcc agcaactatg tgcagtggta ccagcagcgc     120
ccgggcagtt cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgatagcag caatgtggta     300
ttcggcggag ggaccaagct gaccgtccta                                      330
```

<210> SEQ ID NO 46
<211> LENGTH: 363
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 46

```
cagctgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt ggatatatct ataagagtgg gagcgcgtac     180
tacagcccgt ccctcaagag tcgagttacc atatcagtag acacgtctaa gaaccagttc     240
tccctgaagc tgagctctgt gactgccgcg gacacggccg tgtattactg tgcgaggact     300
cctacggtga ccggggactg gttcgacccc tggggccgtg caccctggt caccgtctcc      360 tca                                                                   363
```

<210> SEQ ID NO 47
<211> LENGTH: 330
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 47
aattttatgc tgactcagcc ccactctgtg tcggagtctc cggggaagac ggtaaccatc    60
tcctgcaccc gcagcagtgg cagcattgcc agcaactatg tgcagtggta ccagcagcgc   120
ccgggcagtt cccccaccac tgtgatctat gaggataacc aaagaccctc tggggtccct   180
gatcggttct ctggctccat cgacagctcc tccaactctg cctccctcac catctctgga   240
ctgaagactg aggacgaggc tgactactac tgtcagtctt atgataccag ggatgtcgta   300
ttcggcggag ggaccaagct gaccgtccta                                    330

<210> SEQ ID NO 48
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
cagctgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatt ggatatatct ataagagtgg gagcgcgtac   180
tacagcccgt ccctcaagag tcgagttacc atatcagtag acacgtctaa gaaccagttc   240
tccctgaagc tgagctctgt gactgccgcg gacacggccg tgtattactg tgcgaggact   300
cctacggtga ccggggactg gttcgacccc tggggccgtg caccctggt caccgtctcc   360 tca                                                                 363

<210> SEQ ID NO 49
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
aattttatgc tgactcagcc ccactctgtg tcggagtctc cggggaagac ggtaaccatc    60
tcctgcaccc gcagcagtgg cagcattgcc agcaactatg tgcagtggta ccagcagcgc   120
ccgggcagtt cccccaccac tgtgatctat gaggataacc aaagaccctc tggggtccct   180
gatcggttct ctggctccat cgacagctcc tccaactctg cctccctcac catctctgga   240
ctgaagactg aggacgaggc tgactactac tgtcagactt atgacagcat cgatgtgtat   300
ttcggcggag ggaccaagct gaccgtccta                                    330

<210> SEQ ID NO 50
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
cagctgcagc tgcaggagtc gggcccagga ctggtgaagc cttcacagac cctgtccctc    60
```

```
acctgcactg tctctggtgg ctccatcagc agtggtggtt actactggag ctggatccgc    120
cagcacccag ggaagggcct ggagtggatt ggatatatct ataagagtgg gagcgcgtac    180
tacagcccgt ccctcaagag tcgagttacc atatcagtag acacgtctaa gaaccagttc    240
tccctgaagc tgagctctgt gactgccgcg gacacggccg tgtattactg tgcgaggact    300
cctacggtga ccggggactg gttcgacccc tggggccgtg caccctggt caccgtctcc    360 tca                                                                  363

<210> SEQ ID NO 51
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
aattttatgc tgactcagcc ccactctgtg tcggagtctc ggggaagac ggtaaccatc     60 tcctgcaccc gcagcagtgg cagcattgcc agcaactatg tgcagtggta ccagcagcgc    120
ccgggcagtt cccccaccac tgtgatctat gaggataacc aaagaccctc tggggtccct    180
gatcggttct ctggctccat cgacagctcc tccaactctg cctccctcac catctctgga    240
ctgaagactg aggacgaggc tgactactac tgtcagtctt atgataccct taatgtgtat    300
ttcggcggag ggaccaagct gaccgtccta                                     330

<210> SEQ ID NO 52
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
cagctgcagc tgcaggagtc gggcccagga ctggtgaagc cttcacagac cctgtccctc     60
acctgcactg tctctggtgg ctccatcagc agtggtggtt actactggag ctggatccgc    120
cagcacccag ggaagggcct ggagtggatt ggatacattt attacagcgg gagcaactac    180
tggaatccgt ccctcaagag tcgagttacc atatcagtag acacgtctaa gaaccagttc    240
tccctgaagc tgagctctgt gactgccgcg gacacggccg tgtattactg tgcgaggact    300
cctacggtga ccggggactg gttcgacccc tggggccgtg caccctggt caccgtctcc    360 tca                                                                  363

<210> SEQ ID NO 53
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
aattttatgc tgactcagcc ccactctgtg tcggagtctc ggggaagac ggtaaccatc     60 tcctgcaccc gcagcagtgg cagcattgcc agcaactatg tgcagtggta ccagcagcgc    120
ccgggcagtt cccccaccac tgtgatctat gaggataacc aaagaccctc tggggtccct    180
gatcggttct ctggctccat cgacagctcc tccaactctg cctccctcac catctctgga    240
```

```
ctgaagactg aggacgaggc tgactactac tgtcagtctt atgataccag ggatgtcgta    300
ttcggcggag ggaccaagct gaccgtccta                                     330

<210> SEQ ID NO 54
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
cagctgcagc tgcaggagtc gggcccagga ctggtgaagc cttcacagac cctgtccctc    60
acctgcactg tctctggtgg ctccatcagc agtggtggtt actactggag ctggatccgc    120
cagcacccag ggaagggcct ggagtggatt ggatacattt attacagcgg gagcaactac    180
tggaatccgt ccctcaagag tcgagttacc atatcagtag acacgtctaa gaaccagttc    240
tccctgaagc tgagctctgt gactgccgcg gacacggccg tgtattactg tgcgaggact    300
cctacggtga ccggggactg gttcgacccc tggggccgtg gcaccctggt caccgtctcc    360
tca                                                                  363

<210> SEQ ID NO 55
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
aattttatgc tgactcagcc ccactctgtg tcggagtctc cggggaagac ggtaaccatc    60
tcctgcaccc gcagcagtgg cagcattgcc agcaactatg tgcagtggta ccagcagcgc    120
ccgggcagtt cccccaccac tgtgatctat gaggataacc aaagaccctc tggggtccct    180
gatcggttct ctggctccat cgacagctcc tccaactctg cctccctcac catctctgga    240
ctgaagactg aggacgaggc tgactactac tgtcagactt atgacagcat cgatgtgtat    300
ttcggcggag ggaccaagct gaccgtccta                                     330

<210> SEQ ID NO 56
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
cagctgcagc tgcaggagtc gggcccagga ctggtgaagc cttcacagac cctgtccctc    60
acctgcactg tctctggtgg ctccatcagc agtggtggtt actactggag ctggatccgc    120
cagcacccag ggaagggcct ggagtggatt ggatacattt attacagcgg gagcaactac    180
tggaatccgt ccctcaagag tcgagttacc atatcagtag acacgtctaa gaaccagttc    240
tccctgaagc tgagctctgt gactgccgcg gacacggccg tgtattactg tgcgaggact    300
cctacggtga ccggggactg gttcgacccc tggggccgtg gcaccctggt caccgtctcc    360
tca                                                                  363

<210> SEQ ID NO 57
```

<210> SEQ ID NO 57
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
aattttatgc tgactcagcc ccactctgtg tcggagtctc ggggaagac ggtaaccatc      60 tcctgcaccc gcagcagtgg cagcattgcc agcaactatg tgcagtggta ccagcagcgc    120
ccgggcagtt cccccaccac tgtgatctat gaggataacc aaagaccctc tggggtccct    180
gatcggttct ctggctccat cgacagctcc tccaactctg cctccctcac catctctgga    240
ctgaagactg aggacgaggc tgactactac tgtcagtctt atgataccct taatgtgtat    300
ttcggcggag ggaccaagct gaccgtccta                                    330

<210> SEQ ID NO 58
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
cagctgcagc tgcaggagtc gggcccagga ctggtgaagc cttcacagac cctgtccctc     60
acctgcactg tctctggtgg ctccatcagc agtggtggtt actactggag ctggatccgc    120
cagcacccag ggaagggcct ggagtggatt gggtacatct ataagagcgg gagcaactac    180
tggaacccgt ccctcaagag tcgagttacc atatcagtag acacgtctaa gaaccagttc    240
tccctgaagc tgagctctgt gactgccgcg gacacggccg tgtattactg tgcgaggact    300
cctacggtga ccggggactg gttcgacccc tggggccgtg caccctggt caccgtctcc    360 tca                                                                363

<210> SEQ ID NO 59
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
aattttatgc tgactcagcc ccactctgtg tcggagtctc ggggaagac ggtaaccatc      60 tcctgcaccc gcagcagtgg cagcattgcc agcaactatg tgcagtggta ccagcagcgc    120
ccgggcagtt cccccaccac tgtgatctat gaggataacc aaagaccctc tggggtccct    180
gatcggttct ctggctccat cgacagctcc tccaactctg cctccctcac catctctgga    240
ctgaagactg aggacgaggc tgactactac tgtcagtctt atgataccag ggatgtcgta    300
ttcggcggag ggaccaagct gaccgtccta                                    330

<210> SEQ ID NO 60
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
cagctgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatt gggtacatct ataagagcgg gagcaactac   180
tggaacccgt ccctcaagag tcgagttacc atatcagtag acacgtctaa gaaccagttc   240
tccctgaagc tgagctctgt gactgccgcg gacacggccg tgtattactg tgcgaggact   300
cctacggtga ccggggactg gttcgacccc tggggccgtg gcaccctggt caccgtctcc   360
tca                                                                 363
```

<210> SEQ ID NO 61
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
aattttatgc tgactcagcc ccactctgtg tcggagtctc cggggaagac ggtaaccatc    60
tcctgcaccc gcagcagtgg cagcattgcc agcaactatg tgcagtggta ccagcagcgc   120
ccgggcagtt cccccaccac tgtgatctat gaggataacc aaagaccctc tggggtccct   180
gatcggttct ctggctccat cgacagctcc tccaactctg cctccctcac catctctgga   240
ctgaagactg aggacgaggc tgactactac tgtcagactt atgacagcat cgatgtgtat   300
ttcggcggag ggaccaagct gaccgtccta                                    330
```

<210> SEQ ID NO 62
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
cagctgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatt gggtacatct ataagagcgg gagcaactac   180
tggaacccgt ccctcaagag tcgagttacc atatcagtag acacgtctaa gaaccagttc   240
tccctgaagc tgagctctgt gactgccgcg gacacggccg tgtattactg tgcgaggact   300
cctacggtga ccggggactg gttcgacccc tggggccgtg gcaccctggt caccgtctcc   360
tca                                                                 363
```

<210> SEQ ID NO 63
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
aattttatgc tgactcagcc ccactctgtg tcggagtctc cggggaagac ggtaaccatc    60
tcctgcaccc gcagcagtgg cagcattgcc agcaactatg tgcagtggta ccagcagcgc   120
ccgggcagtt cccccaccac tgtgatctat gaggataacc aaagaccctc tggggtccct   180
```

```
gatcggttct ctggctccat cgacagctcc tccaactctg cctccctcac catctctgga    240
ctgaagactg aggacgaggc tgactactac tgtcagtctt atgatacect taatgtgtat    300 ttcggcggag ggaccaagct gaccgtccta                                     330
```

<210> SEQ ID NO 64
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
gaggtgcagc tggtggagtc gggcccagga ctggtgaagc cttcggagac cctgtccctc    60
acctgcgctg tctctggtta ctccatcagc agtggttact actggggctg gatccggcag    120
cccccaggga aggggctgga gtggattggt ttgagctacc acactcgttc tacctactac    180
gatccgtccc tcaagagtcg agtcaccata tcagtagaca cgtccaagaa ccagttctcc    240
ctgaagctga gctctgtgac cgccgcagac acggccgtgt attactgtgc gagagaggcc    300
tactccgatc gggcttttga tatctggggc caagggacaa tggtcaccgt ctcctca      357
```

<210> SEQ ID NO 65
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
aattttatgc tgactcagcc ccactctgtg tcggagtctc cggggaagac gataaccatc    60
tcctgcaccc gcagcagtgg cagcattgcc agcgactatg tgcagtggta ccagcagcgc    120
ccgggcagtt cccccagcac tgtgatctat gcggataacc aaagacectc tgaagtccct    180 gatcggttct ctggctccat cgacagctcc tccaactctg cctccctcac catctctgga    240
ctgatgactg aggacgaggc tgactactac tgtcagtctt atgatagcaa catcgtgata    300
ttcggcggag ggaccaagct gaccgtccta                                     330
```

<210> SEQ ID NO 66
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
caggtccagc tggtgcagtc tggggctgag gtgaagaagc ctgggtcctc ggtgaaggtc    60
tcctgcaagg cttctggagg caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagtggac    300
cggtattata actggaacta cttttttaggc tcctttgact actggggcca gggaaccctg    360
gtcaccgtct cgagc                                                     375
```

```
<210> SEQ ID NO 67
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
agctatgtgc tgactcagcc accctcagtg tcagtggccc caggaaagac ggccaggatt      60
acctgtgggg gaaacaacat tagaagtaaa agtgtgcact ggtaccagca gaagcccggc     120
caggcccctg tggtggtcat ctattatgat agcgaccggc cctcagggat ccctgagcga     180
atctctgggt ccaactctgg aaacacggcc accctgacca tcagcagggt cgaagccggg     240
gatgaggccg actattttg tcaggtgtgg gatagtagta gtgaccatca tgtattcggc      300
ggagggacca agctgaccgt ccta                                             324

<210> SEQ ID NO 68
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaagc cgctggggca     360
ccgtcagtct tcctcttccc tccaaaaccc aaggacaccc tcatgatctc ccggaccct      420 gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                       990

<210> SEQ ID NO 69
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
cgaactgtgg ctgcaccatc tgtcttcatc ttcccgccat ctgatgagca gttgaaatct      60
```

```
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                               321

<210> SEQ ID NO 70
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
ggtcagccca aggctgcccc ctcggtcact ctgttcccac cctcctctga ggagcttcaa     60
gccaacaagg ccacactggt gtgtctcata agtgacttct acccgggagc cgtgacagtg    120
gcctggaagg cagatagcag ccccgtcaag gcgggagtgg agaccaccac accctccaaa    180
caaagcaaca acaagtacgc ggccagcagc tacctgagcc tgacgcctga gcagtggaag    240
tcccacagaa gctacagctg ccaggtcacg catgaaggga gcaccgtgga agacagtg     300 gcccctacag aatgttca                                                  318

<210> SEQ ID NO 71
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Lys Ser Gly Ser Ala Tyr Tyr Ser Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Thr Val Thr Gly Asp Trp Phe Asp Pro Trp Gly
            100                 105                 110

Arg Gly Thr Leu Val Thr Val Ser Ser
        115                 120

<210> SEQ ID NO 72
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72
```

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Ser
                85                  90                  95

Ile Asp Val Tyr Phe Gly Gly Gly Thr Lys Leu Thr Val Leu
            100                 105                 110
```

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

```
Ser Gly Gly Tyr Tyr Trp Ser
1               5
```

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

```
Gly Ser Ile Ser Ser Gly Gly Tyr
1               5
```

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

```
Gly Ser Ile Ser Ser Gly Gly Tyr Tyr Trp Ser
1               5                   10
```

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

```
Gly Tyr Ile Tyr Tyr Ser Gly Ser Thr Tyr Tyr Asn Pro Ser Leu Lys
1               5                   10                  15

Ser Arg Val
```

```
<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ile Tyr Tyr Ser Gly Ser Thr Tyr
1               5

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Pro Thr Val Thr Gly Asp Trp Phe Asp Pro
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Arg Ser Ser Gly Ser Ile Ala Ser Asn Tyr Val Gln
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Asp Asn Gln Arg Pro Ser
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Ser Tyr Asp Ser Ser Thr Val Val
1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 82

Gly Tyr Tyr Met His
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Tyr Thr Phe Thr Gly Tyr
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Tyr Thr Phe Thr Gly Tyr Tyr Met His
1               5

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Trp Ile Asn Pro Asn Ser Gly Gly Thr Asn Tyr Ala Gln Lys Phe
1               5                   10                  15

Gln Gly Arg Val
            20

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ile Asn Pro Asn Ser Gly Gly Thr Asn
1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Leu Thr Phe Asp Tyr
1               5
```

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Ala Ser Gln Asp Ile Phe Asn Leu Leu Asn
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ala Ser Asn Leu Glu Thr
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Gln Ser Ala Asn Leu Pro Leu Thr
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Gly Gly Tyr Tyr Trp Ser
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ser Ile Ser Ser Gly Gly Tyr
1               5

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 93

Gly Ser Ile Ser Ser Gly Gly Tyr Tyr Trp Ser
1               5                   10

<210> SEQ ID NO 94
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Tyr Ile Tyr Tyr Ser Gly Ser Thr Tyr Tyr Asn Pro Ser Leu Lys
1               5                   10                  15

Ser Arg Val

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ile Tyr Tyr Ser Gly Ser Thr Tyr
1               5

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Pro Thr Val Thr Gly Asp Trp Phe Asp Pro
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Arg Ser Ser Gly Ser Ile Ala Ser Asn Tyr Val Gln
1               5                   10

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Asp Asn Gln Arg Pro Ser
1               5

<210> SEQ ID NO 99
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Ser Tyr Asp Ser Ser Asn Val Val
1               5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Gly Tyr Tyr Trp Gly
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Tyr Ser Ile Ser Ser Gly Tyr
1               5

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Tyr Ser Ile Ser Ser Gly Tyr Tyr Trp Gly
1               5                   10

<210> SEQ ID NO 103
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ser Ile Tyr His Ser Gly Ser Thr Tyr Tyr Asn Pro Ser Leu Lys
1               5                   10                  15

Ser Arg Val

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 104

Ile Tyr His Ser Gly Ser Thr Tyr
1               5

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Glu Ala Tyr Ser Asp Arg Ala Phe Asp Ile
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Thr Arg Ser Ser Gly Ser Ile Ala Ser Asp Tyr Val Gln
1               5                   10

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Asp Asn Gln Arg Pro Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Ser Tyr Asp Ser Asn Ile Val Ile
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Gly Gly Tyr Tyr Trp Ser
1               5

<210> SEQ ID NO 110
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 110

Gly Ser Ile Ser Ser Gly Gly Tyr
1               5

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Ser Ile Ser Ser Gly Gly Tyr Tyr Trp Ser
1               5                   10

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Tyr Ile Tyr Tyr Ser Gly Ser Thr Tyr Tyr Asn Pro Ser Leu Lys
1               5                   10                  15

Ser Arg Val

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ile Tyr Tyr Ser Gly Ser Thr Tyr
1               5

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Pro Thr Val Thr Gly Asp Trp Phe Asp Pro
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115
```

```
Thr Arg Ser Ser Gly Ser Ile Ala Ser Asn Tyr Val Gln
1               5                   10
```

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

```
Glu Asp Asn Gln Arg Pro Ser
1               5
```

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Gln Ser Tyr Asp Ser Ser Asn Val Val
1               5
```

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Ser Gly Gly Tyr Tyr Trp Ser
1               5
```

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Gly Ser Ile Ser Ser Gly Gly Tyr
1               5
```

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Gly Ser Ile Ser Ser Gly Gly Tyr Tyr Trp Ser
1               5                   10
```

<210> SEQ ID NO 121
<211> LENGTH: 19
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 121

Gly Tyr Ile Tyr Lys Ser Gly Ser Ala Tyr Tyr Ser Pro Ser Leu Lys
1               5                   10                  15

Ser Arg Val

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ile Tyr Lys Ser Gly Ser Ala Tyr
1               5

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Thr Pro Thr Val Thr Gly Asp Trp Phe Asp Pro
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Arg Ser Ser Gly Ser Ile Ala Ser Asn Tyr Val Gln
1               5                   10

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Glu Asp Asn Gln Arg Pro Ser
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Ser Tyr Asp Thr Arg Asp Val Val
1               5
```

```
<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Gly Gly Tyr Tyr Trp Ser
1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Ser Ile Ser Ser Gly Gly Tyr
1               5

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Ser Ile Ser Ser Gly Gly Tyr Tyr Trp Ser
1               5                   10

<210> SEQ ID NO 130
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Tyr Ile Tyr Lys Ser Gly Ser Ala Tyr Tyr Ser Pro Ser Leu Lys
1               5                   10                  15

Ser Arg Val

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ile Tyr Lys Ser Gly Ser Ala Tyr
1               5

<210> SEQ ID NO 132
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 132

Thr Pro Thr Val Thr Gly Asp Trp Phe Asp Pro
1               5                   10

<210> SEQ ID NO 133
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Arg Ser Ser Gly Ser Ile Ala Ser Asn Tyr Val Gln
1               5                   10

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Glu Asp Asn Gln Arg Pro Ser
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Thr Tyr Asp Ser Ile Asp Val Tyr
1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Gly Gly Tyr Tyr Trp Ser
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Ser Ile Ser Ser Gly Gly Tyr
1               5
```

```
<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Ser Ile Ser Ser Gly Gly Tyr Tyr Trp Ser
1               5                   10

<210> SEQ ID NO 139
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Tyr Ile Tyr Lys Ser Gly Ser Ala Tyr Tyr Ser Pro Ser Leu Lys
1               5                   10                  15

Ser Arg Val

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ile Tyr Lys Ser Gly Ser Ala Tyr
1               5

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Thr Pro Thr Val Thr Gly Asp Trp Phe Asp Pro
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Thr Arg Ser Ser Gly Ser Ile Ala Ser Asn Tyr Val Gln
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 143

Glu Asp Asn Gln Arg Pro Ser
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Ser Tyr Asp Thr Leu Asn Val Tyr
1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Gly Gly Tyr Tyr Trp Ser
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Ser Ile Ser Ser Gly Gly Tyr
1               5

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Ser Ile Ser Ser Gly Gly Tyr Tyr Trp Ser
1               5                   10

<210> SEQ ID NO 148
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Tyr Ile Tyr Tyr Ser Gly Ser Asn Tyr Trp Asn Pro Ser Leu Lys
1               5                   10                  15

Ser Arg Val
```

```
<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ile Tyr Tyr Ser Gly Ser Asn Tyr
1               5

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Thr Pro Thr Val Thr Gly Asp Trp Phe Asp Pro
1               5                   10

<210> SEQ ID NO 151
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Thr Arg Ser Ser Gly Ser Ile Ala Ser Asn Tyr Val Gln
1               5                   10

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Glu Asp Asn Gln Arg Pro Ser
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Ser Tyr Asp Thr Arg Asp Val Val
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154
```

```
Ser Gly Gly Tyr Tyr Trp Ser
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Ser Ile Ser Ser Gly Gly Tyr
1               5

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Ser Ile Ser Ser Gly Gly Tyr Tyr Trp Ser
1               5                   10

<210> SEQ ID NO 157
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Tyr Ile Tyr Tyr Ser Gly Ser Asn Tyr Trp Asn Pro Ser Leu Lys
1               5                   10                  15

Ser Arg Val

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ile Tyr Tyr Ser Gly Ser Asn Tyr
1               5

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Thr Pro Thr Val Thr Gly Asp Trp Phe Asp Pro
1               5                   10

<210> SEQ ID NO 160
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Arg Ser Ser Gly Ser Ile Ala Ser Asn Tyr Val Gln
1               5                   10

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Glu Asp Asn Gln Arg Pro Ser
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Thr Tyr Asp Ser Ile Asp Val Tyr
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ser Gly Gly Tyr Tyr Trp Ser
1               5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Ser Ile Ser Ser Gly Gly Tyr
1               5

<210> SEQ ID NO 165
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Ser Ile Ser Ser Gly Gly Tyr Tyr Trp Ser
```

<210> SEQ ID NO 166
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Tyr Ile Tyr Tyr Ser Gly Ser Asn Tyr Trp Asn Pro Ser Leu Lys
1               5                   10                  15

Ser Arg Val

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ile Tyr Tyr Ser Gly Ser Asn Tyr
1               5

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Thr Pro Thr Val Thr Gly Asp Trp Phe Asp Pro
1               5                   10

<210> SEQ ID NO 169
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Thr Arg Ser Ser Gly Ser Ile Ala Ser Asn Tyr Val Gln
1               5                   10

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Glu Asp Asn Gln Arg Pro Ser
1               5

<210> SEQ ID NO 171
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 171

Gln Ser Tyr Asp Thr Leu Asn Val Tyr
1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Gly Gly Tyr Tyr Trp Ser
1               5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Ser Ile Ser Ser Gly Gly Tyr
1               5

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Ser Ile Ser Ser Gly Gly Tyr Tyr Trp Ser
1               5                   10

<210> SEQ ID NO 175
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Tyr Ile Tyr Lys Ser Gly Ser Asn Tyr Trp Asn Pro Ser Leu Lys
1               5                   10                  15

Ser Arg Val

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ile Tyr Lys Ser Gly Ser Asn Tyr
```

```
1               5
```

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

```
Thr Pro Thr Val Thr Gly Asp Trp Phe Asp Pro
1               5                   10
```

<210> SEQ ID NO 178
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

```
Thr Arg Ser Ser Gly Ser Ile Ala Ser Asn Tyr Val Gln
1               5                   10
```

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

```
Glu Asp Asn Gln Arg Pro Ser
1               5
```

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

```
Gln Ser Tyr Asp Thr Arg Asp Val Val
1               5
```

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

```
Ser Gly Gly Tyr Tyr Trp Ser
1               5
```

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 182

Gly Ser Ile Ser Ser Gly Gly Tyr
1               5

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Ser Ile Ser Ser Gly Gly Tyr Tyr Trp Ser
1               5                   10

<210> SEQ ID NO 184
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Tyr Ile Tyr Lys Ser Gly Ser Asn Tyr Trp Asn Pro Ser Leu Lys
1               5                   10                  15

Ser Arg Val

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ile Tyr Lys Ser Gly Ser Asn Tyr
1               5

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Thr Pro Thr Val Thr Gly Asp Trp Phe Asp Pro
1               5                   10

<210> SEQ ID NO 187
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Thr Arg Ser Ser Gly Ser Ile Ala Ser Asn Tyr Val Gln
1               5                   10
```

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Glu Asp Asn Gln Arg Pro Ser
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Thr Tyr Asp Ser Ile Asp Val Tyr
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ser Gly Gly Tyr Tyr Trp Ser
1               5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Ser Ile Ser Ser Gly Gly Tyr
1               5

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Ser Ile Ser Ser Gly Gly Tyr Tyr Trp Ser
1               5                   10

<210> SEQ ID NO 193
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 193

Gly Tyr Ile Tyr Lys Ser Gly Ser Asn Tyr Trp Asn Pro Ser Leu Lys
1               5                   10                  15

Ser Arg Val

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ile Tyr Lys Ser Gly Ser Asn Tyr
1               5

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Thr Pro Thr Val Thr Gly Asp Trp Phe Asp Pro
1               5                   10

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Thr Arg Ser Ser Gly Ser Ile Ala Ser Asn Tyr Val Gln
1               5                   10

<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Glu Asp Asn Gln Arg Pro Ser
1               5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gln Ser Tyr Asp Thr Leu Asn Val Tyr
1               5

<210> SEQ ID NO 199
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ser Gly Tyr Tyr Trp Gly
1               5

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Tyr Ser Ile Ser Ser Gly Tyr
1               5

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Tyr Ser Ile Ser Ser Gly Tyr Tyr Trp Gly
1               5                   10

<210> SEQ ID NO 202
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Leu Ser Tyr His Thr Arg Ser Thr Tyr Tyr Asp Pro Ser Leu Lys
1               5                   10                  15

Ser Arg Val

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Tyr His Thr Arg Ser Thr Tyr
1               5

<210> SEQ ID NO 204
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 204

Glu Ala Tyr Ser Asp Arg Ala Phe Asp Ile
1               5                   10

<210> SEQ ID NO 205
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Thr Arg Ser Ser Gly Ser Ile Ala Ser Asp Tyr Val Gln
1               5                   10

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ala Asp Asn Gln Arg Pro Ser
1               5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gln Ser Tyr Asp Ser Asn Ile Val Ile
1               5

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ser Tyr Ala Ile Ser
1               5

<210> SEQ ID NO 209
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Thr Phe Ser Ser Tyr
1               5

<210> SEQ ID NO 210
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 210

Gly Thr Phe Ser Ser Tyr Ala Ile Ser
1               5

<210> SEQ ID NO 211
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Gly Ile Ile Pro Ile Phe Gly Thr Ala Asn Tyr Ala Gln Lys Phe
1               5                   10                  15

Gln Gly Arg Val
            20

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ile Ile Pro Ile Phe Gly Thr Ala Asn
1               5

<210> SEQ ID NO 213
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Val Asp Arg Tyr Tyr Asn Trp Asn Tyr Phe Leu Gly Ser Phe Asp Tyr
1               5                   10                  15

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Gly Asn Asn Ile Arg Ser Lys Ser Val His
1               5                   10

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215
```

```
Tyr Asp Ser Asp Arg Pro Ser
1               5

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gln Val Trp Asp Ser Ser Ser Asp His His Val
1               5                   10

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ser Gly Gly Tyr Tyr Trp Ser
1               5

<210> SEQ ID NO 218
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Tyr Ile Tyr Lys Ser Gly Ser Ala Tyr Tyr Ser Pro Ser Leu Lys
1               5                   10                  15

Ser Arg Val

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Thr Pro Thr Val Thr Gly Asp Trp Phe Asp Pro
1               5                   10

<210> SEQ ID NO 220
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Thr Arg Ser Ser Gly Ser Ile Ala Ser Asn Tyr Val Gln
1               5                   10

<210> SEQ ID NO 221
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Glu Asp Asn Gln Arg Pro Ser
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gln Thr Tyr Asp Ser Ile Asp Val Tyr
1               5

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 223

His His His His His His
1               5

<210> SEQ ID NO 224
<211> LENGTH: 153
<212> TYPE: PRT
<213> ORGANISM: Homo sapiens

<400> SEQUENCE: 224

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 225
```

```
<211> LENGTH: 154
<212> TYPE: PRT
<213> ORGANISM: Macaca fascicularis

<400> SEQUENCE: 225

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Arg His Leu Gln Cys Leu Glu
65                  70                  75                  80

Glu Glu Leu Lys Pro Leu Glu Glu Val Leu Asn Leu Ala Gln Ser Lys
                85                  90                  95

Ser Phe His Leu Arg Asp Thr Lys Asp Leu Ile Ser Asn Ile Asn Val
            100                 105                 110

Ile Val Leu Glu Leu Lys Gly Ser Glu Thr Thr Leu Met Cys Glu Tyr
        115                 120                 125

Ala Asp Glu Thr Ala Thr Ile Val Glu Phe Leu Asn Arg Trp Ile Thr
    130                 135                 140

Phe Cys Gln Ser Ile Ile Ser Thr Leu Thr
145                 150
```